US011850332B2

(12) United States Patent
Shelton, IV et al.

(10) Patent No.: US 11,850,332 B2
(45) Date of Patent: Dec. 26, 2023

(54) METHOD FOR TREATING TISSUE

(71) Applicant: Cilag GmbH International, Zug (CH)

(72) Inventors: Frederick E. Shelton, IV, Hillsboro, OH (US); Michael J. Vendely, Lebanon, OH (US); Jason L. Harris, Lebanon, OH (US); Jacqueline Anim, Springboro, OH (US)

(73) Assignee: Cilag GmbH International, Zug (CH)

( * ) Notice: Subject to any disclaimer, the term of this patent is extended or adjusted under 35 U.S.C. 154(b) by 162 days.

(21) Appl. No.: 17/217,252

(22) Filed: Mar. 30, 2021

(65) Prior Publication Data

US 2022/0313874 A1 Oct. 6, 2022

(51) Int. Cl.
*A61B 17/072* (2006.01)
*A61B 17/00* (2006.01)
(Continued)

(52) U.S. Cl.
CPC ...... *A61L 31/146* (2013.01); *A61B 17/07292* (2013.01); *A61K 33/00* (2013.01);
(Continued)

(58) Field of Classification Search
CPC .......... A61B 17/07292; A61B 17/1155; A61B 2017/00004; A61B 2017/00061;
(Continued)

(56) References Cited

U.S. PATENT DOCUMENTS 5,711,960 A 1/1998 Shikinami
5,833,695 A 11/1998 Yoon
(Continued)

FOREIGN PATENT DOCUMENTS

EP 2113206 A2 11/2009
EP 2333701 A1 6/2011
(Continued)

OTHER PUBLICATIONS

U.S. Appl. No. 17/216,977, filed Mar. 30, 2021, Compressible Adjuncts With Fluid Control Features.
(Continued)

*Primary Examiner* — Ryan J. Severson
(74) *Attorney, Agent, or Firm* — Mintz Levin Cohn Ferris Glovsky and Popeo, P.C.

(57) ABSTRACT

Methods for treating tissue are provided. In one embodiment, an adjunct material, when secured to tissue, can receive at least one physiological element released from the tissue during healing progression of the tissue, and can exhibit first and second stiffnesses in compression that are approximately constant during first and second time periods from contact with the tissue, with the second stiffness decreasing with time as a function of at least one of oxidation, enzyme-catalyzed hydrolysis, and change of pH resulting from interaction with the at least one physiological element. In another embodiment, the adjunct can receive a unit volume of fluid that causes first and second portions of the adjunct to expand according to first and second expansion behaviors that differ from one another to apply different pressures to the tissue.

20 Claims, 47 Drawing Sheets

(51) Int. Cl.
*A61B 17/115* (2006.01)
*A61L 31/14* (2006.01)
*A61L 31/16* (2006.01)
*A61K 38/47* (2006.01)
*A61K 33/00* (2006.01)
*A61K 33/40* (2006.01)

(52) U.S. Cl.
CPC .............. *A61K 33/40* (2013.01); *A61K 38/47* (2013.01); *A61L 31/145* (2013.01); *A61L 31/16* (2013.01); *A61B 17/1155* (2013.01); *A61B 2017/00004* (2013.01); *A61B 2017/00061* (2013.01); *A61B 2017/00084* (2013.01); *A61B 2017/00199* (2013.01); *A61B 2017/00893* (2013.01); *A61B 2017/07271* (2013.01); *A61B 2017/07285* (2013.01); *A61L 2300/10* (2013.01); *A61L 2300/11* (2013.01); *A61L 2300/114* (2013.01); *A61L 2300/254* (2013.01); *A61L 2300/442* (2013.01)

(58) Field of Classification Search
CPC ........... A61B 2017/00893; A61B 2017/07271; A61B 2017/07285; A61K 33/00; A61K 33/40; A61K 38/47; A61L 31/16; A61L 31/146; A61L 31/145; A61L 2300/10; A61L 2300/11; A61L 2300/114; A61L 2300/254; A61L 2300/442
See application file for complete search history.

(56) References Cited

U.S. PATENT DOCUMENTS

| | | | |
|---|---|---|---|
| 6,029,671 | A | 2/2000 | Stevens et al. |
| 7,143,925 | B2 | 12/2006 | Shelton, IV et al. |
| 7,601,118 | B2 | 10/2009 | Smith et al. |
| 8,062,330 | B2 | 11/2011 | Prommersberger et al. |
| 8,317,070 | B2 | 11/2012 | Hueil et al. |
| 8,393,514 | B2 | 3/2013 | Shelton, IV et al. |
| 8,864,007 | B2 | 10/2014 | Widenhouse et al. |
| 9,084,602 | B2 | 7/2015 | Gleiman |
| 9,232,941 | B2 | 1/2016 | Mandakolathur et al. |
| 9,272,406 | B2 | 3/2016 | Aronhalt et al. |
| 9,282,962 | B2 | 3/2016 | Schmid et al. |
| 9,480,476 | B2 | 11/2016 | Aldridge et al. |
| 9,681,936 | B2 | 6/2017 | Hodgkinson et al. |
| 9,913,642 | B2 | 3/2018 | Leimbach et al. |
| 9,999,408 | B2 | 6/2018 | Boudreaux et al. |
| 10,111,661 | B2 | 10/2018 | Widenhouse et al. |
| 10,136,890 | B2 | 11/2018 | Shelton, IV et al. |
| 10,166,023 | B2 | 1/2019 | Vendely et al. |
| 10,172,611 | B2 | 1/2019 | Shelton, IV et al. |
| 10,172,617 | B2 | 1/2019 | Shelton, IV et al. |
| 10,172,618 | B2 | 1/2019 | Shelton, IV et al. |
| 10,251,649 | B2 | 4/2019 | Schellin et al. |
| 10,258,332 | B2 | 4/2019 | Schmid et al. |
| 10,265,091 | B2 | 4/2019 | Nativ et al. |
| 10,285,692 | B2 | 5/2019 | Widenhouse et al. |
| 10,349,939 | B2 | 7/2019 | Shelton, IV et al. |
| 10,368,869 | B2 | 8/2019 | Olson et al. |
| 10,433,846 | B2 | 10/2019 | Vendely et al. |
| 10,517,592 | B2 | 12/2019 | Shelton, IV et al. |
| 10,548,593 | B2 | 2/2020 | Shelton, IV et al. |
| 10,568,621 | B2 | 2/2020 | Shelton, IV et al. |
| 10,569,071 | B2 | 2/2020 | Harris et al. |
| 10,588,623 | B2 | 3/2020 | Schmid et al. |
| 10,772,732 | B1 | 9/2020 | Miller et al. |
| 10,939,911 | B2 | 3/2021 | Huitema et al. |
| 11,116,505 | B2 | 9/2021 | Vendely et al. |
| 11,224,423 | B2 | 1/2022 | Shelton, IV et al. |
| 11,291,449 | B2 | 4/2022 | Swensgard et al. |
| 11,406,377 | B2 | 8/2022 | Schmid et al. |
| 11,504,125 | B2 | 11/2022 | Shelton, IV et al. |
| 2002/0014951 | A1 | 2/2002 | Kramer et al. |
| 2004/0101546 | A1 | 5/2004 | Gorman et al. |
| 2004/0101548 | A1 | 5/2004 | Pendharkar |
| 2005/0070929 | A1 | 3/2005 | Dalessandro et al. |
| 2007/0021760 | A1 | 1/2007 | Kelleher |
| 2007/0034669 | A1 | 2/2007 | De et al. |
| 2007/0179528 | A1 | 8/2007 | Soltz et al. |
| 2007/0251835 | A1 | 11/2007 | Mika et al. |
| 2008/0051866 | A1 | 2/2008 | Chen et al. |
| 2009/0093550 | A1 | 4/2009 | Rolfes et al. |
| 2009/0123517 | A1 | 5/2009 | Flanagan et al. |
| 2009/0206142 | A1 | 8/2009 | Huitema et al. |
| 2009/0209031 | A1 | 8/2009 | Stopek |
| 2010/0331880 | A1 | 12/2010 | Stopek |
| 2012/0083836 | A1 | 4/2012 | Shelton, IV et al. |
| 2012/0100200 | A1 | 4/2012 | Belcheva et al. |
| 2012/0241491 | A1 | 9/2012 | Aldridge et al. |
| 2012/0241497 | A1 | 9/2012 | Mandakolathur Vasudevan et al. |
| 2012/0241498 | A1 | 9/2012 | Gonzalez et al. |
| 2012/0289979 | A1 | 11/2012 | Eskaros et al. |
| 2013/0146643 | A1 | 6/2013 | Schmid et al. |
| 2013/0172929 | A1 | 7/2013 | Hess et al. |
| 2013/0209659 | A1 | 8/2013 | Racenet et al. |
| 2013/0221065 | A1 | 8/2013 | Aronhalt et al. |
| 2013/0256377 | A1 | 10/2013 | Schmid et al. |
| 2014/0166726 | A1 | 6/2014 | Schellin et al. |
| 2014/0205637 | A1 | 7/2014 | Widenhouse et al. |
| 2015/0129634 | A1 | 5/2015 | Shelton, IV et al. |
| 2015/0133995 | A1 | 5/2015 | Shelton, IV et al. |
| 2015/0133996 | A1 | 5/2015 | Shelton, IV et al. |
| 2015/0134076 | A1 | 5/2015 | Shelton, IV et al. |
| 2015/0134077 | A1 | 5/2015 | Shelton, IV et al. |
| 2015/0136831 | A1 | 5/2015 | Baxter, III et al. |
| 2015/0196296 | A1 | 7/2015 | Swayze et al. |
| 2015/0238191 | A1 | 8/2015 | Schellin et al. |
| 2015/0297236 | A1 | 10/2015 | Harris et al. |
| 2015/0351761 | A1 | 12/2015 | Shelton, IV et al. |
| 2015/0351764 | A1* | 12/2015 | Shelton, IV ......... A61B 17/068 227/176.1 |
| 2016/0100839 | A1 | 4/2016 | Marczyk et al. |
| 2016/0106427 | A1 | 4/2016 | Shelton, IV et al. |
| 2016/0345976 | A1 | 12/2016 | Gonzalez et al. |
| 2017/0049448 | A1 | 2/2017 | Widenhouse et al. |
| 2017/0055981 | A1 | 3/2017 | Vendely et al. |
| 2017/0055986 | A1 | 3/2017 | Harris et al. |
| 2017/0055992 | A1 | 3/2017 | Widenhouse et al. |
| 2017/0055994 | A1 | 3/2017 | Vendely et al. |
| 2017/0056018 | A1 | 3/2017 | Zeiner et al. |
| 2017/0056567 | A1 | 3/2017 | Harris et al. |
| 2017/0119391 | A1 | 5/2017 | Schellin et al. |
| 2017/0281181 | A1 | 10/2017 | Matonick et al. |
| 2017/0296213 | A1 | 10/2017 | Swensgard et al. |
| 2018/0085124 | A1 | 3/2018 | Nativ et al. |
| 2018/0235613 | A1 | 8/2018 | Shelton, IV et al. |
| 2018/0235616 | A1 | 8/2018 | Shelton, IV et al. |
| 2018/0235625 | A1 | 8/2018 | Shelton, IV et al. |
| 2018/0353174 | A1 | 12/2018 | Widenhouse et al. |
| 2018/0353175 | A1 | 12/2018 | Widenhouse et al. |
| 2018/0353659 | A1 | 12/2018 | Widenhouse et al. |
| 2019/0200844 | A1 | 7/2019 | Shelton, IV et al. |
| 2019/0200981 | A1 | 7/2019 | Harris et al. |
| 2019/0201140 | A1 | 7/2019 | Yates et al. |
| 2019/0206004 | A1 | 7/2019 | Shelton, IV et al. |
| 2019/0206562 | A1 | 7/2019 | Shelton, IV et al. |
| 2019/0254654 | A1 | 8/2019 | Shelton, IV et al. |
| 2019/0254655 | A1 | 8/2019 | Shelton, IV et al. |
| 2019/0254661 | A1 | 8/2019 | Shelton, IV et al. |
| 2019/0254670 | A1 | 8/2019 | Shelton, IV et al. |
| 2019/0290267 | A1 | 9/2019 | Baxter, III et al. |
| 2019/0328390 | A1 | 10/2019 | Harris et al. |
| 2019/0344064 | A1 | 11/2019 | Buchanan |
| 2020/0205825 | A1 | 7/2020 | Vendely et al. |
| 2020/0238244 | A1 | 7/2020 | Tchakalova et al. |
| 2021/0077094 | A1 | 3/2021 | Harris et al. |
| 2021/0077095 | A1 | 3/2021 | Harris et al. |
| 2021/0077109 | A1 | 3/2021 | Harris et al. |
| 2021/0346015 | A1 | 11/2021 | Krulevitch et al. |
| 2022/0313145 | A1 | 10/2022 | Shelton, IV et al. |
| 2022/0313245 | A1 | 10/2022 | Shelton, IV et al. |
| 2022/0313246 | A1 | 10/2022 | Shelton, IV et al. |

(56) References Cited

U.S. PATENT DOCUMENTS

| | | |
|---|---|---|
| 2022/0313247 A1 | 10/2022 | Shelton, IV et al. |
| 2022/0313248 A1 | 10/2022 | Shelton, IV et al. |
| 2022/0313255 A1 | 10/2022 | Shelton, IV et al. |
| 2022/0313256 A1 | 10/2022 | Shelton, IV et al. |
| 2022/0313257 A1 | 10/2022 | Shelton, IV et al. |
| 2022/0313258 A1 | 10/2022 | Shelton, IV et al. |
| 2022/0313259 A1 | 10/2022 | Shelton, IV et al. |
| 2022/0313260 A1 | 10/2022 | Shelton, IV et al. |
| 2022/0313261 A1 | 10/2022 | Shelton, IV et al. |
| 2022/0313262 A1 | 10/2022 | Shelton, IV et al. |

FOREIGN PATENT DOCUMENTS

| | | |
|---|---|---|
| EP | 2395333 A1 | 12/2011 |
| EP | 2604196 A2 | 6/2013 |
| EP | 2628491 A2 | 8/2013 |
| EP | 3132811 A1 | 2/2017 |
| EP | 3530199 A2 | 8/2019 |
| EP | 3756612 A2 | 12/2020 |
| EP | 3782558 A1 | 2/2021 |
| EP | 3791804 A2 | 3/2021 |
| EP | 3791809 A1 | 3/2021 |
| WO | 9824048 A1 | 6/1998 |
| WO | 2006044490 A2 | 4/2006 |
| WO | 2006068999 A2 | 6/2006 |
| WO | 2015187793 A1 | 12/2015 |
| WO | 2020021433 A1 | 1/2020 |
| WO | 2022079516 A1 | 4/2022 |

OTHER PUBLICATIONS

U.S. Appl. No. 17/216,978, filed Mar. 30, 2021, Compressible Adjuncts With Drug Release Features.
U.S. Appl. No. 17/216,982, filed Mar. 30, 2021, Compressible Adjuncts With Drug Release Features.
U.S. Appl. No. 17/216,985, filed Mar. 30, 2021, Compressible Adjuncts With Drug Dosage Control Features.
U.S. Appl. No. 17/216,994, filed Mar. 30, 2021, Compressible Adjuncts With Different Behavioral Zones.
U.S. Appl. No. 17/216,914, filed Mar. 30, 2021, Smart Packaging for Tissue Adjuncts.
U.S. Appl. No. 17/216,946, filed Mar. 30, 2021, Passively Powered Packaging for Tissue Adjuncts.
U.S. Appl. No. 17/216,953, filed Mar. 30, 2021, Using Smart Packaging in Adjusting Use of Tissue Adjuncts.
U.S. Appl. No. 17/216,960, filed Mar. 30, 2021, Monitoring Healing After Tissue Adjunct Implantation.
U.S. Appl. No. 17/217,578, filed Mar. 30, 2021, Implantable Adjuncts Having Adjustable Degradation Profile.
U.S. Appl. No. 17/217,680, filed Mar. 30, 2021, Compressible Adjuncts With Healing-Dependent Degradation Profile.
U.S. Appl. No. 17/217,736, filed Mar. 30, 2021, Tissue Thickness Compensating Adjuncts Having Regions of Differential Expansion.
U.S. Appl. No. 17/217,784, filed Mar. 30, 2021, Composite Adjuncts That Degrade Through Multiple Different Mechanisms.
International Patent Application No. PCT/IB2020/060710 entitled "Drug Delivery Device Sensing Modules", filed on Nov. 13, 2020, 100 pages.
U.S. Appl. No. 17/022,520 entitled "Method of Applying Buttress to End Effector of Surgical Stapler", filed Sep. 16, 2020, 226 pages.
U.S. Appl. No. 17/068,857 entitled "Adaptive Responses From Smart Packaging of Drug Delivery Absorbable Adjuncts", filed Oct. 13, 2020, 97 pages.
Agren et al. (Jul. 2006) "Action of Matrix Metalloproteinases at Restricted Sites in Colon Anastomosis Repair: An Immunohistochemical and Biochemical Study", Surgery, 140(1):72-82.
Aslanian et al. (Mar.-Apr. 1984) "Dietary Intake and Urinary Excretion of Various Mineral Substances in Patients with Hypertension and Ischemic Heart Disease", Vopr Pitan, (2):16-9(English Abstract).

Bezwada Rao S. (2008) "Controlled Release of Drugs from Novel Absorbable Oligomers and Polymers", White Paper, Bezwada Biomedical, 7 pages.
Bezwada Rao S. (2008) "Functionalized Triclosan for Controlled Release Applications", White Paper, AP Bezwada Biomedical, 6 pages.
Bezwada Rao S. (2010) "Nitric Oxide and Drug Releasing Hydrolysable Macromers, Oligomers and Polymers", Chapter 11 of Biomaterials, ACS Symposium Series, American Chemical Society: Washington, DC, 24 pages.
Bezwada Rao S. (Mar. 2009) "Nitric Oxide and Drug Releasing Hydrolysable Macromers, Oligomers and Polymers", White Paper, Bezwada Biomedical, 9 pages.
Bosmans et al. (2015) "Colorectal Anastomotic Healing: Why the Biological Processes that Lead to Anastomotic Leakage Should Be Revealed Prior to Conducting Intervention Studies", BMC Gastroenterology, 15:180(6 pages).
Broughton et al. (Jun. 2006) "The Basic Science of Wound Healing", Plastic and Reconstructive Surgery, 117(7 Suppl):12S-34S.
Casalani et al. (Oct. 11, 2019) "A Perspective on Polylactic Acid-Based Polymers Use for Nanoparticles Synthesis and Applications", Frontiers in Bioengineering and Biotechnology, 7(259):1-16.
De Hingh et al. (Jun. 21, 2002) "The Matrix Metalloproteinase Inhibitor BB-94 Improves the Strength of Intestinal Anastomoses in the Rat", International Journal of Colorectal Disease, 17(5):348-354.
Fatouros et al. (Oct. 1999) "Influence of Growth Factors Erythropoietin and Granulocyte Macrophage Colony Stimulating Factor on Mechanical Strength and Healing of Colonic Anastomoses in Rats", The European Journal of Surgery, 165(10):986-992.
Gibson et al. (Nov. 2009) "MMPs Made Easy", Wounds International, 1(1):1-6.
Hayden et al. (Jun. 15, 2011) "The Role of Matrix Metalloproteinases in Intestinal Epithelial Wound Healing During Normal and Inflammatory States", Journal of Surgical Research, 168(2):315-324.
Holte et al. (Jun. 2009) "Cyclo-oxygenase 2 Inhibitors and the Risk of Anastomotic Leakage After Fast-Track Colonic Surgery", British Journal of Surgery, 96(6):650-654.
Kaemmer et al. (Oct. 2010) "Erythropoietin (EPO) Influences Colonic Anastomotic Healing in a Rat Model by Modulating Collagen Metabolism", Journal of Surgical Research, 163(2):e67-e72.
Kiyama et al. (Sep. 2002) "Tacrolimus Enhances Colon Anastomotic Healing in Rats", Wound Repair and Regeneration, 10(5):308-313.
Klein et al. (Jan. 2011) "Effect of Diclofenac on Cyclooxygenase-2 Levels and Early Breaking Strength of Experimental Colonic Anastomoses and Skin Incisions", European Surgical Research, 46(1):26-31.
Klein et al. (Jul. 18, 2010) "Physiology and Pathophysiology of Matrix Metalloproteases", Amino Acids, 41(2):271-290.
Krarup et al. (Apr. 26, 2013) "Expression and Inhibition of Matrix Metalloproteinase (MMP)-8, MMP-9 and MMP-12 in Early Colonic Anastomotic Repair", International Journal of Colorectal Disease, 28(8):1151-1159.
Martens et al. (Dec. 1991) "Postoperative changes in collagen synthesis in intestinal anastomoses of the rat: differences between small and large bowel", Gut, 32(12):1482-1487.
Moran et al. (May 15, 2007) "The Effect of Erythropoietin on Healing of Obstructive vs Nonobstructive Left Colonic Anastomosis: An Experimental Study", World Journal of Emergency Surgery, 2:13(6 pages).
Munireddy et al. (Dec. 2010) "Intra-abdominal Healing: Gastrointestinal Tract and Adhesions", Surgical Clinics of North America, 90(6):1227-1236(10 pages).
Øines et al. (Sep. 21, 2014) "Pharmacological Interventions for Improved Colonic Anastomotic Healing: A Meta-Analysis", World Journal of Gastroenterology, 20(35):12637-12648.
Raptis et al. (Mar. 2012) "The Effects of Tacrolimus on Colonic Anastomotic Healing in Rats", International Journal of Colorectal Disease, 27(3):299-308.

(56) References Cited

OTHER PUBLICATIONS

Savage et al. (Aug. 1997) "Role of Matrix Metalloproteinases in Healing of Colonic Anastomosis", Diseases of the Colon & Rectum, 40(8):962-970.
Siemonsma et al. (Mar. 1, 2003) "Doxycycline Improves Wound Strength After Intestinal Anastomosis in the Rat", Surgery, 133(3):268-276.
Thompson et al. (2006) "Clinical Review: Healing in Gastrointestinal Anastomoses, Part I", Microsurgery, 26(3):131-136.
Vandenbroucke et al. (Dec. 2014) "Is There New Hope for Therapeutic Matrix Metalloproteinase Inhibition?", Nature Reviews Drug Discovery, 13(12):904-927.
Witte et al. (Aug. 2003) "Repair of Full-thickness Bowel Injury", Critical Care Medicine, 31(8 Suppl):S538-S546.
U.S. Appl. No. 18/084,102, filed Dec. 19, 2022.
International Search Report and Written Opinion for Patent Application No. PCT/IB2022/052795, dated Oct. 10, 2022, 19 pages.
International Search Report and Written Opinion received for Application No. PCT/IB2022/052796, dated Oct. 11, 2022, 21 pages.
International Search Report and Written Opinion received for Application No. PCT/IB2022/052822, dated Oct. 13, 2022, 20 pages.
International Search Report and Written Opinion received for PCT Application No. PCT/IB2022/052798, dated Aug. 18, 2022, 14 pages.
International Search Report and Written Opinion received for PCT Application No. PCT/IB2022/052804, dated Jul. 8, 2022, 16 pages.
International Search Report and Written Opinion received for PCT Application No. PCT/IB2022/052806, dated Jul. 27, 2022, 17 pages.
International Search Report and Written Opinion received for PCT Application No. PCT/IB2022/052807, dated Jul. 7, 2022, 14 pages.
International Search Report and Written Opinion received for PCT Application No. PCT/IB2022/052809, dated Jul. 27, 2022, 17 pages.
International Search Report and Written Opinion received for PCT Application No. PCT/IB2022/052811, dated Jul. 7, 2022, 18 pages.
International Search Report and Written Opinion received for PCT Application No. PCT/IB2022/052813, dated Jul. 27, 2022, 15 pages.
International Search Report and Written Opinion received for PCT Application No. PCT/IB2022/052815, dated Jul. 20, 2022, 13 pages.
International Search Report and Written Opinion received for PCT Application No. PCT/IB2022/052816, dated Jul. 12, 2022, 16 pages.
International Search Report and Written Opinion received for PCT Application No. PCT/IB2022/052818, dated Aug. 10, 2022, 14 pages.
(Mar. 24, 2022) "What are Stents?", NIH National Heart, Lung, and Blood Institute, 3 pages.
Maurus et al. (2004) "Bioabsorbable Implant Material Review", Operative Techniques in Sports Medicine, 12:158-160.

* cited by examiner

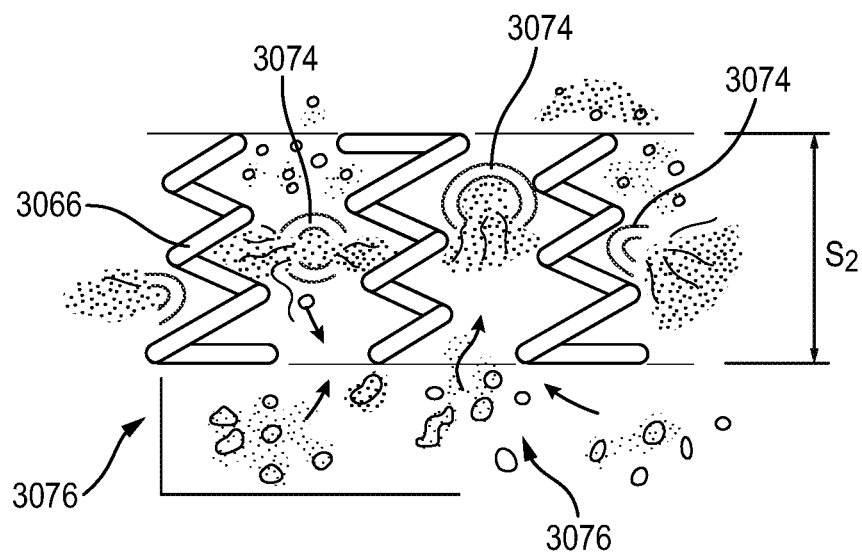
FIG. 77
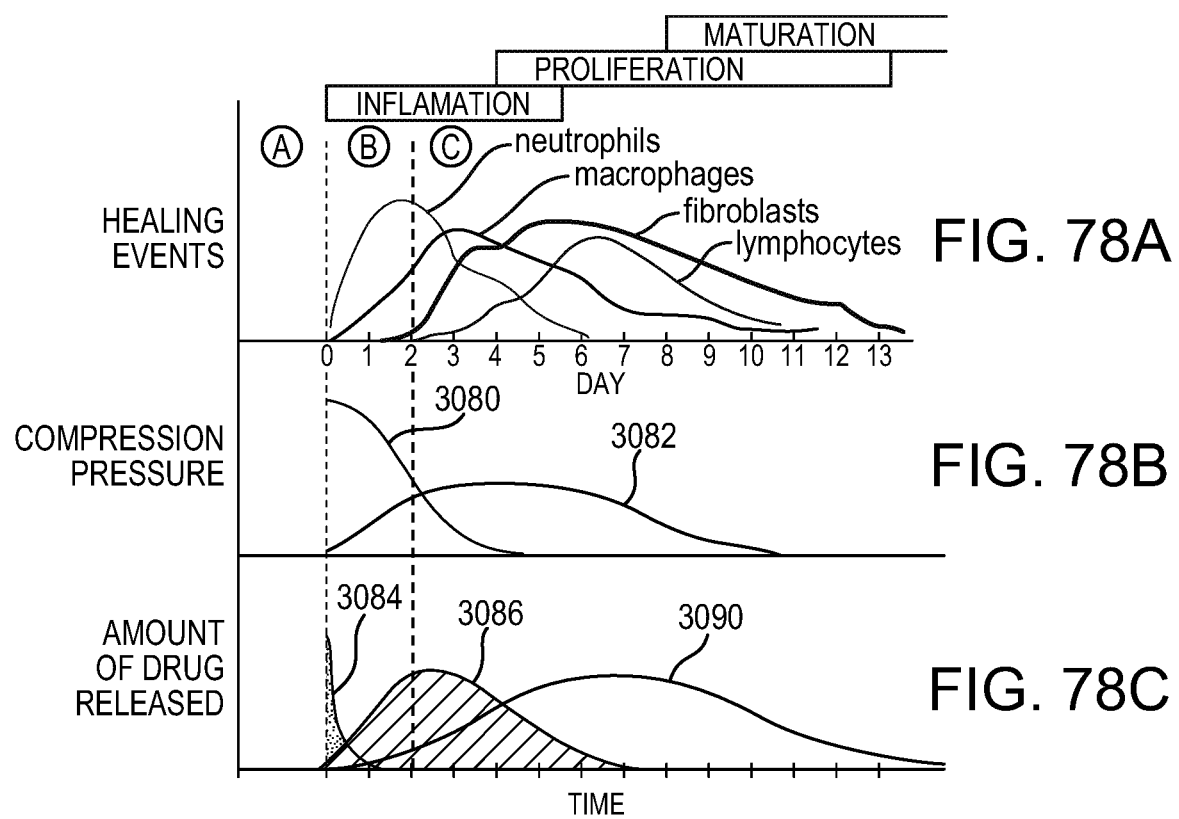
FIG. 78A
FIG. 78B
FIG. 78C

METHOD FOR TREATING TISSUE

FIELD OF THE INVENTION

The present disclosure relates generally to compressible adjuncts and methods of using compressible adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling.

Various implantable materials have been developed for use in combination with stapling tissue, however there remains a need for improved materials that address some of the aforementioned problems.

SUMMARY

Compressible adjuncts for use with a surgical cartridge are provided. In one exemplary embodiment, a compressible adjunct includes a biocompatible adjunct material that is configured to be releasably retained on at least one of a staple cartridge and an anvil and that is configured to be delivered to tissue by deployment of staples in the cartridge. The adjunct material includes a lattice main structure having at least one absorbable sub-structure formed in the lattice main structure, the at least one absorbable sub-structure configured to control fluid movement through the adjunct material such that the fluid movement impacts healing of tissue adjacent the adjunct material when the adjunct material is in a tissue deployed state.

The at least one absorbable sub-structure can have a variety of configurations. In some embodiments, the at least one absorbable sub-structure can include at least one of an active flow control structure and a passive flow control structure. In certain embodiments, the at least one absorbable sub-structure can include at least one of a duck bill valve, a flapper valve, and micro-passageways formed in a sidewall of the lattice main structure. In other embodiments, the at least one absorbable sub-structure includes at least one movable valve. The movable valve can be configured to control fluid movement therethrough. In some embodiments, the at least one absorbable sub-structure includes a plurality of absorbable sub-structures that together control a direction of fluid movement through the adjunct material.

The lattice main structure can have a variety of configurations. In some embodiments, the lattice main structure can include a plurality of hollow struts. In such embodiments, the at least one absorbable sub-structure can be formed in at least one of the hollow struts for controlling fluid flow therethrough.

In other embodiments, the lattice main structure can include a plurality of unit cells having passageways therethrough. In such embodiments, the at least one absorbable sub-structure can include at least one microstructure formed in at least one unit cell of the plurality of unit cells for controlling fluid flow through the respective passageway.

The unit cells can have a variety of configurations. In some embodiments, the plurality of unit cells can include at least one Schwarz-P structure. In certain embodiments, at least a portion of the plurality of unit cells can be configured to deform when the adjunct material is compressed so as to draw fluid into the adjunct material when the adjunct material is in a tissue deployed state, pump fluid out of the adjunct material to tissue adjacent the adjunct material when the adjunct material is in a tissue deployed state, or a combination thereof.

In some embodiments, the plurality of unit cells each include at least one internal stopping element. The at least one internal stopping element can be configured to limit the amount of deformation of the respective unit cell when the adjunct material is being compressed.

In another embodiment, a compressible adjunct for use with a surgical cartridge includes a biocompatible adjunct material that is configured to be releasably retained on at least one of a staple cartridge and an anvil and that is configured to be delivered to tissue by deployment of staples in the cartridge. The adjunct material includes at least one drug disposed therein, an intended cut line that extends along a longitudinal axis extending from a first end to a second end of the adjunct material, a retaining segment on a first side of the intended cut line, and a removing segment on a second side of the intended cut line. The adjunct material has a geometry that is configured to locally deliver or store the at least one drug relative to the intended cut line or relative to the retaining and removing segments such that the adjunct material has an asymmetric drug delivery profile of the at least one drug in at least one predetermined direction when the adjunct material is in a tissue deployed state.

In some embodiments, the compressible adjunct can include an indicator feature. The indicator feature can be configured to indicate at least one of the removing segment of the adjunct material and a location of the at least one drug within the adjunct material.

In some embodiments, the at least one drug can be only disposed within the retaining segment of the adjunct material.

The adjunct material can have a variety of configurations. In some embodiments, the adjunct material can have a tissue-contacting surface and a cartridge-contacting surface that is opposite the tissue-contacting surface. The tissue-contacting surface can differ from the cartridge-contacting surface in at least one of concentration and type of the at least one drug.

Stapling assemblies for use with a surgical stapler are also provided. In one exemplary embodiment, a stapling assembly includes a cartridge and a biocompatible adjunct. The cartridge has a plurality of staples disposed therein, in which the plurality of staples are arranged in staple rows and configured to be deployed into tissue. The biocompatible adjunct is configured to be releasably retained on the cartridge and is configured to be delivered to tissue by deployment of the plurality of staples. The adjunct includes a lattice macrostructure having a plurality of absorbable microstructures formed therein, in which each absorbable microstructure is configured to direct, limit, or prevent fluid movement as fluid flows through the lattice macrostructure.

The plurality of absorbable microstructures can have a variety of configurations. In some embodiments, the plurality of absorbable microstructures can include at least one of an active flow control structure and a passive flow control structure. In other embodiments, the plurality of absorbable microstructures can include movable valves.

The lattice macrostructure can have a variety of configurations. For example, in some embodiments, the lattice macrostructure can include a plurality of Schwarz-P structures having passageways therethrough. The plurality of absorbable microstructures can include at least one microfeature that formed in at least one Schwarz-P structure of the plurality of Schwarz-P structures for controlling fluid flow through the respective passageway. In certain embodiments, at least a portion of the plurality of Schwarz-P structures can be configured to deform when the adjunct is compressed so as to draw fluid into the adjunct when the adjunct is in a tissue deployed state, pump fluid out of the adjunct to tissue adjacent the adjunct when the adjunct is in a tissue deployed state, or a combination thereof. In such embodiments, at least a portion of the plurality of Schwarz-P structures can be positioned within regions of the adjunct that do not overlap with the staple rows when the adjunct is releasably retained on the cartridge.

Compressible adjuncts for use with a surgical cartridge are provided. In one exemplary embodiment, a compressible adjunct includes a biocompatible adjunct material that is configured to be releasably retained on at least one of a staple cartridge and anvil and that is configured to be delivered to tissue by deployment of staples in the cartridge. The adjunct material includes a hollow lattice macrostructure having at least one drug contained therein. The hollow lattice macrostructure is formed of a plurality of unit cells having at least one absorbable sub-structure that is formed in the plurality of unit cells. The at least one absorbable sub-structure is configured to control a rate of fluid movement through the respective unit cell so as to control the release of the at least one drug from the adjunct material when the adjunct material is in a tissue deployed state.

The plurality of unit cells can have a variety of configurations. In some embodiments, each unit cell can have at least one passageway extending therethrough. The at least one passageway can be configured to impact the release of the at least one drug from the adjunct material when the adjunct material is in a tissue deployed state. In such embodiments, the release of the at least one drug from the adjunct material can be in response to an active interaction between the plurality of unit cells and respective passageways. In other embodiments, the at least one passageway can be configured to impact at least one of ingress of fluid into the adjunct material and egress of fluid out of the adjunct material when the adjunct material is in a tissue deployed state.

The at least one absorbable sub-structure can have a variety of configurations. In some embodiments, the at least one absorbable sub-structure can include at least one of a duck bill valve, a flapper valve, and micro-passageways formed in a wall of the unit cell.

The hollow lattice macrostructure can have a variety of configurations. In some embodiments, the hollow lattice macrostructure can include at least one primary reservoir formed in the hollow lattice macrostructure. The at least one primary reservoir can have a first drug of the at least one drug disposed therein. The at least one primary reservoir can be configured to release at least a portion of the first drug therefrom in response to an initial ingress of fluid into the adjunct material when the adjunct material is in a tissue deployed state. In certain embodiments, the hollow lattice macrostructure includes at least one secondary reservoir formed in the hollow lattice macrostructure. The at least one secondary reservoir can have a second drug of the at least one drug disposed therein. The at least one secondary reservoir can be configured to release at least a portion of the second drug therefrom in response to structural degradation of at least a portion of the adjunct material defining the at least one secondary reservoir when the adjunct material is in a tissue deployed state.

The plurality of unit cells can have a variety of configurations. In some embodiments, the plurality of unit cells include at least one Schwarz-P structure. In other embodiments, the plurality of units can include at least one hollow strut. In either embodiment, the at least one absorbable sub-structure can include a one-way valve.

In another embodiment, a compressible adjunct for use with a surgical cartridge includes a biocompatible adjunct material that is configured to be releasably retained on at least one of a staple cartridge and an anvil and that is configured to be delivered to tissue by deployment of staples in the cartridge. The adjunct material includes a lattice main structure having at least one drug therein. The lattice main structure is formed of a plurality of hollow unit cells, in which each hollow unit cell is configured to pump fluid through the adjunct material to at least one of direct drug movement through the adjunct material and control the location of drug elution from the adjunct material when the adjunct material is in a tissue deployed state.

The plurality of hollow unit cells can have a variety of configurations. In some embodiments, each hollow unit cell can have at least one passageway extending therethrough. The at least one passageway can be configured to impact drug elution from the adjunct material when the adjunct material is in a tissue deployed state. In such embodiments, drug elution from the adjunct material can be in response to an active interaction between the plurality of hollow unit cells and respective passageways. In certain embodiments, the plurality of hollow unit cells can include at least one Schwarz-P structure.

The lattice main structure can have a variety of configurations. In some embodiments, the lattice main structure can include at least one absorbable sub-structure that is formed in at least one hollow unit cell of the plurality of hollow unit cells. The at least one absorbable sub-structure can be configured to control drug movement through the adjunct material when the adjunct material is in a tissue deployed state. In such embodiments, the at least one absorbable sub-structure can include at least one movable valve. The at least one movable valve can be configured to control drug movement therethrough.

Stapling assemblies for use with a surgical stapler are also provided. In one exemplary embodiments, a stapling assembly includes a cartridge and a biocompatible adjunct. The cartridge has a plurality of staples disposed therein, in which the plurality of staples being arranged in staple rows and configured to be deployed into tissue. The adjunct is configured to be releasably retained on the cartridge and is configured to be delivered to tissue by deployment of the plurality of staples in the cartridge. The adjunct includes a hollow lattice macrostructure having at least one drug contained therein. The hollow lattice macrostructure is formed of a plurality of Schwarz-P structures, in which each Schwarz-P structure has at least one first absorbable sub-structure formed therein. The at least one first absorbable sub-structure is configured to at least one of direct drug movement through the adjunct and control drug elution from the adjunct when the adjunct is in a tissue deployed state.

In some embodiments, at least a portion of the plurality of Schwarz-P structures can be arranged in regions of the adjunct that do not overlap with the staples rows when the adjunct is releasably retained on the cartridge.

In some embodiments, the cartridge has a knife slot defined therein. In such embodiments, at least a portion of the plurality of Schwarz-P structures can be arranged in regions of the adjunct that do not overlap with the knife slot when the adjunct is releasably retained on the cartridge.

The hollow lattice macrostructure can have a variety of configurations. In some embodiments, the hollow lattice macrostructure include a plurality of connecting structures that extend between and connect adjacent Schwarz-P structures to each other. The at least one connecting structure of the plurality of connecting structures can include at least one second absorbable sub-structure formed therein.

In another exemplary embodiment, a compressible adjunct includes a non-fibrous adjunct material formed of at least one fused bioabsorbable polymer. The adjunct material is configured to be releasably retained on a staple cartridge and is configured to be delivered to tissue by deployment of staples in the cartridge. The adjunct material includes a lattice macrostructure having a plurality of drug delivery microstructures formed in the lattice macrostructure, in which each drug delivery microstructure has drug disposed therein. The plurality of drug delivery microstructures are configured to encapsulate the drug to thereby prevent drug release until the plurality of drug delivery microstructures are at least one of thermally ruptured while the adjunct material is stapled to tissue and mechanically ruptured in response to at least one of clamping, stapling, and cutting of the adjunct material.

In some embodiments, the plurality of drug delivery microstructures can be configured to thermally rupture in response to an increase in temperature. In such embodiments, the increase in temperature can be in response to an infection of the tissue that is stapled to the adjunct material. In other embodiments, the plurality of drug delivery microstructures can be configured to thermally rupture when the adjunct material is at or above an activation temperature.

The plurality of drug delivery microstructures can have a variety of configurations. In some embodiments, the plurality of drug delivery microstructures can include at least one triply periodic minimal surface structure. In certain embodiments, the plurality of drug delivery microstructures can include at least one Schwarz-P structure. In other embodiments, the plurality of drug delivery microstructures can include at least one hollow strut.

The lattice macrostructure can have a variety of configurations. In some embodiments, the lattice macrostructure can include a plurality of connecting structures. The plurality of connecting structures can extend between and connect adjacent drug delivery microstructures to each other. In certain embodiments, at least a portion of the plurality of connecting structures can have drug disposed therein.

Stapling assemblies for use with a surgical stapler are also provided. In one exemplary embodiment, a stapling assembly includes a cartridge and a non-fibrous adjunct formed of at least one fused bioabsorbable polymer. The cartridge has a plurality of staples disposed therein, in which the plurality of staples being configured to be deployed into tissue. The adjunct is configured to be releasably retained on the cartridge such that the adjunct can be attached to tissue by the plurality of staples in the cartridge. The adjunct includes a lattice main structure having a plurality of first microreservoirs formed therein, in which each first microreservoir has drug disposed therein. The plurality of first microreservoirs are each configured to release corresponding drug therefrom in response to at least one of clamping, stapling, and cutting of the adjunct.

In some embodiments, the plurality of first microreservoirs can be positioned within regions of the adjunct that overlap with staple legs of the plurality of staples when the adjunct is releasably retained on the cartridge. The staple legs can be configured to advance through the plurality of first microreservoirs and release drug therefrom and into tissue as the plurality of staples are deployed into tissue.

In some embodiments, the cartridge can include a slot that is defined therein and that can be configured to receive a cutting element. The plurality of first microreservoirs can be positioned within regions of the adjunct that overlap with the slot when the adjunct is releasably retained on the cartridge. The cutting element can be configured sever the plurality of first microreservoirs to cause drug to release therefrom as the cutting element advances through the slot.

The lattice main structure can have a variety of configurations. In some embodiments, the lattice main structure can include a plurality of triply periodic minimal surface structures. Each triply periodic minimal surface structure can define a respective first microreservoir of the plurality of first microreservoirs. In certain embodiments, the plurality of triply periodic minimal surface structures can include at least one Schwarz-P structure. In other embodiments, the lattice main structure can include a plurality of connecting structures. The plurality of connecting structures can extend between and connect adjacent first microreservoirs to each other. In certain embodiments, at least a portion of the plurality of connecting structures can have drug disposed therein. In yet other embodiments, the lattice main structure can include a plurality of hollow struts. Each hollow strut can define a respective first microreservoir of the plurality of first microreservoirs.

In some embodiments, the lattice main structure can include a plurality of second microreservoirs. Each second microreservoir can have drug disposed therein. In certain embodiments, the lattice main structure can include a plurality of Schwarz-P structures, in which at least one of the plurality of first microreservoirs and the plurality of second microreservoirs can be defined by the plurality of Schwarz-P structures. In some embodiments, the cartridge can include a slot that is defined therein and that can be configured to receive a cutting element The plurality of second microreservoirs can be positioned within regions of the adjunct that overlap with the slot when the adjunct is releasably retained on the cartridge. The cutting element can be configured to sever the plurality of second microreservoirs to cause drug to release therefrom as the cutting element advances through the slot.

Compressible adjuncts for use with a staple cartridge are provided. In one exemplary embodiments, the compressible adjunct includes a non-fibrous adjunct material formed of at least one fused bioabsorbable polymer. The adjunct material is configured to be releasably retained on a staple cartridge and is configured to be delivered to tissue by deployment of staples in the cartridge. The adjunct material includes a lattice macrostructure having primary and secondary microreservoirs formed in the lattice macrostructure. The primary microreservoirs and secondary microreservoirs are different in size relative to each other and contain drug disposed therein. The primary microreservoirs are configured to release drug therefrom upon activation and the secondary microreservoirs are configured to release drug therefrom upon degradation of at least one of the at least one fused bioabsorbable polymer so that the combination of the primary and secondary microreservoirs control the dosage of drug being released from the adjunct material when the adjunct material is in a tissue deployed state.

The lattice macrostructure can have a variety of configurations. In some embodiments, the lattice macrostructure can include at least one internal stopping member formed in each primary microreservoir. The at least one internal stopping member can be configured to limit the amount of deformation of the respective primary microreservoir when the adjunct material is being compressed. In certain embodiments, the at least one internal stopping member can be configured to degrade over time while the adjunct material is in a tissue deployed state to thereby allow for greater deformation of the respective primary microreservoir when the adjunct material is being compressed. In certain embodiments, the primary microreservoirs can be formed of a first fused bioabsorbable polymer and the at least one internal stopping member can be formed of a second fused bioabsorbable polymer that degrades faster that the first fused bioabsorbable polymer.

In some embodiments, the lattice macrostructure can include a plurality of triply periodic minimal surface structures. Each triply periodic minimal surface structure can define a respective primary microreservoir of the plurality of primary microreservoirs. The plurality of triply periodic minimal surface structures can at least one Schwarz-P structure. In other embodiments, the lattice macrostructure can include a plurality of hollow struts. Each hollow strut can define a respective secondary microreservoir of the plurality of second microreservoirs.

In another embodiment, a compressible adjunct for use with a staple cartridge includes a non-fibrous adjunct material that is formed of at least one fused bioabsorbable polymer. The adjunct material is configured to be releasably retained on a staple cartridge body and is configured to be delivered to tissue by deployment of staples in the cartridge body. The adjunct material can include a lattice main structure having a plurality of first microstructures formed in the lattice main structure and a plurality of second microstructures formed in the lattice main structure. Each first microstructure has a first drug disposed therein and is configured to encapsulate the first drug to thereby prevent drug release until the first microstructure is compressed from an uncompressed state to a compressed state or is ruptured in response to at least one of clamping, stapling, and cutting of the adjunct material. Each second microstructure has a second drug disposed therein and is configured to encapsulate the second drug to thereby prevent drug release until degradation of at least a portion of a wall that defines the second microreservoir.

The lattice main structure can have a variety of configurations. In some embodiments, the lattice main structures can include at least one internal stopping member formed in each first microstructure. The at least one internal stopping member can be configured to limit the amount of deformation of the respective first microstructure when the adjunct material is being compressed. In certain embodiments, the at least one internal stopping member can be configured to degrade over time while the adjunct material is in a tissue deployed state to thereby allow for greater deformation of the respective first microstructure when the adjunct material is being compressed. In certain embodiments, the plurality of first microstructures can be formed of a first fused bioabsorbable polymer and the at least one internal stopping member can be formed of a second fused bioabsorbable polymer that degrades faster than the first fused bioabsorbable polymer.

The plurality of first microstructures can have a variety of configurations. In some embodiments, the plurality of first microstructures can include at least one triply periodic minimal surface structure. In other embodiments, the plurality of first microstructures can include at least one Schwarz-P structure. In yet other embodiments, the plurality of first microstructures can include at least one hollow strut.

In another embodiment, a compressible adjunct for use with a staple cartridge includes a non-fibrous adjunct material that is formed of at least one fused bioabsorbable polymer. The adjunct material is configured to be releasably retained on a staple cartridge and is configured to be delivered to tissue by deployment of staples in the cartridge. The adjunct material includes a lattice macrostructure formed of a plurality of hollow unit cells, in which each unit cell has an inner layer and an outer layer. The inner layer defines an internal cavity of the unit cell and is formed of a blend of a first fused bioabsorbable polymer and drug, and the outer layer is formed of a second fused bioabsorbable polymer that is configured to degrade at a degradation rate that is less than a degradation rate of the first fused bioabsorbable polymer.

In some embodiments, the first fused bioabsorbable polymer can be configured to undergo degradation when the adjunct material is stapled to tissue so as to release discrete amounts of the drug into the internal cavities of the hollow unit cells over time. In certain embodiments, each hollow unit cell can be configured to deform when the adjunct material is compressed so as to pump at least a portion of the drug that is present in the internal cavity out of adjunct material to tissue adjacent the adjunct material when the adjunct material is in a tissue deployed state.

The plurality of hollow unit cells can have a variety of configurations. In some embodiments, the plurality of hollow unit cells can include at least one Schwarz-P structure. In certain embodiments, the lattice macrostructure can include a plurality of connecting structures that extend between and connect adjacent Schwarz-P structures to each other.

Compressible adjuncts for use with a staple cartridge are provided. In one exemplary embodiment, the compressible adjunct includes a non-fibrous adjunct material formed of at least one fused bioabsorbable polymer. The adjunct material is configured to be releasably retained on a staple cartridge and is configured to be delivered to tissue by deployment of staples in the cartridge The adjunct material includes a lattice macrostructure having at least one drug contained therein. The lattice macrostructure is formed of a plurality of unit cells, in which each unit cell is configured to eject a predetermined amount of drug from the adjunct material and the predetermined amount of the drug being a function of a compression profile of the respective unit cell.

The plurality of unit cells can have a variety of configurations. In some embodiments, at least one unit cell of the plurality of unit cells can have a variable wall thickness. In some embodiments, the plurality of unit cells can include first unit cells and second unit cells. The first unit cells can have a first compression profile and the second unit cells can have a second compression profile that is different than the first compression profile. In some embodiments, each unit cell can have a plurality of compression zones. The plurality of compression zones can include a first compression zone and a second compression zone. The first compression zone can have a first compressive strength and the second compression zone can have a second compressive strength that is different than the first compressive strength. The first compression zone can configured to compress from a first uncompressed height to a first compressed height. The second compression zone can be configured to compress from a second uncompressed height to a second compressed height that is different than the first compressed height.

In some embodiments, each unit cell can include a plurality of sub-structures formed therein. The plurality of sub-structures can be configured to control the deformation behavior of the respective unit cell when the adjunct material is being compressed. The plurality of sub-structures can include first sub-structures and second sub-structures. The first sub-structures can be projections that extend inward from a wall of the unit cell and the second sub-structures can be recesses formed in a wall of the unit cell. In certain embodiments, the plurality of sub-structures can include at least one internal stopping member.

In some embodiments, the plurality of unit cells can include Schwarz-P structures. In such embodiments, the lattice macrostructure can comprise a plurality of connecting structures. The plurality of connecting structures can extend between and connect adjacent Schwarz-P structures to each other.

In another embodiment, a compressible adjunct for use with a staple cartridge includes a non-fibrous adjunct material formed of at least one fused bioabsorbable polymer. The adjunct material is configured to be releasably retained on a staple cartridge and is configured to be delivered to tissue by deployment of staples in the cartridge. The adjunct material includes a lattice main structure having at least one drug contained therein. The lattice main structure can include first sub-structures formed in at least one first portion of the lattice main structure and second sub-structures formed in at least one second portion of the lattice main structure. The first sub-structures and the second sub-structures are configured to control a first release rate and a second release rate, respectively, of the at least one drug from the adjunct material when the adjunct material is compressed and in a tissue deployed state, the first release rate being different than the second release rate.

The first and second portions of the lattice main structure can have a variety of configurations. In some embodiments, the first portion of the lattice main structure can have a first wall thickness and the second portion of the lattice main structure can have a second wall thickness that is different than the first wall thickness. In certain embodiments, the first portion of the lattice main structure can be configured to deform from a first undeformed state to a first deformed state. In such embodiments, the second portion of the lattice main structure can be configured to deform from a second undeformed state to a second deformed state that is different than the first deformed state.

The first sub-structures and the second sub-structures can have a variety of configurations. In some embodiments, the first sub-structures can include at least one of a first projection that extends inward from a wall of the lattice main structure and a first recess formed in a wall of the lattice main structure. In some embodiments, the second sub-structures can include at least one of a second projection that extends inward from a wall of the lattice main structure and a second recess formed in a wall of the lattice main structure. In certain embodiments, at least one of the first sub-structures and the second sub-structures can include at least one internal stopping member.

The lattice main structure can have a variety of configurations. In some embodiments, the lattice main structure can include a plurality of Schwarz-P structures. In such embodiments, the lattice main structure can include a plurality of connecting structures. The connecting structures can extend between and connect adjacent Schwarz-P structures to each other.

Various smart packagings for tissue adjuncts and methods of using smart packagings for tissue adjuncts are provided.

In one aspect, a surgical system is provided that in one embodiment includes a bioabsorbable adjunct configured to be implanted in a body of a patient using a surgical stapler, a medicant releasably retained by the adjunct and configured to be released from the adjunct into the body of the patient, and a packaging unit packaging the adjunct and the medicant. The packaging unit includes a storage device configured to store therein data regarding at least one of the adjunct and the medicant. The data includes at least one of an expiration date, an identification code, a manufacturing date of the adjunct, and a manufacturing date of the medicant. The packaging unit also includes a communications interface configured to communicate the data to an external computer system that is external to the packaging unit.

The surgical system can vary in any number of ways. For example, the surgical system can also include the external computer system, and the external computer system can be configured to receive the data, and, based the received data, at least one of set an operational parameter of the surgical stapler and cause a display to show operational information of the surgical stapler. In some embodiments, the external computer system can be configured to, based the received data, at least set the operational parameter of the surgical stapler; and/or the external computer system can be configured to, based the received data, at least cause the display to show operational information of the surgical stapler, and the operational information can include at least one of steps of using the surgical stapler, an operational status of the surgical stapler, and compatibility of use of the adjunct with the surgical stapler. In some embodiments, the external computer system can include a surgical hub. In some embodiments, the surgical stapler can include the external computer system.

For another example, the storage device and the communications interface can be defined by a Quick Response (QR) code, the storage device and the communications interface can be defined by a radio frequency identification (RFID) tag, or the communications interface can include a Bluetooth communications module.

For yet another example, the surgical system can also include a sensor configured to, with the packaging unit packaging the adjunct and the medicant, gather data regarding an exposure condition of at least one of the adjunct and the medicant, the exposure condition can be a condition that affects performance of at least one of the adjunct in the body of the patient and the medicant in the body of the patient, the packaging unit can include the sensor, the memory can be configured to store the data gathered by the sensor, and the communications interface can be configured to communicate the data gathered by the sensor to the external computer system. In some embodiments, the exposure condition can include at least one of temperature that affects a viability of the medicant, humidity that affects structural resilience of the adjunct, and light that affects the viability of the medicant; the exposure condition can include at least one of ultraviolet that affects a viability of the medicant, oxygen that affects structural resilience of the adjunct, and time that affects an expiration date of the medicant; and/or the surgical system can also include the external computer system, and the external computer system can be configured to analyze the received data gathered by the sensor and thereby determine whether the exposure condition adversely affected performance of the at least one of the adjunct and the medicant. In some embodiments, the external computer system can be configured to, based the determination, at least one of set an operational parameter of the surgical stapler and cause a display to show operational information of the surgical stapler.

For still another example, the surgical system can also include a staple cartridge to which the adjunct is releasably coupled, the packaging unit can also package the staple cartridge, and the data can also include data regarding the staple cartridge.

In another aspect, a surgical method is provided that in one embodiment includes receiving, at a computer system, data from a communications interface of a packaging unit regarding at least one of a bioabsorbable adjunct and a medicant releasably retained by the adjunct. The adjunct is configured to be implanted in a body of a patient using a surgical stapler. The medicant is configured to be released from the adjunct into the body of the patient. The adjunct and medicant are packaged in the packaging unit. The computer system is external to the packaging unit. The data includes at least one of an expiration date, an identification code, a manufacturing date of the adjunct, and a manufacturing date of the medicant. The surgical method also includes causing, using the computer system and based on the received data, at least one of an operational parameter of the surgical stapler to be set and a display to show operational information of the surgical stapler.

The surgical method can have any number of variations. For example, the external computer system can include a surgical hub. For another example, the surgical stapler can include the external computer system. For yet another example, the packaging unit can also package a staple cartridge, and the data can also include data regarding the staple cartridge.

For still another example, the surgical method can also include receiving, at the computer system, data gathered using a sensor packaged by the packaging unit, the gathered data can regard at least one exposure condition of at least one of the adjunct and the medicant, the at least one exposure condition can be a condition that affects performance of at least one of the adjunct in the body of the patient and the medicant in the body of the patient, the surgical method can also include analyzing, at the computer system, the received data gathered by the sensor and thereby determine whether the at least one exposure condition adversely affected performance of the at least one of the adjunct and the medicant, and the surgical method can also include, based the determination, causing, using the computer system, at least one of an operational parameter of the surgical stapler to be set and a display to show operational information of the surgical stapler. In some embodiments, the at least one exposure condition can include at least one of temperature that affects a viability of the medicant, humidity that affects structural resilience of the adjunct, light that affects the viability of the medicant, ultraviolet that affects the viability of the medicant, oxygen that affects structural resilience of the adjunct, and time that affects an expiration date of the medicant.

Various passively powered smart packagings for tissue adjuncts and methods of using passively powered smart packagings for tissue adjuncts are provided.

In one aspect, a surgical system is provided that in one embodiment includes a packaging unit packaging a bioabsorbable adjunct configured to be implanted in a body of a patient using a surgical stapler, a medicant releasably retained by the adjunct and configured to be released from the adjunct into the body of the patient, a degradable element configured to degrade in response to exposure to an environmental condition, and a light sensitive element configured to be powered in response to the packaging unit being opened and exposing the light sensitive element to light. The surgical system also includes a communications interface configured to, with the communications interface receiving power from the powered light sensitive element, communicate data regarding a state of the degradable element to a computer system external to the packaging unit.

The surgical system can vary in any number of ways. For example, the packaging unit can also package a circuit that is closed with the degradable element being in a non-degraded state and that is open with the degradable element being in a degraded state, and the circuit being closed or open can indicate the state of the degradable element that is communicated by the communications interface. For another example, the environmental condition can include humidity, temperature, oxygen, and/or irradiation. For yet another example, the light sensitive element can include a solar cell. For still another example, the computer system can include a surgical hub. For another example, the surgical system can also include a light configured to, with the communications interface receiving power from the powered light sensitive element, illuminate in a first color corresponding to the degradable element being in a non-degraded state and illuminate in a second, different color corresponding to the degradable element being in a degraded state. For yet another example, the packaging unit can include a sensor configured to gather data regarding the environmental condition, and the communications interface can be configured to, with the communications interface receiving power from the powered light sensitive element, communicate the gathered data to the computer system.

In another embodiment, a surgical system includes a packaging unit packaging a bioabsorbable adjunct configured to be implanted in a body of a patient using a surgical stapler, a medicant releasably retained by the adjunct and configured to be released from the adjunct into the body of the patient, a light sensitive element configured to be powered in response to the packaging unit being opened and exposing the light sensitive element to light, a conductive element configured to degrade in response to exposure to an environmental condition, and a communications interface in series with the conductive element and the light sensitive element. The communications interface is configured to, with the communications interface receiving power from the powered light sensitive element, communicate data regarding an amount of degradation of the conductive element to a computer system external to the packaging unit.

The surgical system can vary in any number of ways. For example, a conductivity of the conductive element can be proportional to the amount of degradation of the conductive element. For another example, the packaging unit can also package a sensor configured to gather data regarding the environmental condition, and the communications interface can be configured to, with the communications interface receiving power from the powered light sensitive element, communicate the gathered data to the computer system. For yet another example, the environmental condition can include at least one of humidity, temperature, oxygen, and irradiation. For still another example, the light sensitive element can include a solar cell. For another example, the computer system can include a surgical hub.

In another aspect, a surgical method is provided that in one embodiment includes opening a packaging unit packaging a bioabsorbable adjunct configured to be implanted in a body of a patient using a surgical stapler, a medicant releasably retained by the adjunct and configured to be released from the adjunct into the body of the patient, and a degradable element configured to degrade in response to exposure to an environmental condition. The opening of the packaging unit exposes a light sensitive element to light and thereby powers the light sensitive element, and triggers a communications interface, with the communications interface receiving power from the powered light sensitive element, to communicate data regarding a state of the degradable element to a computer system external to the packaging unit.

The surgical method can have any number of variations. For example, the environmental condition can include at least one of humidity, temperature, oxygen, and irradiation. For another example, the computer system can be configured to, based on the received data regarding the state of the degradable element cause at least one of an operational parameter of the surgical stapler to be set and a display to show operational information of the surgical stapler. For yet another example, the opening of the packaging unit can trigger the communications interface to communicate, to the computer system, data gathered by a sensor regarding exposure of the packaging unit to the environmental condition.

Various systems and methods of using smart packagings in adjusting use of tissue adjuncts are provided.

In one aspect, a surgical system is provided that in one embodiment includes a bioabsorbable adjunct configured to be implanted in a body of a patient using a surgical stapler, a medicant releasably retained by the adjunct and configured to be released from the adjunct into the body of the patient, a packaging unit packaging the adjunct and the medicant, and a sensor configured to, with the packaging unit packaging the adjunct and the medicant, gather data regarding an exposure condition of at least one of the adjunct and the medicant. The exposure condition is a condition that affects performance of at least one of the adjunct in the body of the patient and the medicant in the body of the patient. The surgical system also includes a processor configured to receive the data gathered by the sensor, determine a recommendation of use of the adjunct and the medicant in a surgical procedure based on the received data and on a requirement of the surgical procedure, and cause notice of the recommendation to be provided to a medical practitioner associated with the surgical procedure.

The surgical system can have any number of variations. For example, the recommendation can include a recommended shelf-life of the adjunct and the medicant. For another example, the recommendation can include a recommended indication of the adjunct and the medicant. For yet another example, the recommendation can include a recommended contraindication of the adjunct and the medicant. For still another example, the recommendation can include a recommended shelf-life of the adjunct and the medicant that is based at least on the gathered data regarding the exposure condition, the recommendation can include at least one of a recommended indication and a recommended contraindication of the adjunct and the medicant, and the at least one of the recommended indication and the recommended contraindication can be based at least on the requirement of the surgical procedure. For another example, the recommendation can include a recommended time after opening of the packaging unit within which the adjunct should be implanted in the body of the patient in the surgical procedure. For still another example, the requirement of the surgical procedure can be specific to a threshold adjunct durability for a type of the surgical procedure, and determining the recommendation can include comparing the threshold adjunct durability with a durability of the adjunct as indicated by the gathered data regarding the exposure condition. For yet another example, the environmental condition can include at least one of light and temperature. For still another example, the environmental condition can include at least one of humidity, oxygen, time, light, vibration, and atmospheric pressure. For another example, the packaging unit can include the sensor. For yet another example, a surgical hub that is external to the packaging unit can include the processor. For still another example, the processor can be configured to, based the received data, set an operational parameter of the surgical stapler.

In another aspect, a surgical method is provided that in one embodiment includes receiving at a computer system external to a packaging unit, from a communications interface of the packaging unit packaging a bioabsorbable adjunct that releasably retains a medicant therein and that is configured to be implanted using a surgical stapler, data gathered by a sensor of the packaging unit indicative of an exposure condition of the packaging unit. The exposure condition is a condition that affects performance of at least one of the adjunct in a patient and the medicant in the patient. The surgical method also includes determining, at the computer system, a recommendation of use of the adjunct and the medicant in a surgical procedure based on the received data indicative of the exposure condition, and a requirement of the surgical procedure. The surgical method also includes providing notice of the recommendation to a medical practitioner associated with the surgical procedure.

The surgical method can vary in any number of ways. For example, the recommendation can include a recommended shelf-life of the adjunct and the medicant. For another example, the recommendation can include a recommended indication of the adjunct and the medicant. For yet another example, the recommendation can include a recommended contraindication of the adjunct and the medicant. For still another example, the recommendation can include a recommended time after opening of the packaging unit within which the adjunct should be implanted in the body of the patient in the surgical procedure. For another example, the requirement of the surgical procedure can be specific to a threshold adjunct durability for a type of the surgical procedure, and determining the recommendation can include comparing the threshold adjunct durability with a durability of the adjunct as indicated by the gathered data regarding the exposure condition. For still another example, the requirement of the surgical procedure can be specific to at least one of a patient on which the surgical procedure is to be performed and a surgeon to perform the surgical procedure. For another example, the surgical method can also include gathering the data, using the sensor of the packaging unit, prior to opening of the packaging unit, and transmitting, using a communications interface of the packaging unit, the data to be received at the computer system. For yet another example, the environmental condition can include at least one of light, temperature, humidity, oxygen, time, light, vibration, and atmospheric pressure. For still another example, the surgical method can also include the processor setting, based the received data, an operational parameter of the surgical stapler.

Various systems and methods of monitoring healing after tissue adjunct implantation are provided.

In one aspect, a medical method is provided that in one embodiment includes, after implantation of a bioabsorbable adjunct into a body of a patient, monitoring degradation of the adjunct in the body of the patient from outside of the patient. The monitoring includes at least one of imaging the adjunct for visualization of radio-opaque markers releasable from the adjunct in the body of the patient, tracking a waste byproduct of the adjunct that is releasable from the implanted adjunct into the body of the patient, monitoring waste of the patient, and tracking a trackable element delivered to the patient from a surgical stapler that stapled the adjunct in the patient.

The medical method can have any number of variations. For example, the monitoring can include at least imaging the adjunct, the adjunct as implanted can include the radio-opaque markers therein, and imaging the adjunct can allow for visualization of the radio-opaque markers to monitor degradation of the adjunct in the body of the patient. In some embodiments, imaging the adjunct can include imaging the adjunct at a plurality of different times, and monitoring degradation of the adjunct can include comparing the different images to identify movement of the radio-opaque markers in the body of the patient.

For another example, the adjunct can include the waste byproduct releasable from the implanted adjunct into the body of the patient, and the monitoring can include at least tracking the waste byproduct of the adjunct. In some embodiments, the waste byproduct can include a ferrous material or a radioactive material, and/or tracking the waste byproduct of the adjunct can include using a monitor wearable by the patient to track the waste byproduct in the body of the patient.

For yet another example, the monitoring can include at least monitoring the waste of the patient. In some embodiments, monitoring the waste of the patient can include gathering data using a monitor mounted in a toilet and transmitting the gathered data to a computer system external to the toilet.

For still another example, the monitoring can include at least tracking the trackable element. In some embodiments, the adjunct can be stapled to a colon, and the trackable element can be configured to interact with a microbiome of the colon, and/or the trackable element can be delivered to the patient from the surgical stapler separately from the adjunct.

For another example, the implanted adjunct can retain therein a medicant releasable from the adjunct and into the patient having the adjunct implanted therein.

In another aspect, a medical method is provided that in one embodiment includes, after stapling a bioabsorbable adjunct to tissue of a patient, non-invasively monitoring healing of the tissue by at least one of imaging the adjunct for visualization of radio-opaque markers releasable from the adjunct in the body of the patient, tracking a waste byproduct of the adjunct that is releasable from the implanted adjunct into the body of the patient, monitoring waste of the patient, and tracking a trackable element delivered to the patient from a surgical stapler that stapled the adjunct in the patient.

The medical method can vary in any number of ways. For example, the monitoring can include at least imaging the adjunct, the adjunct as implanted can include the radio-opaque markers therein, and imaging the adjunct can allow for visualization of the radio-opaque markers to monitor degradation of the adjunct in the body of the patient.

For another example, the adjunct can include the waste byproduct releasable from the implanted adjunct into the body of the patient, and the monitoring can include at least tracking the waste byproduct of the adjunct. In some embodiments, the waste byproduct can include a ferrous material or a radioactive material, and tracking the waste byproduct of the adjunct can include using a monitor wearable by the patient to track the waste byproduct in the body of the patient.

For yet another example, the monitoring can include at least monitoring the waste of the patient.

For still another example, the monitoring can include at least tracking the trackable element. In some embodiments, the adjunct can be stapled to a colon, and the trackable element can be configured to interact with a microbiome of the colon.

For another example, the implanted adjunct can retain therein a medicant releasable from the adjunct and into the patient having the adjunct implanted therein.

In general, compressible adjuncts and methods for repairing tissue are provided. In one embodiment, a compressible adjunct kit for use with a staple cartridge is provided and includes a biocompatible adjunct material and a pretreatment fluid. The biocompatible adjunct material is configured to be releasably retained on a staple cartridge and is configured to be delivered to tissue by deployment of staples in the staple cartridge. The adjunct material can be in the form of a porous polymer body. The pretreatment fluid is configured to be applied to the adjunct material to change the adjunct material from an untreated state to a treated state. The adjunct material in the untreated state is configured to exhibit a first degradation profile when delivered to tissue. The adjunct material in the treated state is configured to exhibit a second degradation profile, different from the first degradation profile, when delivered to tissue.

The pretreatment fluid can have a variety of configurations. In one embodiment, the pretreatment fluid can be configured to increase a rate of degradation of the second degradation profile with respect to the first degradation profile. In another embodiment, the pretreatment fluid can be configured to cause the adjunct in the treated state to increase a pH adjacent to the adjunct when delivered to tissue. In other aspects, the pretreatment fluid can be configured to increase a degree of hydrophilicity of the adjunct in the treated state. In another embodiment, the pretreatment fluid can be configured to decrease a rate of degradation of the second degradation profile with respect to the first degradation profile. In another embodiment, the pretreatment fluid can be configured to form a coating that is deposited on at least a portion of the adjunct in the treated state. In yet another embodiment, the pretreatment fluid can be configured to react with the adjunct material to change a terminal functional group of at least a portion of a polymer chain forming the porous polymer body in the treated state. In other aspects, the pretreatment fluid can be configured to increase a degree of hydrophobicity of the adjunct in the treated state as compared to the untreated state. In yet another embodiment, the pretreatment fluid can be configured to form a sealant that seals at least a portion of pores in the porous polymer body. In other aspects, the pretreatment can be configured to terminate at least a portion of a plurality of polymer chains of the porous polymer body such that an average length of the plurality of polymer chains of the polymer body in the treated state is less than an average length of the plurality of polymer chains of the polymer body in the untreated state.

In another embodiment, a surgical method is provided and includes treating an untreated biocompatible adjunct material including a porous polymer body to produce a treated adjunct material having an altered degradation profile with respect to the untreated adjunct material. The method also includes releasably retaining the treated adjunct material on a staple cartridge, and actuating a surgical stapling device having the staple cartridge and treated adjunct material thereon to staple the treated adjunct material to tissue.

In one embodiment, treating the biocompatible adjunct material includes immersing the adjunct material within a pretreatment fluid. The altered degradation profile can have a rate of degradation that is greater than a degradation profile of the untreated adjunct material. In other embodiments, treating the adjunct material causes the adjunct material to increase a pH adjacent to the treated adjunct material when delivered to tissue. In another embodiment, treating the adjunct material increases a degree of hydrophilicity of the treated adjunct material as compared to an untreated adjunct material. In another embodiment, the altered degradation profile has a rate of degradation that is less than a degradation profile of the untreated adjunct material.

In another embodiment, treating the adjunct material applies a coating to at least a portion of the adjunct material. In another embodiment, treating the adjunct material includes apply a pretreatment fluid that reacts with the porous polymer body of the adjunct material and changes a terminal functional group of polymer chains forming the polymer body. In another embodiment, treating the adjunct material increases a degree of hydrophobicity of the treated adjunct material as compared to an untreated adjunct material. In another embodiment, treating the adjunct material includes apply a pretreatment fluid that forms a sealant that seals at least a portion of pores of the porous body.

In another embodiment, treating the adjunct material includes apply a pretreatment fluid that terminates at least a portion of the polymer chains of the polymer body such that an average length of polymer chains of the polymer body of the treated adjunct material is less than an average length of polymer chains of the polymer body of the untreated adjunct material. A rate of degradation of the second degradation profile is increased with respect to the first degradation profile.

In another embodiment, a compressible adjunct for use with a staple cartridge is provided and includes a biocompatible adjunct material configured to be releasably retained on a staple cartridge and configured to be delivered to tissue by deployment of staples in the staple cartridge. The adjunct material is formed from a porous polymer body and is configured to exhibit a first stiffness in compression that is approximately constant during a first time period from contact with the tissue. The adjunct material is further configured to exhibit a second stiffness in compression during a second time period following the first time period. The second stiffness is less than the first stiffness and is configured to decrease with time as a function of at least one of oxidation, enzyme-catalyzed hydrolysis, and change of pH resulting from interaction with at least one physiological element released from the tissue during healing progression of the tissue.

In one embodiment, the adjunct is configured to adopt the second stiffness in response to oxidation resulting from reaction with the physiological element comprising a reactive oxygen species. In another embodiment, the adjunct is configured to oxidize in response to reaction with a reactive oxygen species released by a mature blood cell or a fybrocyte. The reactive oxygen species can include a superoxide. In another embodiment, the adjunct is configured to oxidize in response to reaction with a reactive oxygen species released by an inflammatory cell. The inflammatory cell can be at least one of a leukocyte, a neutrophil, a basophil, an eosinophil, a lymphocyte, a monocytes, and a macrophage. In another embodiment, the reactive oxygen species is at least one of an oxygen containing enzyme, a free radical, a superoxide, and a peroxide. In another embodiment, the reactive oxygen species is at least one of $O_2^-$, $H_2O_2$, NO, and HOCl.

In another embodiment, the adjunct is configured adopt the second stiffness in response to hydrolysis catalyzed by an enzyme. The enzyme can be a lysozyme. In another embodiment, the adjunct is configured to adopt the second stiffness in response to a decrease in pH resulting from the presence of the at least one physiological element.

In other aspects, a method for treating tissue is provided. The method includes securing, by one or more staples, a biocompatible porous polymer adjunct material to tissue. The adjunct material receives at least one physiological element released from the tissue during healing progression of the tissue, and exhibits a first stiffness in compression that is approximately constant during a first time period from contact with the tissue, and exhibits a second stiffness in compression during a second time period following the first time period. The second stiffness can be less than the first stiffness and can decrease with time as a function of at least one of oxidation, enzyme-catalyzed hydrolysis, and change of pH resulting from interaction with the at least one physiological element.

In one embodiment, the adjunct can oxidize in response to reaction with a reactive oxygen species released by an inflammatory cell. In another embodiment, the adjunct can adopt the second stiffness in response to oxidation of the adjunct due to reaction with the physiological element comprising a reactive oxygen species.

In another embodiment, the adjunct can oxidize in response to reaction with the reactive oxygen species released by an inflammatory cell. The inflammatory cell can be at least one of a leukocyte and a macrophage. The reactive oxygen species can be at least one of an oxygen containing enzyme, a free radical, a superoxide, and a peroxide. In another embodiment, the reactive oxygen species can be at least one of $O_2^-$, $H_2O_2$, NO, and HOCl.

In another embodiment, the adjunct can adopt the second stiffness in response to hydrolysis catalyzed by an enzyme. The enzyme can be a lysozyme.

In another embodiment, the adjunct can adopt the second stiffness in response to a decrease in pH resulting from the presence of the at least one physiological element.

In other aspects, a stapling assembly is provided and includes a staple cartridge, an anvil, and an adjunct. The staple cartridge has a plurality of staples disposed therein that are arranged in staple rows and configured to be deployed into tissue. The staple cartridge also includes a knife slot extending therethrough between the staple rows for receiving a knife to cut tissue along a cut line. The anvil is positioned opposite the staple cartridge. The adjunct is configured to be releasably retained on the staple cartridge or the anvil. The adjunct can be in the form of a biocompatible porous polymer material configured to be delivered to tissue by deployment of the plurality of staples from the staple cartridge. The adjunct can have a first shape, and at least one first portion of the adjunct can be configured to exhibit a first expansion behavior in response to receipt of a unit volume of fluid, and at least one second portion of the adjunct can be configured to exhibit a second expansion behavior, different from the first expansion behavior, in response to receipt of the unit volume of fluid such that the adjunct adopts a second shape that is different from the first shape. The difference between the first and second expansion behavior can be configured to apply different pressures to different portions of tissue having the adjunct stapled thereto.

In one embodiment, an amount of expansion of the adjunct is configured to provide hemostasis at the cut line. In another embodiment, an amount of expansion of the adjunct is configured to seals holes created in the issue by the plurality of staples when the staples are ejected into tissue.

In another embodiment, the at least one second portion of the adjunct is positioned adjacent to the knife slot and the at least one first portion of the adjunct is spaced a distance from the knife slot, and the second shape can be configured to apply a greater pressure than the first shape.

In another embodiment, the at least one second portion includes a swellable material that differs from the biocompatible porous polymer material. The swellable material can include a hydrogel. In another embodiment, the swellable material includes a porous, solid material, and the swellable material is housed in a compressed state within a fluid-soluble capsule. The capsule can be configured to release the swellable material after a predetermined time period from contact with the fluid.

In another embodiment, a rate of expansion of the at least one second portion of the adjunct in response to receipt of the unit volume of fluid is greater than a rate of expansion of the at least one first portion of the adjunct in response to receipt of the unit volume of fluid.

In another embodiment, at least one staple of the plurality of staples includes at least one leg including a plurality of barbs. When the plurality of staples are ejected into the adjunct and tissue, the plurality of barbs are configured to permit expansion of adjunct in a first direction and inhibit retraction of the adjunct in a second direction, opposite the first direction.

In another embodiment, the at least one second portion includes a film overlying a surface of the adjunct.

In another embodiment, the adjunct further includes a color transition dye that changes color during expansion of the adjunct. The color transition dye can be a hydrochromic ink configured to change color in response to contact with at least one of a fluid and lipids.

Surgical methods are also provided, and in one embodiment a surgical method can include clamping tissue and a biocompatible porous polymer adjunct between opposed first and second jaws, and firing a plurality of staples from one of the first and second jaws, through the adjunct, and into the tissue to thereby staple the adjunct to the tissue. The adjunct, after being stapled to the tissue, receives a unit volume of fluid that causes at least one first portion of the adjunct to expand according to a first expansion behavior to thereby apply a first pressure to the tissue, and that causes at least one second portion of the adjunct to expand according to a second expansion behavior that is different from the first expansion behavior to thereby apply a second pressure to the tissue that is different than the first pressure.

In one embodiment, one of the first and second jaws includes a staple cartridge having a knife slot, and the at least one first portion of the adjunct is positioned adjacent to the knife slot, and the at least one second portion of the adjunct is spaced apart from the knife slot.

In another embodiment, the one or more second portions of the adjunct include a swellable material, different from the adjunct material, positioned at the one or more second portions. The swellable material can be at least a hydrogel. The swellable material can include a porous, solid material and the swellable material is housed in a compressed state within a fluid-soluble capsule. The capsule can release the swellable material after a predetermined time period from contact with the fluid.

In another embodiment, a rate of expansion of the one or more second portions of the adjunct in response to receipt of a unit volume of fluid is greater than that within the one or more first portions of the adjunct. In another embodiment, a rate of expansion of the one or more second portions of the adjunct in response to receipt of a unit volume of fluid is less than that within the one or more first portions of the adjunct.

In another embodiment, the amount of expansion of the adjunct is sufficient to provide hemostasis when the tissue is cut. In another embodiment, the amount of expansion of the adjunct is sufficient to seal holes created by staples when ejected therethrough.

In another embodiment, at least one staple of the plurality of staples includes at least one leg including a plurality of barbs. When the plurality of staples are ejected into the adjunct and tissue, the barbs permit expansion of adjunct in a first direction towards the tissue and inhibit retraction of the adjunct in a second direction, opposite the first direction.

In an embodiment, the at least one second portion of the adjunct includes a film overlying a surface of the adjunct.

In other aspects, the adjunct includes a color transition dye and the method further includes changing, by the dye, the color of the adjunct during expansion. The color transition dye can be a hydrochromic ink that changes color in response to contact with at least one of a fluid and lipids.

In another embodiment, an adjunct for use with a staple cartridge is provided. The adjunct includes a biocompatible adjunct configured to be releasably retained on a staple cartridge body and configured to be delivered to tissue by deployment of staples in the cartridge body. The adjunct is formed as a porous body including a first polymer and a second polymer. The first polymer is configured to degrade according to a first degradation profile as a function of at least one of hydrolysis in response to interaction with water and heating to a physiological temperature. The second polymer is configured to degrade according to a second degradation profile as a function of at least one of oxidation, enzyme-catalyzed hydrolysis, and change of pH resulting from interaction with at least one physiological element released from the tissue during healing progression of the tissue.

In one aspect, the first polymer is configured to expand in response to absorption of water and to exert a first compressive pressure on the tissue having a magnitude that is dependent upon the first degradation profile, the second polymer is configured to expand in response to degradation of the first polymer and to exert a second compressive pressure on the tissue having a magnitude that is dependent upon the first and second degradation profiles, and a maximum magnitude of the second compressive pressure is less than a maximum magnitude of the first compressive pressure.

In another embodiment, the first polymer is configured to inhibit interaction of the second polymer with at least a portion of the at least one physiological element. The first polymer can overlay the second polymer.

In another embodiment, a degradation rate of the first polymer according to the first degradation profile is greater than a degradation rate of the second polymer according to the second degradation profile.

In another embodiment, the first polymer is a moisture absorbing powder or foam.

In another embodiment, the at least one physiological element includes a reactive oxygen species. The reactive oxygen species can include at least one of an oxygen containing enzyme, a free radical, a superoxide, and a peroxide.

In another embodiment, the adjunct includes a first drug retained by the first polymer and configured for release during degradation of the first polymer. The first drug can include a hemostatic drug. The adjunct can further include a second drug retained by the second polymer and configured for release during degradation of the second polymer. The second drug can be configured to promote tissue remodeling. In another embodiment, the second drug is configured for at least one of bolus release and gradual release based upon a geometry of the second polymer.

In an embodiment, a method for treating tissue is provided. The method includes securing, by one or more staples, a porous biocompatible adjunct to tissue. The adjunct can include a first polymer and a second polymer. The adjunct receives at least one of water and heat sufficient to raise a temperature of the adjunct to a physiological temperature, thereby causing the first polymer to degrade according to a first degradation profile. The adjunct receives at least one physiological element released from the tissue during healing progression of the tissue, thereby causing the second polymer to degrade according to a second degradation profile as a function of at least one of oxidation, enzyme-catalyzed hydrolysis, and change of pH resulting from interaction with the at least one physiological element.

In one embodiment, the first polymer expands in response to receipt of the water to exert a first compressive pressure on the tissue having a magnitude that is dependent upon the first degradation profile, and the second polymer expands in response to degradation of the first polymer and exerts a second compressive pressure on the tissue having a magnitude that is dependent at least upon the first and second degradation profiles. A maximum magnitude of the second compressive pressure is less than a maximum magnitude of the first compressive pressure.

In another embodiment, the second compressive pressure is dependent upon the first degradation profile and the second degradation profile.

In another embodiment, the first polymer inhibits interaction of the second polymer with at least a portion of the at least one physiological element. The at least one physiological element can include a reactive oxygen species.

In another embodiment, the first polymer overlies the second polymer. In another embodiment, the first polymer is at least one of moisture absorbing powder and a foam.

In another embodiment, a degradation rate of the first polymer according to the first degradation profile is greater than a degradation rate of the second polymer according to the second degradation profile.

In another embodiment, the adjunct further includes a first drug retained by the first polymer that is released during degradation of the first polymer. The first drug can be a hemostatic drug.

In another embodiment, the adjunct further includes a second drug retained by the second polymer that is released during degradation of the second polymer. The second drug can promote tissue remodeling.

In another embodiment, the method further includes at least one of a bolus release and a gradual release of the second drug based upon a geometry of the second polymer.

BRIEF DESCRIPTION OF THE DRAWINGS

This invention will be more fully understood from the following detailed description taken in conjunction with the accompanying drawings, in which:

FIG. 77 is a schematic diagram illustrating a side cross-sectional view of the composite adjunct of FIG. 76;

FIG. 78A is a plot illustrating healing events within the tissue coupled to the composite adjunct as a function of time;

FIG. 78B is a plot illustrating compressive pressure applied by the first and second polymers of the composite adjunct of FIG. 73 to the tissue, respectively, as a function of time; and FIG. 78C is a plot illustrating release rates of first and second drugs retained by the first and second polymers of the composite adjunct of FIG. 73, respectively, as a function of time.

DETAILED DESCRIPTION

Figure 1:
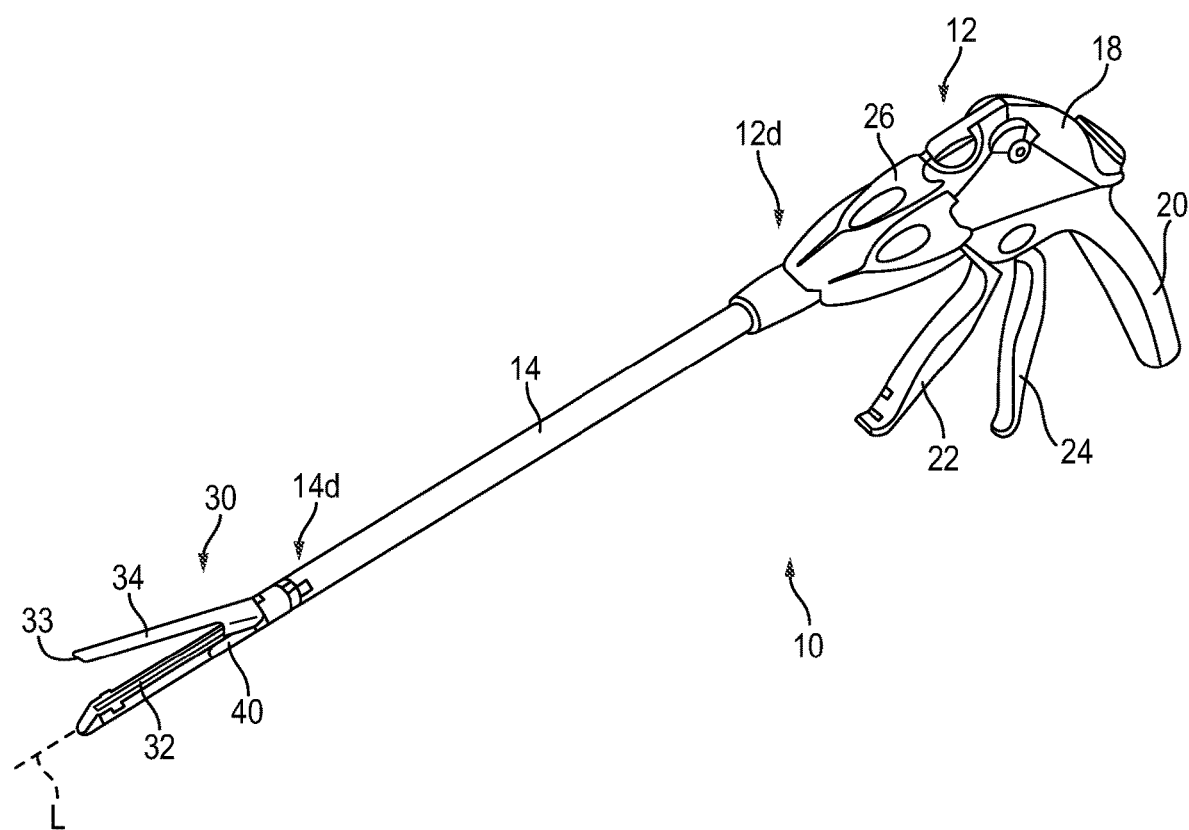
FIG. 1 is a perspective view of one exemplary embodiment of a conventional surgical stapling and severing instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, referred to herein as "adjuncts," in conjunction with surgical instruments to help improve surgical procedures. "Adjuncts" are also referred to herein as "adjunct materials." While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing, and/or is experiencing another tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissue's movement around these puncture sites can minimize the size the holes may grow to under tension. In some instances, the adjunct(s) can be configured to wick or absorb beneficial fluids, e.g., sealants, blood, glues, and the like, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts.

In other embodiments, the adjunct(s) can be used with surgical instruments that are configured to seal tissue without using staples (e.g., by using energy, such as RF or ultrasound), for example, as described in U.S. Pat. No. 10,172,611, which is incorporated by reference herein in its entirety.

In some instances, the adjunct(s) can be configured to compensate for variations in tissue thickness when the adjunct(s) are stapled to tissue. In such instances, the adjunct can be also be referred to as a "tissue thickness compensator." A tissue thickness compensator has an uncompressed (undeformed), or pre-deployed, height that is greater than the height of a staple that is in a formed configuration. Additional details on exemplary tissue thickness compensators can be found in, for example, U.S. Pat. No. 8,864,007, which is incorporated by reference herein in its entirety. A tissue thickness compensator can be attached and released from a staple cartridge in a variety of ways, for example, as described in U.S. Pat. Nos. 9,272,406, and 10,136,890, each of which is incorporated by reference herein in its entirety.

In addition to the disclosures herein, additional details pertaining to the adjunct(s) and other exemplary adjuncts can be found in, for example, U.S. Pat. Nos. 10,172,611 and 10,433,846 and U.S. patent application Ser. No. 17/009,769, filed on Sep. 1, 2020, and entitled "Compressible Non-Fibrous Adjuncts," each of which is incorporated herein by reference in its entirety.

Alternatively or in addition, the adjunct(s) can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Alternatively or in addition, the adjunct(s) can have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc. In addition to the disclosures herein, additional details on drug eluting adjuncts can be found in U.S. Pat. Nos. 9,232,941 and 10,569,071, each of which is incorporated herein by reference in its entirety.

Surgical Stapling Instruments

A variety of surgical instruments can be used in conjunction with the adjunct(s) and/or medicant(s) disclosed herein. The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
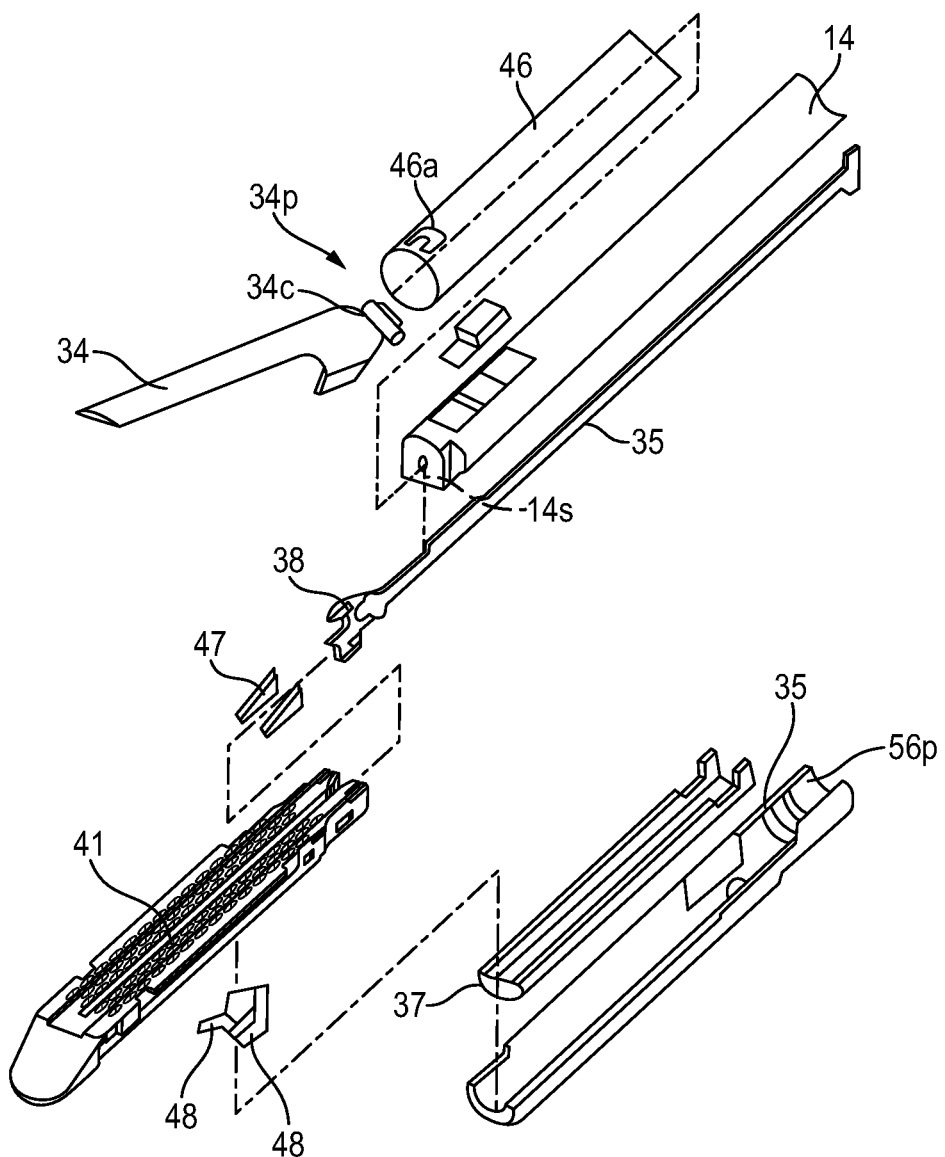
FIG. 2 is a top view of a staple cartridge for use with the surgical stapling and severing instrument of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement with the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
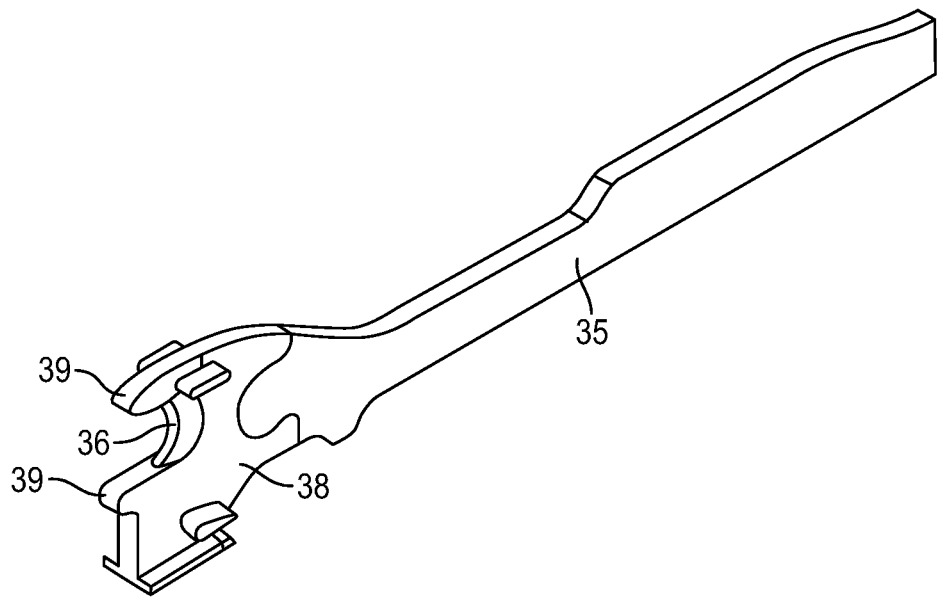
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
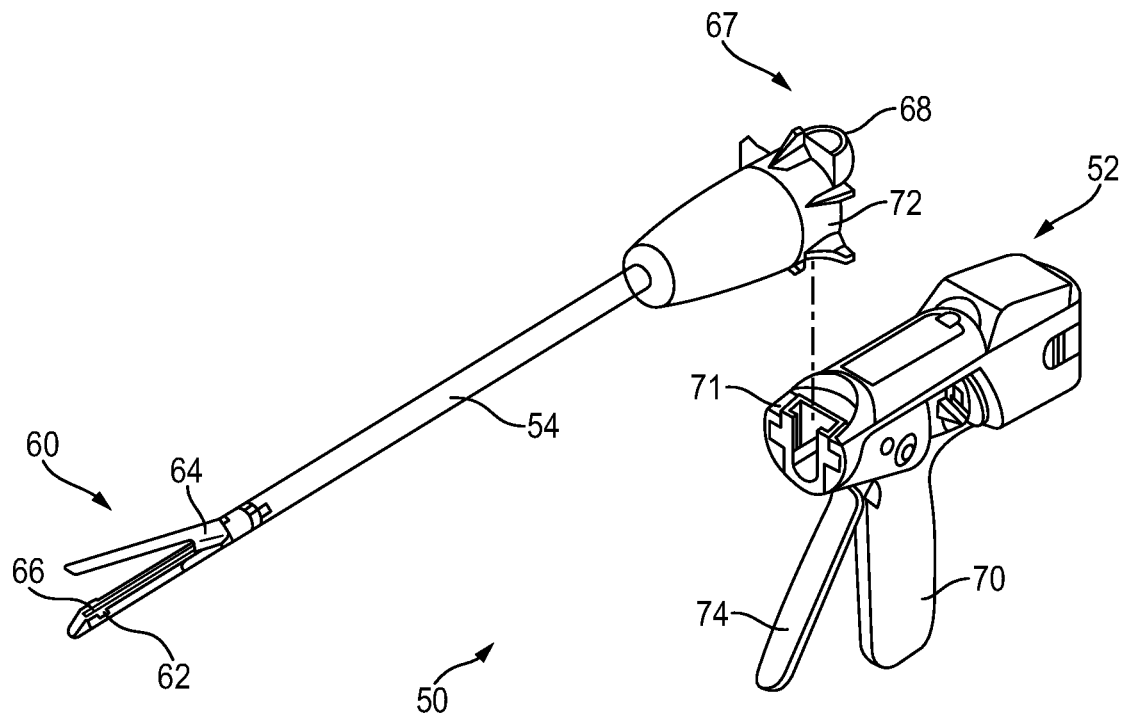
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
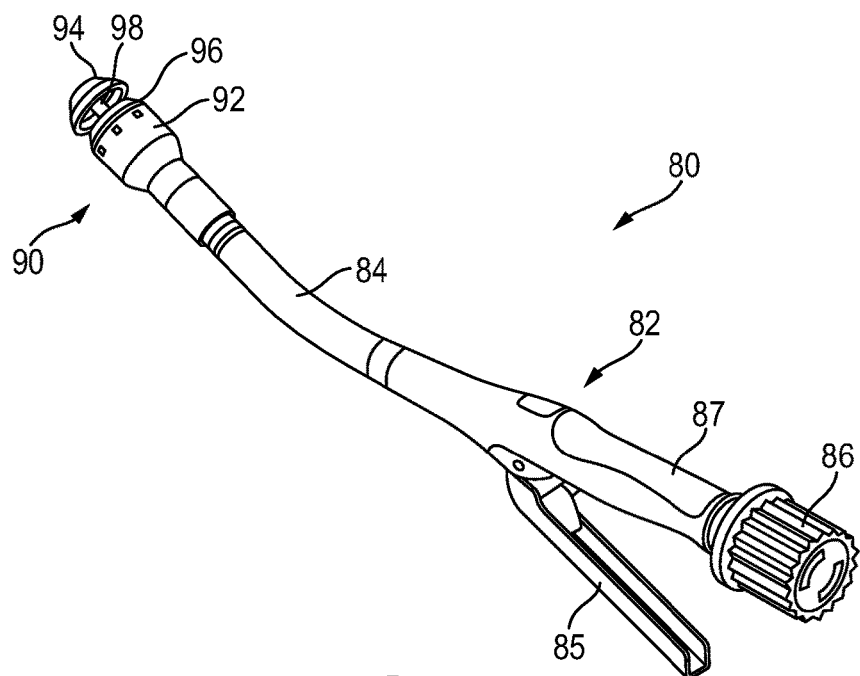
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, e.g., move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076 entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

Implantable Adjuncts

Figure 6:
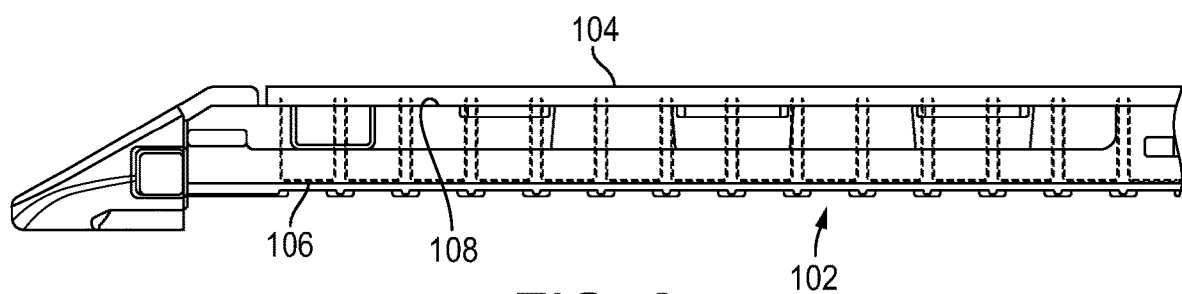
FIG. 6 is a longitudinal cross-sectional view of an exemplary embodiment of a staple cartridge having an exemplary adjunct attached to a top or deck surface thereof.

As indicated above, various implantable adjuncts are provided for use in conjunction with surgical stapling instruments. When used in conjunction with a surgical stapler, the adjunct(s) can be disposed between and/or on jaws of the stapler, incorporated into a staple cartridge disposed in the jaws, or otherwise placed in proximity to the staples. For example, as shown in FIG. 6, an adjunct 104 is positioned against a staple cartridge 102. For sake of simplicity, the adjunct 104 is generally illustrated in FIG. 6, and various structural configurations of the adjunct are described in more detail below. While partially obstructed in FIG. 6, the staple cartridge 102 includes staples 106 that are configured to be deployed into tissue. The staples 106 can have any suitable unformed (pre-deployed) height. For example, the staples 106 can have an unformed height between about 2 mm and 4.8 mm. Prior to deployment, the crowns of the staples can be supported by staple drivers (not shown).

In the illustrated embodiment, the adjunct 104 can be releasably mated to at least a portion of the top surface or deck surface 108 of the staple cartridge 102. In some embodiments, the top surface 108 of the staple cartridge 102 can include one or more surface features. Alternatively, or in addition, one or more adhesives can be used to releasably mate the adjunct to the staple cartridge 102. The one or more surface features and/or the one or more adhesives can be configured to engage the adjunct 104 to avoid undesirable movements of the adjunct 104 relative to the staple cartridge 102 and/or to prevent premature release of the adjunct 104 from the staple cartridge 102. Exemplary surface features are described in U.S. Patent Publication No. 2016/0106427, which is incorporated by reference herein in its entirety. Additional details on adhesives for temporary attachment to instruments and other exemplary adhesives can be found in U.S. Pat. Nos. 9,282,962, 10,172,617, 10,172,618, 10,258, 332, 10,517,592, 10,548,593, 10,568,621, and 10,588,623, each of which is incorporated by reference herein in its entirety. Additional details on attachment methods and other exemplary methods can be found in U.S. Pat. Nos. 10,166, 023 and 10,349,939 and U.S. patent application Ser. No. 17/022,520, filed on Sep. 16, 2020, and entitled "Method of Applying Buttress to End Effector of Surgical Stapler," each of which is incorporated by reference herein in its entirety.

Figure 7:
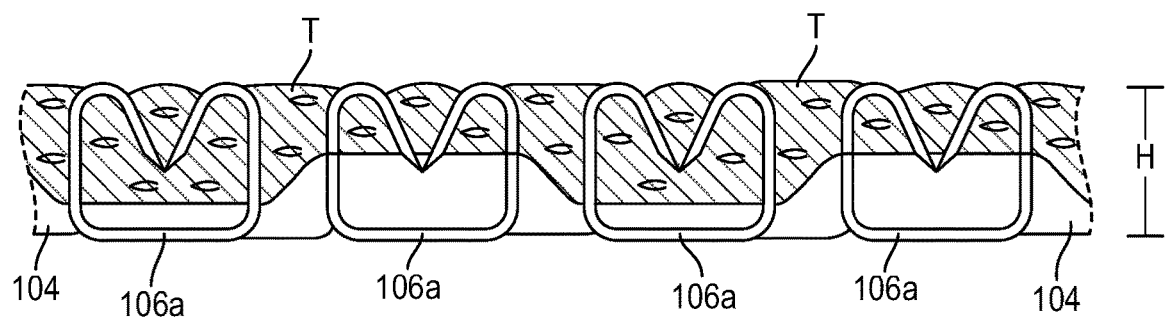
FIG. 7 is a partial-schematic illustrating the adjunct of FIG. 6 in a tissue deployed condition.

In certain instances, the adjunct can be compressible to permit the adjunct to compress to varying heights to thereby compensate for different tissue thickness that are captured within a deployed staple. For example, as illustrated in FIG. 6, the adjunct 104 has an uncompressed (undeformed), or pre-deployed, height and is configured to deform to one of a plurality of compressed (deformed), or deployed, heights. As such, the adjunct 104 can have an uncompressed height which is greater than the fired height of the staples 106 disposed within the staple cartridge 102 (e.g., the height (H) of the fired staple 106a in FIG. 7). That is, the adjunct 104 can have an undeformed state in which a maximum height of the adjunct 104 is greater than a maximum height of a fired staple (e.g., a staple that is in a formed configuration). In such instances, the adjunct can be referred to as a "tissue thickness compensator." In one embodiment, the uncompressed height of the adjunct 104 can be about 10% taller, about 20% taller, about 30% taller, about 40% taller, about 50% taller, about 60% taller, about 70% taller, about 80% taller, about 90% taller, or about 100% taller than the fired height of the staples 106. In certain embodiments, the uncompressed height of the adjunct 104 can be over 100% taller than the fired height of the staples 106, for example.

The adjuncts can have a variety of configurations, and can be formed from various materials. In general, an adjunct can be formed from one or more of a film, a foam, an injection molded thermoplastic, a vacuum thermoformed material, a fibrous structure, an additive manufacturing material, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010, which is incorporated by reference herein in its entirety.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

In other embodiments, the adjunct can be formed using a 3D printing process(es) compatible with absorbable polymers. Non-limiting examples of suitable 3D printing processes include stereolithography (SLA or SL), material jetting, selective laser sintering (SLS), and fused filament fabrication as understood by a person skilled in the art.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA) (e.g., Dexon and Neoveil), poly(lactic-co-glycolic acid) (PLGA), polycaprolactone (PCL), polyglycolide (PGL), trimethylene carbonate (TMC), polylactic acid (PLA) (e.g., Linvatec Bioscrew and Bionx Implants Smart Screw), poly(trimethylene carbonate (PTMC), polyethylene diglycolate (PEDG), poly(propylene fumarate) (PPF), polyethylene ether (PEE), poly(ethylene glycol) (PEG), poly(N-isopropylacrylamide, poly(amino acid), poly(epoxycarbonate), poly(2-oxypropylene carbonate), poly(diol citrates), polymethacrylate anhydrides, poly(ethoxyethylene diglycolate), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides (e.g., REVA ReZolve Stents), and tyrosine-based polyesteramides (e.g., TYRX). The copolymers can also include poly(lactic acid-co-polycaprolactone) (PLA/PCL) (e.g., 16-18 month hydrolyzed), poly (L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), LPLA/DLPLA (e.g., Optima), PLGA-PCL (e.g., 15:85 (PCL: 50% D,L-Lactide: 50% Glycolide), 40:60 (PCL: 50% D,L-Lactide: 50% Glycolide), and 40:60 (PCL: 85% D,L-Lactide: 15% Glycolide), PLGA-PCL-PLGA, and PLGA-PEG-PLGA.

An adjunct can also include special polymer terminations, including (meth)acrylate and organically-derived polymers. Non-limiting examples of organically-derived polymers include those derived from collagen (e.g., Avitene, Endoavitene, Instat, Integran, Veritas, and Microfibrillar Collagen (MFC)).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+ Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, NeoRecormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids agents that inhibit mitosis and microtubule formation (e.g., Vinblastine, Vincristine, Vindesine, Vinorelbine), angiostatic inhibiting agents that inhibit cell growths or cell expansion (e.g., Axitinib (Inlyta), Bevacizumab (Avastin), Cabozantinib (Cometriq), Everolimus (Afinitor, Zortress) Lenalidomide (Revlimid), Pazopanib (Votrient), Ramucirumab (Cyramza), Regorafenib (Stivarga), Sorafenib (Nexavar), Sunitinib (Sutent), Thalidomide (Synovir, Thalomid), Vandetanib (Caprelsa), Zib-aflibercept (Zaltrap), antiangiogenic polysaccharide, aplidine (dehydrodidemnin B), sapogenins viz. 20(S)-protopanaxadiol, and 20(S)-protopanaxatriol), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and antiangiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Exemplary medicants also include agents that encourage blood supply regeneration following coronary artery disease (CAD) (e.g., $VEGF_{165}$ protein, $AdVEGF_{165}$, $AdVEGF_{121}$, and $VEGF_{165}$ plasmid) or periphery artery disease (PAD) (e.g., $VEGF_{165}$ plasmid, $AdVEGF_{121}$, SB-509 (SFP-VEGF plasmid), $AdVEGF_{165}$, and Ad2-HIF1α-VP16 (WALK trial)).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Fluid Control Features and Drug Release Features

In certain embodiments, the adjuncts can have a variety of configurations that are designed to control fluid movement into, out of, and/or through the adjuncts when the adjuncts are in a tissue deployed state (e.g., stapled to tissue in vivo). This fluid control can encourage the mobility of cells and bi-products into and out of the adjunct during tissue remodeling while the adjunct is in a tissue deployed state. Further, this fluid control can impact the ion level of the tissue that is stapled to the adjunct such that the fluid movement through the adjunct can disrupt or enhance environment effects on tissue remodeling.

The adjuncts can generally be formed from a biocompatible adjunct material that is configured to be releasably retained on a staple cartridge and that is configured to be delivered to tissue by deployment of staples in the cartridge. In an exemplary embodiment, the adjunct material can include a lattice main structure having at least one absorbable sub-structure formed in the lattice main structure. The at least one absorbable sub-structure can be configured to control fluid movement into, out of, and/or through the adjunct material such that the fluid movement impacts healing of tissue adjacent the adjunct material when the adjunct material is in a tissue deployed state. As used herein, the terms "lattice main structure" and "absorbable sub-structure" are used synonymously with the terms "lattice macrostructure" and "absorbable microstructure," respectively.

In order to enable formation of macro and micro structures, the adjuncts can be non-fibrous adjuncts. Unlike conventional adjuncts (e.g., adjuncts that are not three-dimensionally printed, such as foam adjuncts and woven/non-woven fibrous adjuncts), the non-fibrous adjuncts are three-dimensionally (3D) printed and therefore can be formed with microstructures (units or sub-structures) that are consistent and reproducible. In certain embodiments, however, the non-fibrous adjuncts can include separate fibrous features to help enhance tissue ingrowth within the adjunct.

As described above, the fluid control structures are configured to impact fluid movement into, out of, and/or through the adjunct. Fluid movement can also be used to control drug release from the adjunct (e.g., when the adjunct contains at least one drug disposed therein and is in a tissue deployed state) and/or to control drug flow through the adjunct. For example, in embodiments wherein the adjunct contains at least one drug disposed therein, fluid ingress could control the saturation of the at least one drug and the fluid egress can control the drug dosage being released. As such, controlling the fluid movement (e.g., rate and/or volume) could therefore drive the drug dosage being released from the adjunct. Further, since fluid can serve as the carrier for the at least one drug, directing fluid movement in predetermined direction(s) through the adjunct can be used to define the drug release location(s) of the adjunct. As such, a person skilled in the art will therefore appreciate that any of the fluid control features disclosed herein (e.g., absorbable sub-structures) can be used in combination with drug(s) retained within the adjunct for the transport thereof to tissue adjacent the adjunct when the adjunct is in a tissue deployed state.

In certain embodiments, the at least one absorbable sub-structure can include two or more absorbable sub-structures that together control a direction of fluid movement through the adjunct material. The absorbable sub-structures can have generally uniform configurations (e.g., uniform within manufacturing tolerances) or different configurations. In one embodiment, the absorbable sub-structures include first absorbable sub-structures having a first configuration and second absorbable sub-structures having a second configuration that is different than the first configuration.

The at least one absorbable sub-structure can be an active flow control structure (e.g., a structure that operates in response to an outside energy input to manipulate fluid flow) or a passive flow control structure (e.g., a structure that operates without an outside energy input to manipulate fluid flow). In certain embodiments, the at least one absorbable sub-structure can include first absorbable sub-structures that are active flow control structures and second absorbable sub-structures that are passive flow control structures. Non-limiting examples of active flow control structures include structures that are configured to undergo a deformation upon an applied outside force to the adjunct (e.g., the force being applied by tissue that is stapled to the adjunct) so as to pump fluid out of the adjunct or draw fluid into the adjunct. These structures can include, for example, seals, degradable walls, valves and other features (e.g., unit cells or portions thereof) that change state as the adjunct undergoes shape changes as the adjunct, or portion(s) thereof, is exposed to externally applied force(s). These structures can act as fluid pumps, vacuum chambers, one-way valving, or the like to encourage large boluses of fluid(s) to move dependent on the structure's exposure to outside forces and movements. Non-limiting examples of passive flow control structures include wicking structures, micro-passageways, or other structures that direct fluid through the adjunct without any outside intervention (e.g., in response to a pressure differential within the adjunct). Further, such structures can be used to create continuous directional fluid transport.

The at least one absorbable sub-structure can have a variety of configurations. For example, in some embodiments, the at least one absorbable sub-structure can be designed as a movable valve that is configured to control fluid movement therethrough. Non-limiting examples of a movable valve include a duck bill valve, a flapper valve, and the like. Alternatively, or in addition, the at least one absorbable sub-structure can include micro-passageways formed in a sidewall of the lattice main structure. The micro-passageways can be formed on an interior surface, an exterior surface of the sidewall, or a combination thereof. For example, first micro-passageways can be formed on inner surface of the wall and second micro-passageways can be formed on the outer surface of the sidewall. In certain embodiments, the micro-passageways can be configured to draw fluid therethrough via capillary action.

The fluid direction through the micro-passageways can be controlled or uncontrolled allowing for homogenous or directed flow. In some embodiments, the micro-passageways can include at least one microfeature that is configured to direct fluid in a predefined direction though the respective micro-passageway. For example, the at least one microfeature can include flexible wicking elements that extend from the sidewall of the lattice main structure and into respective micro-passageways. The flexible wicking elements can extend at any suitable angle relative to the sidewall such that the flexible wicking elements can direct fluid through the micro-passageways and thus, through the respective portions of the lattice main structure, in one or more predefined directions. A person skilled in the art will appreciate that the angle(s) at which the flexible wicking elements extend depend at least in part on desired direction of flow through the respective micro-passageway and the structural configuration of the respective sidewall of the lattice main structure.

The lattice main structure can be formed of unit cells. The unit cells can have a variety of configurations. The unit cells can be formed of strut-based unit cells, which are characterized by the presence of sharp corners or angles, or non-strut-based unit cells can be characterized by curved surfaces. In some embodiments, with strut-based unit cells, the unit cells can be formed of hollow struts. For example, the hollow struts can be in the form of hollow tubes, which have higher bending strength that solid tubes of the same mass. Hollow tubes can therefore reduce the total amount of material of the implanted adjunct while also maintaining a high enough compressive strength. Further, in certain embodiments, the hollow tubes can in the form of an "I" shape or any other suitable that can move material away from its neutral axis.

With non-strut based unit cells, the unit cells, for example, can be based on triply periodic minimal surfaces (TPMS). TPMS is a minimal surface that repeats itself in three dimensions. The term "minimal surface" as used in this description refers to a minimal surface as known in mathematics. As such, in some embodiments, the unit cell can be a triply periodic minimal surface structure (e.g., Schwarz-P, Schwarz Diamond, and the like) having passageways extending therethrough. For example, the non-strut based unit cells can be a hollow structure. Additional details on triply periodic minimal surface structures, such as Schwarz-P structures can be found in previously mentioned U.S. patent application Ser. No. 17/009,740, filed Sep. 1, 2020, and entitled "Compressible Non-Fibrous Adjuncts," which is incorporated herein by reference in its entirety. In certain embodiments, the lattice main structure can include a combination of strut-based unit cells (e.g., hollow struts) and non-strut based unit cells (e.g., one or more triply periodic minimal surface structures).

The structural configurations of the unit cells disclosed herein can be tailored to enhance cellular ingrowth within the adjunct. For example, the sizes of the voids or passageways through the unit cells can be tailored to such to a size that has the least impact on cellular mobility therethrough (e.g., about 50 microns to 75 microns). Alternatively, or in addition, the adjunct can be designed with a maximum closed porosity that does not substantially interfere with tissue ingrowth (e.g., tissue granulation or filing, bridging or healing within the open spaces of the adjunct). For example, in some embodiments, the maximum closed porosity of the adjunct can be about 500 microns.

Further, the internal cavities and/or internal surfaces of the unit cells and/or interstitial space between the unit cells can include fibrous features to encourage tissue ingrowth. In some embodiments, fibers can be disposed with the internal cavity of one or more unit cells (e.g., surgical fibrillary can be loosely packed within an internal cavity of a unit cell). Alternatively, or in addition, fibers can be disposed within the interstitial spaces (e.g., concave areas) between the unit cells. Further, alternatively or in addition, fiber-like structures can be printed onto the internal surface(s) of one or more unit cells and/or the internal surface(s) of one or more unit cells can be textured.

The structural configurations of the unit cells disclosed herein can also be tailored to effect variable mechanical responses within the same adjunct, e.g., in the lateral and/or longitudinal directions (e.g., y- and/or z-directions, respectively). For example, an adjunct can be formed of at least two or more different lattice structures, each exhibiting a different compressive behavior. In some embodiments, the perimeter of the adjunct could be more compliant while stiffer regions are located closer to the intended cut line of the adjunct. By way of example, the wall adjacent to the intended cut line itself could be mostly solid or rigid thereby allowing for a more controlled and cleaner cut of the adjunct along the intended cut line. Further, the softer perimeter of the adjunct could protect tissue outside of and adjacent to the jaws (e.g., the jaws of a surgical stapler) from collateral compressive damage.

In some embodiments, the unit cells can be defined by one or more walls, in which some of the walls are hollow (e.g., having void space between opposing exterior surfaces) and others are solid, thereby creating preferential wall bending among the one or more walls. In certain embodiments, any solid wall of the unit cells can include internal voids that create flex zones where the solid wall initially bends prior to the wall bending as a whole (e.g., when a force is applied to the adjunct).

In some embodiments, the one or more walls of the unit cell can be populated with small non-interconnected voids (e.g., in the form of spheres and/or cylinders) that create a substantially incompressible outer shell that is flexible. That is, the small non-interconnected voids would allow the mostly rigid polymer of the one or more walls to be more flexible since these voids could enable bending without direct compressions of the internal aspects of the one or more walls. In such embodiments, the bi-modal nature of the outer shell can be increased such that the unit cell can more easily move between two different states based on a pre-defined force.

The adjuncts disclosed herein can also include internal and/or external features that promote or inhibit selective deformation of the adjunct (e.g., stretching, bending, compressing, and the like). For example, the adjuncts can include one or more internal stopping elements that are configured to limit the amount of deformation of the adjunct when the adjunct is being compressed. Alternatively, or in addition, the adjunct can include surface features that prevent the adjunct from stretching while releasably retained on a cartridge of a stapling assembly. Alternatively, or in addition, the adjunct can include surface features (e.g., surface friction features) that are configured to minimize slippage of the adjunct relative to a top surface of a staple cartridge when the adjunct is releasably retained thereon and/or relative to tissue when the adjunct is stapled thereto. Additional details on and other exemplary embodiments of internal features and surface features that are suitable to promote or inhibit selective deformation of an adjunct disclosed herein can be found in U.S. patent application Ser. No. 15/901,087, filed on Feb. 21, 2018, and entitled "Three Dimensional Adjuncts," and previously mentioned U.S. patent application Ser. No. 17/009,769, filed on Sep. 1, 2020, and entitled "Compressible Non-Fibrous Adjuncts," each of which is incorporated herein by reference in its entirety.

In certain embodiments, the at least one absorbable sub-structure can include at least one microstructure formed in at least one unit cell for controlling fluid flow through the respective passageway. For example, the at least one microstructure can be a micro-passageway that is formed in the sidewall of the unit cell. The micro-passageway can be in fluid communication with the passageway of the respective unit cell. In other embodiments, the at least one absorbable sub-structure can include other fluid control structures, such as a movable valve (e.g., duck bill valve, a flapper valve, and the like) that is formed in at least one of the unit cells.

In certain embodiments, at least a portion of the unit cells can be configured to deform when the adjunct material is compressed so as to draw fluid into the adjunct material (e.g., when the adjunct material is in a tissue deployed state) and/or to drive fluid out of the adjunct material to tissue adjacent the adjunct material (e.g., when the adjunct material is in a tissue deployed state). As such, this portion of unit cells can serve as pumping elements within the lattice main structure to drive fluid flow through the adjunct material. In such embodiments, this portion of unit cells can be concentrated outside of the staple puncture zones of the adjunct material (e.g., zones or regions of the adjunct material that are configured to overlap with staples disposed in a cartridge that the adjunct material is to be releasably retained thereto).

Further, in some embodiments, lattice main structure can include connecting structures that extend between and connect adjacent unit cells to each other. The connecting structures can be in the form of hollow tubes. As such, the connecting structures can serve as channeling elements within the lattice main structure to direct fluid flow through the adjunct material. Alternatively or in addition, the connecting structures can serve as pumping elements within the lattice main structure.

In some embodiments, the lattice main structure can include hollow struts. In certain embodiments, the at least one absorbable sub-structure can be formed within at least one of the hollow struts for controlling fluid flow therethrough. In one embodiment, the hollow struts are the connecting structures that extend between and connect adjacent unit cells to each other.

Each exemplary adjunct as described below is illustrated in partial form (e.g., not in full-length), and therefore a person skilled in the art will appreciate that the adjunct can be longer in length, e.g., along its longitudinal axis ($L_A$) as identified in each embodiment. The length can vary based on a length of the staple cartridge or anvil. The width can also vary as needed. Further, each exemplary adjunct is configured to be positioned atop a cartridge or anvil surface such that the longitudinal axis L of each adjunct is aligned with and extends along the longitudinal axis ($L_A$) of the cartridge or anvil. These adjuncts are structured so as to compress when exposed to compressive forces (e.g., stress or load).

Figure 8:
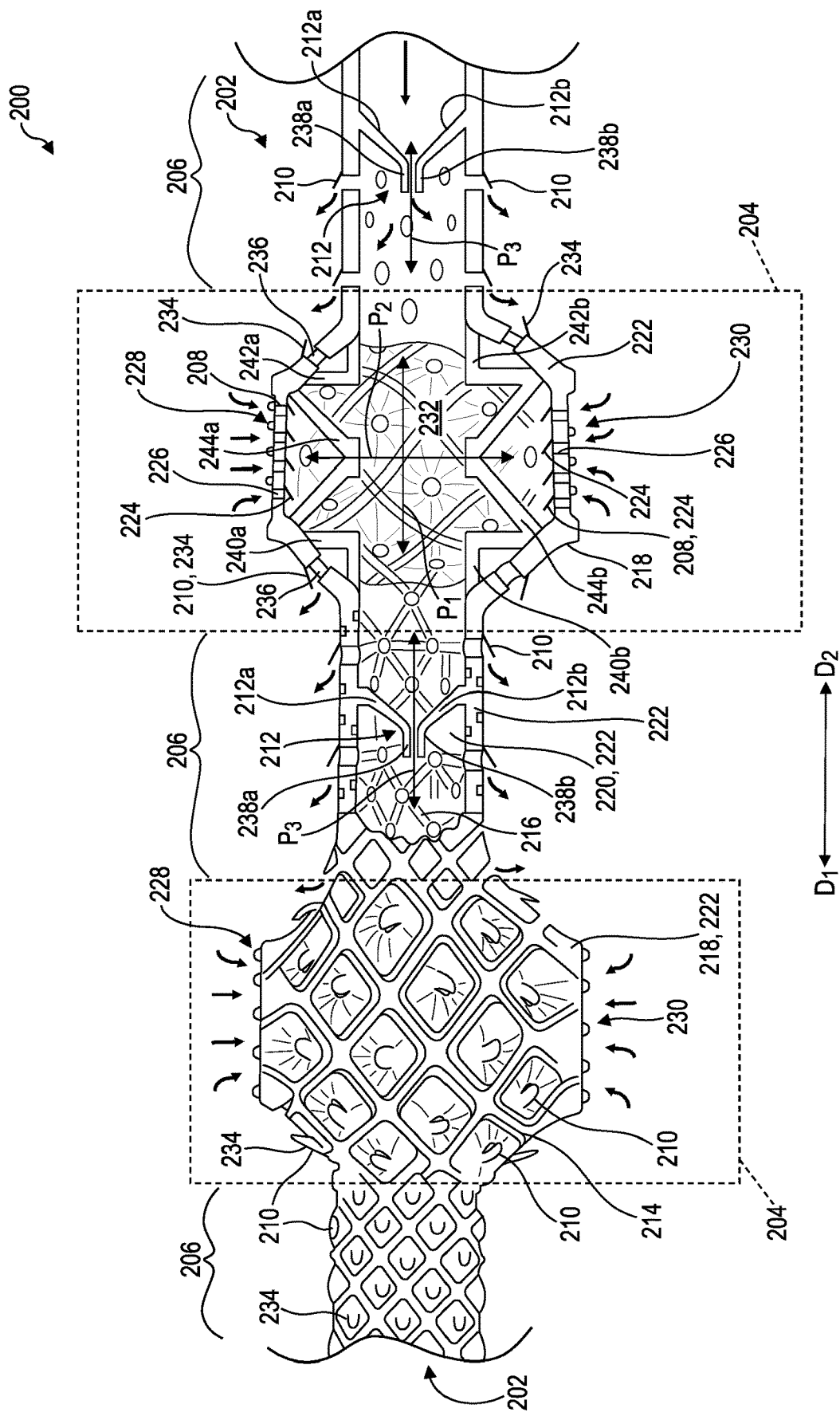
FIG. 8 is a partial cut-away side view of an exemplary adjunct having at least one fluid control feature.

FIG. 8 illustrates one embodiment of an adjunct 200 having a lattice main structure 202 that is formed of unit cells 204. While not shown, the adjunct 200 can be positioned atop an anvil surface of an anvil, like anvil 34 shown in FIG. 1, and/or a top or deck surface of a staple cartridge, like staple cartridge 40 and 102 shown in FIGS. 1 and 6, respectively. In this illustrated embodiment, the unit cells 204 are hollow with passageways, e.g., first passageway denoted by arrow $P_1$ and second passageway denoted by arrow $P_2$, extending therethrough. In use, when a force is applied to the adjunct 200, the unit cells 204 are configured to deform or compress. In this way, the unit cells 204 can function as pumping elements that drive fluid into and out of the adjunct 200. The unit cells 204 are connected to each other via connecting structures 206 that are in the form of hollow tubes with passageways, e.g., passageways denoted by arrow $P_3$, extending therethrough. As a result, the unit cells 204 are in fluid communication with each other such that a continuous network of pathways are present within the adjunct 200. Further, since the connecting structures 206 are in the form of hollow tubes, the connecting structures 206 can also serve as pumping features when the adjunct is being compressed. For purposes of clarity, only unit cells 204 and three connecting structures 206 are being illustrated.

The adjunct 200 can include at least one absorbable sub-structure 208, 210, 212, 214, 216 that is formed in the lattice main structure 202. The at least one absorbable sub-structure 208, 210, 212, 214, 216 can have a variety of configurations. For example, in this illustrated embodiment, the lattice main structure 202 is illustrated as having a variety of different absorbable sub-structures 208, 210, 212, 214, 216 formed therein. More specifically, the absorbable sub-structures 208, 210, 212, 214, 216 include first flapper valves 208, second flapper valves 210, duck bill valves 212, first microchannels 214 that are defined within an exterior surface 218 of a sidewall 222 of the lattice main structure 202, and second microchannels 216 that are defined within interior surface 220 of the sidewall 222 of the lattice main structure 202. The first and second microchannels 214, 216 are each configured to direct fluid therethrough. While a variety of different absorbable sub-structures are illustrated, a person skilled the art will appreciate that the type(s) of absorbable sub-structures and the number of absorbable sub-structures can depend at least upon the size and shape of lattice main structure, and therefore, the adjunct is not limited to the types and number of absorbable sub-structures illustrated in the figures. Further, while a variety of different absorbable sub-structures are illustrated, in other embodiments, the lattice main structure can have any suitable type and number of absorbable sub-structures.

While not illustrated, the adjunct 200 can include at least one drug disposed within the lattice main structure 202. In such instances, a person skilled in the art will appreciate that the fluid can serve as a carrier vehicle for the at least one drug. As such, fluid movement through and out of the adjunct would therefore include drug movement and as a result, it can affect the rate and/or location of drug release from the adjunct.

The first flapper valves 208 can have a variety of configurations. For example, as shown in FIG. 8, the first flapper valves 208 each include a first flap 224, e.g., a movable polymer flap, that is placed over a respective first opening 226 that completely extends through the sidewall 222 of the lattice main structure 202. While the first openings 226 can be positioned at various locations in the sidewall, in this illustrated embodiment, the first openings are positioned at the top portion 228 and the bottom portion 230 of the unit cells 204. In use, the first flap 224 is configured to move from a closed position to an open positon. When the first flap 224 is in an open position, as shown in FIG. 8, fluid (denoted by the arrows) can pass through the respective first opening and into an internal volume 232 of the respective unit cell 204. When the first flap 224 is in a closed position, the first flap 224 creates a seal, and as a result, any fluid within the internal volume 232 of the respective unit cell 204 is inhibited from passing through the respective first opening 226 and out of the adjunct 200. As such, the first flapper valves 208 are configured as one-way self-sealing valves that only allow fluid ingress.

The second flapper valves 210 can have a variety of configurations. For example, as shown in FIG. 8, the second flapper valves 210 each include a second flap 234, e.g., a movable polymer flap, that is placed over a respective second opening 236 that completely extends through the sidewall 222 of the lattice main structure 202. While the second openings 236 can be positioned at various locations in the sidewall 222, in this illustrated embodiment, the second openings 236 are along the sides of the unit cells 204 and around the connecting structures 206. The second flap 234 is configured to move from a closed position to an open position. When the second flap 234 is in an open position, as shown in FIG. 8, fluid (denoted by a black arrow) can pass out of the unit cells 204 and the connecting structures 206, through the respective second openings 236 and out of the adjunct 200. When the second flap 234 is in a closed position, the second flap 234 creates a seal, and as a result, any fluid outside of the adjunct 200 is inhibited from passing through the respective second opening 236 and into the unit cells 204 and the connecting structures 206. As such, the second flapper valves 210 are configured as one-way self-sealing valves that only allow fluid egress.

Figure 9:
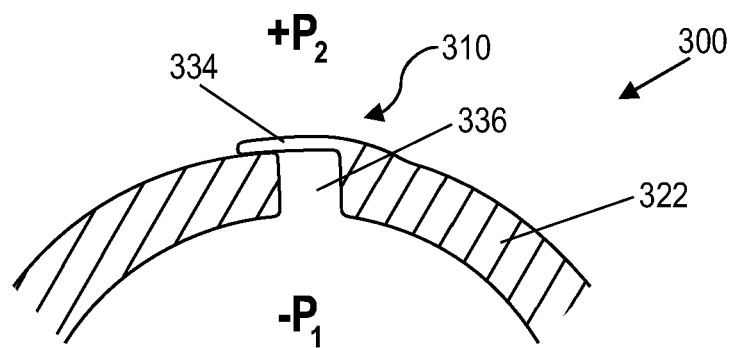
FIG. 9 is a cross-sectional view of a portion of another embodiment of an adjunct having at least one fluid control feature, showing the at least fluid control feature in a closed position.
Figure 10:
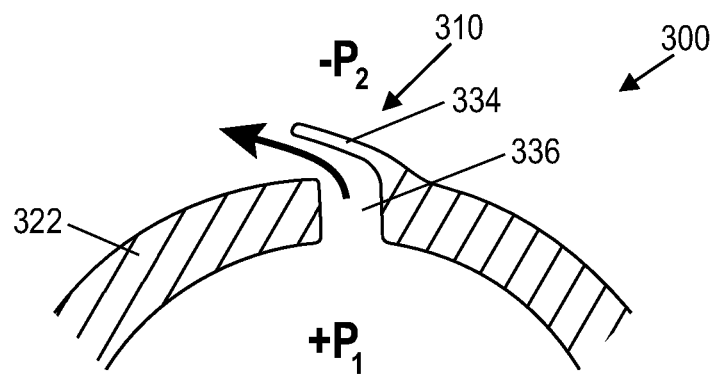
FIG. 10 is a cross-sectional view of the portion of the adjunct of FIG. 9, showing the at least one fluid control feature in an open position.

FIG. 9 and FIG. 10 illustrate another embodiment adjunct 300 with a flapper valve 310, like second flapper valves 210 shown in FIG. 8, that is designed to use a constricting physical bias to allow fluid to move in one direction but prevent movement in the opposite direction. While not shown, the adjunct 300 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For sake of simplicity, a cross-sectional view of a portion of the adjunct 300 is shown in FIG. 9 and FIG. 10. The flapper valve 310 includes a flap 334 that is bias to a closed position (FIG. 9) to seal an opening 336 through a sidewall 322 of the adjunct 300 when the internal pressure $P_1$ (e.g., pressure inside of the adjunct) is less than the external pressure $P_2$. (e.g., pressure outside of the adjunct). However, when the internal pressure $P_1$ is greater than then external pressure $P_2$, the flap 334 is configured to move to an open position (FIG. 10) thereby allowing at least a portion of the contents, e.g., fluid (denoted by a black arrow) within the adjunct 1000 to flow through the opening 336 and out of the adjunct 300. In some embodiments, the pressure differential is created by the fluid present on both sides of the opening 336. As such, when an exterior force is applied to the adjunct 300, the internal pressure $P_1$ can increase to thereby cause the flapper valve 310 to move from a closed position to an open position.

Referring back to FIG. 8, duck bill valves 212 are positioned within the connecting structures 206 that are used to control fluid movement through the connecting structures 206. Each duck bill valve 212 includes a pair of opposing leaflets 212a, 212b that are attached to and extend from the sidewall 222 of the lattice main structure 202 that define the respective connecting structures 206. The leaflets 212a, 212b are configured to move from a closed position, in which the free ends 238a, 238b of the leaflets 212a, 212b are in contact with each other, to an open position, as shown in FIG. 8, in which the free ends 238a, 238b of the leaflets 212a, 212b are spaced apart from one another. When the duck bill valve 212 is in an open position, the space between the free ends 238a, 238b of the leaflets 212a, 212b allow fluid to pass through the respective connecting structure 206 in one direction $D_1$. When the duck bill valve 312 is in a closed position, the contact between the free ends 238a, 238b of the leaflets 212a, 212b, prevent fluid from passing through the respecting connecting structure 206 in the opposite direction $D_2$.

Figure 11:
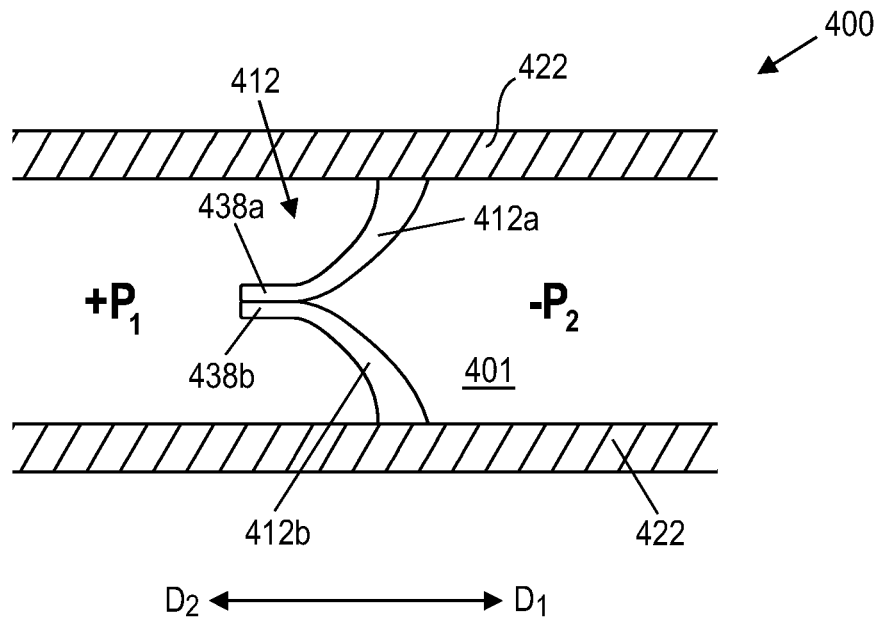
FIG. 11 is a cross-sectional view of a portion of another embodiment of an adjunct having at least one fluid control feature, showing the at least fluid control feature in a closed position.
Figure 12:
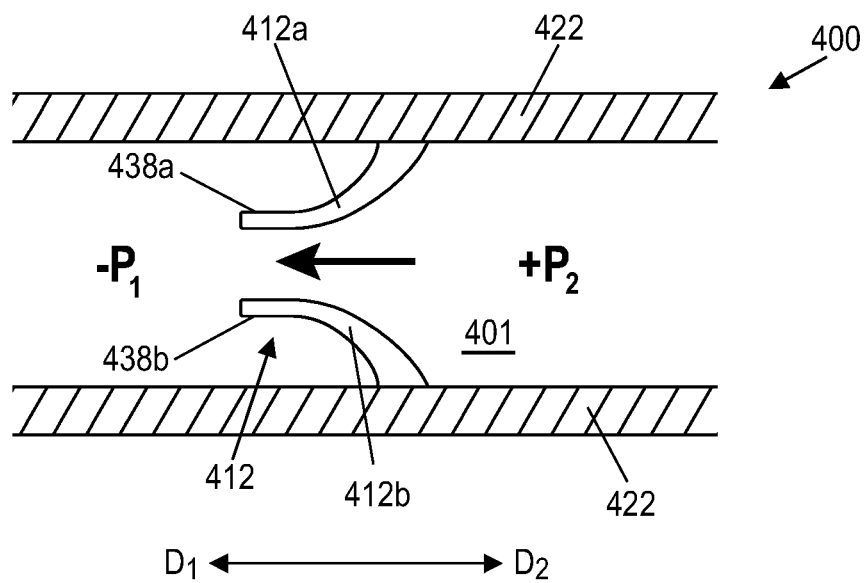
FIG. 12 is a cross-sectional view of the portion of the adjunct of FIG. 11, showing the at least one fluid control feature in an open position.

FIG. 11 and FIG. 12 illustrate another embodiment of an adjunct 400 with a duck bill valve 412, like duck bill valves 212 shown in FIG. 8, that is designed to use a constricting physical bias to allow fluid to move in one direction but prevent movement in the opposite direction. While not shown, the adjunct 400 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For sake of simplicity, a cross-sectional view of a portion of the adjunct 400 with a single duck bill valve 412 is shown in FIG. 11 and FIG. 12. The duck bill valve 412 generally includes two opposing flaps 412a, 412b extending from an annular sidewall 422 of the adjunct 400, in which each flap 412a, 412b has a flattened or bent free end 438a, 438b. As shown in FIG. 11, the flattened or bent free ends 438a, 438b are bias to a closed position (FIG. 11) to seal a passageway 401 through the adjunct 400 when a first pressure $P_1$ on one side of the duck bill valve (e.g., the right side of the duck bill valve) is greater than a second pressure on the opposite side of the duck bill valve (e.g., the left side of the duck bill valve). This prevents fluid from flowing through the valve in a first direction $D_1$. However, when the first pressure $P_1$ is greater than then second pressure $P_2$, the flattened or bent free ends 428a, 438b are configured to move to an open position (FIG. 12) to thereby allow fluid (denoted by a black arrow) to flow through the duck bill valve, and thus through the passageway 401 of the adjunct in a second direction $D_2$. In some embodiments, when an exterior pressure is applied to the adjunct 400, the internal pressure, e.g., the second pressure $P_2$, can increase to thereby cause the duck bill valve to move from a closed position to an open position.

Referring back to FIG. 8, the adjunct 200 can include internal stopping elements 240a, 240b, 242a, 242b, 244a, 244b that are formed in the unit cells 204 and extend into the internal volume 232. These internal stopping elements 240a, 240b, 242a, 242b, 244a, 244b are configured to come into contact with each other to thereby limit the amount of deformation of the respective unit cell 204 while the adjunct 200 is being compressed. While the adjunct 200 can include any number of internal stopping elements, in this illustrated embodiment, the adjunct includes three sets of internal stopping elements 240a, 240b, 242a, 242b, 244a, 244b.

The internal stopping elements 240a, 240b, 242a, 242b, 244a, 244b can have a variety of configurations. Further, the internal stopping elements can have the same or different structural configurations. As shown in FIG. 8, the first set of elements include first and second opposing stopping elements 240a, 240b, each having a L-shaped configuration in which the first stopping element 240a is positioned proximate to the top portion 228 of the unit cell 204 and the second stopping element 240b is positioned proximate to the bottom portion 230 of the unit cell 204. The second set of elements include third and fourth opposing stopping elements 242a, 242b, each having a L-shaped configuration in which the third stopping element 242a is positioned proximate to the top portion 228 of the unit cell 204 and the fourth stopping element 242b is positioned proximate to the bottom portion 230 of the unit cell 204. The first and second sets of elements are positioned on opposite sides of the internal surface of the unit cell 204. The third set of elements include fifth and sixth opposing stopping elements 244a, 244b, each having a V-shaped configuration in which the fifth stopping element 244a is positioned proximate to the top portion 228 of the unit cell 204 and the sixth stopping element 244b is positioned proximate to the bottom portion 230 of the unit cell 204. The third set of elements are positioned between the first and second sets of elements. A person skilled in the art will appreciate that the number and structural configurations of the internal stopping elements depend at least upon the structural configuration and size of the unit cell, and therefore, in other embodiments, a unit cell can have a different number of internal stopping elements and/or internal stopping elements having other suitable shapes and sizes.

Figure 13:
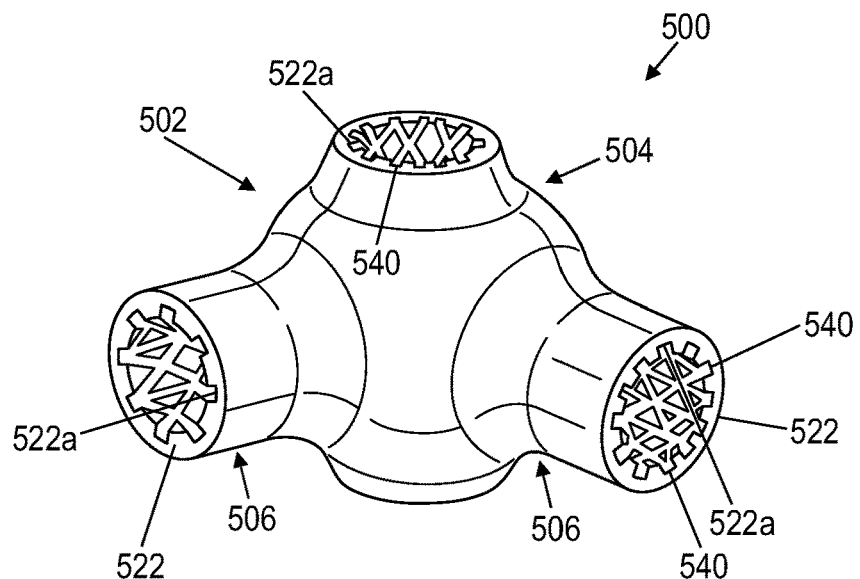
FIG. 13 is a perspective side view of a portion of another exemplary embodiment of an adjunct having at least one fluid control feature.
Figure 14:
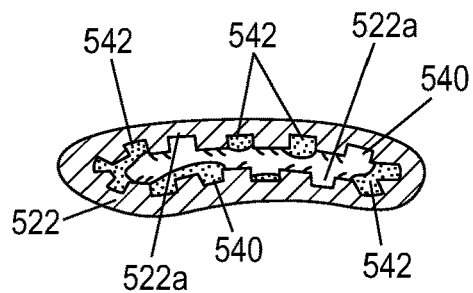
FIG. 14 is a cross-sectional front view of one of a connecting structure of the adjunct of FIG. 13 with fluid within at least one fluid control feature, showing the adjunct in a compressed state.

FIG. 13 illustrates another embodiment of an adjunct 500 having a lattice main structure 502 that is formed of interconnected unit cells 504. While not shown, the adjunct 500 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For sake of simplicity, only one unit cell 504 and a portion of two connecting structures 506 are being illustrated. While the unit cell 504 and the two connecting structures 506 can have a variety of configurations, in this illustrated embodiment, the unit cell 504 is a hollow structure and the two connecting structures 506 are each a hollow tube. As shown in FIG. 5, the unit cell 504 and the hollow tubes 506 each have microchannels 540 formed therein, i.e., smaller channels located within the macrochannels defined by the hollow tubes. That is, the microchannels 540 are formed within the sidewall 522 of the lattice main structure 502 that define the unit cell 504 and the two hollow tubes 506. In this illustrated embodiment, the microchannels 540 form part of the internal surface 522a of the sidewall 522. In use, when the adjunct 500 is compressed, the fluid 542 within the adjunct 500 can be directed via the microchannels 540, for example, as shown in FIG. 14.

Figure 15:
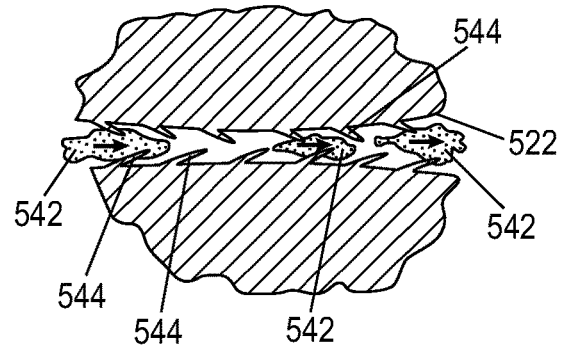
FIG. 15 is a magnified cross-sectional side view of one of the at least fluid control feature of FIG. 14 having an additional fluid control features formed therein, showing fluid movement through the at least one fluid control feature.

In certain embodiments, the microchannels 540 can include microfeature(s) that are oriented within the microchannels 540 so as to direct fluid 542 therethrough in a predefined direction. For example, as illustrated in FIG. 15, a microchannel 540 can include flexible wicking elements 544 that are configured to direct fluid 542 though the microchannel 540 in a first direction $D_1$. A person skilled in the art will appreciate that the orientation of the microfeature(s) depend at least upon the structural configuration of the microchannel and the desired direction of fluid flow therethrough.

In some embodiments, the microchannels can be configured to wick fluid therethrough via capillary action. For example, the microchannels can have a width of about 10 micrometers to 500 micrometers so as to wick fluids therethrough via capillary action. In other embodiments, the microchannels can include knitted or woven construction of filaments that are configured to wick fluids therethrough.

Figure 16:
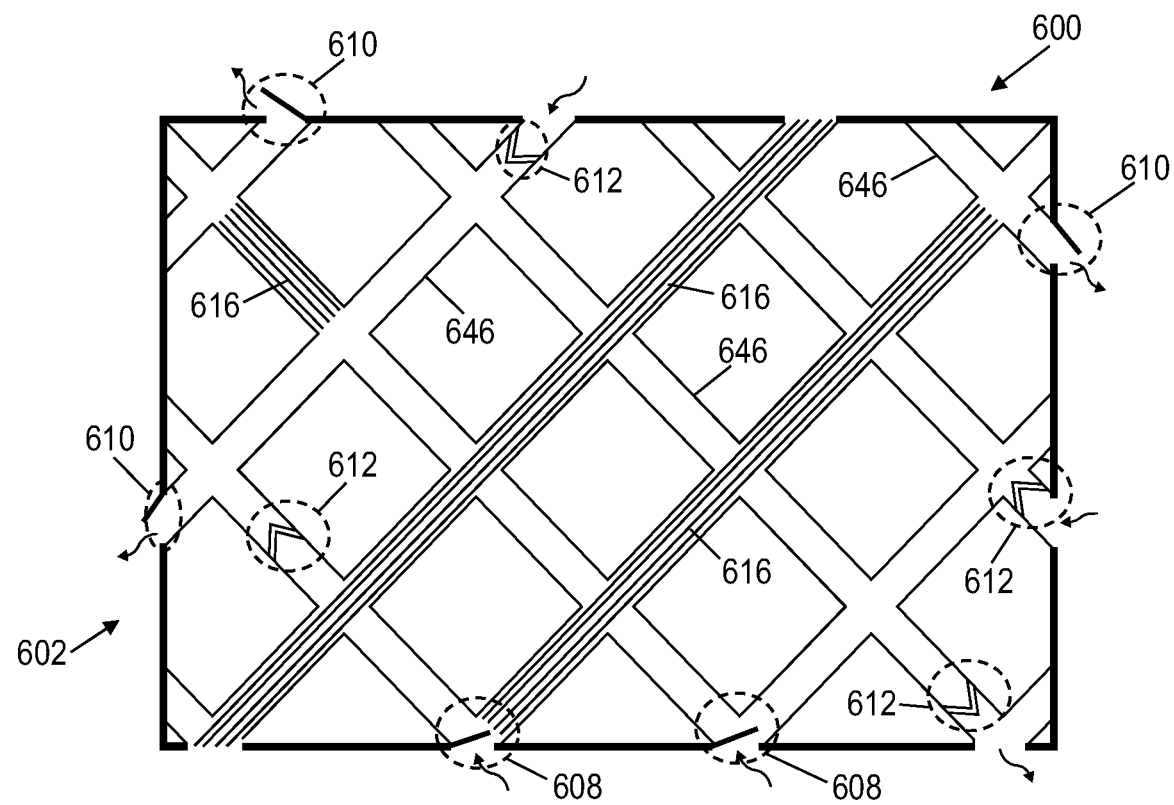
FIG. 16 is a cross-sectional side view of another exemplary embodiment of an adjunct having at least one control feature.

FIG. 16 illustrates another exemplary embodiment of an adjunct 600 having a lattice main structure 602 with absorbable sub-structures 608, 610, 612, 616 that are formed in the lattice main structure 602. While not shown, the adjunct 600 can be positioned atop an anvil surface of an anvil, like anvil 34 shown in FIG. 1, and/or a top or deck surface of a staple cartridge, like staple cartridge 40 and 102 shown in FIGS. 1 and 6, respectively. The lattice main structure includes hollow struts 1646 in which the absorbable sub-structures are formed for controlling fluid flow therethrough. While the absorbable sub-structures 608, 610, 612, 616 can have a variety of configurations, in this illustrated embodiment, the absorbable sub-structures 608, 610, 612, 616 include first flapper valves 608, second flapper valves 610, duck bill valves 612, and microchannels 616. Fluid flow into and out of the adjunct is denoted by the arrows. The first flapper valves 608, the second flapper valves 610, the duck bill valves 612, and the microchannels 616 are similar in structural configuration and/or function to the first flapper valves 208, the second flapper valves 210, the duck bill valves 212, and the second microchannels 216 shown in FIG. 8 and therefore are not described in detail herein.

Figure 17:
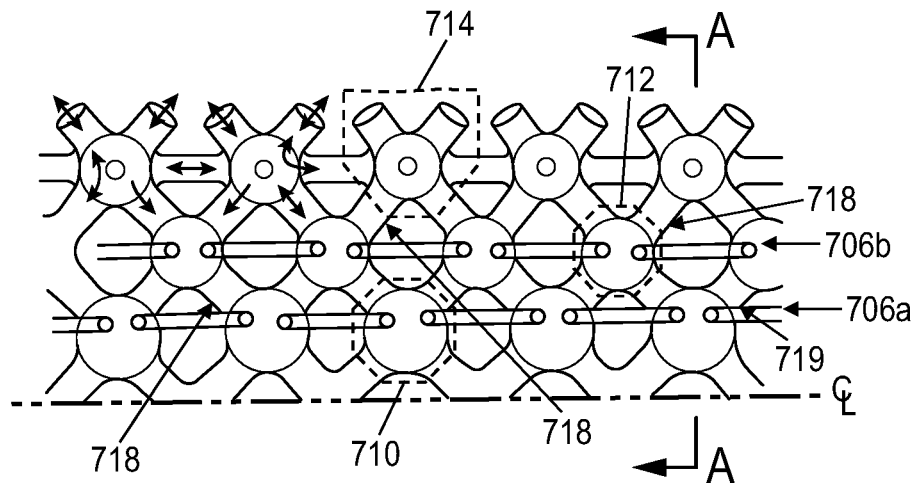
FIG. 17 is a top-down view of an exemplary embodiment of a stapling assembly having an adjunct releasably retained on a staple cartridge, showing only a portion of the stapling assembly.
Figure 18:
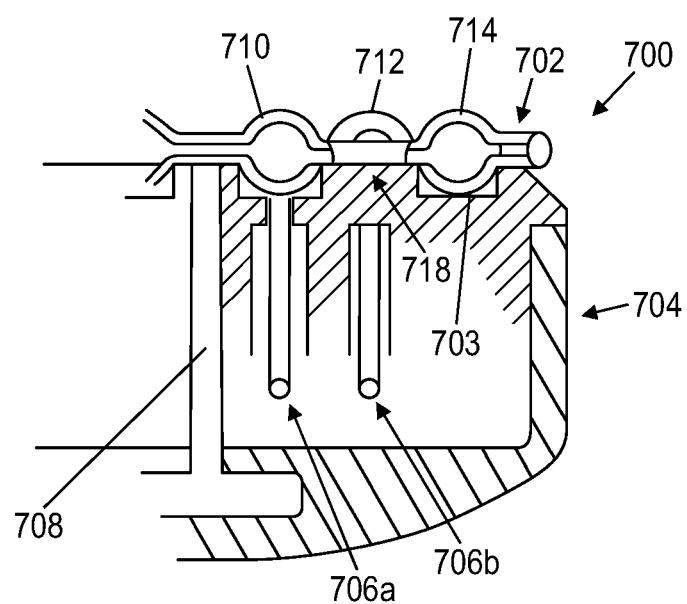
FIG. 18 is a cross-sectional view of the stapling assembly of FIG. 17 taken at A-A.

In some embodiments, at least a portion of the unit cells of an adjunct can be positioned within regions of the adjunct that do not overlap with staple rows of a cartridge when the adjunct is released retained thereto, for example as shown in FIG. 17 and FIG. 18. As such, in use, the non-overlapping unit cells can serve as pumping elements that are configured to drive fluid out of the adjunct when the unit cells are being compressed, draw fluid into the adjunct when the unit cells are expanding back to their uncompressed configuration, or a combination thereof.

FIG. 17 and FIG. 18 illustrate an exemplary embodiment of a stapling assembly 700 having an adjunct 702 releasably retained on a top or deck surface 703 of a staple cartridge 704 (e.g., the cartridge surface that faces the anvil). As shown, only one half (e.g., the right half) of the adjunct 702 is illustrated on the staple cartridge 704 with two rows of staples 706a, 706b disposed within the staple cartridge 704. As shown in FIG. 18, the inner most staple row 706a is adjacent a knife slot 708 defined within the cartridge 704.

While the adjunct 702 can have a variety of configurations, the adjunct 702 is formed of interconnected unit cells (e.g., Schwarz-P structures) that are arranged in two sets of three longitudinal arrays, with the first set positioned on a first side of the intended cut line CL of the adjunct 702 and the second set (not shown) positioned on the second side of the intended cut line CL of the adjunct 702. Since both sets are the same, only unit cells 710, 712, 714 of one set of the three longitudinal arrays are illustrated in FIG. 17 and FIG. 18. Further, adjacent unit cells are connected to each other via connecting structures 718.

As shown in FIG. 17 and FIG. 18, the inner-most longitudinal array of unit cells 710 overlap with the first staple row 706a (e.g., the inner-most staple row) and the intermediate longitudinal array of unit cells 712 overlap with the second staple row 706b (e.g., the outer-most staple row). Further, the outer-most longitudinal array of unit cells 714 do not overlap with any of the staple rows 706a, 706b. Further, the outer-most longitudinal array of unit cells 714 do not overlap with intended cut line CL of the adjunct or the knife slot 708 of the cartridge 704. As a result, in use, when the adjunct 702 is stapled and cut, the staples 706a, 706b and cutting element (not shown) do not puncture and cut, respectively, the outer-most longitudinal array of unit cells 714. This allows the structural integrity of the outer-most longitudinal array of unit cells 714 to remain intact. As such, at least the outer-most longitudinal array of unit cells 714 can draw fluid into the adjunct when being compressed, drive fluid out of the adjunct when expanding to uncompressed configuration, or a combination thereof, as denoted by the arrows in FIG. 17.

Figure 19:
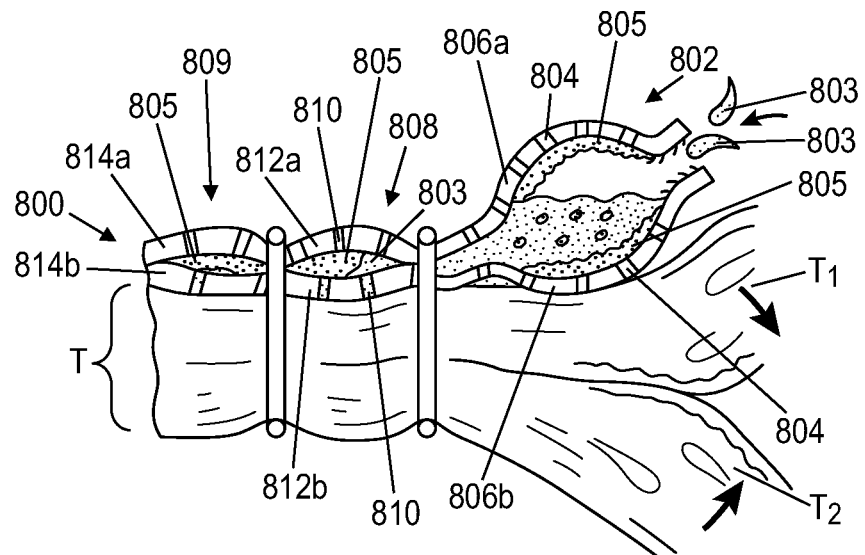
FIG. 19 is a partial-schematic illustrating an exemplary embodiment of an adjunct in a tissue deployed state, showing the tissue in a first position.
Figure 20:
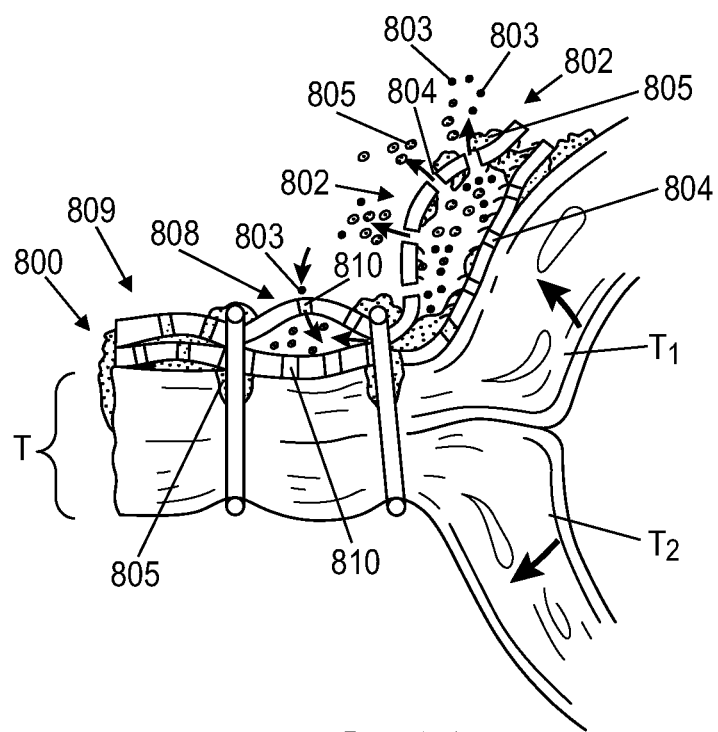
FIG. 20 is a partial-schematic illustrating the adjunct of FIG. 19, showing the tissue in a second position.

In certain embodiments, as tissue moves, the non-overlapping unit cells of the adjunct relative to the staple rows and knife slot of the cartridge can be configured to draw fluid into the adjunct or pump out fluid and/or fluid/drug mixture to surrounding tissue. For example, in FIG. 19, an adjunct 800 is stapled to tissue T. As shown, the non-overlapping unit cells 802 (e.g., the outer-most longitudinal array of unit cells), only one of which is illustrated, can draw fluid 803 into the adjunct 800 when segments of the tissue $T_1$ and $T_2$ move towards each other. The drawn fluid can be used to saturate the at least one drug 805 (e.g., powdered drug) that is positioned along the inner surface 802a of the unit cell 802. When segments of the tissue $T_1$ and $T_2$ move away from each other, as shown in FIG. 20, the non-overlapping unit cell 802 can be configured to pump fluid 803 and the at least one drug 805 out of the adjunct 800, e.g., through microholes 804 extending through the top and bottom walls 806a, 806b of the unit cell 802. Further, other unit cells, e.g., adjacent unit cell 808, 809, can be configured to draw fluid into and out of the adjunct, e.g., through microholes 810 extending through respective top and bottom walls 812a, 812b, 814a, 814b. As such, the drawn fluid can be used to saturate the at least one drug 805 positioned with the respective unit cells 808, 809 of the unit cell 802, and thus, as shown in FIG. 20, the respective unit cells 808, 809 can be configured to pump the fluid 803 and the at least one drug 805 therefrom.

As noted above, the present adjuncts can contain at least one drug. The at least one drug can be positioned at various locations within the adjunct (e.g., within one or more reservoirs that are formed within the adjunct). For example, in embodiments wherein the adjunct includes hollow unit cells, the at least one drug can be contained within the internal volume of the unit cell. Alternatively, or in addition, the at least one drug can be contained within a void or pocket defined within a wall of the unit cell. In some embodiments, a first drug of the at least one drug can be positioned within the adjunct such that it is free to be expelled in response to fluid ingress into and through the adjunct, and a second drug of the at least one drug can be positioned within the adjunct such that it is expelled in response to structural degradation of at least a portion of the adjunct. As a result, in certain embodiments, drug delivery can be dependent not only on fluid movement, but in some instances, time (hydrolysis) and/or oxygen level (e.g., enzyme degradation).

Figure 21:
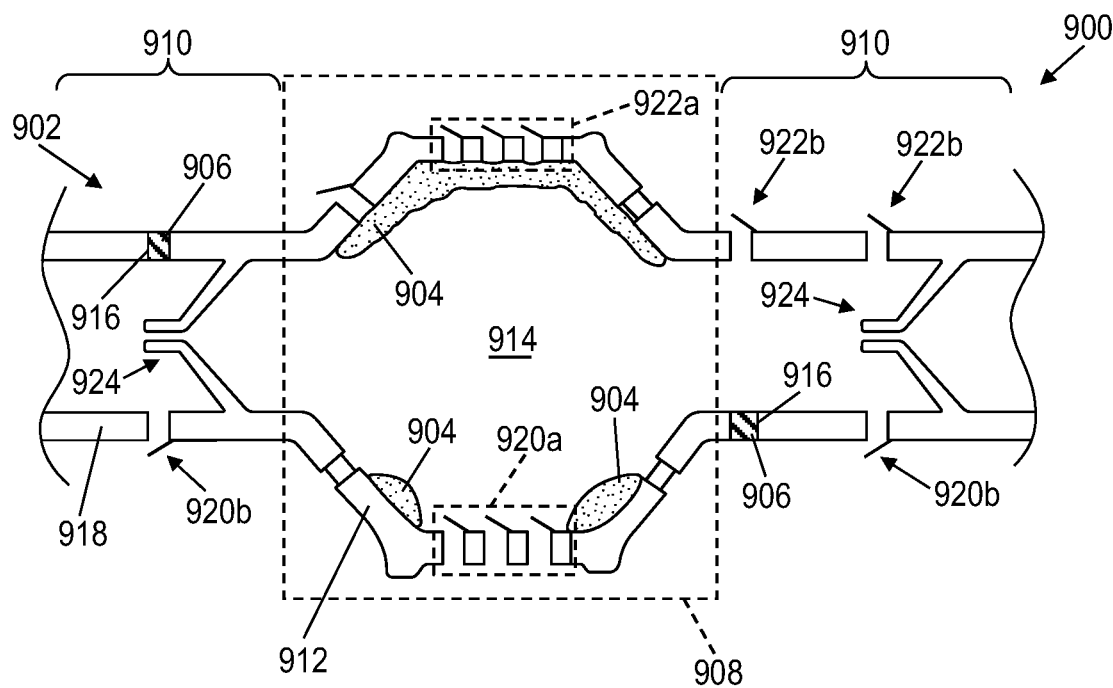
FIG. 21 is a cross-sectional view of a portion of another exemplary embodiment of an adjunct having at least one drug disposed therein and at least one fluid control feature.

FIG. 21 illustrates an exemplary embodiment of an adjunct 900 having a hollow lattice macrostructure 902 with at least one drug 904, 906 contained therein. While not shown, the adjunct 900 can be positioned atop an anvil surface of an anvil, like anvil 34 shown in FIG. 1, and/or a top or deck surface of a staple cartridge, like staple cartridge 40 and 102 shown in FIGS. 1 and 6, respectively. The hollow lattice macrostructure 902 is formed of unit cells 908 that are connected to each other via connecting structures 910. While the unit cells 908 and connecting structures 910 can have a variety of configurations, in this illustrated embodiment, the unit cells 908 have an outer wall 912 that defines an internal cavity 914, and the connecting structures 910 are in the form of hollow tubes. For purposes of simplicity, only one unit cell 908 and two connecting structures 910 are illustrated. As shown, a first drug 904 is disposed within the internal cavity 914 (e.g., a primary reservoir) of the unit cell 908, and a second drug 906 is disposed within voids 916 (e.g., a secondary reservoir) defined within the wall 918 of the connecting structures 910. In certain embodiments, the internal cavity 914 is configured to release at least a portion of the first drug 904 therefrom in response to an initial ingress of fluid into the unit cell 908, whereas the voids 916 can be configured to release at least a portion of the second drug 906 therefrom in response to structural degradation of the portions of the wall 918 that define the voids 916.

As further shown, absorbable sub-structures 920a, 920b, 922a, 922b, 924 are formed in hollow lattice macrostructure 902. More specifically, absorbable sub-structures 920a, 922a are formed in the unit cell 908 and absorbable sub-structures 920b, 922b, 924 are formed in the connecting structures 910. While the absorbable sub-structures 920a, 920b, 922a, 922b, 924 can have a variety of configurations, in this illustrated embodiment, the absorbable sub-structures 920a, 920b, 922a, 922b, 924 include first flapper valves 920a, 920b, second flapper valves 922a, 922b, and duck bill valves 924. The first flapper valves 920a, 920b, the second flapper valves 922a, 922b, and the duck bill valves 924 are similar in structural configuration and/or function to the first flapper valves 208, the second flapper valves 210, and the duck bill valves 212 shown in FIG. 8 and therefore are not described in detail herein.

In use, when a force is applied to the adjunct 900, the unit cells 908 are configured to deform or compress. In this way, the unit cells 908 can function as pumping elements that draw fluid into and out of the adjunct 900. The influx of fluid can be directed through the adjunct 900 to thereby mix with at least the first drug 904 and/or the second drug 906. The resulting fluid/drug mixture can then be subsequently driven out of the adjunct 200 via, e.g., the pumping action of the unit cells 908. As such, the unit cells 908 can direct drug movement through the adjunct 900 and control the location of drug elution from the adjunct 900. Further, the flow of the fluid and/or the fluid/drug mixture can be further controlled by the absorbable sub-structures 920a, 920b, 922a, 922b, 924. That is, the absorbable sub-structures 920a, 920b, 922a, 922b, 924 can also be used to control the rate and/or direction of drug movement through and out of the adjunct 900. As such, the combination of the unit cells with the absorbable sub-structures can effect controlled drug delivery of the first and second drugs from the adjunct.

Figure 22:
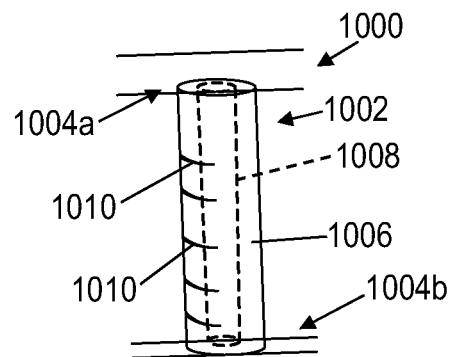
FIG. 22 is a cross-sectional view of a portion of another exemplary embodiment of an adjunct, showing the adjunct in an uncompressed state.
Figure 23:
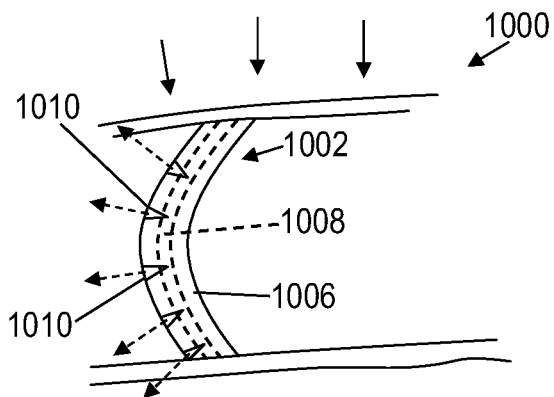
FIG. 23 is a cross-sectional view of the adjunct of FIG. 22, showing the adjunct in a compressed state.

Other structural configurations and mechanisms can be used for adjunct drug delivery. For example, as shown in FIG. 22 and FIG. 23, an adjunct 1000 can include buckling columns 1002, only one of which is illustrated, that extend from a first end 1004a to a second end 1004b with a longitudinal axis $L_A$ extending therebetween. While not shown, the adjunct 1000 can be positioned atop an anvil surface of an anvil, like anvil 34 shown in FIG. 1, and/or a top or deck surface of a staple cartridge, like staple cartridge 40 and 102 shown in FIGS. 1 and 6, respectively. While the buckling columns 1002 can have a variety of configurations, in this illustrated embodiment, the buckling column 1002 has an elongated cylindrical body 1006 with a longitudinal channel 1008 that extends from the first end 1004a to the second end 1004b of the body 1006. The longitudinal channel 1008 is configured to draw fluid therein and thus into the adjunct 1000 (e.g., when the adjunct 1000 is stapled to tissue). The buckling column 1002 also includes lateral slots 1010 that are defined within the body 1006 and are in fluid communication with the longitudinal channel 1008. The lateral slots 1010 are configured to house at least one drug (not shown). As shown in FIG. 22, when the adjunct 1000 is uncompressed (e.g., without having a force applied to it), the buckling column 1002 is in a generally straight configuration. As a result, the lateral slots 1010 are closed, and therefore drug contained therein would be sealed within the respective lateral slot 1010.

Once a force (depicted as solid arrows) is applied to the adjunct 1000, as shown in FIG. 22, the adjunct compresses causing the buckling column to bend (e.g., into a convex configuration) and the lateral slots 1010 to open. This causes the at least one drug contained within the lateral slots 1010, now open, and fluid present within the longitudinal channel 1008 to be expelled (depicted as dotted arrows) from the adjunct 1000. That is, once the lateral slots 1010 are open, the expulsion of the fluid present within the longitudinal channel 1008 through the lateral slots 1010 causes the at least one drug to be released from the buckling columns 1002, and thus out of the adjunct 1000. While only five lateral slots are illustrated in FIG. 22 and FIG. 23, a person skilled in the art will appreciate that the number of lateral slots can vary and can depend at least upon the structural configuration of the buckling column, and therefore the number of lateral slots are not limited to what is illustrated in the figures. It is also contemplated herein that in other embodiments, the at least one drug can be omitted from at least one or more lateral slots within the buckling columns and/or the adjunct can also additional buckling columns with lateral slots that do not contain any drug therein.

Figure 24:
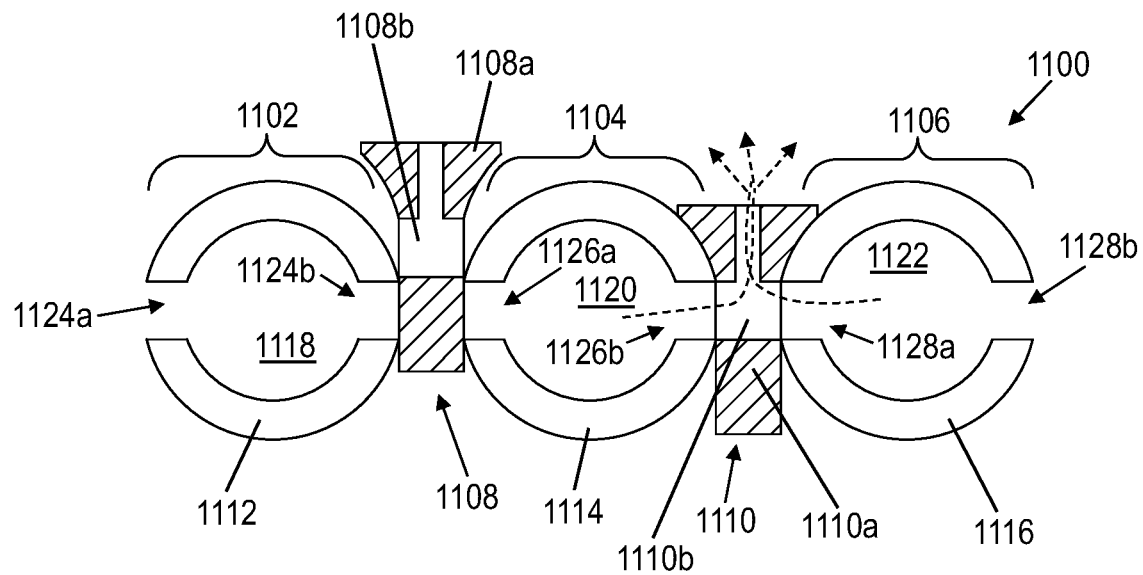
FIG. 24 is a cross-sectional view of another exemplary embodiment of an adjunct having a least one control feature.

In other embodiments, the adjunct can include sliding valves that open under pressure (e.g., pressure exerted during stapling or by the tissue stapled to the adjunct). For example, as shown in FIG. 24, an adjunct 1100 is formed of unit cells 1102, 1104, 1106 with drug (not shown) disposed therein and sliding valves 1108, 1110. While not shown, the adjunct 1100 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For simplicity, only three unit cells 1102, 1104, 1106 and two sliding valves 1108, 1110 are illustrated. More specifically, sliding valve 1108, which is shown in a closed position, is located between adjacent unit cells 1102 and 1104, and sliding valve 1110, which is shown in an open position, is located between adjacent unit cells 1104 and 1106.

While the unit cells 1102, 1104, 1106 can have variety of configurations, each unit cell is defined by a respective wall 1112, 1114, 1116 having a circular-shaped configuration with an internal cavity 1118, 1120, 1122 defined therein. Each wall 1112, 1114, 1116 also includes two opposing channels 1124a, 1124b, 1126a, 1126b, 1128a, 1128b. Further, while the sliding valves 1108, 1110 can have a variety of configuration, as shown in FIG. 24, each sliding valve 1108, 1110 has a body 1108a, 1110a with a T-shaped channel 1108b, 1110b defined therein that is configured to allow fluid flow through the sliding valve 1108, 1110. In use, the sliding valves 1108, 1110 move up and down relative to the unit cells 1102, 1104, 1106 when a force is being applied to the adjunct 1100 (e.g., during stapling or by tissue when the adjunct is stapled thereto). As such, when the sliding valves 1108, 1110 are in a closed position, such as illustrated sliding valve 1108, the T-shaped channel 1108b is not aligned, and therefore not in fluid communication with the channels 1124b, 1126a of the adjacent unit cells 1102, 1104. As a result, this prevents the fluid or fluid/drug mixture that is present within the unit cells 1102, 1104 from being released from the adjunct 1100. However, when the sliding valves 1108, 110 are in an open position, such illustrated sliding valve 1110, the T-shaped channel 1110b is aligned with, and therefore in fluid communication with the channels 1126b, 1128a of the adjacent unit cells 1104, 1106. As a result, the fluid or fluid/drug mixture that is present within the adjacent unit cells 1104, 1106 can be released (depicted as dotted arrows) from the adjunct 1100.

Figure 25:
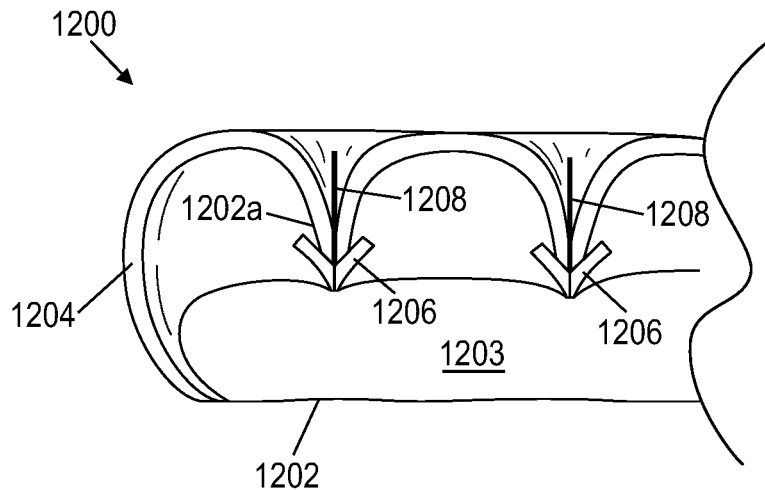
FIG. 25 is a side view of an exemplary embodiment of an adjunct drug delivery system, showing the system in an uncompressed state.
Figure 26:
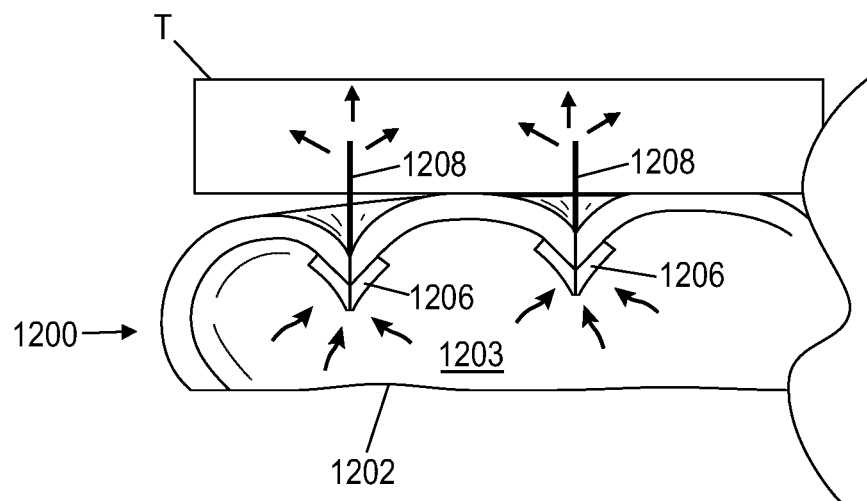
FIG. 26 is a side view of the adjunct drug delivery system of FIG. 25, showing the system in a compressed state.

In some embodiments, adjunct drug delivery systems can be configured to administer drugs directly into the tissue, as opposed to just onto the tissue surface. For example, as shown in FIG. 25 and FIG. 26, an adjunct drug delivery system 1200 can include a compressible drug pouch 1202 having an internal cavity 1203 that houses at least one drug (not shown) therein. The system 1200 also includes a needle carrier 1204 that is coupled to the drug pouch 1202. The needle carrier 1204 includes piercing members 1206 with at least one drug delivery needle 1208 attached thereto. As shown, the needle carrier curves about the drug pouch 1202 such that the piercing members face the top surface 1202a of the drug pouch 1202. When the adjunct drug delivery system 1200 is compressed (e.g., when stapled to tissue), for example, as shown in FIG. 26, the piercing members 1206 pierce through the top surface 1202a and into the internal cavity 1203 of the drug pouch 1202. As a result, the internal cavity 1203 of the drug pouch 1202 and the drug delivery needles 1208 are then in fluid communication with each other to thereby allow the at least one drug to be expelled from the drug pouch 1202. Further, when the adjunct system 1200 is placed and compressed against tissue T, as shown in FIG. 26, the drug delivery needles 1208 pierce into the tissue and therefore deliver the at least one drug directly into the tissue T (depicted as solid arrows). While not shown, the adjunct drug delivery system 1200 can be positioned atop an anvil surface of an anvil, like anvil 34 shown in FIG. 1, and/or a top or deck surface of a staple cartridge, like staple cartridge 40 and 102 shown in FIGS. 1 and 6, respectively.

In other embodiments, adjuncts can be configured to apply medicants to staples as the staples are deployed therethrough. For example, the unit cells 710 shown in FIG. 17 and FIG. 18 that overlap staple rows 706a, 706b can be configured to house drug therein. In this way, as the staples deploy through respective unit cells 710, the drug can be applied to the staples.

Figure 29:
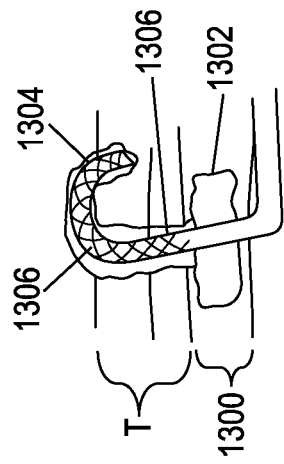
FIG. 29 is a cross-sectional view of the adjunct of FIG. 28, showing the staple leg in a completely deployed state.
Figure 28:
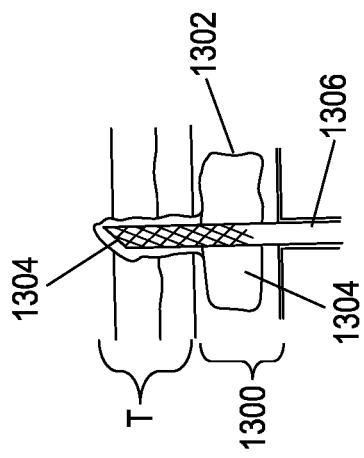
FIG. 28 is a cross-sectional view of the adjunct of FIG. 27 showing the adjunct placed against tissue and the staple leg in a partially deployed state.
Figure 27:
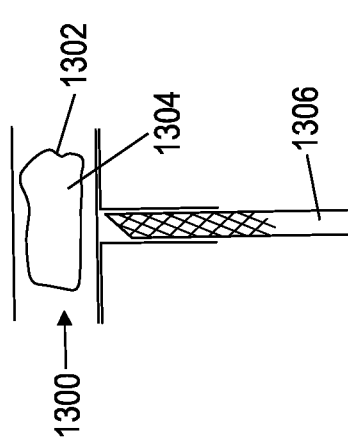
FIG. 27 is a cross-sectional side view of a portion of another exemplary embodiment of an adjunct having at least one drug pocket, showing the portion of the adjunct placed over a staple leg.

In another example, as illustrated in FIG. 27, FIG. 28, and FIG. 29, an adjunct 1300 can include drug pockets 1302 defined therein and that are configured to house drug 1304. As shown, the drug pockets 1302 are positioned within regions of the adjunct 1300 that overlap with staple legs 1306 (e.g., staple legs disposed within a staple cartridge). For simplicity only, one drug pocket 1302 and one staple leg 1306 is illustrated. As a result, when the staple leg 1306 is deployed, the staple leg 1306 penetrates through the drug pocket 1302 (FIG. 28 and FIG. 29) such that the drug 1304 coats onto the staple leg 1306. This allows penetration of drug directly into the tissue T via the coated staple leg 1306 (see FIG. 28 and FIG. 29). Further, in certain embodiments, at least a portion of the staple legs can be textured (illustrated as hatch marking in FIG. 27, FIG. 28, and FIG. 29) to enhance the coating of the drug to the staple legs as they pass though the drug pockets. For example, the textured surface can make the staples hydrophilic or allow the drug to otherwise stick to the staples.

Asymmetric Drug Delivery

As noted above, in certain embodiments, the adjunct can have at least one drug disposed therein. While the adjunct can be configured to release the at least one drug in a variety of ways, in certain embodiments, the adjunct be configured to have an asymmetric drug delivery profile relative to the geometry of the adjunct. For example, the adjunct can have an intended cut line that extends along a longitudinal axis extending from a first end to a second end of the adjunct material, a retaining segment on a first side of the intended cut line and a removing segment on a second side of the intended cut line. In such instances, the adjunct material can have a geometry that is configured to locally deliver or store the at least one drug relative to the intended cut line or relative to the retaining and removing segments. As a result, the adjunct has an asymmetric drug delivery profile of the at least one drug in at least one predetermined direction when the adjunct material is in a tissue deployed state. Stated differently, the at least one drug can be non-uniformly dispersed throughout the adjunct and/or non-uniformly directed through the adjunct such that the drug release profile of the at least one drug from the adjunct in at least one predetermined direction differs along the adjunct.

Figure 30:
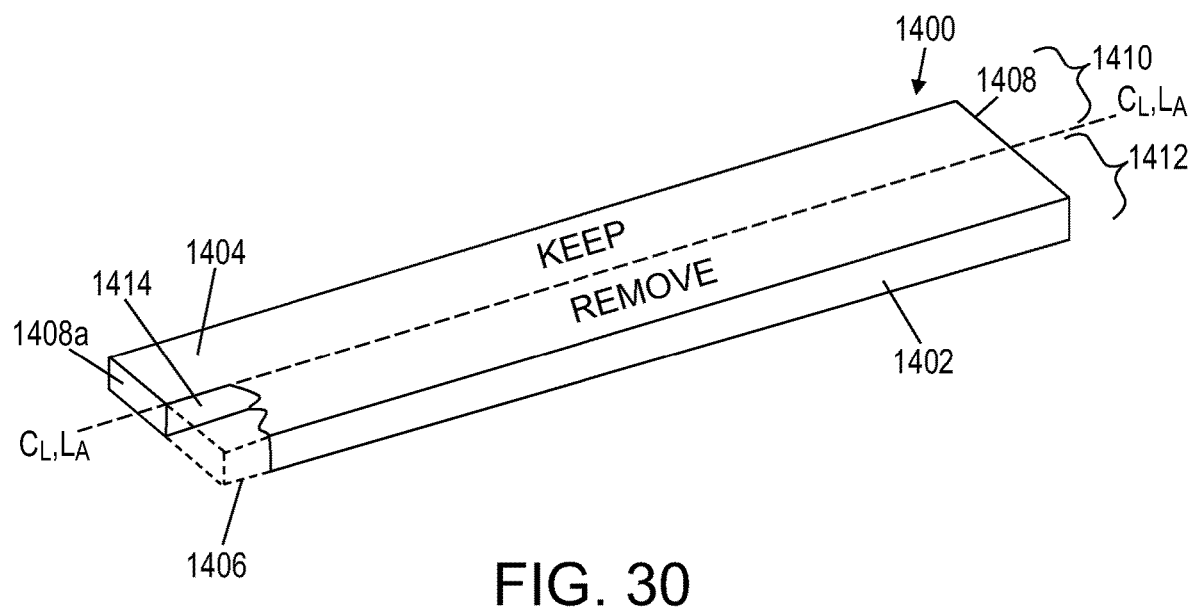
FIG. 30 is perspective view of another exemplary embodiment of an adjunct.

FIG. 30 illustrates an exemplary embodiment of an adjunct 1400 having a lattice structure 1402 with a tissue-contacting surface 1404 and a cartridge-contacting surface 1406 that is opposite the tissue-contacting surface 1404. While not shown, the adjunct 1400 can be positioned atop an anvil surface of an anvil, like anvil 34 shown in FIG. 1, and/or a top or deck surface of a staple cartridge, like staple cartridge 40 and 102 shown in FIGS. 1 and 6, respectively. Since the lattice structure 1402 can be formed by any of the unit cells disclosed herein, the lattice structure 1402 is generally illustrated without any specific unit cells. A person skilled in the art will appreciate that the lattice structure can be formed of strut-based unit cells (e.g., defined by planar hollow struts), strut-less based unit cells (e.g., defined by Schwarz-P structures), or a combination thereof.

As shown, the adjunct 1400 has an intended cut line CL that extends along a longitudinal axis $L_A$ that extends from a first end 1408a to a second end 1408b of the adjunct 1400. In this illustrated embodiment, the intended cut line CL divides the adjunct 1400 into a retaining segment 1410 that is configured to remain with the patient (e.g., once the adjunct 1400 is stapled to tissue and cut) and a removing segment 1412 that is configured to be removed from the patient (e.g., once the adjunct 1400 is stapled to tissue and cut). Thus, the retaining segment 1410 remains at the surgical site.

The adjunct 1400 can include at least one drug (not shown) disposed therein. In such embodiments, the at least on drug can be stronger on one side of the adjunct 1400, only present on one side of the adjunct 1400, or have differing effects from one side to the adjacent side of the adjunct 1400. This can result in an asymmetric drug release profile of the at least one drug in at least one predetermined direction from the adjunct 1400. For example, in some embodiments, only the retaining segment 1410 of the adjunct 1400 has at least one drug disposed therein. In this way, the removing segment 1412 does not include the at least one drug, thereby reducing manufacturing costs of the adjunct. The lack of drug within the removing segment 1412 can also prevent the tissue specimen stapled to the removing segment 1412 from being compromised by the at least one drug, and therefore, the tissue specimen would be "cleaner" for biopsy purposes. In other embodiments, the retaining segment 1410 and the removing segment 1412 can be different in at least one of concentration and type of the at least one drug. In certain embodiments, the tissue-contacting surface 1404 of the retaining segment 1410 can have a first drug (e.g., a therapeutic agent) disposed thereon and a portion 1414 of the retaining segment 1410 along the intended cut line CL can have a second drug disposed thereon (e.g., a hemostatic agent).

In other embodiments, the tissue-contacting surface 1404 and cartridge-contacting surface 1406 can differ from each other in at least of concentration and type of the at least one drug. This can result in asymmetric doses of the at least one drug relative to the geometry of the adjunct 1400. For example, in certain embodiments, the tissue-contacting surface 1404 can have a first drug disposed thereon and the cartridge-contacting surface 1406 can have a second drug disposed thereon that is different than the first drug. For example, the first drug can be healing promoting agent(s) and the second drug can be anti-adhesion medicant(s). In some embodiments, the tissue-contacting surface 1404 can be designed with larger pores and more compliance compared to that of the cartridge-contacting surface 1406, which can be designed to prevent staple leg pull through or tearing.

Figure 31:
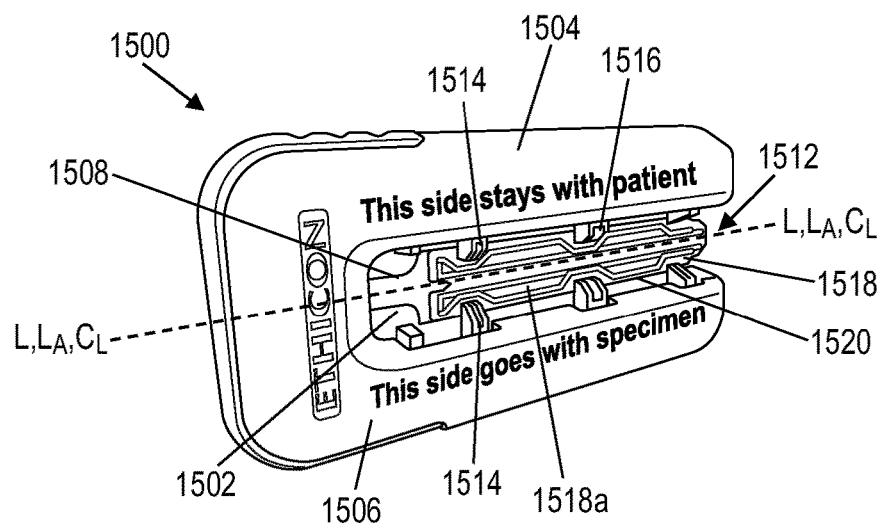
FIG. 31 is a perspective view of an exemplary embodiment of an adjunct applicator having an exemplary embodiment of an adjunct releasably retained thereon.

In some embodiments, the adjunct 1400 can include an indicator feature that is configured to indicate at least one of the retaining segment 1410 of the adjunct 1400 and the location of the at least one drug within the adjunct 1400. The indicator feature can be a visual indication, such an indicia (FIG. 30) or a color (FIG. 31). For example, as shown in FIG. 30, the retaining segment 1410 of the adjunct 1400 includes, and therefore is indicated by, the word "KEEP" printed thereon, and the removing segment 1412 of the adjunct 1400 includes, and therefore is indicated by, the word "REMOVE" printed thereon. Alternatively, or in addition, the indicator feature can configured to indicate the side of the adjunct that is applied to a staple cartridge (e.g., a cartridge-contacting surface), the side of the adjunct that is applied to a tissue (e.g., a tissue-contacting surface), or a combination thereof. As such, the adjunct can include indicator features that are configured to identify the proper orientation of the adjunct relative to a staple cartridge, the patient, or a combination thereof.

In some embodiments, adjuncts can be applied to a staple cartridge and/or an anvil using an adjunct applicator as shown, for example, in FIG. 31. FIG. 31 illustrates an embodiment of an adjunct applicator 1500 having a U-shaped configuration with a channel 1502 extending therethrough. The channel 1502 extends longitudinally along the longitudinal axis L of the adjunct applicator 1500 and divides the adjunct applicator 1500 into a first longitudinal segment 1504 and a second longitudinal segment 1506. An elongated base member 1508 is positioned within and extends along the channel 1502. The adjunct applicator 1500 has a cartridge-facing side 1515 and an anvil-facing side (obstructed) that is opposite the cartridge-facing side. For sake of simplicity, only the cartridge-facing side 1515 of the adjunct applicator 1500 is illustrated. The anvil-facing side of the adjunct applicator is similar to the cartridge-facing side, and therefore a person skilled in the art will appreciate that the following description is also applicable to the anvil-facing side. Further, a person skilled in the art will appreciate that only one side of the adjunct applicator can include an adjunct, and therefore in other embodiments, an adjunct can be disposed on only one of the cartridge-facing side and the anvil-facing side.

As shown in FIG. 31, an adjunct 1512 is positioned on the elongated base member 1508 and is releasably retained to the elongated base member 1508 via movable attachment elements 1514. The adjunct 1512 has an intended cut line CL that extends along the longitudinal axis $L_A$ of the adjunct 1512, and thus along the longitudinal axis L of the adjunct applicator 1500. The intended cut line divides the adjunct 1512 into a retaining segment 1516 and a removing segment 1518. The retaining segment 1516 and the removing segment 1518 are similar to the retaining segment 1410 and the removing segment 1412 of adjunct 1400 in FIG. 30, except that a color indicator feature 1520 is printed on the tissue-contacting surface 1518a of the retaining segment 1516. As a result, the color indicator feature 1520 identifies the removing segment 1518 for the user. Further, in use, this color indicator feature 1520 allows a user to choose which side of the adjunct (e.g., relative to the intended cut line CL) stays with the patient and which side of adjunct is removed from the surgical site. In certain embodiment, the color indicator feature can also be used to identify the location of one or more drugs disposed within the adjunct and/or the drug delivery side of the adjunct.

Alternatively, or in addition, the first longitudinal segment 1504 and/or the second longitudinal segment 1506 can include an indicator feature that can be used to identify the retaining segment 1516 and/or removing segments 1518 of the adjunct 1512. For example, as shown in FIG. 31, the first longitudinal segment 1504 of the adjunct applicator 1500 includes the following indicia printed on a surface thereof: "This side stays with patient." Since the retaining segment 1516 is positioned directly adjacent to the first longitudinal segment 1504, this indicia can be used to identify the retaining segment 1516 of the adjunct 1512. As further shown, the second longitudinal segment 1506 of the adjunct applicator 1500 includes the following indicia printed on a surface thereof: "This side goes with specimen." Since the removing segment 1518 is positioned directly adjacent to the second longitudinal segment 1506, this indicia can be used to identify the removing segment 1518 of the adjunct 1512. In other embodiments, only one of the first longitudinal segment and the second longitudinal segment includes an indicator feature. In other embodiments, an indicator feature on either the first longitudinal segment, the second longitudinal segment, or both, can be used to determine the drug delivery side of the adjunct.

Drug Release Features

In certain embodiments, the adjuncts can have configurations designed to control drug movement though and out of the adjuncts when the adjuncts are in a tissue deployed state (e.g., stapled to tissue in vivo). As discussed below, the adjuncts can include active drug release features that are designed to effect drug release from the adjuncts in a controlled and tailored manner when such features are activated (e.g., thermal and/or mechanical activation). That is, unless activated, the active drug release features are configured to encapsulate the drug and therefore inhibit drug from being released from the adjunct. In this way, the active drug release features can help prevent premature drug release from the adjuncts.

The adjuncts can generally be formed at least one fused bioabsorbable polymer that is configured to be releasably retained on a staple cartridge and that is configured to be delivered to tissue by deployment of staples in the cartridge. In an exemplary embodiment, the adjunct material can include a lattice macrostructure having drug delivery microstructures formed in the lattice macrostructure, and each drug delivery microstructure can have drug disposed therein. The drug delivery microstructures can be configured to encapsulate the drug to thereby prevent drug release until the plurality of drug delivery microstructures are thermally ruptured in response to changes in body temperature and/or mechanically ruptured in response to at least one of clamping, stapling, and cutting of the adjunct material (e.g., mechanical failure). In certain embodiments, the drug delivery microstructures can have an internal cavity (e.g., microreservoir) defined therein. As used herein, the term "lattice macrostructure" is used synonymously with the term "lattice main structure."

In order to enable formation of macro and micro structures, the adjuncts can be non-fibrous adjuncts. Unlike conventional adjuncts (e.g., adjuncts that are not three-dimensionally printed, such as foam adjuncts and woven/non-woven fibrous adjuncts), the non-fibrous adjuncts are three-dimensionally (3D) printed and therefore can be formed with microstructures (units) that are consistent and reproducible. That is, unlike with other methods of manufacture, 3D printing significantly improves control over microstructural features such as placement and connection of elements. As a result, variability in both the microstructure(s) and attendant properties of the present adjuncts is decreased, as compared to conventional adjuncts. Further, 3D printing can create adjuncts with microstructural features that could not otherwise be formed or generated within conventional adjuncts. The present non-fibrous adjuncts can also be adapted for use with a variety of staples and tissue types.

In certain embodiments, the drug delivery microstructures can be thermally ruptured in response to a variety temperature related events (e.g., a temperature increase or decrease). In some embodiments, the drug delivery microstructures can be configured to thermally rupture in response to an increase in temperature.

The increase in temperature can be in response to an infection of the stapled tissue. That is, once the adjunct is in a tissue deployed state (e.g., stapled to tissue in vivo), the temperature at or proximate to the stapled adjunct can increase due to infected tissue (e.g., due to swelling and/or localized increased in blood flow). As a result, this increase in temperature can initiate the release of the drug from one or more of the drug delivery microstructures. For example, in some embodiments, the drug delivery microstructures can in the form of microcontainers that are sealed with a material that is configured to break down or liquefy at an elevated body temperature (e.g., greater than about 37° C.). Once the microcontainers are unsealed, the drug can be released out of the adjunct, and in certain embodiments, the drug (e.g., antibiotic(s)) can be used to treat the infection. In certain embodiments, the microcontainers are sealed with a plug that is formed of the material. Alternatively, or in addition, where the initial release of the drug one or more drug delivery microstructures are already thermally ruptured, the temperature increase can be used to accelerate the release of the drug from the drug delivery microstructures.

In some embodiments, the drug delivery microstructures can be configured to thermally rupture when the adjunct material is at or above an activation temperature. The activation temperature can be associated with body temperature (e.g., about 37° C.). As a result, the body temperature can be used as a gating key that can initiate the release of the drug from one or more of the drug delivery microstructures. For example, in some embodiments, the drug delivery microstructures can be in the form of microcontainers that are sealed with a material that is configured to break down or liquefy when exposed to body temperature and/or in the presence of humidity. In certain embodiments, the microcontainers can be sealed with a plug that is formed of the material. In other embodiments, the drug delivery microstructures can be formed of a structure (e.g., formed of a shape memory material) having initially sealed pores, and once the adjunct is in a tissue deployed state, the exposure to body temperature can cause the sealed pores to open and release drug therefrom.

In some embodiments, daily temperature variation at or proximate to the stapled tissue can be used to control the rate of drug release from the drug delivery microstructures. For example, a combination of time and temperature dependent release features could allow the administration of drug to the patient over multiple days at approximately the same time. In one embodiment, temperature activated release feature(s) can be encapsulated in different thicknesses of time dependent release materials. In another embodiment, the drug delivery microstructures can be in the form of microcontainers that are sealed with a different material(s) or material thicknesses that are configured to release at body temperature. These microcontainers can be sealed with plugs having different thicknesses and/or formed of different materials relative to each other. In one embodiment, first microcontainers can be sealed with first plugs and second microcontainers can be sealed with second plugs that differ from the first plugs in material and/or thickness.

In other embodiments, the drug delivery microstructures can be mechanically ruptured in response to clamping, stapling, and/or cutting the adjunct (e.g., mechanical failure). For example, in use, once the adjunct is releasably retained to a staple cartridge of a surgical end effector, the clamping of the adjunct between opposing jaws of the end effector (e.g., first jaw (e.g., anvil) compression of the adjunct, prior to trocar introduction, or first compression with tissue between the jaws) can cause at least a portion of the drug delivery microstructures to rupture (e.g., shear, fracture, or otherwise open). Once ruptured, drug that was otherwise encapsulated within these drug delivery microstructures can then be released. The encapsulated drug can be in a variety of forms, for example, in an inter-powder form (e.g., dry or freeze dried), a polymer interaction form (e.g., pendent molecule on a polymer strand), or liquid form (e.g., a liquid that is does interact with the base polymer of the adjunct (e.g., oil based for a hydrolyses polymer or water based in an enzyme degradable polymer). Alternatively, or in addition, once the adjunct is releasably retained on the cartridge, any drug delivery microstructures that overlap with the staples disposed within the cartridge can be punctured during stapling of the adjunct. As a result, drug release from the overlapping drug delivery microstructures can be effected by staple advancement through the adjunct. Alternatively, or in addition, once the adjunct is releasably retained on the cartridge, any drug delivery microstructures that overlap with a slot of the cartridge that is configured to receive a cutting element can be severed by the cutting element as it advances through the slot during cutting of the adjunct. As a result, drug release from the overlapping drug delivery microstructures can be effected by advancement of a cutting element through the adjunct.

Drug can be incorporated into the adjuncts in a variety of ways and at different times. In some embodiments, drug can be incorporated into an adjunct prior the adjunct being releasably retained on the staple cartridge and/or anvil. In other embodiments, drug can be incorporated into an adjunct after the adjunct is releasably retained on the staple cartridge and/or anvil adjuncts. For example, in one embodiment, once an adjunct is applied to the staple cartridge and/or anvil (e.g., via an adjunct applicator), a user can clamp onto a drug delivery device (e.g., a sponge containing the drug, e.g., a drug in the form of a liquid, that is removably coupled to the adjunct) to apply at least one drug to the adjunct. In another embodiments, the drug delivery device can be a 3D printed bottle or container having at least one drug disposed therein. The 3D printed container can be attached to the adjunct and configured to delivery drug to the adjunct upon compression of the 3D printed container (e.g., squeezing). In certain embodiments, the 3D printed container is attached to the adjunct and remains attached when the adjunct is stapled to tissue. In one embodiment, the 3D printed container includes a one-way valve that retains at least one drug within the 3D printed container and only allows the at least one drug to exit when the 3D printed container is compressed. Alternatively, or in addition, the 3D printed container can include a cap that is configured to be cut off by a cutting element as the cutting element advances through the staple cartridge. Alternatively, or in addition, compression of the 3D printed container can be effected by swelling of the tissue that is stapled to the adjunct during healing or during an infection.

The drug delivery microstructures can have a variety of configurations. In certain embodiments, the drug delivery microstructures can be strut-based unit cells characterized by the presence of sharp corners or angles, non-strut-based unit cells characterized by curved surface, or a combination thereof. With non-strut based unit cells, the unit cells, for example, can be based on triply periodic minimal surfaces (TPMS). TPMS is a minimal surface that repeats itself in three dimensions. The term "minimal surface" as used in this description refers to a minimal surface as known in mathematics. As such, in some embodiments, the unit cell can be a triply periodic minimal surface structure (e.g., Schwarz-P, Schwarz Diamond, and the like) having passageways extending therethrough. For example, the non-strut based unit cells can be a hollow structure. Additional details on triply periodic minimal surface structures, such as Schwarz-P structures can be found in previously mentioned U.S. patent application Ser. No. 17/009,740, filed Sep. 1, 2020, and entitled "Compressible Non-Fibrous Adjuncts," which is incorporated herein by reference in its entirety. In certain embodiments, the lattice main structure can include a combination of strut-based unit cells (e.g., hollow struts) and non-strut based unit cells (e.g., one or more triply periodic minimal surface structures). In one embodiment, the non-strut based unit cells are interconnected to each other via connecting structures. These connecting structures can take the form of hollow tubes or struts. In certain embodiments, the unit cell(s) can include the connecting structures.

Each exemplary adjunct as described below is illustrated in partial form (e.g., not in full-length), and therefore a person skilled in the art will appreciate that the adjunct can be longer in length, e.g., along its longitudinal axis ($L_A$) as identified in each embodiment. The length can vary based on a length of the staple cartridge or anvil. The width can also vary as needed. Further, each exemplary adjunct is configured to be positioned atop a cartridge or anvil surface such that the longitudinal axis L of each adjunct is aligned with and extends along the longitudinal axis ($L_A$) of the cartridge or anvil. These adjuncts are structured so as to compress when exposed to compressive forces (e.g., stress or load).

Figure 32:
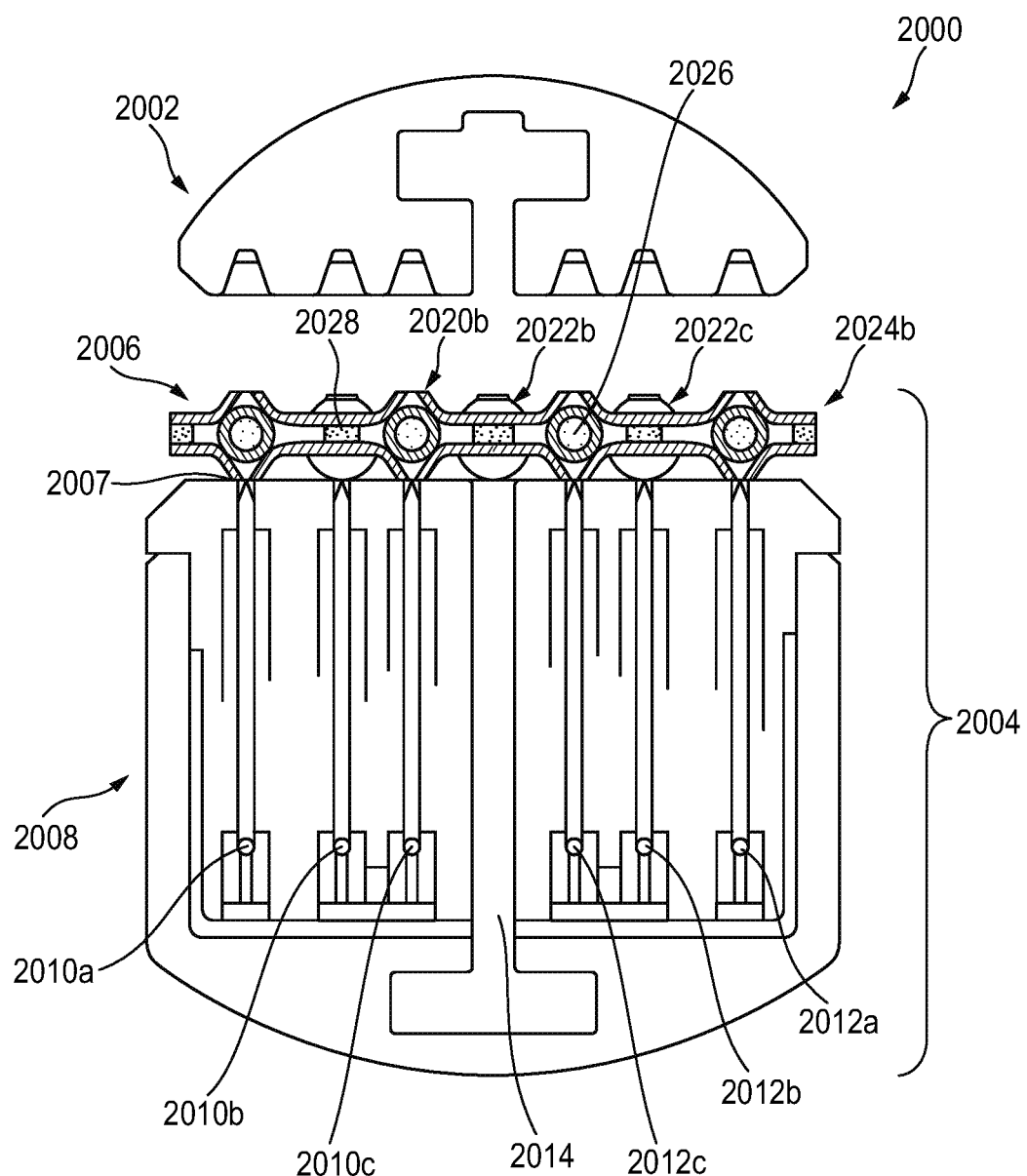
FIG. 32 is a cross-sectional front view of an exemplary embodiment of a surgical end effector having an anvil and a stapling assembly, the stapling assembly having an exemplary embodiment of an adjunct releasably retained on a staple cartridge, showing the surgical end effector in a closed positioned without tissue positioned between the anvil and the stapling assembly.
Figure 33:
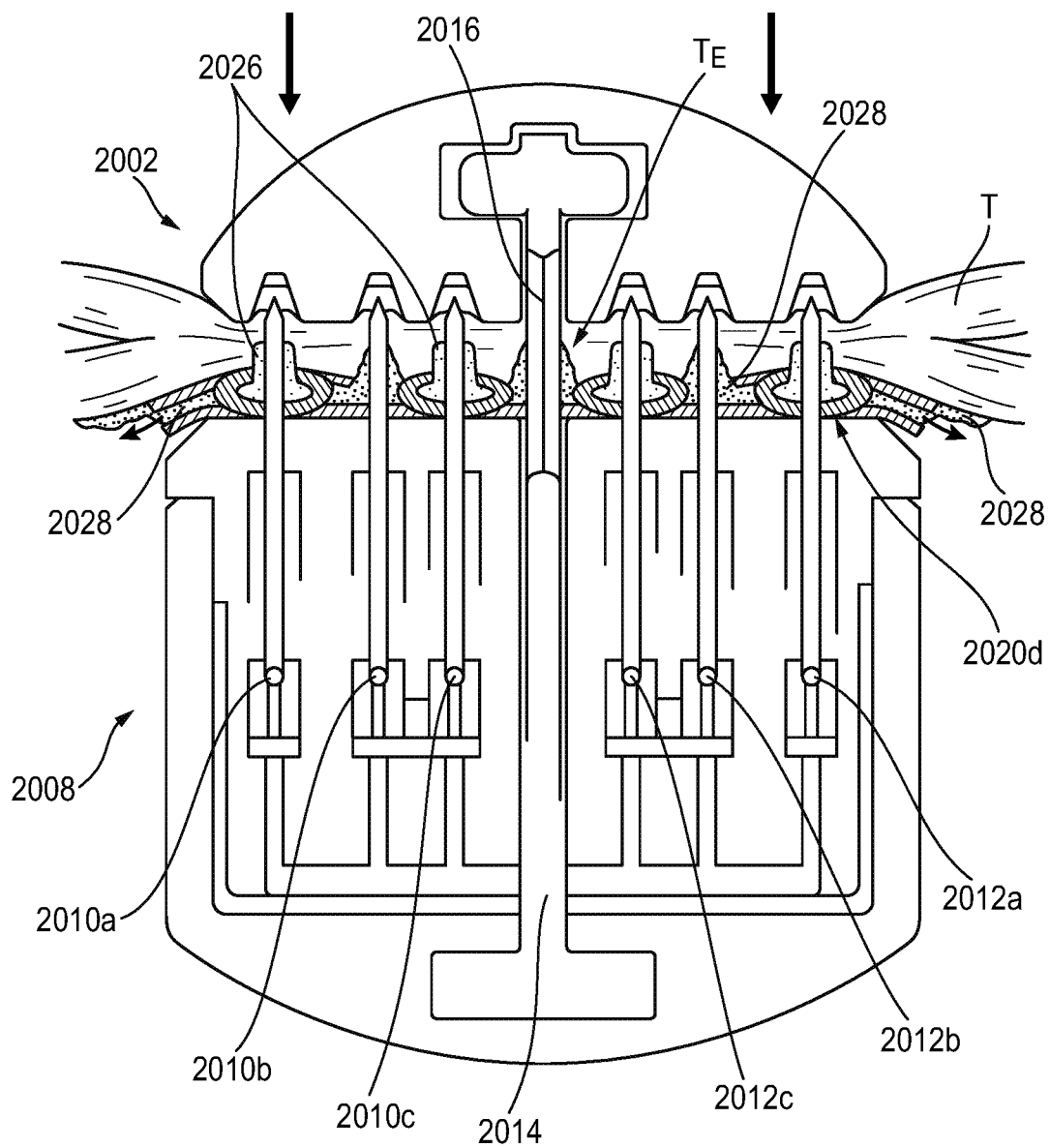
FIG. 33 is a cross-sectional front view of the surgical end effector of FIG. 32, showing tissue clamped between the anvil and the stapling assembly and the tissue being stapled to the compressible non-fibrous adjunct.

FIG. 32 and FIG. 33 illustrate an exemplary embodiment of a surgical end effector 2000 having an anvil 2002 and a stapling assembly 2004. The stapling assembly 2004 includes an adjunct 2006 releasably retained on a top or deck surface 2007 of a staple cartridge 2008 (e.g., the cartridge surface that faces the anvil). The cartridge 2008 has two sets of three rows of staples (only three staples 2010a, 2010b, 2010c, 2012a, 2012b, 2012c from each set are illustrated) that are disposed within the staple cartridge 2008, and a slot 2014 defined within the staple cartridge 2008 that is configured to receive a cutting element 2016 (see FIG. 33). FIG. 32 illustrates the surgical end effector 2000, and thus the anvil 2002, in a fully closed position, whereas FIG. 33 illustrates tissue T being clamped between the anvil 2002 and stapling assembly 2004, being stapled to the adjunct 2006 via staples 2010a, 2010b, 2010c, 2012a, 2012b, 2012c, and the tissue T and the adjunct 2006 being cut via cutting element 2016. While not illustrated, the anvil 2002 is pivotally coupled to an elongate staple channel and the stapling assembly 2004 is positioned within and coupled to elongate staple channel.

Figure 34:
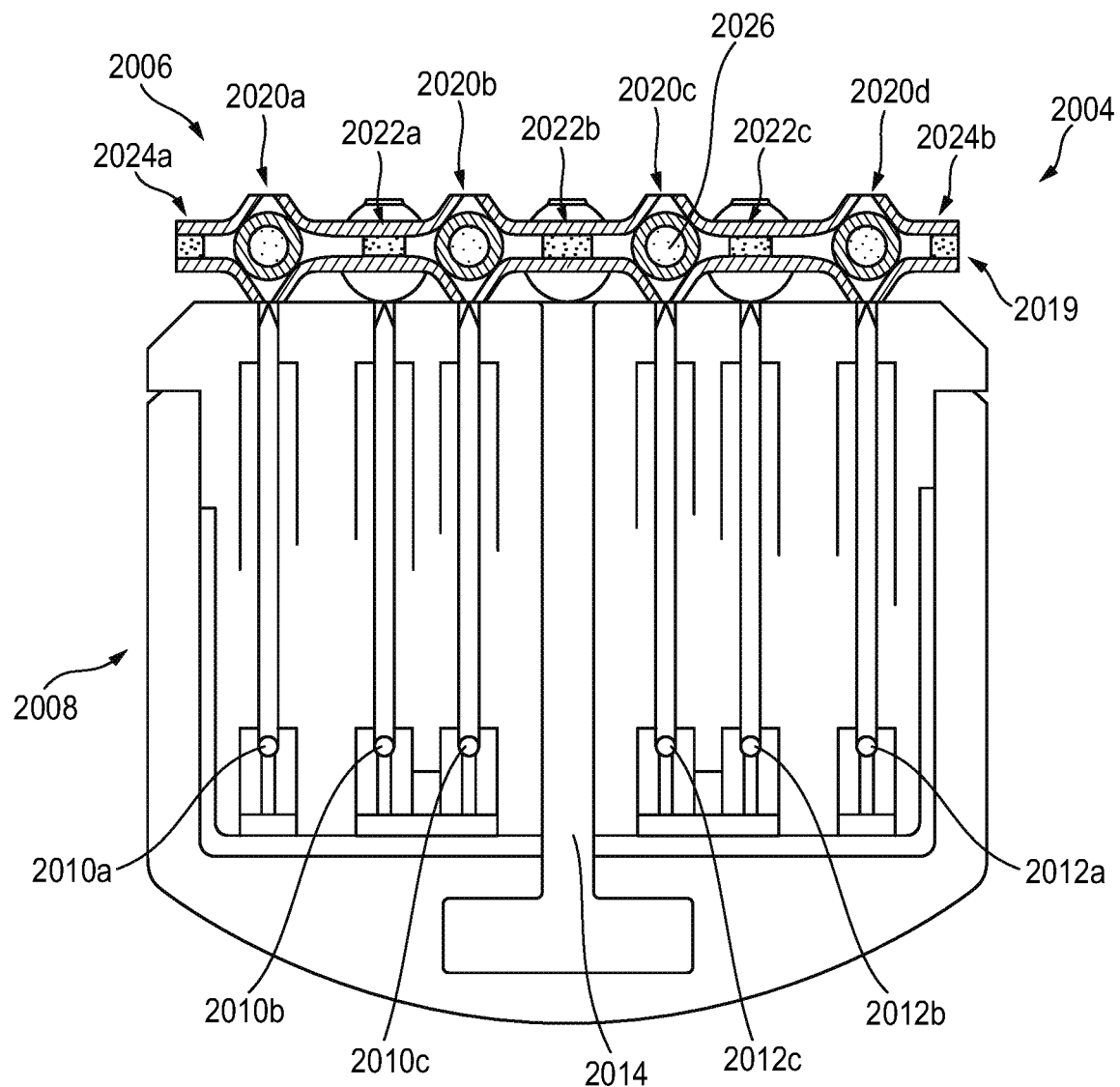
FIG. 34 is a cross-sectional front view of only the stapling assembly of FIG. 32.

While the adjunct 2006 can have a variety of configurations, as shown in FIG. 32, and in more detail in FIG. 34, the adjunct 2006 has a lattice macrostructure 2019 with drug delivery microstructures formed therein (only nine drug delivery microstructures 2020a, 2020b, 2020c, 2020d, 2022a, 2022b, 2022c, 2024a, 2024b are shown). While the drug delivery microstructures 2020a, 2020b, 2020c, 2020d, 2022a, 2022b, 2022c, 2024a, 2024b can have a variety of configurations, in this illustrated embodiment, lattice macrostructure 2019 includes first drug delivery microstructures 2020a, 2020b, 2020c, 2020d, each having a first drug 2026 disposed therein, and second drug delivery microstructures 2022a, 2022b, 2022c, 2024a, 2024b, each having a second drug 2028 disposed therein. The first and second drug delivery microstructures 2020a, 2020b, 2020c, 2020d, 2022a, 2022b, 2022c, 2024a, 2024b are each configured to encapsulate the respective first and second drugs 2026, 2028 therein (FIG. 32 and FIG. 34 until the first and second drug delivery microstructures 2020a, 2020b, 2020c, 2020d, 2022a, 2022b, 2022c, 2024a, 2024b are mechanically ruptured (FIG. 33). In some embodiments, the first drug and second drug can be different, whereas in other embodiments, the first drug and second drug can be the same. Further, in embodiments where the first and second drugs are different, one portion of the first drug delivery microstructures and/or second drug delivery microstructures can include the first drug and another portion of the first drug delivery microstructures and/or second drug delivery microstructures can include the second drug.

The first and second drug delivery microstructures 2020a, 2020b, 2020c, 2020d, 2022a, 2022b, 2022c, 2024a, 2024b can have a variety of configurations. In this illustrated embodiment, the first drug delivery microstructures 2020a, 2020b, 2020c, 2020d are in the form of hollow unit cells each with an internal cavity (e.g., a microreservoir) defined therein. The second drug delivery microstructures are in the form of internal hollow tubes (drug delivery microstructures 2022a, 2022b, 2022c) and external hollow tubes (drug delivery microstructures 2024a, 2024b) each having an internal cavity (e.g., a microreservoir). The internal hollow tubes 2022a, 2022b, 2022c extend between and connect adjacent hollow unit cells to each other, whereas the external hollow tubes 2024a, 2024b extend outward from the outer-most hollow unit cells (drug delivery microstructures 2020a, 2020d). As a result, the hollow unit cells (drug delivery microstructures 2020a, 2020b, 2020c, 2020d) are in fluid communication with each other such that a continuous network of pathways are present within the adjunct 2006. A person skilled the art will appreciate that the structural configuration and number of the first and second drug delivery microstructures can depend at least upon the size and shape of lattice macrostructure and the structural configuration of the staple cartridge the adjunct is to be releasably retained thereto, and therefore, the adjunct is not limited to the structure and number of drug delivery microstructures illustrated in the figures. Further, while two different drug delivery microstructures are illustrated, in other embodiments, the lattice macrostructure can include any suitable type and number of drug delivery microstructures.

The first and second drug delivery microstructures 2020a, 2020b, 2020c, 2020d, 2022a, 2022b, 2022c, 2024a, 2024b can be positioned within different regions of the adjunct 2006 such that drug release from the microstructures can be effected by different activation mechanism (e.g., clamping, stapling, and/or cutting of the adjunct). In this illustrated embodiment, the first drug delivery microstructures 2020a, 2020b, 2020c, 2020d are positioned at regions of the adjunct 2006 that overlap with the inner and outer staple rows 2010a, 2010c, 2012a, 2012c of the staple cartridge 2008. More specifically, the outer-most hollow unit cells (first drug delivery microstructures 2020a, 2020d) overlap with outer-most staple rows 2010a, 2012a, respectively, and the inner-most hollow unit cells (first drug delivery microstructure 2020b, 2020c) overlap with inner-most staple rows 2010c, 2012c, respectively. Further, the outer-most internal hollow tubes (second drug delivery microstructures 2022a, 2022c) overlap with intermediate staple rows 2010b, 2012b, respectively. As a result, as shown in FIG. 33, as the staples 2010a, 2010b, 2010c, 2012a, 2012b, 2012c advance through the respective overlapping drug delivery microstructures 2020a, 2020b, 2020c, 2020d, 2022a, 2022b, 2022c, the staples puncture, and thus cause mechanical rupture of these drug delivery microstructures. As such, drug can then be released from these drug delivery microstructures 2020a, 2020b, 2020c, 2020d, 2022a, 2022b, 2022c and into the tissue (e.g., at or around the staples holes created within the tissue) as shown in FIG. 33. Further, the clamping of the adjunct 2006 between the anvil 2002 and the staple cartridge 2008 during staple deployment can help facilitate drug release from the punctured drug delivery microstructures 2022a, 2022b, 2020c, 2020d, 2022a, 2022b, 2022c.

As further shown in FIG. 32 and FIG. 34, the inner-most internal hollow tube (drug delivery microstructure 2022b) is positioned within the region of the adjunct 2006 that overlaps with the slot 2014 of the staple cartridge 2008. As a result, in use, as shown in FIG. 33, as the cutting element 2016 advances through the slot 2014, the overlapping drug delivery microstructure 2022b is severed, and thus mechanically ruptured. As such, drug can then be released from drug delivery microstructure 2022b and into the tissue (e.g., along the severed edges TE of the tissue T) as shown in FIG. 33.

Further, in this illustrated embodiment, the external hollow tubes (drug delivery microstructures 2024a, 2024b) are positioned within the outer-most regions of the adjunct and therefore are adjacent to the outer-most staple rows 2010a, 2012a. As a result, in use, as shown in FIG. 33, when the adjunct 2006 and tissue T are clamped between the anvil 2002 and the staple cartridge 2008, the resulting force applied to the adjunct 2006 can thereby cause drug disposed within the external hollow tubes (drug delivery microstructures 2024a, 2024b) to be released therefrom and into the tissue T. A person skilled in the art will appreciate that in other embodiments, clamping of the adjunct can by itself cause mechanical rupture of any of the drug delivery microstructures within the adjunct.

In some embodiments, the adjunct can include drug release features that can be configured to control the dosage release of the drug from the adjunct when the adjunct is in a tissue deployed state. For example, in certain embodiments, the drug release features can be configured to effect a metered drug dosage over time while the adjunct is in a tissue deployed state. In other embodiments, the drug release features can be configured to effect a variable drug dosage over time while the adjunct is in a tissue deployed state. For example, the drug release features can allow for an initial bolus dosage of drug, followed by subsequent metered dosages of drug (e.g., based on a timeframe relative to expected healing profiles of the tissue that is stapled to the adjunct). Alternatively, or in addition, the adjunct can include one or more materials (e.g., hydrogels) that are positioned within passageways formed the adjunct. These materials can serve as a type of drug release feature(s) that is configured to inhibit drug movement through the respective passageways for a predetermined period of time.

For example, in one exemplary embodiment, the adjunct can be formed of at least one fused bioabsorbable polymer and can have a lattice macrostructure having primary and secondary microreservoirs formed in the lattice macrostructure. The primary microreservoirs and secondary microreservoirs differ in size relative to each other and can contain drug disposed therein. The primary microreservoirs can be configured to release drug therefrom upon activation and the secondary microreservoirs can be configured to release drug therefrom upon degradation of at least one of the at least one fused bioabsorbable polymer so that the combination of the primary and secondary microreservoirs control the dosage of drug being released from the adjunct when the adjunct is in a tissue deployed state. As such, the primary microreservoirs can serve as active drug release features and the secondary microreservoirs can serve as passive drug release features.

Activation (e.g., mechanical failure) of the primary microreservoirs can occur in a variety ways. For example, the primary reservoirs can be configured to be punctured (e.g., by stapling the adjunct as discussed above), fractured (e.g., by clamping the adjunct as discussed above), severed (e.g., by cutting the adjunct ad discussed above), or any combination thereof.

In certain embodiments, the lattice macrostructure can include at least one internal stopping member formed in each primary microreservoir. The at least one internal stopping member can be configured to limit the amount of deformation of the respective primary microreservoir when the adjunct material is being compressed. In some embodiments, the at least one internal stopping member can be configured to degrade over time while the adjunct material is in a tissue deployed state to thereby allow for greater deformation of the respective primary microreservoir when the adjunct material is being compressed. In certain embodiments, the primary microreservoirs can be formed of a first fused bioabsorbable polymer and the at least one internal stopping member can be formed of a second fused bioabsorbable polymer that degrades faster that the first fused bioabsorbable polymer.

Depending on the form of drug disposed within the primary microreservoirs, the primary microreservoirs can be sealed, or otherwise capped off. For example, in embodiments where the drug is in a liquid form, the primary microreservoir can be sealed so as to prevent the drug from premature release from the adjunct. The primary microreservoir can be sealed in any suitable manner (e.g., the seal can be 3D printed or jetted/extruded/rolled into place (BAM)). In embodiments where the drug is in a powered form, the primary microreservoir can be unsealed, or otherwise open. Further, in certain embodiments, the primary microreservoirs can be unsealed when the drug is in a vicious liquid form.

The primary and secondary microreservoirs can each be defined by respective microstructures that are formed within the lattice macrostructure. In some embodiments, the primary microreservoirs can be defined by respective hollow unit cells or hollow tubes. That is, the internal cavity of a hollow unit cell or hollow tube can serve as a primary microreservoir. In some embodiments, the secondary microreservoirs can be voids or openings that are defined within a wall of the lattice macrostructure.

Figure 35:
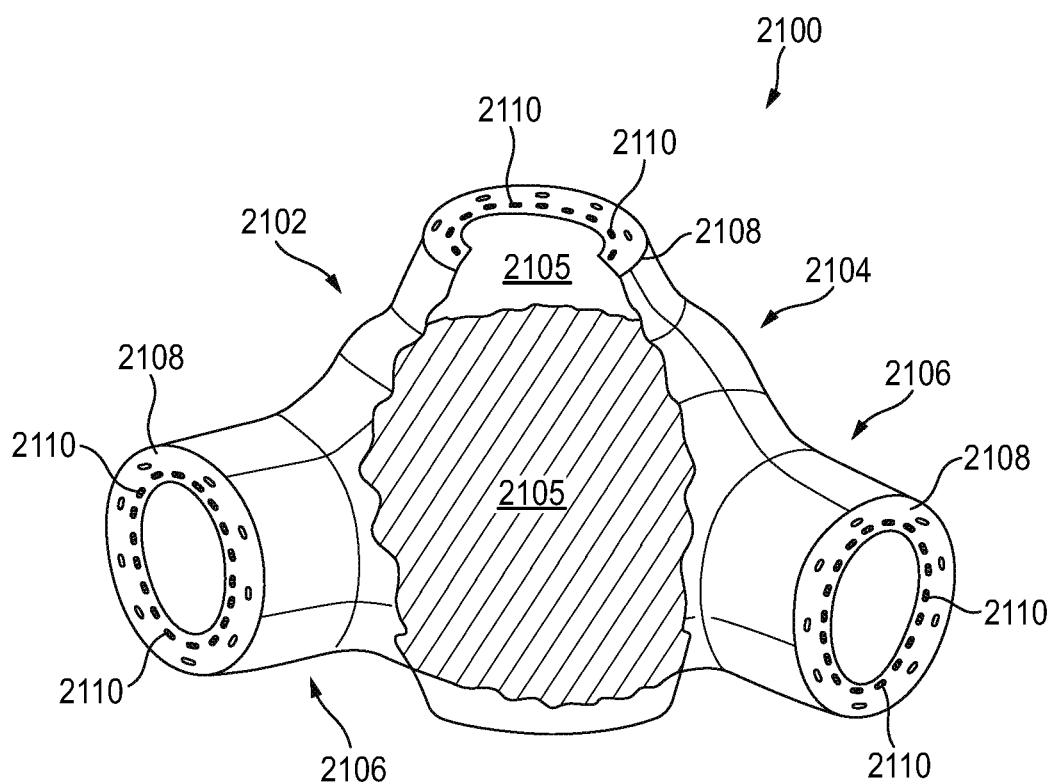
FIG. 35 is a partial cut-away perspective view of a portion of another embodiment of an adjunct.

FIG. 35 illustrates another embodiment of an adjunct 2100 having a lattice macrostructure 2102 that is formed of unit cells 2104 (e.g., Schwarz-P structures) that connected to each other via connecting structures 2106. For sake of simplicity, only one unit cell 2104 and a portion of two connecting structures 2106 are being illustrated. While the unit cell 2104 and two connecting structures 2106 can have a variety of configurations, in this illustrated embodiment, the unit cell 2104 is a hollow structure with an internal cavity 2105 defined therein and the two connecting structures 2106 are each a hollow tube. As a result, the unit cells 2104 are in fluid communication with each other such that a continuous network of pathways can be present or formed within the adjunct 2100.

As shown, a first drug (depicted as hatch markings) is disposed within the internal cavity 2105 (e.g., a primary microreservoir) of the unit cell 2104. The unit cell 2104 can be configured to encapsulate the first drug within its internal cavity 2105 until the unit cell is activated. Thus, in use, once the unit cell 2104 is activated, (e.g., compressed from an uncompressed state to a compressed state or is ruptured in response to at least one of clamping, stapling, and cutting of the adjunct 2100), the first drug can be released therefrom and into tissue.

As further shown in FIG. 35, voids 2010 (e.g., secondary microreservoirs) are defined within the walls 2108 of the lattice macrostructure 2102. Each void 2010 has a second drug disposed therein, and each void 2010 is configured to release the second drug therefrom in response to at least partial degradation or erosion of the defining portion of the respective wall 2108. Stated differently, each void 2010 is configured to encapsulate the second drug to thereby prevent drug release therefrom until structural degradation of at least a portion of the defining wall 2108. As a result, the combination of the internal cavities 2105 (e.g., primary microreservoirs) of the unit cells 2104 and the voids 2010 (e.g., secondary microreservoirs) within the walls 2108 of the lattice macrostructure 2102 can control the dosage of drug that is released from the adjunct 2100 when the adjunct 2100 is in a tissue deployed state.

While the internal cavities 2105 (e.g., primary microreservoirs) and the voids 2110 (e.g., secondary microreservoirs)

can have a variety of shapes and sizes, as shown, the internal cavities 2105 are larger in size, and thus have larger drug loading capacity, compared to that of the voids 2110. This can allow for a large bolus of the first drug to be released upon activation of the unit cells 2104, followed by smaller doses of the second drug to be released upon structural degradation of the walls 2108 of the lattice macrostructure 2102.

Further, while not illustrated, the adjunct 2100 can include at least one internal stopping member (e.g., like internal stopping members 2314, 2316 shown in FIG. 38) formed within the unit cells 2104. The at least one internal stopping member can be configured to limit the amount of deformation of the respective unit cells when the adjunct is being compressed. For example, in some embodiments, with the at least one internal stopping member in place, each activation of the unit cell can eject a smaller bolus of the first drug. In other embodiments, the at least one internal stopping member can be configured to degrade over time while the adjunct is in a tissue deployed state. As a result, during one or more subsequent activations of the unit cell, this degradation can allow a greater amount of drug to be released (e.g., compared to the amount(s) of drug prior to degradation). In other words, as degradation progresses, drug release can increase. Thus, the bolus of drug released from the adjunct 2100 can vary in response to changes in the geometry of the unit cells during activation. In certain embodiments, the adjunct 2100 can include one or more hydrogels (e.g., disposed within one or more passageways of the adjunct) that can function to inhibit flow therethrough for a predetermined period of time.

In certain embodiments, the adjunct can include first and second voids (e.g., secondary microreservoirs) that are positioned within different regions of the walls of the lattice macrostructure. For example, FIG. 36 illustrates a portion of a connector of a unit cell of an adjunct 2200 that is similar to the adjunct 2100 in FIG. 35, except that the adjunct 2200 includes first voids 2202 with a first drug 2204 disposed therein and second voids 2206 with a second drug 2208 disposed therein.

Figure 36:
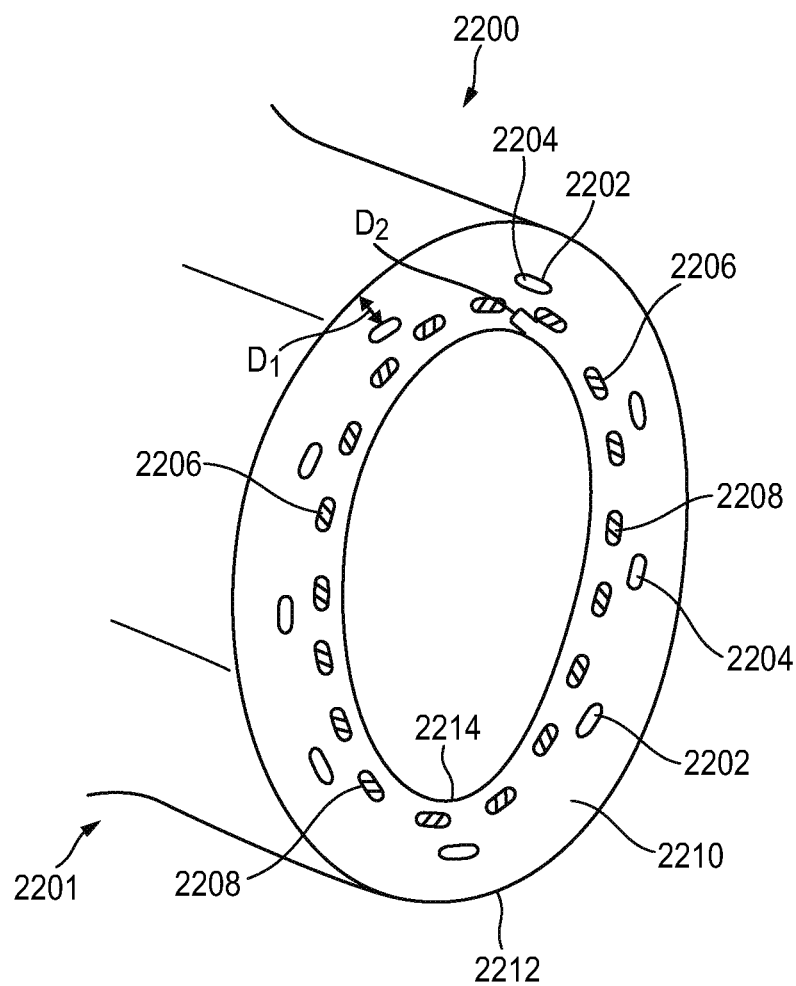
FIG. 36 is a magnified cross-sectional side view of another embodiment of an adjunct, showing the adjunct in an initial state (t=0)
Figure 37:
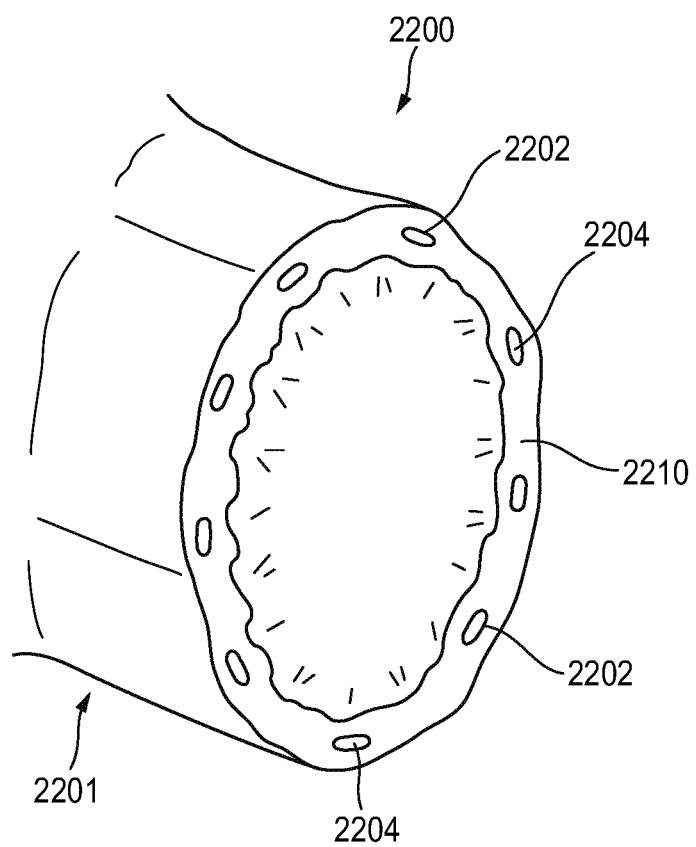
FIG. 37 is the adjunct of FIG. 36, showing the adjunct in a partially degraded state (t>0)

As shown in FIG. 36, the first voids 2202 are positioned proximate to the outer surface 2212 of the wall 2210, and the second voids 2206 are positioned proximate to the inner surface 2214 of the wall 2210. In this illustrated embodiment, the first voids 2202 (e.g., outer voids) encircle the second voids 2206 (e.g., inner voids). Further, as shown, the distance $D_1$ between the first voids 2202 and the outer surface 2212 of the wall 2210 is greater than the distance $D_2$ between the second voids 2206 and the inner surface 2214 of the wall 2210. As a result, as shown in FIG. 37, as the wall 2210 degrades the second drug 2208 is released from the adjunct 2100 prior to the first drug. That is, drug release from the first and second voids 2202, 2206 can therefore be a function of their respective position within the wall(s) 2210 (e.g., relative to the inner or outer wall surface). In some embodiments, the first and second drugs can be the same with a metered release from the adjunct. In other embodiments, the first and second drugs can be different so as to fulfill different needs based on different time periods or events while the adjunct is stapled to tissue (e.g., time periods relative to expected healing profiles of the stapled tissue that).

Figure 38:
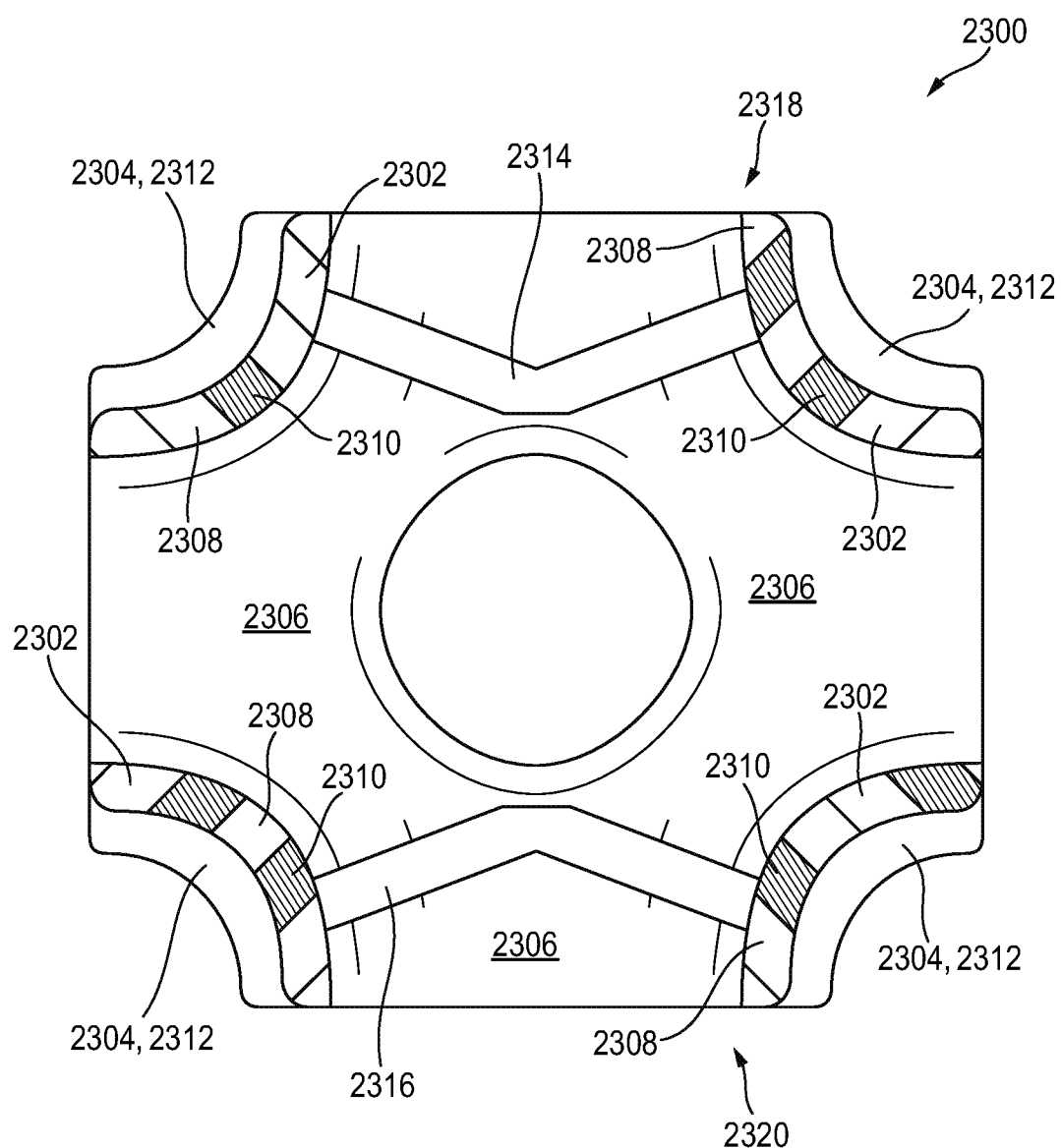
FIG. 38 is cross-sectional view of an exemplary embodiment of a multi-layered unit cell.

In some embodiments, the adjunct can be formed from multi-layered unit cells such that drug dosage can vary in response to polymer erosion of one or more layers of the unit cell. For example, FIG. 38 illustrates an exemplary embodiment of a multi-layered unit cell 2300 that can be used to form any adjunct described herein. While the unit cell 2300 can have a variety of configurations, in this illustrated embodiment, the unit cell 2300 is a Schwarz-P structure having an inner layer 2302 and an outer layer 2304. As shown, the illustrated Schwarz-P structure is a hollow in which the inner layer 2302 defines an internal cavity 2306 of the Schwarz-P structure.

The inner layer 2302 and the outer layer 2304 can be formed of a variety of materials. The inner layer 2302 can formed of a blend of a first fused bioabsorbable polymer 2308 and drug 2310. In some embodiments, as shown in FIG. 38, drug 2310 can be discretely embedded within portions of the inner layer 2302. In other embodiments, the drug can be homogenously dispersed throughout the first fused bioabsorbable polymer. In either embodiment, the first fused bioabsorbable polymer 2308 can be configured to undergo degradation when the adjunct is stapled to tissue so as to release discrete amounts of the drug into the internal cavities 2305 of the unit cells 2300 over time.

The outer layer 2304 can be formed of a second fused bioabsorbable polymer 2312 that is different than the first fused bioabsorbable polymer 2308. In some embodiments, the second fused bioabsorbable polymer 2312 can be configured to degrade at a degradation rate that is less than a degradation rate of the first fused bioabsorbable polymer 2308. In such embodiments, the outer layer 2304 can maintain the structural integrity of the overall unit cell 2300 while the inner layer 2302 degrades. As a result, the unit cell 2300 can function as a pump when the adjunct is being compressed. That is, when a force is applied to the adjunct, the unit cell 2300 can be configured to deform or compress so as to drive at least a portion of the drug that is present in the internal cavity 2306 (e.g., due to erosion of at least a portion of the inner layer 2302) out of the adjunct and to adjacent tissue when the adjunct is in a tissue deployed state.

As further shown in FIG. 38, the unit cell 2300 can include internal stopping members 2314, 2316 that are formed therein and that extend into the internal cavity 2306. These internal stopping members 2314, 2316 are configured to contact each other when the unit cell 2300 is being compressed to limit the amount of deformation of the unit cell 2300. While the unit cell 2300 can include any number of internal stopping members, in this illustrated embodiment, the unit cell 2300 includes one set of internal stopping members 2314, 2316.

The internal stopping members 2314, 2316 can have a variety of configurations. Further, the internal stopping members can have the same or different structural configurations. As shown in FIG. 38, the one set of members include first and second opposing stopping members 2314, 2316, each having a V-shaped configuration in which the first stopping member 2314 is positioned proximate to a top portion 2318 of the unit cell 2300 and the second stopping member 2316 is positioned proximate to a bottom portion 2320 of the unit cell 2300. A person skilled in the art will appreciate that the number and structural configurations of the internal stopping members depend at least upon the structural configuration and size of the unit cell, and therefore, in other embodiments, a unit cell can have a different number of internal stopping members and/or internal stopping members having other suitable shapes and sizes.

In other embodiments, adjuncts are provided having microstructures (units) with sub-structures formed in the microstructures to thereby create differing zones exhibiting different mechanical behavior within the adjuncts when the adjuncts are in a tissue deployed state. For example, the interconnections or geometries of the microstructures can have pre-defined bend zones, flexion shapes, deflection stops, elongation zones, or other variable geometry to thereby encourage a first portion of the adjunct to move or deform differently than other portion(s). The structural configuration of the microstructures can therefore be tailored to have respective compression profiles that control the flow of drug (e.g., volume and/or flow rate) being ejected therefrom. As a result, the microstructures can create different drug release responses in different portions of an adjunct.

For example, in one exemplary embodiment, the adjunct can be formed of at least one fused bioabsorbable polymer and can have a lattice macrostructure having at least one drug contained therein. The lattice macrostructure can be formed of unit cells, and each unit cell can be configured to eject a predetermined amount of drug from the adjunct and the predetermined amount of the drug being a function of a compression profile of the respective unit cell. As such, drug delivery can therefore be controlled by the compression profiles of the unit cells.

The unit cells can have a variety of configurations. For example, in some embodiments, the unit cells are Schwarz-P structures. In one embodiment, the Schwarz-P structures are hollow. In certain embodiments, the lattice microstructure includes connecting structures that extend between and connect adjacent Schwarz-P structures to each other. In one embodiment, the connecting structures are in the form of hollow tubes. In such embodiments, the Schwarz-P structures can be in fluid communication with each other such that a continuous network of pathways are present or formed within the adjunct.

In some embodiments, the adjunct can include first unit cells having a first compression profile and second unit cells having a second compression profile that is different than the first compression profile. As such, different portions of the adjunct can therefore have different drug release rates. For example, the portions of the adjunct that are formed of the first unit cells can have a first release rate of drug that is a function of the first compression profile and the portions of the adjunct that are formed of the second unit cells can have a second release rate of drug that is a function of the second compression profile.

One or more of unit cells of an adjunct can have different compression zones. For example, in some embodiments, a unit cell can include two compression zones, in which the first compression zone has a first compressive strength and the second compression zone has a second compressive strength that is different than the first compressive strength. The first compression zone can be configured to compress from a first uncompressed height to a first compressed height. The second compression zone can be configured to compress from a second uncompressed height to a second compressed height that is different than the first compressed height. A person skilled in the art will appreciate that the compressive strength of the respective compression zone of a unit zone can depend at least upon the location of the unit cell within the adjunct (e.g., relative to an intended cut line of the adjunct) and/or the intended drug delivery site.

In some embodiments, the deformation properties of an adjunct can be controlled by sub-structures formed in one or more unit cells. For example, the sub-structures can be configured to change the deformation properties, deformation limits, bulk modulus, etc. of the unit cells relative to the intended staple line(s) and/or the intended cut line of the adjunct so as to create differing mechanical responses in different portions of the adjunct. As such, this can allow for a non-uniform pressure distribution against tissue that is stapled to the adjunct. Moreover, since drug is contained within one or more unit cells, this can create different drug release properties laterally relative to the intended cut line of the adjunct. The zones of healing from the cut line to the unrestrained portion of the tissue can require differing drug and doses to induce the proper healing. In one embodiment, unit cells can differ in size, release mechanism (e.g., bolus vs graduated release), and/or drug or drug combinations (e.g., the unit cells can differ laterally along the adjunct in a y-direction).

In one embodiment, the sub-structures can be configured to contact each other as the adjunct compresses. This resulting contact can either increase the bias (e.g., stiffness) of the adjunct, or alternatively, inhibit or stop any further compression or collapse of the adjunct. Alternatively, or in addition, the overall geometry of the unit cells can impact the deformation properties of the adjunct. For example, in one embodiment, one or more unit cells can have a variable wall thickness In another embodiment, one or more unit cells can have a thinner wall thickness and have an integral structure (e.g., a living hinge or like structure) that is configured to induce bending in a predefined location.

Figure 39:
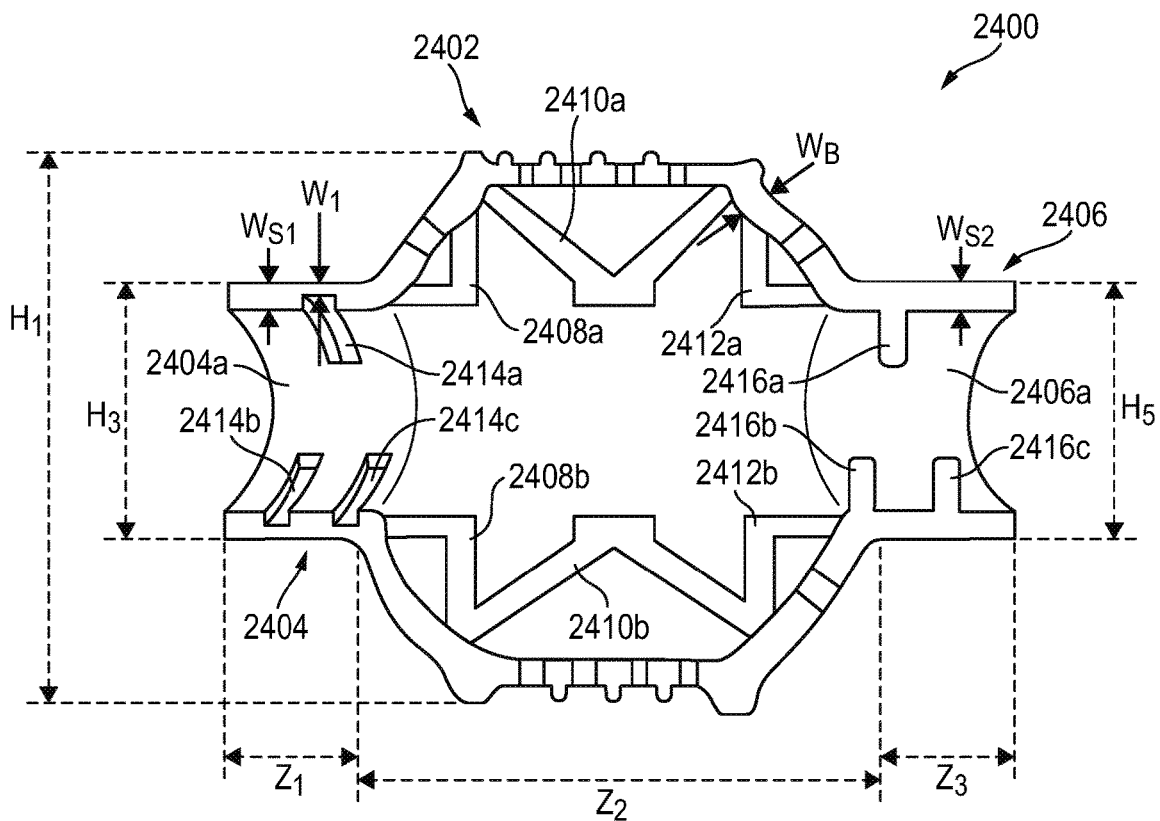
FIG. 39 is a cross-sectional view of a portion of another embodiment of adjunct, showing the adjunct in an uncompressed state.
Figure 40:
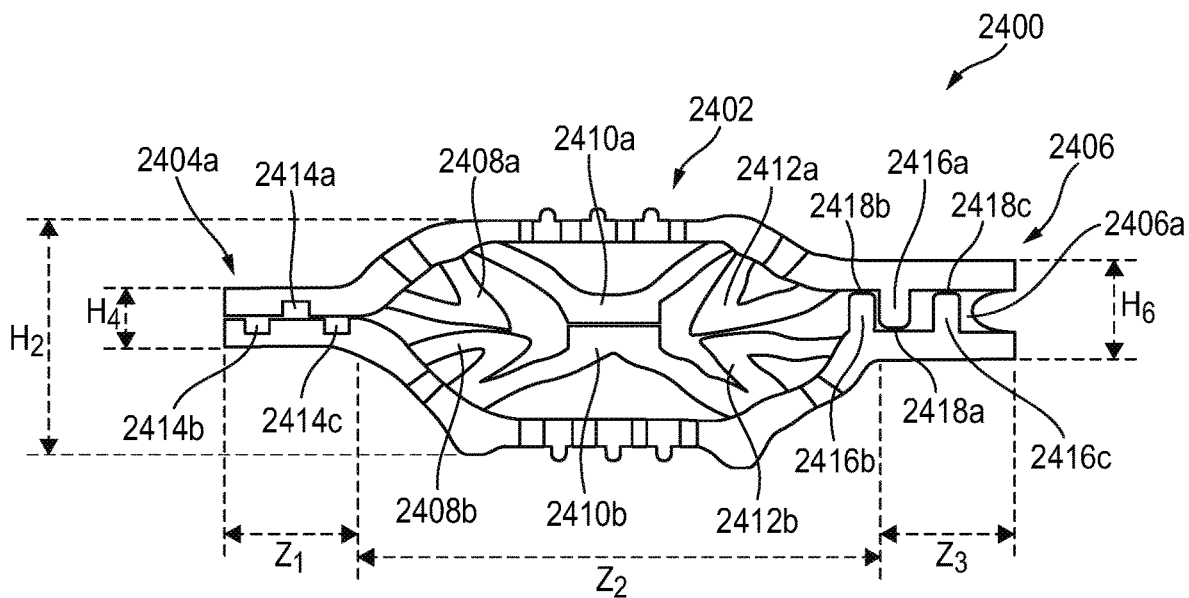
FIG. 40 is the adjunct of FIG. 39, showing the adjunct in a compressed state.

FIG. 39 and FIG. 40 illustrate an exemplary embodiment of a unit cell 2400 (e.g., microstructure) that can be configured to eject a predetermined amount of drug (not shown). While the unit cell 2400 can have a variety of configurations, in this illustrated embodiment, the unit cell 2400 is hollow and has a base structure 2402 with first and second side structures 2404, 2406. The first and second side structures 2404, 2406 extend outward from opposite sides of the base structure 2402. While the structural configurations of the base structure 2402 and the first and second side structures 2404, 2406 can vary, in this illustrated embodiment, the base structure 2402 has a generally spherical shape and the first and second side structures 2404, 2406 each have a generally cylindrical shape. Further, the unit cell 2400 can have a variable wall thickness, in which the base structure 2402 has a maximum wall thickness WB that is greater than the maximum wall thickness $W_{S1}$ of the first side structure 2404 and the maximum wall thickness $W_{S2}$ of the second side structure 2406.

As further shown, the unit cell 2400 includes sub-structures that are formed in different sections of the unit cell 2400. More specifically, the unit cell 2400 includes first sub-structures 2408a, 2408b, second sub-structures 2410a, 2410b, and third sub-structures 2412a, 2412b that are formed in the base structure 2402, fourth sub-structures 2414a, 2414b, 2414c that are formed in the first side structure 2404, and fifth sub-structures 2416a, 2416b, 2416c that are formed in second side structure 2406. These sub-structures are configured to effect different mechanical behaviors within the unit cell 2400 when the unit cell 2400 is being compressed (see FIG. 40). As a result, the unit cell 2400 has three different compression zones Z1, Z2, Z3, each having a different compressive strength. These three compression zones Z1, Z2, Z3 together define the compression profile of the unit cell 2400. In can be appreciated that the amount of compression experienced by the respective compression zones Z1, Z2, Z3 will therefore dictate the driving force applied to the drug retained therein. Accordingly, the compression profile can be used control the release rate of the drug from unit cell 2400.

The sub-structures can have a variety of configurations. In this illustrated embodiment, the first, second, and third sub-structures 2408a, 2408b, 2410a, 2410b, 2412a, 2412b are each internal stopping members, the fourth sub-structures 2414a, 2414b, 2414c are recesses that are defined within the wall 2404a of the first side structure 2404, and the fifth sub-structures 2416a, 2416b, 2416c are projections that partially extend inward from the wall 2406a of the second side structure 2406. The internal stopping members are configured to limit the amount of compression of the base structure when the unit cell is being compressed. In use, as shown in FIG. 40, the first internal stopping members 2408a, 2408b contact each other, the second internal stopping members 2410a, 2410b, and the third internal stopping members 2412a, 2412b contact each other, thereby increasing the stiffness of the base structure 2402 as it is compressed from an uncompressed height $H_1$ (FIG. 39) to a compressed height $H_2$. The recesses 2414a, 2414b, 2414c create weakened portions within the wall 2406a and therefore are configured to decrease the stiffness of the first side structure 2404. In use, as shown in FIG. 40, the first side structure 2404 fully compresses from an uncompressed height $H_3$ (FIG. 39) to a compressed height $H_4$. The projections 2416a, 2416b, 2416c within the second side structure 2406 form partial walls that are configured to limit the amount of compression of the second side structure 2406 when the unit cell 2400 is being compressed. In use, as shown in FIG. 40, the free ends 2418a, 2418b, 2418c of the projections 2416a, 2416b, 2416c come in contact with respective facing portions of the wall 2406a. As such, the projections 2416a, 2416b, 2416c thereby increase the stiffness of the second side structure 2406 as it is compressed from an uncompressed height $H_5$ (FIG. 39) to a compressed height $H_6$.

In certain embodiments, the adjuncts can be designed such that they possess rate dependent compressive properties. For example, an adjunct can include a series of interconnected fluid pockets (fluid filled) that are configured to transfer volume from one to another during compression, e.g., to thereby overcome or resist tissue flow. In one embodiment, two interconnected pockets exhibiting differing stiffness can transfer volume from the less stiff pocket to the more stiff pocket during tissue compression. This volume transfer could be used to prevent tissue from flowing away from a cutting element when the adjunct and tissue are being severed. In certain embodiments, a one-way valve between adjacent pockets can be configured to prevent backflow.

Figure 41:
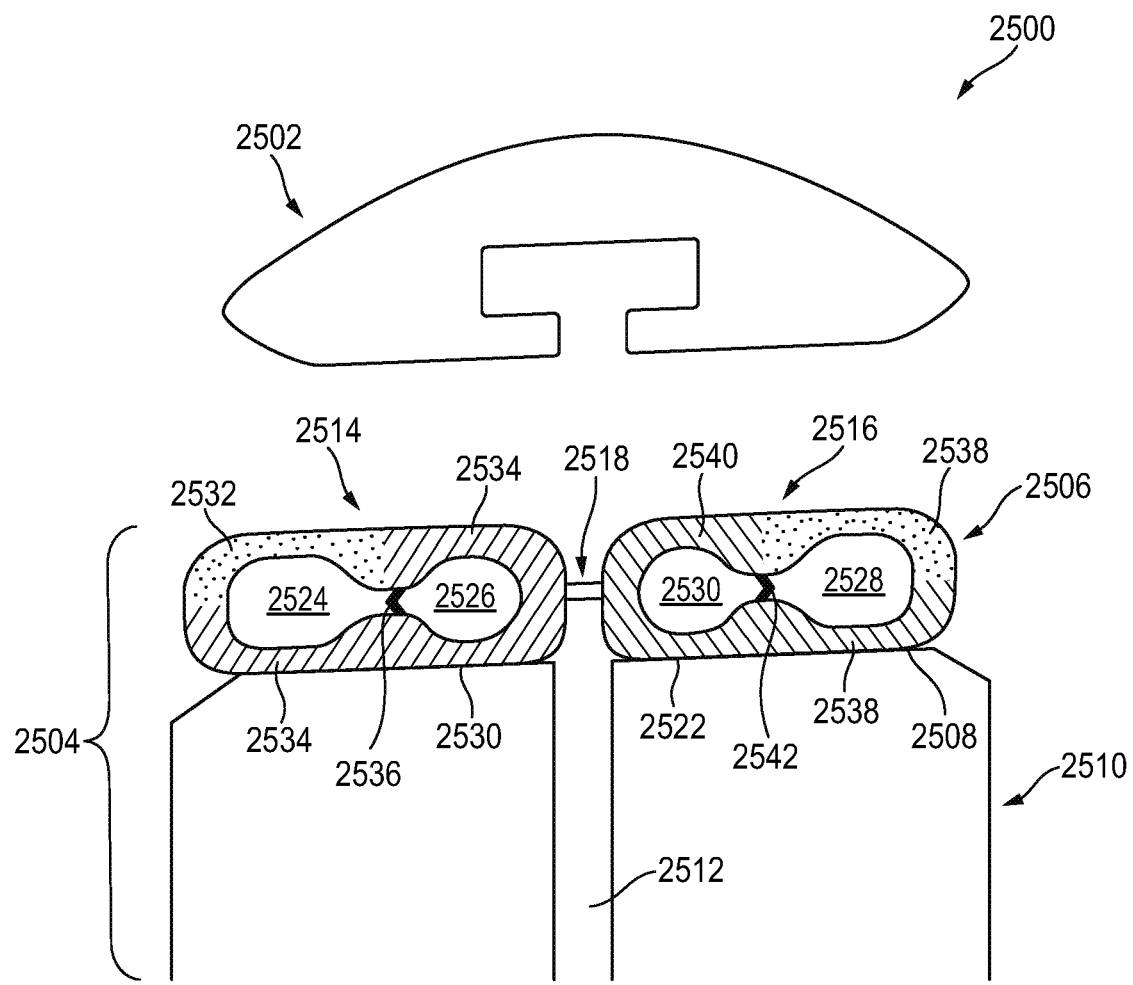
FIG. 41 is a cross-sectional front view of another embodiment of a surgical end effector having an anvil and a stapling assembly, the stapling assembly having an another embodiment of an adjunct releasably retained on a staple cartridge, showing the surgical end effector in a closed positioned without tissue positioned between the anvil and the stapling assembly.

FIG. 41 illustrates another exemplary embodiment of a surgical end effector 2500 having an anvil 2502 and a stapling assembly 2504. The stapling assembly 2504 includes an adjunct 2506 releasably retained on a top or deck surface 2508 of a staple cartridge 2510 (e.g., the cartridge surface that faces the anvil). As shown, the cartridge 2510 has a slot 2512 that is defined within the cartridge 2510 and is configured to receive a cutting element (not illustrated). While not illustrated, the anvil 2502 is pivotally coupled to an elongate staple channel and the stapling assembly 2504 is positioned within and coupled to elongate staple channel.

The adjunct 2506 can have a variety of configurations. In this illustrated embodiment, the adjunct 2506 has a first longitudinal segment 2514 and an opposing, second longitudinal segment 2516 that are interconnected to each other via a connecting structure 2518 that extends therebetween. As shown in FIG. 41, the first longitudinal segment 2514 is positioned on a first side 2520 of the slot 2512, the second longitudinal segment 2516 is positioned on a second, opposing side 2522 of the slot 2512, and the connecting structure 2518 overlaps with the slot 2512.

The first longitudinal segment 2514 and the second longitudinal segment 2516 can have a variety of configurations. In this illustrated embodiment, the first longitudinal segment 2514 includes first and second interconnected pockets 2525, 2526 defined therein, and the second longitudinal segment 2516 includes third and fourth interconnected pockets 2528, 2530 defined therein. The first and second interconnected pockets 2525, 2526 are fluid filled and are configured to transfer volume(s) of the fluid between each other during compression of the adjunct 2506 (e.g., during clamping, stapling, and/or cutting and/or when the adjunct is in a tissue deployed state). As a result, fluid transfer between the first and second interconnected pockets 2525, 2526 can inhibit or resist tissue flow in undesirable directions (e.g., in a direction away from the slot 2512 and/or cutting element).

Similarly, the third and fourth interconnected pockets 2528, 2530 are fluid filled and are configured to transfer volume(s) of the fluid between each other during compression of the adjunct 2506 (e.g., during clamping, stapling, and/or cutting and/or when the adjunct is in a tissue deployed state). As a result, fluid transfer between third and fourth interconnected pockets 2528, 2530 can inhibit or resist tissue flow in undesirable directions (e.g., in a direction away from the slot 2512 and/or cutting element).

In certain embodiments, the first and second interconnected pockets 2525, 2526 can be configured to exhibit differing stiffness. For example, as shown in FIG. 41, the first interconnected pocket 2525 is bounded by a first wall 2532 formed of a first material (illustrated by stippling) and a second material (illustrated by hatching), whereas the second interconnected pocket 2526 is bounded by a second wall 2534 formed of only the second material (illustrated by hatching). In some embodiments, the first material is stiffer than the second material, whereas in other embodiments, the second material is stiffer the first material. In this illustrated embodiment, the second material is stiffer than the first material. Further, to prevent backflow, a one-way valve 2536 (e.g., a flapper valve, a duckbill valve, and the like) can be positioned between the first and second interconnected pockets. As shown, the one-way valve 2532 is configured to allow fluid to transfer from only the second interconnected pocket 2526 to the first interconnected pocket 2525.

Similarly, in certain embodiments, the third and fourth interconnected pockets 2528, 2530 can be configured to exhibit differing stiffness. For example, as shown in FIG. 41, the third interconnected pocket 2528 is bounded by a third wall 2538 formed of a first material (illustrated by stippling) and a second material (illustrated by hatching), whereas the fourth interconnected pocket 2530 is bounded by a fourth wall 2540 formed of only the second material (illustrated by hatching). In some embodiments, the first material is stiffer than the second material, whereas in other embodiments, the second material is stiffer the first material. In this illustrated embodiment, the second material is stiffer than the first material. Further, to prevent backflow, a one-way valve 2542 (e.g., a flapper valve, a duckbill valve, and the like) can be positioned between the first and second interconnected pockets. As shown, the one-way valve 2542 is configured to allow fluid to transfer from only the fourth interconnected pocket 2530 to the third interconnected pocket 2528.

The adjunct can be configured to exhibit rate dependent compressible properties that can be used as a mechanism for controlling tissue flow during compression. By way of example, FIG. 42 illustrates a surgical end effector 2600 having that is similar to the surgical end effector 2500 in FIG. 41 except for the differences described below.

Figure 42:
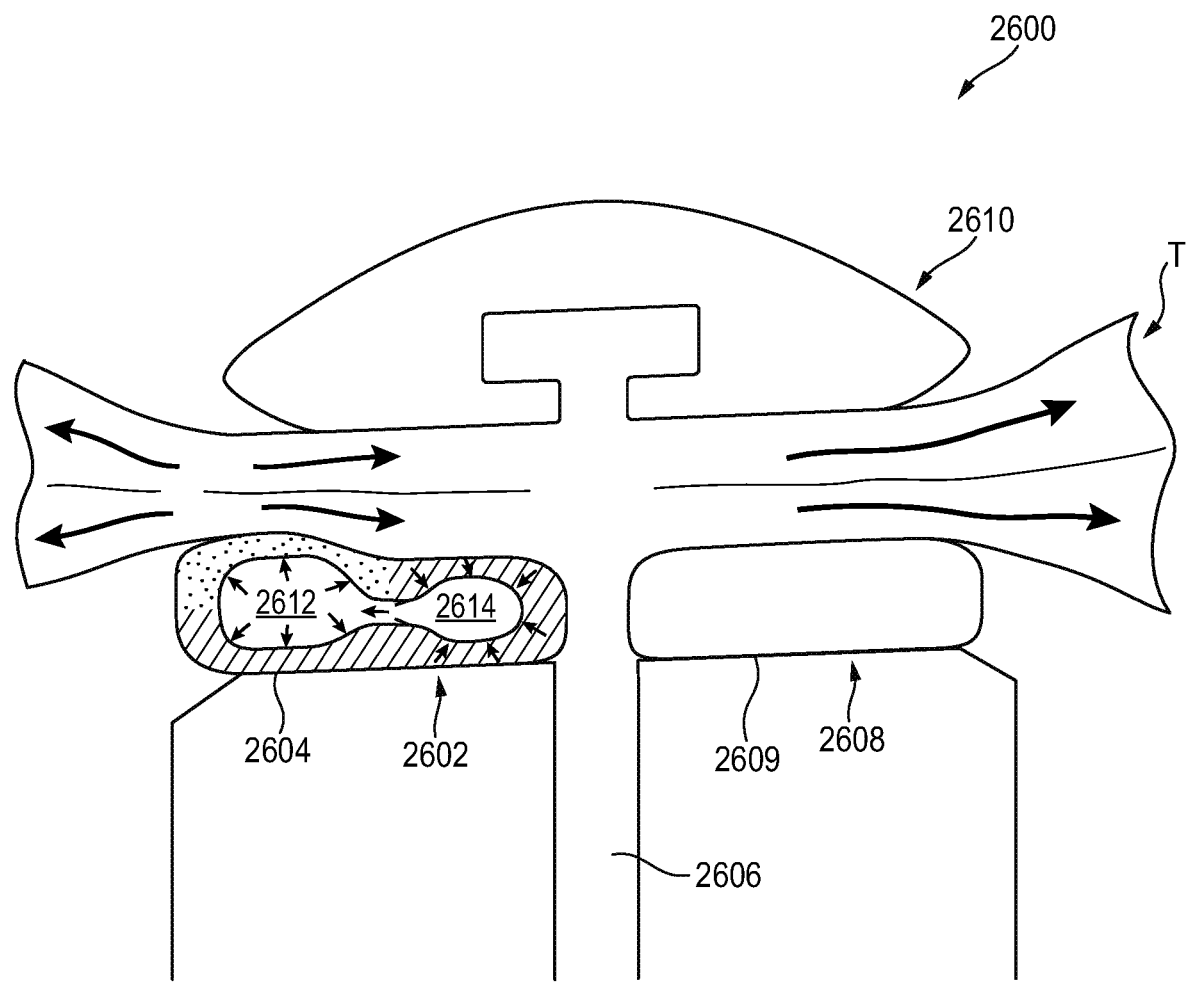
FIG. 42 is a cross-sectional front view of another embodiment of a surgical end effector having an anvil and a stapling assembly, the stapling assembly having an another embodiment of an adjunct releasably retained on a staple cartridge, showing the surgical end effector in a closed positioned without tissue positioned between the anvil and the stapling assembly.

As shown in FIG. 42, a first adjunct 2602 with rate dependent compressible properties is disposed on a first side 2604 of the slot 2606 and a second adjunct 2608 without rate dependent compressible properties is shown on the second, opposing side 2609 of the slot 2606. The first adjunct 2602 is structurally similar to the first longitudinal segment 2414 of the adjunct 2506 in FIG. 41, and therefore, common features are not described in detail herein. As shown, when tissue T is clamped between the anvil 2610 and the first adjunct 2602, the rate dependent compressible properties of the first adjunct 2602 minimize tissue flow away from the slot 2606. More specifically, upon compression, fluid transfer from the second interconnected pocket 2614 to the first interconnected pocket 2612 occurs thereby causing the first interconnected pocket 2612 to expand. As a result, tissue flow (depicted as dashed arrows) can be partially redirected back towards the slot 2606. By way of comparison, upon compression of the second adjunct 2608, as shown in FIG. 42, redirection of tissue flow (e.g., toward the slot 2606) does not otherwise occur.

Exposure Condition Monitoring

Monitoring and/or tracking exposure of an adjunct and any medicant(s) retained therein to one or more exposure conditions can provide any number of benefits. Exposure conditions, also referred to as environmental condition, can affect performance of the adjunct, e.g., longevity, and/or can affect performance of the medicant(s) retained therein, e.g., viability, longevity, and potency. Viability of a medicant generally refers to efficacy of the medicant, e.g., the medicant's ability to produce a particular effect. Longevity of an adjunct generally refers to a length of time the adjunct can produce a particular effect, such as the adjunct's ability to degrade or dissolve in a patient's body and thereby release medicant(s) from the adjunct. Longevity of a medicant generally refers to a length of time the medicant can produce a particular effect. Potency of a medicant generally refers to an amount of the medicant needed to produce a particular effect. The monitoring or tracking of the adjunct and the medicant(s) retained therein from the point of packaging to administration, or a portion thereof, can allow for early identification of non-viable adjunct and non-viable medicants, as well as modification of a patient's treatment, e.g., providing additional medicant dosage to a patient to compensate for a medicant having experienced an exposure condition adversely affecting the medicant's performance, and/or shelf-life based upon the exposure monitoring or tracking. Thus, monitoring and/or tracking exposure of an adjunct and any medicant(s) retained therein may reduce the risk of implanting an adjunct that has been rendered ineffective due to exposure conditions, may reduce the risk of administering a medicant at a dosage that has been rendered ineffective due to exposure conditions, and may reduce the risk of a non-viable medicant being administered to a patient via implantation of the adjunct that retains the medicant therein.

In general, systems and methods described herein include active or passive sensing mechanisms, such as sensors, that can monitor at least one exposure condition of an adjunct and any medicant(s) retained therein. In some instances, the active or passive sensing mechanisms can also track the extent of the adjunct's and medicant(s)'s exposure, e.g., frequency, intensity, and/or duration. As a result, the information related to the exposure condition itself and/or the extent of exposure can be used to determine the effectiveness of the adjunct and any medicant(s) retained therein prior to implantation of the adjunct and/or prior to distribution in commerce of the adjunct that retains the medicant(s) therein.

Systems and methods described herein including an active or passive sensing mechanism can include a staple cartridge and an adjunct releasably coupled to the staple cartridge, such as any one or more of the staple cartridges and any one or more of the adjuncts discussed above. As also discussed above, the adjunct can retain one or more medicants therein, and the staple cartridge either can be fixedly coupled to a jaw of a surgical stapler or can be configured to be removably and replaceably coupled to a jaw of a surgical stapler. The medicants can include any one or more of the medicants discussed above.

In an exemplary embodiment, a packaging unit that packages the adjunct and the medicant(s) retained therein includes at least one active or passing sensing mechanism. At least one exposure condition of the adjunct and the medicant(s) retained therein can thus be monitored along the supply chain from when the adjunct and the medicant(s) retained therein are packaged by the packaging unit until removal of the adjunct and the medicant(s) retained therein from the packaging unit.

A packaging unit can package an adjunct with at least one medicant releasably retained therein with the adjunct being configured to be releasably coupled to a staple cartridge after the packaging unit is opened. Alternatively, a packaging unit can package an adjunct with at least one medicant releasably retained therein with the adjunct releasably coupled to a staple cartridge such that the packaging unit packages the adjunct, the at least one medicant, and the staple cartridge. In such embodiments, the staple cartridge having the adjunct releasably coupled thereto can be configured to be seated in an end effector of a surgical stapler after the packaging unit is opened, or the packaging unit can also package the surgical stapler with the staple cartridge seated in the stapler's end effector or with the staple cartridge being seatable in the stapler's end effector after the packaging unit is opened. In some embodiments, a packaging unit can package a plurality of adjuncts each having at least one medicant retained therein, and can optionally also package a plurality of staple cartridges each with one of the adjuncts releasably coupled thereto. Providing a plurality of adjuncts in a packaging unit may allow for different staples cartridges to be provided so a surgeon or other medical professional can choose an appropriately sized staple cartridge for use in a particular procedure, as staple cartridges are typically offered in different sizes for different surgical staplers and/or with differently sized staples and/or a different number of staples. Providing a plurality of adjuncts in a packaging unit may allow for a plurality of the same adjuncts to be provided to ease reloading of a surgical stapler during a surgical procedure with a series of the same adjuncts. Regardless of the elements packaged by a packaging unit, in an exemplary embodiment, the packaging unit is sterile to help ensure safe use of the packaged element(s) with a patient.

As mentioned above, a sensor can be configured to monitor or detect at least one exposure condition of an adjunct and any medicant(s) retained therein. Examples of exposure conditions include geographic location (e.g., as sensed by a location sensor configured to sense GPS or other location), time (e.g., as sensed by a timer or a clock device such as an atomic clock), date (e.g., as sensed by a timer), temperature (e.g., as sensed by a temperature sensor), ultraviolet (UV) exposure (e.g., as sensed by a UV sensor configured to sense UV level), pH (e.g., as sensed by a pH sensor configured to sense pH level), humidity (e.g., as sensed by a humidity sensor configured to sense humidity level), light (e.g., as sensed by a photo detector configured to sense light level), oxygen exposure (e.g., as sensed by an oxygen ($O_2$) sensor configured to sense oxygen level), vibration (e.g., as sensed by a vibration sensor, accelerometer, etc. configured to sense vibration), and atmospheric pressure (e.g., as sensed by a barometric pressure sensor configured to sense barometric pressure or an atmospheric pressure sensor configured to sense air pressure of ambient air). Alternatively, or in addition, the sensor can be configured to track the frequency, duration, and/or intensity of an adverse exposure event experienced by the adjunct and any medicant(s) retained therein prior to implantation of the adjunct, e.g., a spike of an exposure condition during transport or storage of the adjunct and any medicant(s) retained therein as sensed by a sensor configured to sense the exposure condition and a timer configured to provide date and time stamp data for the sensed data. One or more sensors can be used to monitor the at least one exposure condition. A sensor can configured to monitor a single exposure condition (e.g., monitor only time, monitor only geographic location, monitor only pH, monitor only light, etc.) or can be configured to sense at least two exposure conditions (e.g., monitor temperature and humidity, monitor time, date, and at least one other exposure condition, monitor light and UV light, etc.). U.S. Pat. Pub. No. 2002/0014951 entitled "Remote Control For A Hospital Bed" published Feb. 7, 2002 and U.S. Pat. Pub. No. 2007/0251835 entitled "Sub-network Synchronization And Variable Transmit Synchronization Techniques For A Wireless Medical Device Network" published Nov. 1, 2007 further discuss various exemplary sensors and are incorporated by reference herein in their entireties.

Temperature can adversely affect performance of an adjunct. For example, a temperature above a predetermined maximum threshold temperature or below a predetermined minimum threshold temperature can cause the adjunct to begin to degrade before implantation of the adjunct in a body of a patient and that, therefore, the adjunct should no longer be used. Temperature can also adversely affect performance of a medicant. For example, a temperature above a predetermined maximum threshold temperature or below a predetermined minimum threshold temperature, as appropriate for a particular medicant, can cause the medicant to lose potency and that, therefore, the adjunct having the medicant retained therein should no longer be used or, before the medicant is retained in the adjunct, that the medicant should not be retained in the adjunct.

UV exposure can adversely affect performance of an adjunct. For example, a UV level above a predetermined maximum threshold UV level or below a predetermined minimum threshold UV level, as appropriate for a particular adjunct's material(s), can cause the adjunct to begin to degrade before implantation of the adjunct in a body of a patient and that, therefore, the adjunct should no longer be used. UV level can also adversely affect performance of a medicant. For example, a UV level above a predetermined maximum threshold UV level or below a predetermined minimum threshold UV level, as appropriate for a particular medicant, can cause the medicant to lose potency and that, therefore, the adjunct having the medicant retained therein should no longer be used or, before the medicant is retained in the adjunct, that the medicant should not be retained in the adjunct.

Humidity can adversely affect performance of an adjunct. For example, a humidity above a predetermined maximum threshold humidity or below a predetermined minimum threshold humidity, as appropriate for a particular adjunct's material(s), can cause the adjunct to begin to degrade before implantation of the adjunct in a body of a patient and that, therefore, the adjunct should no longer be used. Humidity can also adversely affect performance of a medicant. For example, a humidity above a predetermined maximum threshold temperature or below a predetermined minimum threshold humidity, as appropriate for a particular medicant, can cause the medicant to lose potency and that, therefore, the adjunct having the medicant retained therein should no longer be used or, before the medicant is retained in the adjunct, that the medicant should not be retained in the adjunct.

Geographic location can be indicative of temperature and/or humidity exposure since temperature and humidity can be known for a particular location at a particular date and time. Geographic location can also be indicative of whether a medicant is approved for use in its current location, e.g., whether or not a medicant is exposed to an inappropriate geographic location and should thus not be used.

Light can adversely affect performance of a medicant. For example, a light level above a predetermined maximum threshold light level can cause the medicant to lose potency and that, therefore, the adjunct having the medicant retained therein should no longer be used or, before the medicant is retained in the adjunct, that the medicant should not be retained in the adjunct.

Oxygen can adversely affect performance of an adjunct. For example, exposure of the adjunct to an oxygen level above a predetermined maximum threshold oxygen level can cause the adjunct to lose sterility and/or begin to degrade before implantation of the adjunct in a body of a patient and that, therefore, the adjunct should no longer be used. If the adjunct is sealed in a sterile packaging unit, the oxygen exposure of the adjunct should not change until the packaging unit is opened for use. Thus, oxygen level being above a predetermined maximum threshold oxygen level at a particular date/time stamp can be indicative of sterility of the adjunct being lost such that the adjunct should no longer be used and/or that the adjunct may have started to degrade such that the adjunct should no longer be used.

Vibration can adversely affect performance of an adjunct. For example, exposure of an adjunct to vibration above a predetermined maximum vibration is indicative of the adjunct being impacted with force. The force may cause the adjunct to become compressed prematurely, e.g., before implantation, and thus not be able to properly compress and conform in a patient's body.

Atmospheric pressure can adversely affect performance of a medicant. For example, exposure of the medicant to an atmospheric pressure above a predetermined maximum threshold atmospheric pressure can cause the medicant to lose potency and that, therefore, the adjunct retaining the medicant therein should no longer be used.

Rushes or delays in the supply chain can have an impact on adjuncts and medicants. For example, production or storage delays of the adjunct and the medicant(s) retained therein can negatively affect the shelf-life of the adjunct or the medicant.

As mentioned above, a system can include one or more sensors. A sensor can be associated with at least one adjunct (and thus also with any medicants retained therein) and/or a packaging unit for the at least one adjunct (and thus also with any medicants retained therein). As discussed above, the one or more adjuncts in the packaging unit can be standalone elements or can be releasably coupled to a staple cartridge, which can be in the packaging unit as a standalone unit configured to be removably and replaceably seated in a jaw of an end effector of a surgical stapler or can be in the packaging unit already coupled to an end effector of a surgical stapler, such as by being fixedly seated in a jaw of the end effector or by being removably and replaceably seated in the jaw of the end effector.

The sensor can be used to monitor exposure conditions of the adjunct and any medicant(s) retained therein prior to the adjunct being implanted in a patient and thus before the medicant(s) are administered to a patient. This may help ensure that at the time of implantation the adjunct(s) can effectively release the medicant(s) and that at the time of medicant administration upon adjunct implantation and/or at time(s) thereafter, each of the one or more medicants is viable and is delivered at an effective dosage. Moreover, this monitoring may also aid in detection of non-viable adjuncts and/or non-viable medicants early on in the supply chain. As a result, manufacturers can recall non-viable adjuncts (and thus any medicant(s) retained therein) at an early stage, e.g., prior to packaging and/or distribution, which may lead to decreased recall costs and avoid the potential health risks to the patients.

The sensor can be configured to monitor at least one exposure condition of the adjunct and any medicants retained therein while the adjunct is seated in a staple cartridge (whether or not the staple cartridge is seated in a jaw of an end effector). Alternatively, or in addition, the sensor can be configured to monitor at least one exposure condition of the adjunct and any medicants retained therein while the adjunct and any medicants retained therein are within the packaging unit, e.g., whether or not the adjunct is packaged already attached to the staple cartridge. As such, the sensor can be configured to monitor at least one exposure condition of the medicant(s) after the medicant(s) are associated with the adjunct, e.g., after the medicant(s) have been retained by the adjunct but before the adjunct has been implanted in a patient. As a result, the sensor can function as a shelf-life monitor for the adjunct having the medicant(s) retained therein and as a shelf-life monitor for the medicant(s) once the medicant(s) are retained by the adjunct.

Data acquired by the sensor can be communicated to a processor through a communications interface. In an exemplary embodiment, the communications interface is associated with the adjunct or a staple cartridge seating the adjunct therein, and a packaging unit packaging the adjunct and the medicant(s) retained therein includes the communications interface, as discussed herein. The processor can be remote from or local to the adjunct and thus remote from or local to the packaging unit packaging the adjunct.

In use, once the data is received by the processor, the processor can process the data and provide a data output. In one example, the data output can be an expiration date of a medicant retained by an adjunct, which can be determined by taking into account the data acquired by the sensor. The processor can be configured to similarly process the data and provide a data output regarding the adjunct. For example, the processor can be configured to determine the expiration date by determining an elapsed amount of time after the medicant and adjunct have been packaged, as indicated by the sensor. The processor can also be configured to compare the determined elapsed amount of time with the medicant's and/or adjunct's predetermined expiration date as set by the manufacturer (or other quality controller) to determine whether the expiration date has passed. The processor can also be configured to adjust the elapsed amount of time based on the data acquired by the sensor to account for intensity and duration of any exposure condition of the packaged medicant and adjunct. The processor can be configured to access a lookup table that is stored in a memory and that store predetermined metrics for the medicant and/or the adjunct. The predetermined metrics can associate the medicant and/or the adjunct with each of one or more exposure conditions and indicate the exposure condition's effect on the medicant's and/or the adjunct's expiration date, e.g., by indicating how much time the medicant's and/or the adjunct's expiration date should be adjusted downward (if at all) for particular time durations of the exposure condition.

In some embodiments, the medicant's expiration date can be for a batch of the medicant. The processor can be configured to provide a data output indicating that the batch of the medicant, and thus that the medicant retained by the adjunct, is beyond its expiration date. For example, the data output can be in the form of a warning, such as a warning configured to be communicated via text and/or image display to a user such as by text message, email, display on a computer system's display screen, etc. The adjunct's expiration date can similarly be for a batch of adjuncts.

A warning as discussed herein can be to a user of the adjunct (and thus of the medicant retained by the adjunct) and/or to a third party, e.g., a manufacturer of the adjunct and/or the medicant, a cloud service configured to communicate with hospitals and/or other medical facilities that provide adjuncts to users, etc. Providing a warning to the user may help prevent the adjunct from being implanted, thereby helping prevent the adjunct and the medicant from being delivered to a patient, and thus help avoid adverse patient effects and/or allow the user to obtain a new adjunct for implantation. Providing a warning to the third party as a cloud service may (1) facilitate automatic product replacement by allowing the cloud service to automatically reorder the adjunct, staple cartridge coupled to the adjunct, and/or surgical stapler coupled to the staple cartridge that is coupled to the adjunct, (2) allow the cloud service to automatically generate a complaint report that is transmitted from the cloud service to another third party, e.g., a manufacturer of the adjunct and/or the medicant, a medical professional intended to implant the adjunct, etc., that the other third party may use to evaluate their business, take remedial action, etc., (3) allow the cloud service to automatically generate a request to a quality control unit, such as a quality control team at the adjunct's and/or medicant's manufacturer, for consultation of what step(s) the user, the user's health care provider (HCP), the adjunct's manufacturer, the medicant's manufacturer, and/or another party should take, and/or (4) associate the particular adjunct (e.g., as identified with a product identification code included in the warning) with a serialization that can be traced to a specific distribution leg in the supply chain, should the excursion happen with the user then the adjunct and/or the medicant retained therein may not be refundable or replaced due to a history of known user error and/or the user can be reminded of appropriate storage conditions for the adjunct, e.g., message shown on a display of a computer system, email sent to the user associated with the adjunct (and thus the medicant retained by the adjunct), a hospital or other medical care facility being informed of the user error(s) for discussion with the one or more parties responsible for proper storage and/or transport of the adjunct at the medical care facility, etc.

The warning can indicate that an adjunct (and thus any medicants retained by the adjunct) should not be used, e.g., because of adverse exposure condition(s) experienced by the adjunct (and any medicants retained by the adjunct). If an adjunct (and thus any medicants retained by the adjunct) is still usable but has experienced at least one adverse exposure condition, the warning can provide a recommendation of use that reflects the adverse exposure condition(s), such as a time period from the current time in which the adjunct should be implanted so the adjunct (and thus any medicants retained by the adjunct) maintain sufficient effectiveness. A warning may be provided even if an adjunct (and thus any medicants retained by the adjunct) has not experienced any exposure condition(s) that adversely affect its use in a surgical procedure, such as a time period from the current time in which the adjunct should be implanted so the adjunct (and thus any medicants retained by the adjunct) maintain sufficient effectiveness. For example, such a recommendation may be beneficial for an adjunct and/or a medicant that is adversely affected by light exposure. When a packaging unit that packages the adjunct and medicant(s) retained by the adjunct is opened, the adjunct and the medicant(s) are exposed to light, which may then start a time period in which the adjunct (and thus the medicant(s)) should be implanted before the adjunct and medicant(s) are exposed to too much light. For another example, such a recommendation may be beneficial for an adjunct and/or a medicant that is adversely affected by temperature and/or humidity exposure. An operating room can have a temperature sensor and/or a humidity sensor in communication with the processor providing the warning such that the warning can take into account the operating room's temperature and/or humidity to provide a time period from the current time in which the adjunct should be implanted so the adjunct (and thus any medicants retained by the adjunct) maintain sufficient effectiveness given its current exposure to conditions in the operating room.

Another example of the data output of the processor after the processor processes the data is an excursion condition state, which can be determined by taking into account the data acquired by the sensor. For example, the processor can be configured to compare data received from the sensor with a predetermined threshold or range indicative of a safe exposure condition. If the received data is outside of the predetermined safe range, above the predetermined safe threshold, or below the predetermined safe threshold as appropriate for the particular exposure condition, the data output can be in the form of a warning indicating that the packaging unit, and thus the adjunct(s) and any medicants retained by the adjunct(s), has experienced at least one exposure condition during its life so far in the supply chain that its performance has been adversely affected enough such that the packaged adjunct(s) retaining the medicant(s) therein should not be implanted.

Figure 43:
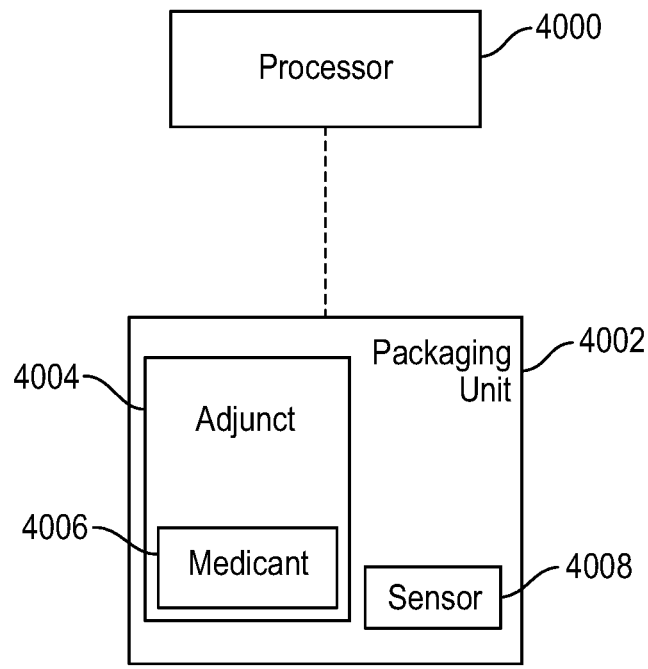
FIG. 43 is a schematic view of one exemplary embodiment of communication network including a processor and one exemplary embodiment of a packaging unit.

FIG. 43 shows an embodiment of a processor 4000 configured to communicate with a packaging unit 4002 packaging an adjunct 4004 retaining a medicant 4006 therein. The packaging unit 4002 in this illustrated embodiment is in the form of a blister pack, but other types of packaging units can be used. A sensor 4008 attached to the packaging unit 4002 is configured to monitor at least one exposure condition, as discussed herein, and incorporates a communications interface therein, e.g., an RFID sensor tag, a microcontroller including a sensor, power source, and a wireless transmitter, a flex circuit including a sensor, battery, and a wireless transmitter, etc., although a packaging unit can include a separate sensor and communications interface. The sensor 4008, e.g., the communications interface thereof, is configured to communicate data wirelessly with the processor 4000. The sensor 4008 can be attached to the packaging unit 4002 in any of a variety of ways, such as by being embedded in a material (e.g., a polymer, a reinforced cardboard, glass, etc.) forming the packaging unit 4002, being adhered to an inner surface or an outer surface of the packaging unit 4002 using adhesive, adhered to a label or sticker on the packaging unit 4002, or by being attached to the packaging unit 4002 using another attachment mechanism.

Figure 44:
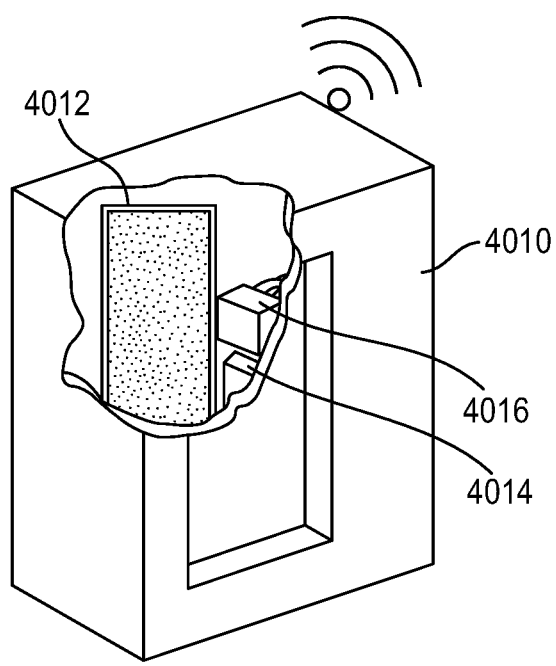
FIG. 44 is a partial-cutaway perspective view of another embodiment of a packaging unit.

FIG. 44 illustrates another embodiment of a packaging unit 4010 configured to communicate with a processor (not shown). The packaging unit 4010 in this illustrated embodiment is in the form of a box, but other types of packaging units can be used. The packaging unit 4010 in this illustrated embodiment packages an adjunct 4012 retaining a medicant (obscured in FIG. 44) therein. A sensor 4014 attached to the packaging unit 4010 is configured to monitor at least one exposure condition, as discussed herein. The packaging unit 4010 also includes an electrical contact 1016 that is configured to read the sensed data from the sensor 4012. The sensor 4014 and the electrical contact 1016 are contained in the packaging unit 4010 with the adjunct 4012. The sensor 1014 is positioned in close proximity to the electrical contact 1016. As such, once the sensor 1014 is positioned close to or in direct contact with the electrical contact 1016, the sensor 1014 is read by the electrical contact 1016 (e.g., a reader) and the data from the sensor 1014 can be transmitted via a communications interface of the packaging unit to a processor, as discussed herein. In this illustrated embodiment, the data is wirelessly transmitted to the processor using the packaging unit's communications interface, which is part of the electrical contact 1016 in this illustrated embodiment.

Figure 45:
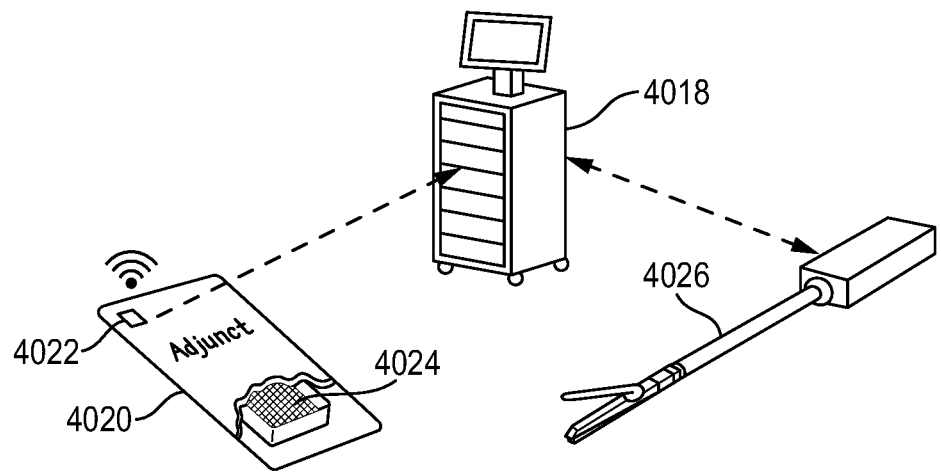
FIG. 45 is a perspective view of another embodiment of a communication network including another embodiment of a packaging unit, one exemplary embodiment of a surgical hub, and another embodiment of a surgical stapler.

A processor configured to communicate with a packaging unit can be a component of a computer system, such as an embodiment of a computer system 4018 shown in FIG. 45. The computer system 4018 is configured to communicate wirelessly with a packaging unit 4020, e.g., the packaging unit 4002 of FIG. 43, the packaging unit 4010 of FIG. 44, or other packaging unit, via a communications interface 4022, e.g., a QR code, an RFID tag, etc., of the packaging unit 4012. The communications interface 4022 can be part of a multi-functional component, such as a sensor including communications technology, a microcontroller including sensing and communicating technology, etc., or a separate sensor configured to communicate gathered data to the communications interface can be attached to the packaging unit 4020. The packaging unit 40202 in this illustrated embodiment packages an adjunct 4024 retaining a medicant (obscured in FIG. 45) therein. The computer system 4018 is also configured to communicate wirelessly with a surgical instrument 4026, e.g., via a communications interface (obscured in FIG. 45) of the surgical instrument 4026, which in this illustrated embodiment includes a linear surgical stapler but can be another type of surgical instrument as discussed herein. The computer system 4018 can have a variety of configurations, such as computer systems 4028, 4030 shown in FIG. 46 and FIG. 47, which are discussed further below. The computer system 4018 in this illustrated embodiment includes a surgical hub. Surgical hubs are also discussed further below.

In some embodiments, a packaging unit can package a plurality of other packaging units, e.g., package a plurality of the packaging units 4010 of FIG. 44, package a plurality of the packaging units 4020 of FIG. 45, package a plurality of the packaging units 4010 of FIG. 44, and a plurality of the packaging units 4020 of FIG. 45, package a plurality of the packaging units 4002 of FIG. 43, or package a plurality of some other combination and/or type of packaging units. Such a packaging unit packaging a plurality of packaging units is generally referred to herein as a "bulk packaging unit." The bulk packaging unit can include a sensor and communications interface as described herein and thus serve as an exposure condition monitor for all of the packaging units packaged in the bulk packaging unit. Such a configuration may reduce overall cost since each of the packaging units packaged in the bulk packaging unit need not include a sensor and communications interface as described herein.

However, for added reliability and/or to account for exposure after a packaging unit is removed from the bulk packaging unit, each of the packaging units packaged in the case can include a sensor and communications interface as described herein. The bulk packaging unit including the sensor and communications interface may help reduce concerns such as over-pressurization of a packaging unit's foil pouch that could break the pouch's sterile seal since the foil pouch will be in the bulk packaging unit when travelling long distances via air travel and thus have some protection from over-pressurization. A medicant may prematurely release if subjected to over-pressurization, so the bulk packaging unit may also help prevent premature medicant release.

Computer Systems

Figure 46:
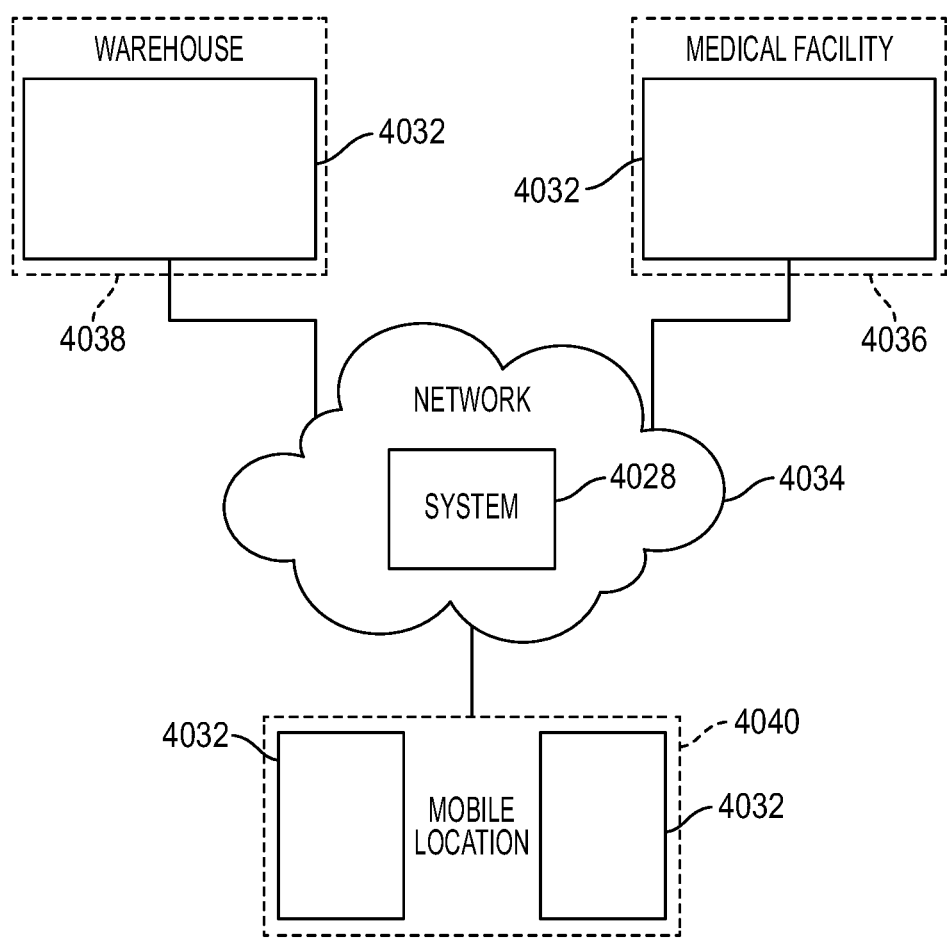
FIG. 46 is a schematic view of another embodiment of a communication network.

As mentioned above, a communications interface can be associated with an adjunct and/or a medicant retained by an adjunct, such as by a packaging unit that packages the adjunct and any medicants retained therein including the communications interface. Such a communications interface can be configured to communicate with a computer system, such a central computer system 4028 shown in FIG. 46. As shown in FIG. 46, a communications interface associated with a packaging unit 4032 packaging an adjunct having a medicant retained therein is configured to communicate with the central computer system 4028 through a communications network 4034 from any number of locations such as a medical facility 4036 (e.g., a hospital or other medical care facility), a warehouse 4038 (e.g., a distribution center or other stop in the packaging unit's supply chain), or a mobile location 4040 (e.g., between stops along the packaging unit's supply chain). The communications interface can be configured to access the computer system 4028 through a wired and/or wireless connection to the network 4034. In an exemplary embodiment, the communications interface is configured to access the computer system 4028 wirelessly, e.g., through Wi-Fi connection(s), which can facilitate accessibility of the computer system 4034 from almost any location in the world.

A person skilled in the art will appreciate that the computer system 4034 can include security features such that the aspects of the computer system 4034 available to any particular node can be determined based on, e.g., the identity of the node and/or the location from which the node is accessing the system. To that end, each node can have a unique key, username, password, and/or other security credentials to facilitate access to the computer system 4034. The received security parameter information can be checked against a database of authorized nodes to determine whether the node is authorized and to what extent the node is permitted to interact with the computer system 4034, view information stored in the computer system 4034, and so forth.

As discussed herein, one or more aspects or features of the subject matter described herein, for example components of the central computer system 4034 and sensors, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As discussed herein, this feedback may be provided as a warning.

Figure 47:
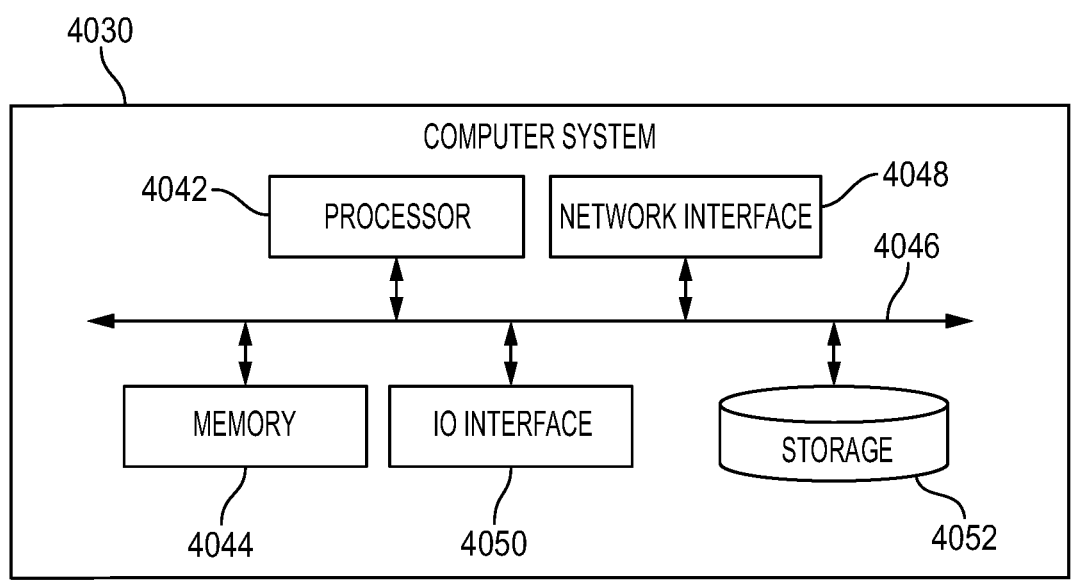
FIG. 47 is a schematic view of one exemplary embodiment of a computer system.

FIG. 47 illustrates one exemplary embodiment of the computer system 4028, depicted as computer system 4030. The computer system includes one or more processors 4042 configured to control the operation of the computer system 4030. The processor(s) 4042 can include any type of microprocessor or central processing unit (CPU), including programmable general-purpose or special-purpose microprocessors and/or any one of a variety of proprietary or commercially available single or multi-processor systems. The computer system 4030 also includes one or more memories 4044 configured to provide temporary storage for code to be executed by the processor(s) 4042 or for data acquired from one or more users, storage devices, and/or databases. The memory 4044 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 4046. The illustrated bus system 4046 is an abstraction that represents any one or more separate physical busses, communication lines/interfaces, and/or multi-drop or point-to-point connections, connected by appropriate bridges, adapters, and/or controllers. The computer system 4030 also includes one or more network interface(s) 4048 (also referred to herein as a communications interface), one or more input/output (IO) interface(s) 4050, and one or more storage device(s) 4052.

The communications interface(s) 4048 are configured to enable the computer system to communicate with remote devices, e.g., other communications interfaces or other computer systems, over a network, and can be, for example, remote desktop connection interfaces, Ethernet adapters, and/or other local area network (LAN) adapters. The IO interface(s) 4050 include one or more interface components to connect the computer system 4030 with other electronic equipment. For example, the IO interface(s) 4050 can include high speed data ports, such as universal serial bus (USB) ports, 1394 ports, Wi-Fi, Bluetooth, etc. Additionally, the computer system 4030 can be accessible to a human user, and thus the IO interface(s) 4050 can include displays, speakers, keyboards, pointing devices, and/or various other video, audio, or alphanumeric interfaces. The storage device(s) 4052, which may also be categorized as a memory, include any conventional medium for storing data in a non-volatile and/or non-transient manner. The storage device(s) 4052 are thus configured to hold data and/or instructions in a persistent state in which the value(s) are retained despite interruption of power to the computer system. The storage device(s) 4052 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 4052 include a tangible or non-transitory computer readable medium configured to store data, e.g., a hard disk drive, a flash drive, a USB drive, an optical drive, a media card, a diskette, or a compact disc.

The elements illustrated in FIG. 47 can be some or all of the elements of a single physical machine. In addition, not all of the illustrated elements need to be located on or in the same physical machine.

The computer system 4030 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 4030 can also include a web server for generating and/or delivering the web pages to client computer systems.

As shown in FIG. 46, the computer system 4030 of FIG. 47 as described above may form the components of the central computer system 4028 which is in communication with one or more communication interfaces each associated with at least one packaging unit. Data can be exchanged between the central computer system 4030 and the one or more communications interfaces. The computer system 4030 can also be configured to communicate with one or more additional computer systems.

In an exemplary embodiment, the computer system 4030 can be a single unit, e.g., a single server, a single desktop computer, a single laptop, a single mobile phone, a single electronic tablet, a single smart watch, a single tower, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 4030 can also include any of a variety of other software and/or hardware components, including by way of example, operating systems and database management systems. Although an exemplary computer system is depicted and described herein, it will be appreciated that this is for sake of generality and convenience. In other embodiments, the computer system may differ in architecture and operation from that shown and described here. For example, the memory 4044 and storage device 4052 can be integrated together or a sensor can be included with the computer system 4030.

In an exemplary embodiment, a computer system to which data, e.g., data acquired by a sensor associated with an adjunct and/or regarding a medicant retained by an adjunct, includes a surgical hub. Exemplary embodiments of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020, which are incorporated by reference herein in their entireties.

In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as surgical devices that are used to conduct medical procedures on patients, sensors configured to monitor exposure conditions, etc. The surgical hubs provide a wide array of functionality to improve the outcomes of medical procedures. The data generated by the various surgical devices, sensors, and surgical hubs about the patient and the medical procedure may be transmitted to the cloud-based medical analytics system. This data may then be aggregated with similar data gathered from many other surgical hubs, sensors, and surgical devices located at other medical facilities. Various patterns and correlations may be found through the cloud-based analytics system analyzing the collected data. Improvements in the techniques used to generate the data may be generated as a result, and these improvements may then be disseminated to the various surgical hubs and surgical devices. Due to the interconnectedness of all of the aforementioned components, improvements in medical procedures and practices may be found that otherwise may not be found if the many components were not so interconnected. Various examples of structures and functions of these various components are described in more detail in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020.

Figure 48:
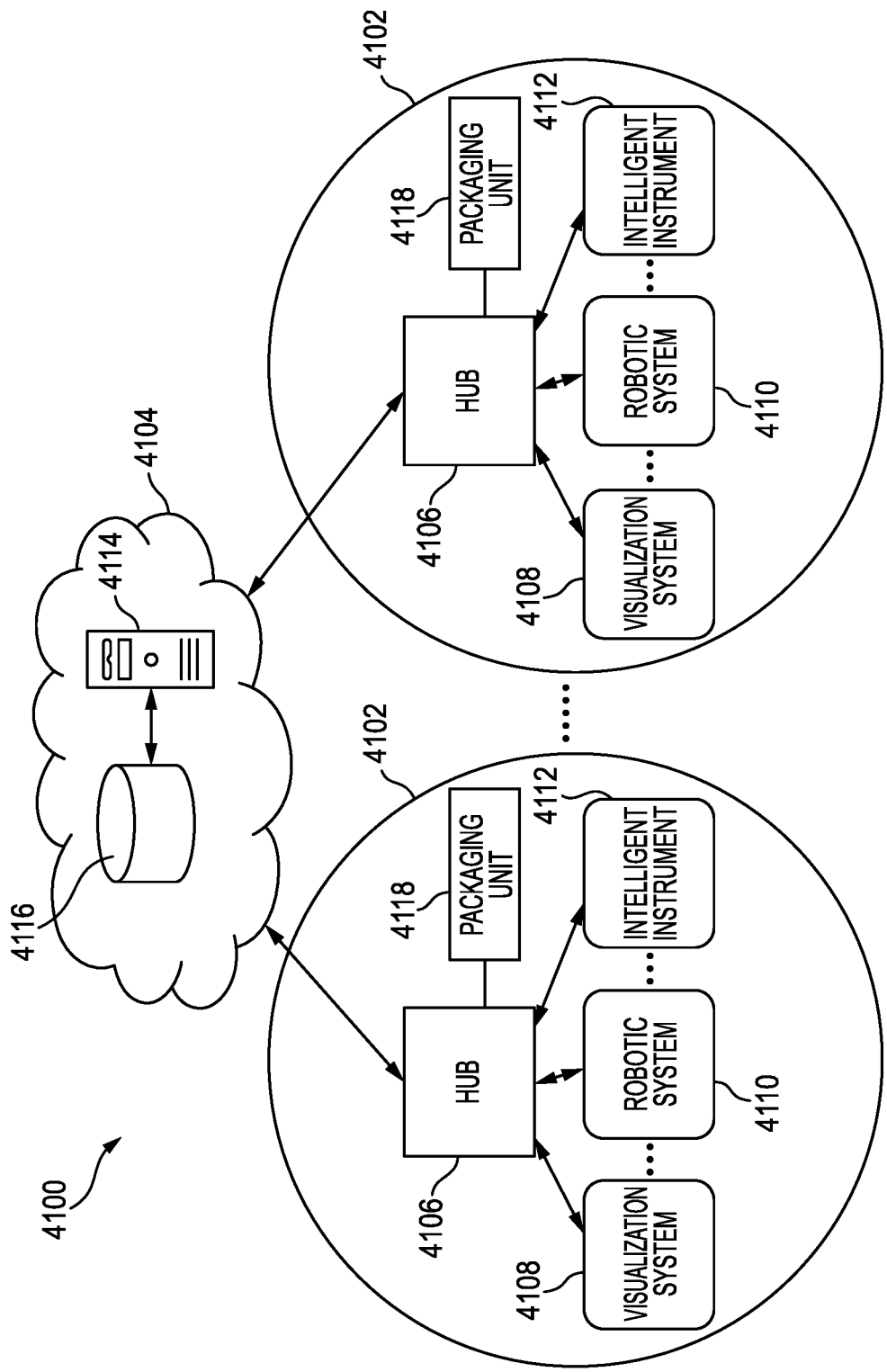
FIG. 48 is a schematic view of one exemplary embodiment of a computer-implemented interactive surgical system.

FIG. 48 illustrates an embodiment of a computer-implemented interactive surgical system 4100 that includes one or more surgical systems 4102 and a cloud-based system (e.g., a cloud 4104 that can include a remote computer system 4114 (a server in this illustrated embodiment) coupled to a storage device 4116). Each surgical system 4102 includes at least one surgical hub 4106 in communication with the cloud 4104. In one example, as illustrated in FIG. 48, the surgical system 4102 includes a visualization system 4108, a robotic system 4110, an intelligent surgical instrument 4112, and a packaging unit 4118 (e.g., packaging an adjunct having a medicant retained therein) which are configured to communicate with one another and/or the hub 4106. As discussed herein, in an exemplary embodiment, the packaging unit 4118 is configured to communicate with the surgical hub 4106, which can communicate with each of the visualization system 4108, the robotic system 4110, the intelligent surgical instrument 4112, and the packaging unit 4118. The surgical system 4102 can include an M number of hubs 4106, an N number of visualization systems 4108, an O number of robotic systems 4110, 4 a P number of 4 intelligent surgical instruments 4112, and a Q number of packaging units 4118, where M, N, O, P, and Q are integers greater than or equal to one that may or may not be equal to any one or more of each other. Various exemplary examples of suitable robotic systems, visualization systems, cloud-based analytics, and intelligent surgical instruments that can be used in a computer-implemented interactive surgical system are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020.

The surgical instruments 4112 in the system 4100 can be various types of tools. In an exemplary embodiment, the surgical instruments 4112 include surgical staplers configured to deliver an adjunct to tissue, such as the various surgical staplers and adjuncts discussed above. Thus, exposure conditions associated with adjuncts and medicant(s) retained therein can be communicated from the packaging units 4118 to their associated hubs 4106 and from the hubs 4106 to the cloud 4104, such as by communication interfaces of the packaging units 4118 each being configured to communicate sensed exposure condition data to the their associated one of the hubs 4106. The packaging units 4118 can also each be configured to communicate other data to the their associated one of the hubs 4106. The other data can include, for example, identification data that uniquely identifies the packaging unit 4118 and/or any one of more components packaged in and/or attached to the packaging unit 4118. Identification data can facilitate analysis of various useful metrics, such as surgical procedure outcomes, record of medicant delivery to the patient, record of adjunct delivery to the patient, etc. Data analysis may further employ outcome analytics processing, and using standardized approaches may provide beneficial feedback to either confirm surgical treatments and adjunct and/or medicant effectiveness or suggest modifications to surgical treatments, surgeon behavior, adjuncts, and/or medicants. For example, as discussed above, exposure conditions experienced by adjuncts and any medicant(s) retained therein can be monitored and tracked, which may facilitate analysis of how exposure conditions experienced by the adjunct and/or the medicant(s) retained by the adjunct affected surgical procedure outcomes, e.g., longer or shorter healing times, premature or delayed medicant release from the adjunct, etc., that can be used to modify a patient's post-operative treatment and/or to modify future evaluation of exposure conditions to help post-operatively observed adverse effects due to exposure conditions be accounted for in the future by, e.g., changing thresholds for exposure conditions.

Figure 49:
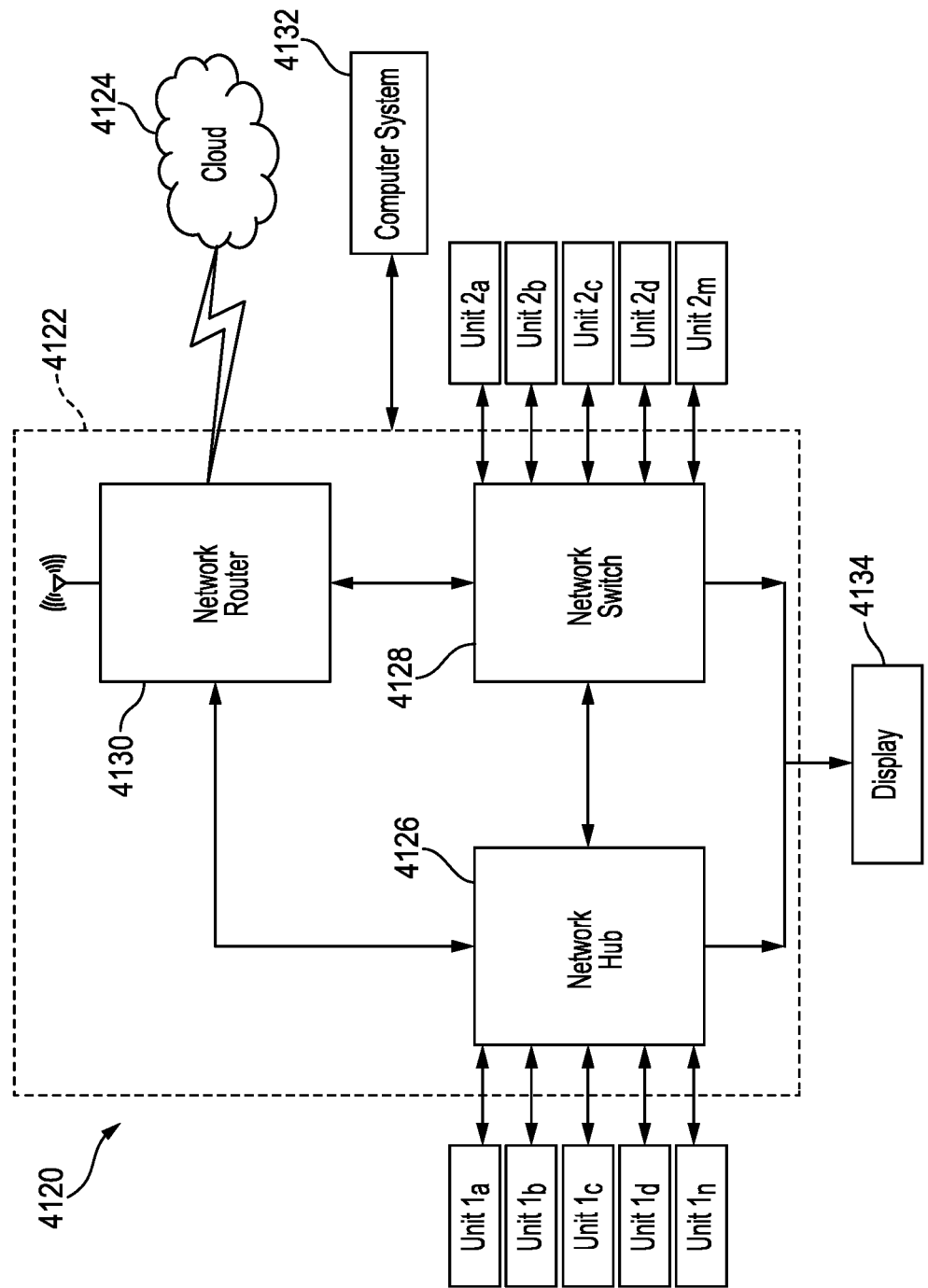
FIG. 49 is a schematic view of one exemplary embodiment of a surgical data network.

FIG. 49 illustrates one example of a surgical data network 4120 comprising a modular communication hub 4122, e.g., the hub 4106, configured to connect modular devices located in one or more operating theaters of a healthcare facility, or any room in a healthcare facility specially equipped for surgical operations, to a cloud-based system including a cloud 4124 that includes a remote server coupled to a storage device, e.g., the cloud 4104 that includes the remote server 4114 coupled to the storage device 4116. The modular communication hub 4122 includes a network hub 4126 and/or a network switch 4128 in communication with a network router 4130. The network hub 4126, the network switch 4128, and the network router 4130 define the communication hub's communications interface. The modular communication hub 4122 also can be coupled to a local computer system 4132 to provide local computer processing and data manipulation. The surgical data network 4120 can be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 4126 or network switch 4128. An "intelligent surgical data network" may be referred to as a "manageable hub" or "manageable switch." A switching hub reads the destination address of each packet and then forwards the packet to the correct port.

Modular units $1_a$-$1_n$, e.g., any number of packaging units such the packaging unit 4002 of FIG. 43, the packaging unit 4010 of FIG. 44, or other packaging unit, located in the operating theater can be coupled to the modular communication hub 4122. The network hub 4126 and/or the network switch 4128 can be coupled to the network router 4130 to connect the units $1_a$-$1_n$ to the cloud 4124 or the local computer system 4132. Data associated with the units $1_a$-$1_n$ can be transferred to cloud-based computers, e.g., to the cloud 4124, via the router 4130 for remote data processing and manipulation. Data associated with the units $1_a$-$1_n$ can also be transferred to the local computer system 4132 for local data processing and manipulation. Modular units $2_a$-$2_m$ located in the same operating theater also can be coupled to a network switch 4128. The network switch 4128 can be coupled to the network hub 4126 and/or the network router 4130 to connect to the units $2_a$-$2_m$ to the cloud 4124. Data associated with the units $2_a$-$2_n$ can be transferred to the cloud 4124 via the network router 4130 for data processing and manipulation. Data associated with the units $2_a$-$2_m$ can also be transferred to the local computer system 4132 for local data processing and manipulation. The numbers n, m of the units $1_a$-$1_n$/$2_a$-$2_m$ can be the same as or different from one another.

A person skilled in the art will appreciate that the surgical data network 4120 can be expanded by interconnecting multiple network hubs 4126 and/or multiple network switches 4128 with multiple network routers 4130. The modular communication hub 4122 can be contained in a modular control tower configured to receive multiple units $1_a$-$1_n$/$2_a$-$2_m$. The local computer system 4132 also can be contained in a modular control tower. The modular communication hub 4122 is connected to a display 4134 configured to display data obtained by at least some of the units $1_a$-$1_n$/$2_a$-$2_m$, and/or such data (and/or other data) analyzed by the cloud 4124 and/or the local computer system 4132, for example during surgical procedures.

The surgical data network 4120 can include a combination of network hub(s), network switch(es), and network router(s) connecting the units $1_a$-$1_n$/$2_a$-$2_m$ to the cloud 4124. Any one of or all of the units $1_a$-$1_n$/$2_a$-$2_m$ coupled to the network hub 4126 or network switch 4128 can collect data in real time and transfer the data to cloud computers for data processing and manipulation. Alternatively or in addition, any one or all of the units $1_a$-$1_n$/$2_a$-$2_m$ coupled to the network hub 4126 or network switch 4128 can transfer previously collected data, such as exposure condition data, to cloud computers for data processing and manipulation, e.g., once the one or all of the units $1_a$-$1_n$/$2_a$-$2_m$ is operatively connected to the cloud 4126 via the communication hub 4122. A person skilled in the art will appreciate that cloud computing relies on sharing computing resources rather than having local servers or personal devices to handle software applications. The term "cloud" can be used as a metaphor for "the Internet," although the term is not limited as such. Accordingly, the term "cloud computing" may be used herein to refer to "a type of Internet-based computing," where different services, such as servers, storage, and applications, are delivered to the modular communication hub 4122 and/or the computer system 4132 located in the surgical theater (e.g., a fixed, mobile, temporary, or field operating room or space) and to devices connected to the modular communication hub 4122 and/or the computer system 4132 through the Internet. The cloud infrastructure can be maintained by a cloud service provider. In this context, the cloud service provider can be the entity that coordinates the usage and control of the units $1_a$-$1_n$/$2_a$-$2_m$ located in one or more operating theaters. The cloud computing services can perform a large number of calculations based on the data gathered by packaging units, robots, and other computerized devices located in the operating theater. The hub hardware enables multiple devices or connections to be connected to a computer that communicates with the cloud computing resources and storage. Applying cloud computer data processing techniques on the data collected by the units $1_a$-$1_n$/$2_a$-$2_m$, the surgical data network may provide improved surgical outcomes, reduced costs, and/or improved patient satisfaction.

The operating theater devices $1_a$-$1_n$ can be connected to the modular communication hub 4122 over a wired channel or a wireless channel depending on the configuration of the units $1_a$-$1_n$ to a network hub, although as mentioned above wireless communication is used with packaging units in an exemplary embodiment. The network hub 4126 can be implemented as a local network broadcast device that works on the physical layer of the Open System Interconnection (OSI) model. The network hub 4126 provides connectivity to the units $1_a$-$1_n$ located in the same operating theater network. The network hub 4126 collects data in the form of packets and sends them to the router 4130 in half duplex mode. The network hub 4126 does not store any media access control/Internet Protocol (MAC/IP) to transfer the device data. Only one of the unit $1_a$-$1_n$ can send data at a time through the network hub 4126. The network hub 4126 has no routing tables or intelligence regarding where to send information and broadcasts all network data across each connection and to a remote server over the cloud 4124. The network hub 4126 can detect basic network errors such as collisions, but having all information broadcast to multiple ports can be a security risk and cause bottlenecks.

The units $2_a$-$2_m$ can be connected to the network switch 4128 over a wired channel or a wireless channel, although as mentioned above wireless communication is used with packaging units in an exemplary embodiment. The network switch 4128 works in the data link layer of the OSI model. The network switch 4128 is a multicast device for connecting the units $2_a$-$2_m$ located in the same operating theater to the network. The network switch 4128 sends data in the form of frames to the network router 4130 and works in full duplex mode. Multiple units $2_a$-$2_m$ can send data at the same time through the network switch 4128. The network switch 4128 can store and use MAC addresses of the units $2_a$-$2_m$ to transfer data.

The network hub 4126 and/or the network switch 4128 are coupled to the network router 4130 for connection to the cloud 4124. The network router 4130 works in the network layer of the OSI model. The network router 4130 creates a route for transmitting data packets received from the network hub 4126 and/or the network switch 4128 to cloud-based computer resources for further processing and manipulation of the data collected by any one of or all the units $1_a$-$1_n$/$2_a$-$2_m$. The network router 4130 can be employed to connect two or more different networks located in different locations, such as, for example, different operating theaters of the same healthcare facility or different networks located in different operating theaters of different healthcare facilities. The network router 4130 sends data in the form of packets to the cloud 4124 and works in full duplex mode. Multiple units can send data at the same time. The network router 4130 uses IP addresses to transfer data.

In one example, the network hub 4126 can be implemented as a USB hub, which allows multiple USB devices to be connected to a host computer. The USB hub can expand a single USB port into several tiers so that there are more ports available to connect units to the host system computer. The network hub 4126 can include wired or wireless capabilities to receive information over a wired channel or a wireless channel. A wireless USB short-range, high-bandwidth wireless radio communication protocol can be employed for communication between the units $1_a\text{-}1_n$ and units $2_a\text{-}2_m$ located in the operating theater.

In other examples, the units $1_a\text{-}1_n/2_a\text{-}2_m$ can communicate to the modular communication hub 4122 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the units $1_a\text{-}1_n/2_a\text{-}2_m$ can communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module can include a plurality of communication modules. For example, a first communication module may be dedicated to shorter-range wireless communications such as Wi-Fi and Bluetooth, and a second communication module can be dedicated to longer-range wireless communications such as GPS, EDGE, GPRS, CDMA, WiMAX, LTE, Ev-DO, and others.

The modular communication hub 4122 can serve as a central connection for one or all of the operating theater units $1_a\text{-}1_n/2_a\text{-}2_m$ and handle a data type known as frames. Frames carry the data generated by the units $1_a\text{-}1_n/2_a\text{-}2_m$. When a frame is received by the modular communication hub 4122, it is amplified and transmitted to the network router 4130, which transfers the data to the cloud computing resources by using a number of wireless or wired communication standards or protocols, as described herein.

The modular communication hub 4122 can be used as a standalone device or be connected to compatible network hubs and network switches to form a larger network. The modular communication hub 4122 is generally easy to install, configure, and maintain, making it a good option for networking the units $1_a\text{-}1_n/2_a\text{-}2_m$.

Figure 50:
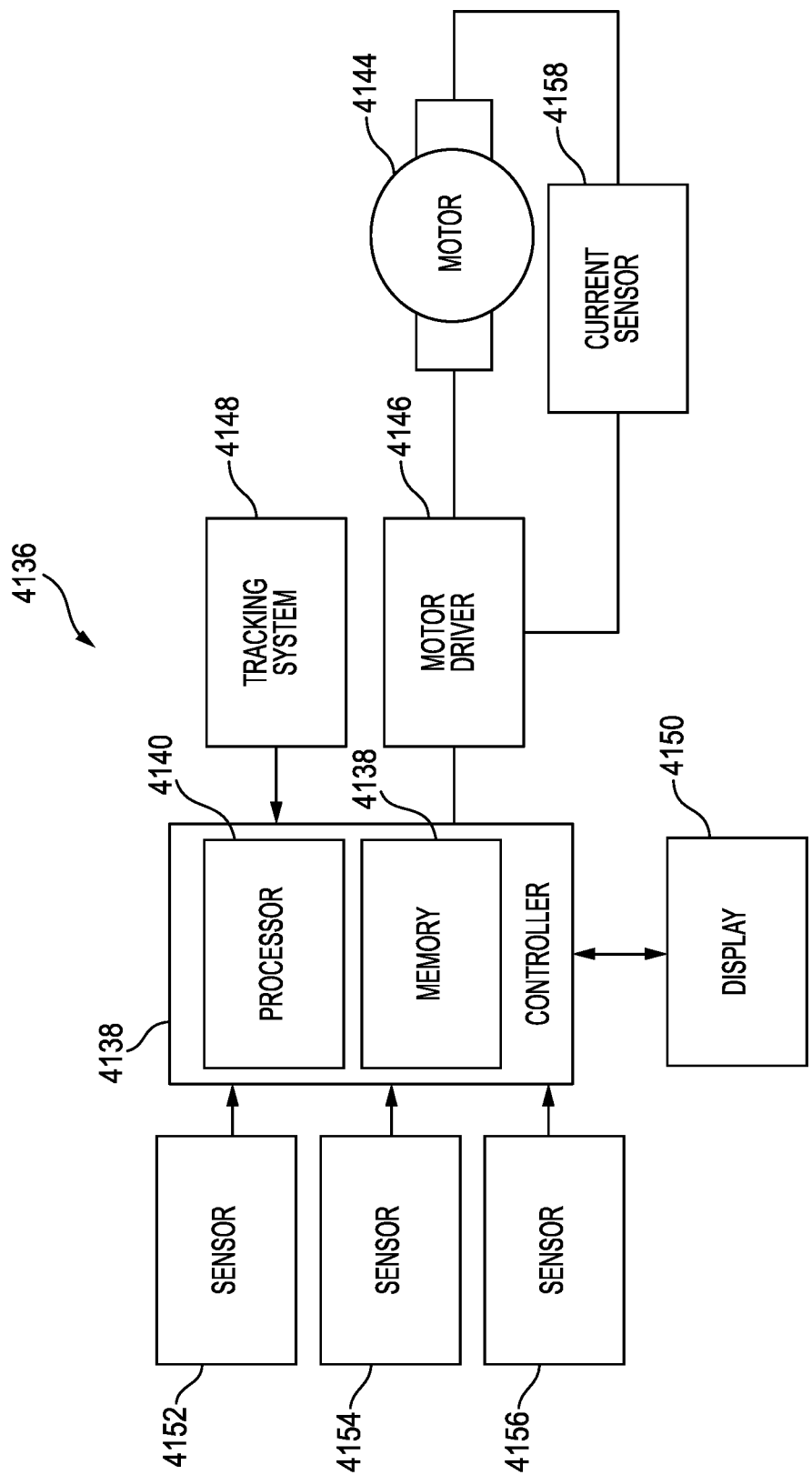
FIG. 50 is a logic diagram of one exemplary embodiment of a control system of a surgical instrument.

FIG. 50 illustrates an embodiment of a control system 4136 of a surgical instrument or tool, e.g., a surgical stapler as described herein. The control system 4136 includes a control circuit. The control circuit includes a controller that in this illustrated embodiment includes a microcontroller 4138 including a processor 4140 and a memory 4142. The microcontroller 4138 can be any single-core or multicore processor such as those known under the trade name ARM Cortex by Texas Instruments. A motor 4144, driven by a motor driver 4146, operably couples a longitudinally movable displacement member, such as a closure tube, a firing bar, an E-beam, and/or a knife, to fire staples, close jaws, and/or cut tissue, as discussed above. A tracking system 4148 is configured to determine the position of the longitudinally movable displacement member. The position information is provided to the processor 4140, which can be programmed or configured to determine the position of the longitudinally movable displacement member. Additional motors can be provided at the tool driver interface to control firing, closure tube travel, shaft rotation, and articulation. A display 4150 displays a variety of operating conditions of the instrument and can include touch screen functionality for data input. Information displayed on the display 4150 can be overlaid with images acquired via endoscopic imaging modules.

The microcontroller 4138 can be programmed to perform various functions such as precise control over the speed and position of knife and end effector articulation systems. The microcontroller 4138 can be configured to compute a response in the software of the microcontroller 4138. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor 4144 can be a brushed direct current (DC) motor with a gearbox and mechanical links to an articulation or knife system. The motor driver 4146 can be an A3941 available from Allegro Microsystems, Inc. Other motor drivers can be readily substituted for use in the tracking system 4148 including an absolute positioning system. Further description of absolute positioning systems is provided in U.S. Pat. Pub. No. 2017/0296213 entitled "Systems And Methods For Controlling A Surgical Stapling And Cutting Instrument" published Oct. 19, 2017, which is incorporated by reference herein in its entirety.

The motor 4144 can be controlled by the motor driver 4146 and can be employed by the firing system of the surgical instrument or tool. In various forms, the motor 4144 can be a brushed DC driving motor having a maximum rotational speed of approximately 25,000 RPM. In other arrangements, the motor 4144 can include a brushless motor, a cordless motor, a synchronous motor, a stepper motor, or any other suitable electric motor. The motor driver 4146 can include an H-bridge driver comprising field-effect transistors (FETs), for example. The motor 4144 can be powered by a power assembly releasably mounted to the handle assembly or tool housing for supplying control power to the surgical instrument. The power assembly can include a battery, which can include a number of battery cells connected in series that can be used as the power source to power the surgical instrument. In certain circumstances, the battery cells of the power assembly can be replaceable and/or rechargeable. For example, the battery cells can be lithium-ion batteries which can be couplable to and separable from the power assembly. The motor driver 4146 can be, for example, an A3941 available from Allegro Microsystems, Inc.

One or more of the control system's sensors 4152, 4154, 4156, 4158 can be configured to provide real-time feedback to the processor 4140. At least one of the sensors 4152, 4154, 4156, 4158 can be configured to monitor at least one operational parameter related to operation of the surgical instrument during a surgical procedure.

One example of a sensor configured to monitor an operational parameter includes a positon sensor configured to provide a unique position signal corresponding to the location of a displacement member, such as by being configured to measure linear displacement. Linear displacement sensors can include contact or non-contact displacement sensors. Examples of linear displacement sensors include linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, and any combination thereof.

Another example of a sensor configured to monitor an operational parameter is a strain gauge or a micro-strain gauge configured to measure one or more parameters of the surgical instrument's end effector. The measured strain is converted to a digital signal and provided to the processor 4140. For example, the strain gauge or micro-strain gauge can be configured to measure an amplitude of strain exerted on the surgical instrument's anvil during a clamping operation, which can be indicative of closure forces applied to the anvil and indicative of tissue compression. For example, the strain gauge or micro-strain gauge can be configured to measure a force applied to tissue by the surgical instrument's end effector.

Another example of a sensor configured to monitor an operational parameter is a load sensor configured to measure the closure force applied by the surgical instrument's closure drive system to the anvil. The load sensor can be configured to measure a firing force applied to an E-beam (or an I-beam) in a firing stroke of the surgical instrument.

Another example of a sensor configured to monitor an operational parameter is a load sensor configured to measure a force used to operate the cutting element, e.g., knife, of the surgical instrument that cuts tissue captured between the end effector's jaws.

Another example of a sensor configured to monitor an operational parameter is a magnetic field sensor configured to measure thickness of tissue captured between the end effector's jaws. The measurement of the magnetic field sensor can be converted to a digital signal and provided to the processor 4140.

Another example of a sensor configured to monitor an operational parameter is a current sensor 4158 configured to measure current drawn by the motor 4144. A force required to advance the firing member can correspond to the current drawn by the motor 4144, for example. The measured force is converted to a digital signal and provided to the processor 4140.

Measurements of tissue compression, tissue thickness, and/or force required to close the end effector on tissue can be used by the microcontroller 4138 to characterize the selected position of the firing member, the corresponding value of the speed of the firing member, and/or motor power level. For example, the memory 4142 can store a technique, an equation, and/or a lookup table which can be employed by the microcontroller 4138 in the assessment.

Sensors configured to sense operational parameters and uses of sensor-measured data, including to control operation of the surgical instrument using a robotic surgical system, are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020.

The control system 4136 of the surgical instrument can include a wired or wireless communications interface configured to communicate with a modular communication hub, such as the modular communication hub 4122 of FIG. 49.

Analysis of Exposure Conditions

As discussed above, one or more exposure conditions of an adjunct and any medicant(s) therein can be monitored, such as by using one or more sensors of a packaging unit, and a processor, such as of a surgical hub or other computer system, can be configured to receive data gathered by the one or more sensors regarding the one or more exposure conditions. As also discussed above, the processor can be in operative communication with a memory configured to store data therein. The stored data can include predetermined threshold(s) for each of one or more exposure conditions that the processor may receive data regarding from a data module. Each of the predetermined threshold(s) can be associated with a particular medicant (or family of related medicants) and/or a particular adjunct (or family of related adjuncts, such as adjuncts all made from a same material). The processor can be configured to compare received exposure condition data to the predetermined threshold for the corresponding exposure condition and element (medicant and/or adjunct), and provide data output.

Figure 51:
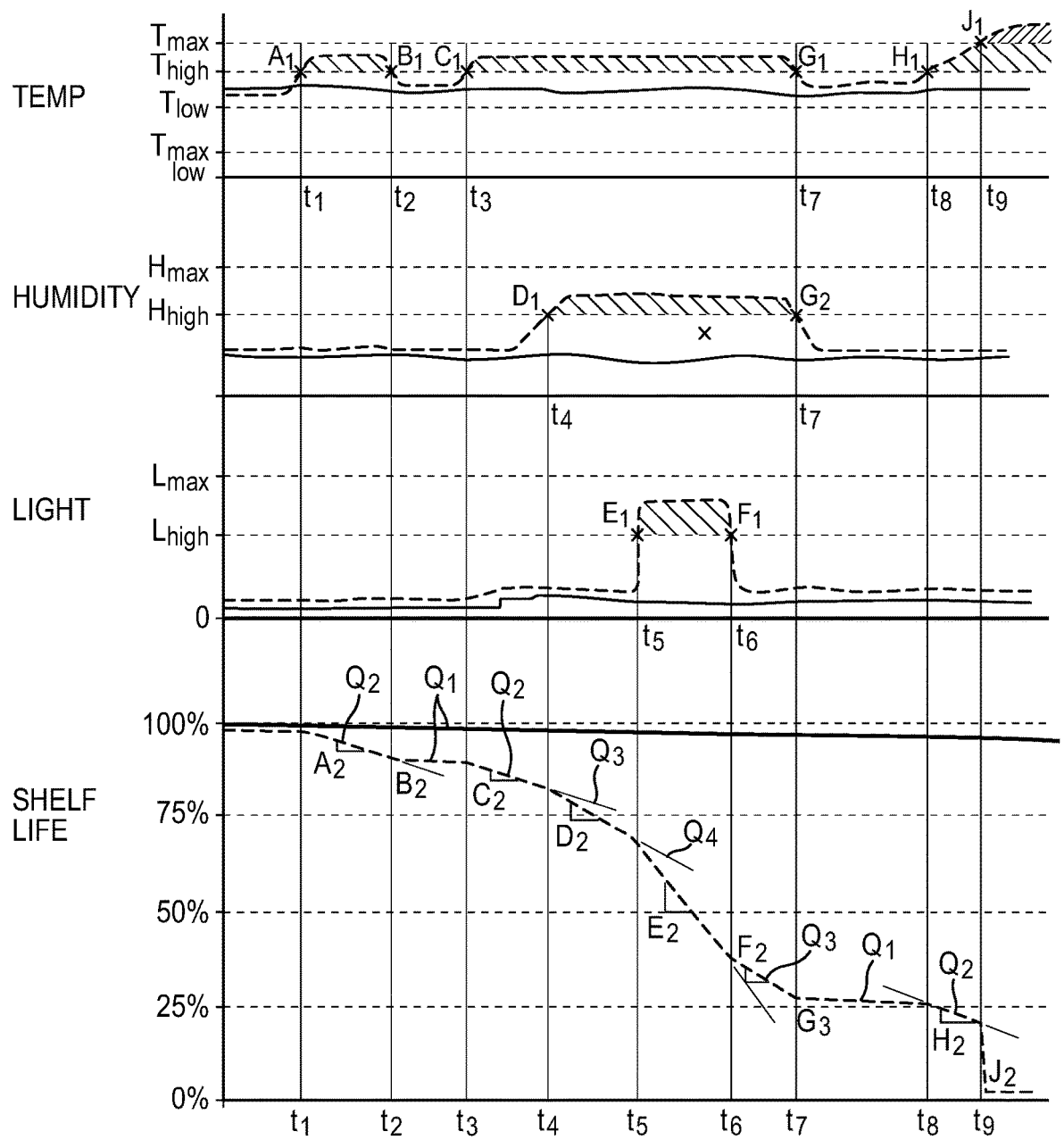
FIG. 51 is a graph showing exposure conditions and shelf life over time.

One embodiment of exposure condition data and processor analysis is shown in FIG. 51. In this illustrated embodiment, the processor is configured to determine a rate of shelf life degradation of an adjunct packaged by a packaging unit based on measurements of temperature, humidity, and light. As discussed above, the adjunct has at least one medicant retained therein, and the packaging unit can package other components therein such as at least one cartridge body, one or more additional adjuncts, etc. As shown in FIG. 51, a sensor of the packaging unit, e.g., the sensor 4008 of FIG. 43, the sensor 4014 of FIG. 44, the sensor 4022 of FIG. 45, etc., can be configured to track temperature, humidity, and light exposure over nine different time intervals $t_1$, $t_2$, $t_3$, $t_4$, $t_5$, $t_6$, $t_7$, $t_8$, $t_9$. As mentioned above, the sensor can be a single sensor configured to monitor multiple exposure conditions or can be a plurality of sensors each configured to sense at least one of the exposure conditions. The following discussion is also applicable to other exposure conditions, e.g., ultraviolet, pressure, etc.

A memory operably coupled to the processor has predetermined thresholds stored therein for each of temperature, light, and humidity. For temperature, the predetermined thresholds include a low temperature maximum $T_{MaxLow}$, a low temperature $T_{Low}$, a high temperature $T_{high}$, and a high temperature maximum $T_{Max}$. A temperature range between the low temperature $T_{Low}$ and the high temperature $T_{high}$ is an acceptable temperature range for the adjunct in which the temperature will not adversely affect shelf life. A temperature below the low temperature $T_{Low}$, and/or below the temperature maximum $T_{MaxLow}$ will adversely affect shelf life. A temperature below the temperature maximum $T_{MaxLow}$ indicates that the adjunct has been exposed to an adverse enough temperature that the adjunct not be used. A temperature above the high temperature $T_{High}$ and/or above the high temperature maximum $T_{Max}$ will adversely affect shelf life. A temperature above the high temperature maximum $T_{Max}$ indicates that the adjunct has been exposed to an adverse enough temperature that the adjunct not be used. As shown in FIG. 51, from time zero to time $t_1$, between time $t_2$ and time $t_3$, and between time $t_7$ and time $t_8$ the temperature is sensed to be in the acceptable range; between time $t_1$ and time $t_2$, between time $t_3$ and time $t_7$, and between time $t_8$ and $t_9$ the temperature is sensed to be above the high temperature $T_{High}$ and below the high temperature maximum $T_{Max}$, and after time $t_9$ the temperature is sensed to be above the high temperature maximum $T_{Max}$.

For humidity, the predetermined thresholds include a high humidity $H_{High}$ and a humidity maximum $H_{max}$. A humidity above the high humidity $H_{High}$ and/or above the humidity maximum $H_{max}$ will adversely affect shelf life. A humidity above the humidity maximum $H_{max}$ indicates that the adjunct has been exposed to an adverse enough humidity that the adjunct not be used. As shown in FIG. 51, from time zero to time $t_4$ and from time $t_7$ forward the humidity is sensed to be in the acceptable range below the high humidity $H_{High}$, and from time $t_4$ to time $t_7$ the humidity is sensed to be above the above the high humidity $H_{High}$ and below the humidity maximum $H_{max}$.

For light, the predetermined thresholds include a high light $L_{High}$ and a light maximum $L_{Max}$. Zero light indicates darkness (no light exposure). A light above the high light $L_{High}$ and/or above the light maximum $L_{Max}$ will adversely affect shelf life. A light above the light maximum $L_{Max}$ indicates that the adjunct has been exposed to an adverse enough light that the adjunct not be used. As shown in FIG. 51, from time zero to time $t_5$ and from time $t_6$ forward the light is sensed to be in the acceptable range below the high light $L_{High}$, and from time $t_5$ to time $t_6$ the light is sensed to be above the high light $L_{High}$ and below the light maximum $L_{Max}$.

In general, the shelf life of the adjunct is affected adversely at a first rate when only one of the exposure conditions is outside the acceptable range at the same time, is affected at a second rate greater than the first rate when two of the three of the exposure conditions are outside the acceptable range at the same time, and is affected at a third rate greater than the second rate when all three of the exposure conditions are outside the acceptable range at the same time. For example, as shown in FIG. 51, the shelf life of the adjunct decreases at a first, very low rate $Q_1$ when all of temperature, humidity, and light are sensed to be in their respective acceptable ranges from time zero to time $t_1$, from time $t_2$ to time $t_3$, and time $t_7$ to time $t_8$. The passage of time accounts for the first rate $Q_1$ of shelf life reduction. When only temperature is sensed to be outside the acceptable temperature range from time $t_1$ to time $t_2$, from time $t_3$ to time $t_4$, and from time $t_8$ forward, the shelf life of the adjunct reduces at a second rate $Q_2$ that is greater than the first rate $Q_1$. When each of temperature and humidity are sensed to be outside their respective acceptable ranges and light is sensed to be within its acceptable range from time $t_4$ to time $t_5$, the shelf life of the adjunct reduces at a third rate $Q_3$ that is greater than the second rate $Q_2$. The third rate $Q_3$ is about three times greater than the first rate $Q_1$ in this illustrated embodiment where the adverse exposure conditions are temperature and humidity. When all of temperature, humidity, and light are sensed to be outside their respective acceptable ranges from time $t_5$ to time $t_6$, the shelf life of the adjunct reduces at a fourth rate $Q_4$ that is greater than the third rate $Q_3$. The fourth rate $Q_4$ is about five times greater than the first rate $Q_1$ in this illustrated embodiment where the adverse exposure conditions are temperature, light, and humidity. When the shelf life reaches 0%, the processor determines that the adjunct is no longer fit for use. If before the shelf life reaches 0% the adjunct experiences a fatal exposure event, the processor determines that the adjunct is no longer fit for use. In this illustrated embodiment, the adjunct experiences a fatal exposure event before the shelf life reaches 0% by the temperature being sensed to be above the high temperature maximum $T_{Max}$ at time $t_9$. The processor thus determines that the adjunct is no longer fit for use after $t_9$. In some embodiments, instead of waiting until the shelf life reaches 0% to determine that the adjunct is no longer fit for use, the percentage threshold for such an unfit determination can be a percentage above zero, such as 15%, 10%, 5%, 8%, 3%, 2%, etc. The unfit threshold percentage being above 0% reflects that even though the adjunct has some remaining shelf life, the life is low enough that an adjunct with greater shelf life should be used to help ensure adjunct effectiveness in a patient.

If the processor determines that the adjunct is unfit for use, e.g., has a shelf life of 0% (or other predetermined threshold for non-viability) or any one or more of the exposure conditions has been sensed to be at a fatal level (temperature above the high temperature maximum $T_{Max}$, humidity above the humidity maximum $H_{Max}$, light above the light maximum $L_{Max}$, the processor is configured to transmit a data output characterizing the determination so that a warning to not use the adjunct can be provided as discussed herein (e.g., email warning, visual warning on a display, audible warning, tactile warning, etc.) and/or to transmit a data output causing such a warning to be provided. The processor can be similarly configured to transmit a data output to indicate an adjunct's current determined shelf life, which may help a surgeon or other medical professional decide whether or not to use the adjunct. The processor can be similarly configured to transmit a data output to indicate any times when the adjunct experiences an adverse exposure event and indications of the exposure event, which may help a manufacturer, distributor, or other provider evaluate storage conditions and/or transport options for its packaging unit.

Figure 52:
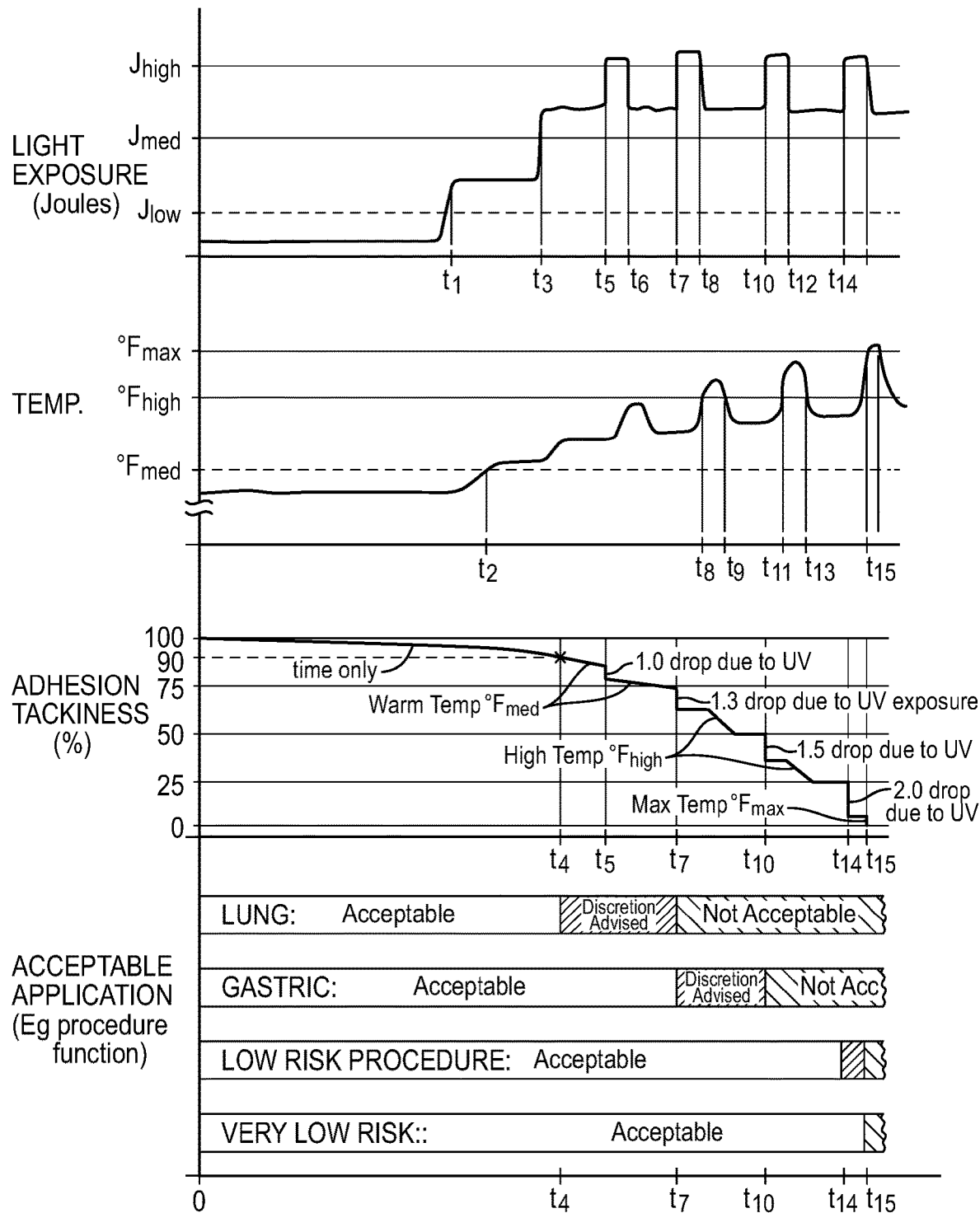
FIG. 52 is a graph showing exposure conditions, adhesion tackiness, and acceptable application over time.

Another embodiment of exposure condition data and processor analysis is shown in FIG. 52. In this illustrated embodiment, the processor is configured to determine indications and contraindications of an adjunct packaged by a packaging unit based on measurements of temperature and light. As discussed above, the adjunct has at least one medicant retained therein, and the packaging unit can package other components therein such as at least one cartridge body, one or more additional adjuncts, etc. As shown in FIG. 52, a sensor of the packaging unit, e.g., the sensor 4008 of FIG. 43, the sensor 4014 of FIG. 44, the sensor 4022 of FIG. 45, etc., can be configured to track temperature and light exposure over fifteen different time intervals (time zero to $t_{15}$). As mentioned above, the sensor can be a single sensor configured to monitor multiple exposure conditions or can be a plurality of sensors each configured to sense at least one of the exposure conditions. The following discussion is also applicable to other exposure conditions, e.g., ultraviolet, pressure, humidity, etc.

A memory operably coupled to the processor has predetermined thresholds stored therein for each of temperature and light similar to that discussed above regarding FIG. 51. In this illustrated embodiment, for temperature, the predetermined thresholds include a medium temperature $F_{med}$, a high temperature $F_{high}$, and a high temperature maximum $F_{max}$. A temperature range below the medium temperature $F_{med}$ is an acceptable temperature range for the adjunct in which the temperature will not adversely affect the adjunct's indications or contraindications. A temperature above the medium temperature $F_{med}$ and below the high temperature $F_{high}$ will degrade the adjunct at a first, medium level of degradation. A temperature above the high temperature $F_{high}$ and below the high temperature maximum $F_{max}$ will degrade the adjunct at a second, high level of degradation that is greater than the first level of degradation. A temperature above the high temperature maximum $F_{max}$ indicates that the adjunct has been exposed to an adverse enough temperature that the adjunct has been contraindicated and should not be used.

For light, the predetermined thresholds include a low light $J_{low}$, a medium light $J_{med}$, and a high light $J_{high}$. A light range below the low light $J_{low}$ is an acceptable light range for the adjunct in which the light will not adversely affect the adjunct's indications or contraindications. A light above the low light $J_{low}$ and below the medium light $J_{med}$ will degrade the adjunct at a first, low level of degradation. A light above the medium light $J_{med}$ and below the high light $J_{high}$ will degrade the adjunct at a second, medium level of degradation that is greater than the first level of degradation. A temperature above the high light $J_{high}$ indicates that the adjunct has been exposed to an adverse enough light that the adjunct has been contraindicated and should not be used. In this illustrated embodiment, the light range below the low light $J_{low}$ corresponds to darkness (no light exposure), light above the low light $J_{low}$ and below the medium light $J_{med}$ corresponds to indoor lighting exposure, light above the medium light $J_{med}$ and below the high light $J_{high}$ corresponds to indirect sunlight exposure, and light above the high light $J_{high}$ corresponds to direct sunlight exposure.

In general, FIG. 52 illustrates attachment adhesive degradation of the adjunct and its relationship to a surgical procedure in which the adjunct is planned to be used. The processor adjusts a durability threshold for the adjunct and compares the durability threshold to predetermined durability requirements of the surgical procedure. The comparison results in a data output of the processor that includes a recommendation or a change in the adjunct's usage status, procedure indications, or steps-of-use of the adjunct.

In this illustrated embodiment, the processor determines that the adjunct is acceptable for use in lung applications, gastric applications, low risk procedures, and very low risk procedures until time $t_4$. The data output of the processor would thus be "acceptable" for use of the adjunct. At time $t_4$, the adjunct has been experiencing a temperature above the medium temperature $F_{med}$ and below the high temperature $F_{high}$ since time $t_2$ and has been experiencing indoor lighting exposure since time $t_3$. The adjunct's adhesion tackiness has thus been reduced from 100% at time $t_2$ to 90% at time $t_4$. Adhesion tackiness of 90% is acceptable for gastric applications, low risk procedures, and very low risk procedures but is questionable for lung applications where tackiness has greater importance due to the particular importance of any leaks in the lung because of the adverse effect of leaks on breathing. The data output of the processor would thus be "acceptable" for use of the adjunct in gastric applications, low risk procedures, and very low risk procedures and "discretion advised" in lung applications. These indications and contraindications remain until time $t_7$, when the adjunct's exposures to light and temperature have reduced the adjunct's tackiness to 60%. Adhesion tackiness of 60% to 90% is acceptable for gastric applications, low risk procedures, and very low risk procedures but is questionable for lung applications. Adhesion tackiness below 60% is unacceptable for lung applications. The data output of the processor would thus be "unacceptable" for use of the adjunct in lung applications. Adhesion tackiness reducing to 60% does not change the adjunct's effectiveness for low risk procedures or very low risk procedures but does change the adjunct's effectiveness for gastric applications where the adjunct's tackiness may begin to be low enough to adversely affect proper gastric function with the adjunct implanted in the patient. The output of the processor would thus be "acceptable" for use of the adjunct in low risk procedures and very low risk procedures and "discretion advised" in gastric applications. These indications and contraindications remain until time $t_{10}$, when the adjunct's exposures to light and temperature have reduced the adjunct's tackiness to 40%. Adhesion tackiness below 40% is unacceptable for gastric applications. The data output of the processor would thus be "unacceptable" for use of the adjunct in gastric applications (as well as in lung applications, as above). Adhesion tackiness reducing to 40% does not change the adjunct's effectiveness for low risk procedures or very low risk procedures. The output of the processor would thus be "acceptable" for use of the adjunct in low risk procedures and very low risk procedures. These indications and contraindications remain until time $t_{14}$, when the adjunct's exposures to light and temperature have reduced the adjunct's tackiness to 25%. Adhesion tackiness reducing to 25% does not change the adjunct's effectiveness for very low risk procedures but does change the adjunct's effectiveness for low risk procedures. The output of the processor would thus be "acceptable" for use of the adjunct in very low risk procedures and "discretion advised" in low risk procedures. These indications and contraindications remain until time $t_{15}$, when the adjunct is exposed to a temperature above the high temperature maximum $F_{max}$. The adjunct is thus deemed unfit for use in any application. The output of the processor would thus be "unacceptable" for all procedures.

FIG. 51 and FIG. 52 are discussed with respect to exposure conditions' effect on an adjunct, but exposure conditions can be similarly processed for a medicant in addition to or instead of exposure conditions for an adjunct. An adjunct can therefore be determined to be unfit for use based the adjunct's exposure to one or more adverse exposure conditions and/or the medicant's exposure to one or more adverse exposure conditions.

Adjunct, Staple Cartridge, and Stapler Compatibility

In some instances, an adjunct and a medicant retained therein may not have experienced any exposure conditions that adversely affect their performance but may still be unsuitable for use. Compatibility can be determined in addition to exposure condition monitoring and analysis discussed above or can be determined without any exposure condition monitoring and analysis. Determining compatibility without any exposure condition monitoring and analysis may allow a packaging unit to be less costly and/or easier to manufacture since sensing capability need not be included.

In embodiments in which a staple cartridge is configured to be removably and replaceably coupled to an end effector of a surgical stapler, staples can only be fired out of the staple cartridge properly and/or safely if the staple cartridge is compatible with the surgical stapler. Staple cartridges have different sizes, so the staple cartridge removably and replaceably coupled to the end effector should have a size compatible with the particular end effector to which the staple cartridge is being coupled. Some surgical staplers may not be compatible with staple cartridges having an adjunct releasably coupled thereto, such as because the presence of the adjunct prevents the stapler's jaws from closing properly, because the presence of the adjunct prevents proper firing of staples because the stapler cannot provide sufficient force to drive the staples through the adjunct, because the cartridge is for a different kind of stapler (e.g., linear versus circular), and/or because the stapler's knife does not have sufficient sharpness and/or strength to cut the adjunct. It can therefore be important to establish compatibility between a surgical stapler and a staple cartridge having an adjunct releasably coupled thereto.

Establishing compatibility of a surgical stapler and a staple cartridge having an adjunct releasably coupled thereto generally involves determining whether the stapler, the staple cartridge, and the adjunct are predetermined to be suitable for use with one another. The establishment of compatibility before staples are attempted to be fired from the stapler may help ensure that the stapler and the adjunct can each function properly and/or help ensure that the patient is not injured or otherwise harmed by use of a stapler that includes a staple cartridge and/or adjunct that is incompatible therewith and should not be used with the stapler. In an exemplary embodiment, the compatibility is established before the staple cartridge is coupled to the stapler, e.g., before the staple cartridge is seated in the stapler's end effector, so as to necessarily be before the stapler attempts to fire staples from the staple cartridge.

In an exemplary embodiment, a method of establishing compatibility of a surgical stapler and a staple cartridge having an adjunct releasably coupled thereto includes a processor, e.g., of a surgical hub or other computer system, acquiring component data relating to the adjunct releasably coupled thereto from a packaging unit packaging the adjunct and comparing the component data with acceptable component data. The component data can be transmitted from the packaging unit using a communications interface of the packaging unit as discussed above, e.g., the communications interface transmitting stored data to an external device. In response to the component data not matching the acceptable component data, the processor can cause a warning to be provided indicating incompatibility. A user can thus be warned to not use incompatible components before attempting to use the components. A confirmation notification indicating compatibility can be provided in response to in response to the component data matching the acceptable component data. In some embodiments, the packaging unit packages the adjunct without the adjunct yet being releasably attached to the staple cartridge, with or without the packaging unit also packaging the adjunct. In other embodiments, the packaging unit packages the adjunct with the adjunct releasably attached to the staple cartridge, with the packaging unit not packaging the surgical stapler since the staple cartridge and the stapler being packaged together would indicate compatibility without component data comparison.

The method of establishing compatibility of a surgical stapler and a staple cartridge having an adjunct releasably coupled thereto may ensure that the correct staple cartridge and adjunct is utilized with the stapler. This may reduce a risk of inadvertently using unsuitable components that may lead to malfunction of the stapler, cartridge and/or adjunct, to improper or entirely absent staple deployment, and/or to incorrect implantation of the adjunct, each of which may be dangerous for the patient.

When a stapler is operated according to stored control parameters, establishing compatibility of components may ensure compatibility with the control parameters. For example, if the stapler has control parameters that indicate a maximum cutting element speed, establishing compatibility of components may ensure that the components are compatible with the cutting element speed and that, e.g., the adjunct will be cut as appropriate and will not unexpectedly tear or otherwise be unintentionally damaged in response to movement of the cutting element therethrough. The control parameters can be stored in a memory of the stapler or of an external device, and the comparison of whether the control parameters are suitable or need to be changed given the component data can be carried out by the processor.

The method can establish the compatibility of the stapler with only one of the cartridge and the adjunct releasably coupled to the adjunct or can establish the compatibility of the stapler with each of the cartridge and the adjunct releasably coupled to the adjunct. The stapler being compatible with only one of the cartridge and the adjunct releasably coupled to the adjunct can be indicative of the other of the cartridge and the adjunct releasably coupled to the adjunct being compatible with the stapler, e.g., because only certain size adjuncts can be used with certain size cartridges, because only certain adjuncts can be used with certain cartridges, etc.

Comparing the component data with the acceptable component data can include comparing component parameter(s), e.g., a number, a code, text, etc., of the component data with acceptable parameter(s), e.g., a number, a code, text, etc., of the acceptable component data stored at the external device that includes the processor and/or that is stored in a memory external to but accessible to the external device. The comparison includes determining whether each of one or more component parameters in the component data matches a corresponding parameter in the acceptable component data, with a match indicating compatibility and a mismatch indicating incompatibility. The acceptable component data can be stored, for example, in the form of a lookup table in which each possible component data receivable from a packaging unit is associated with acceptable staplers and/or cartridges. For another example, the acceptable component table can be stored as a lookup table that correlates adjuncts and/or staple cartridges usable with a particular surgical stapler to allow received component data to either be found in the table, indicating compatibility, or not found in the table, indicating incompatibility.

The acceptable component data can be updatable. Therefore, the suitability of the stapler with various cartridges and adjuncts can be updated based on developments in relation to the cartridge and adjunct and the stapler. For example, a lookup table stored in a memory of a surgical hub or other external device can be regularly updated with acceptable component data. For another example, an electronic instructions for user (eIFU) stored in a memory of a surgical hub or other external device can be regularly updated to include acceptable component data.

The component data stored at the packaging unit can include one or more component parameters. Examples of component parameters include adjunct manufacturer, adjunct model number, adjunct serial number, adjunct material, adjunct thickness, cartridge manufacturer, cartridge model number, cartridge serial number, and other parameters.

The component data can include an indication of compatible firing parameters. In this way, the first component data can indicate what one or more firing settings, e.g., motor speed, cutting element speed, tissue clamping force, etc., are suitable for operating with the component.

In addition to assessing the compatibility of the components, other approaches can be used for ensuring that only compatible devices are utilized. For example, a physical interface between the components can be sized and shaped to limit the physical compatibility to include components that are known to be compatible, such as by a staple cartridge and a jaw of an end effector having complementary mating features. In this way, the number of staple cartridges, and thus adjuncts releasably coupled to the cartridges, that are able to be coupled to the stapler is restricted and thereby reduces the possibility of utilizing non-compatible components.

In addition to component data, the packaging unit can be configured to transmit expiration date data to the external device that indicates an expiration date of the adjunct and/or of the medicant(s) retained by the adjunct. If the expiration date has passed based on a comparison with the current date, the processor can cause a warning to be provided indicating that the adjunct and/or medicant(s) have expired and that the adjunct should therefore not be used.

In addition to component data, the packaging unit can be configured to transmit sub-component data to the external device that indicates lot information for each packaged component, e.g., each adjunct, each medicant, each staple cartridge, each component part of the staple cartridge, etc. If any of the sub-component data indicates that a particular sub-component is faulty, based on a comparison with stored known faulty sub-component data, the processor can cause a warning to be provided indicating that the adjunct, the staple cartridge, the stapler, and/or medicant(s) should not be used and/or should be returned for maintenance or replacement. Comparing sub-component data may be useful if a lot of sub-components is found to be faulty but only some of the lot was incorporated into a small portion of a lot of end product, e.g., faulty staples used with only some staple cartridges in a lot, faulty cutting blade used with only some staple cartridges in a lot, faulty medicant used with only some adjuncts in a lot, etc., the recall could be targeted at just the devices that include the faulty sub-component. The processor can thus check to make sure that all components and sub-components are from good lots.

In some embodiments, the packaging unit is configured to transmit sub-component data but not component data. In some embodiments, the packaging unit is configured to transmit expiration date data but not component data. In some embodiments, the packaging unit is configured to transmit expiration date data and sub-component data but not component data. In some embodiments, the packaging unit is configured to transmit expiration date data and component data but not sub-component data. In some embodiments, the packaging unit is configured to transmit component data and sub-component data but not expiration date data.

Figure 53:
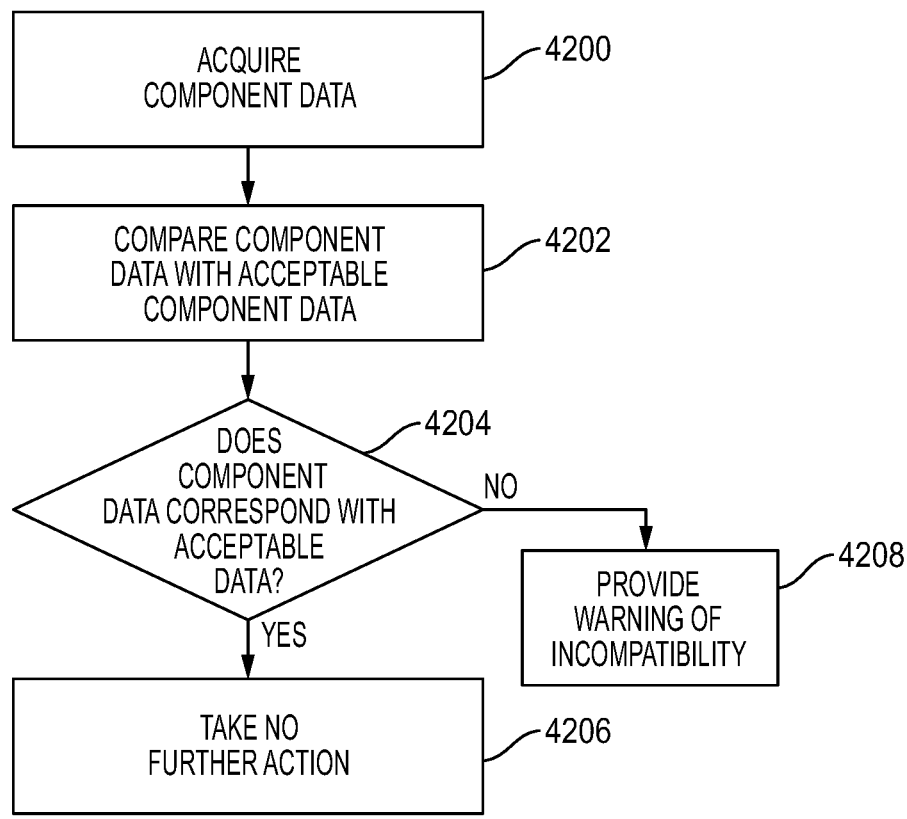
FIG. 53 is a flowchart of one exemplary embodiment of a method of establishing compatibility of components.

FIG. 53 illustrates an embodiment of a method of establishing compatibility of components. As shown, the component data is acquired 4200. As noted herein, the acquisition can occur by the component data being communicated from a packaging unit to an external device. The component data is then compared 4202 with acceptable component data. As noted herein, this comparison can be carried out using a processor, e.g., a processor of a surgical hub or other external device. The acceptable component data can be stored in a memory associated with the processor, and the processor can compare the acquired component data with the acceptable component data present in the memory. Based on this comparison, the processor determines 4204 whether the component data corresponds with the acceptable component data. In the situation that the component data is determined 4204 to correspond with the acceptable component data, the processor can take no further action 4206 since no incompatibility was detected. The relevant component can thus be used for staple and adjunct delivery. The processor can, however, provide a notification of compatibility. If the component data is determined 4204 to not correspond with acceptable first component data, then the processor causes 4208 a warning to be provided, as discussed herein, indicating incompatibility.

Figure 54:
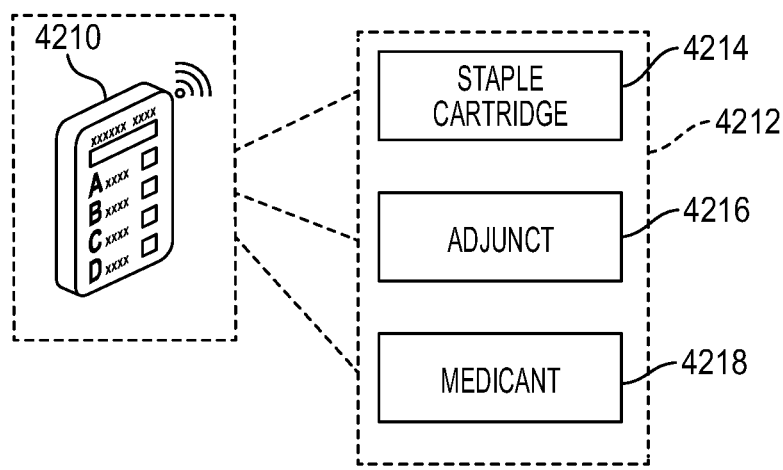
FIG. 54 is a schematic view of another embodiment of a communication network including another embodiment of a packaging unit and another embodiment of a computer system.

FIG. 54 illustrates an embodiment of a verification system including an external device 4210. The external device 4210 in this embodiment is in the form of a mobile phone configured to wirelessly interact with a packaging unit 4212, e.g., the packaging unit 4002 of FIG. 43, the packaging unit 4010 of FIG. 44, or other packaging unit. The packaging unit 4202 in this illustrated embodiment packages a staple cartridge 4214, an adjunct 4216, and a medicant 4218 releasably retained by the adjunct 4216. The staple cartridge 4214 can be packaged with the adjunct 4216 already releasably attached thereto. The external device 4210 is configured to acquire the component data, sub-component data, and/or expiration date data from the packaging unit 4202 as discussed herein and to analyze the received data as also discussed herein.

Packaging Unit Power

In some embodiments, a packaging unit can operate in a single power mode regardless of where the packaging unit is in its supply chain and whether or not the packaging unit has been opened. A sensor of the packaging unit can thus be "on" gathering data for an entire shelf life of the packaging unit, and a communications interface of the packaging unit can always have sufficient power to transmit data to an external device. Data may thus be assured of being gathered and communicated at all relevant times.

In other embodiments, a packaging unit can be configured to operate in a low power mode and in a high power mode. In the low power mode, a sensor of the packaging unit is provided with sufficient power from an on-board power source for the sensor to monitor data as discussed herein, and a communications interface of the packaging unit does not have sufficient power to transmit data to an external device. In the high power mode, the sensor and the communications interface are each provided with sufficient power. Less power is required from a power source for data gathering than for the data gathering in addition to allowing for data communication, so the low power mode may help conserve power and thereby help ensure that the power source has sufficient power throughout data communication in the high power mode. In an exemplary embodiment, opening the packaging unit is configured to move the packaging unit from the lower power mode to the high power mode. Until the packaging unit is opened, the packaging unit will continue to be potentially exposed to adverse exposure condition(s), so waiting until the packaging unit is opened to allow for data communication may help ensure that all relevant data is communication to an external device for analysis.

To facilitate movement from the low power mode to the high power mode, the packaging unit can include a tab configured to be automatically moved in response to opening of the packaging unit. Removing the tab fully "wakes up" the packaging unit's power source so the power source is providing power to the sensor to gather data (as in the low power mode) and to the communications interface to allow for data communication. The tab can be attached, for example, across a top box seam of a packaging unit and be configured to be automatically moved and/or broken when the box top is opened. For another example, the tab can be attached over a sealed opening of a foil pouch of a packaging unit and be configured to automatically moved and/or broken when the sealed opening is opened. The power source can include a first power source configured to provide power to the sensor in the low and high power modes and a second power source configured to only provide power to the communications interface in the high power mode. The tab can act as an insulator that prevents the second power source from providing power to the communications interface until the tab is removed, e.g., in response to the packaging unit being opened and causing the tab to move. In other words, the tab can be configured to prevent a circuit from being completed until the tab is removed. In some embodiments, the tab can include a conductive trace configured to facilitate circuit completion and prevention. Exemplary embodiments of tabs configured to be moved to cause movement from a low power mode to a high power mode are further described in Intl. Pat. App. No. PCT/IB2020/060710 entitled "Drug Delivery Device Sensing Modules" filed Nov. 13, 2020, which is hereby incorporated by reference in its entirety.

Instead of including a tab, a packaging unit can include a photosensor configured to facilitate movement of the packaging unit from a low power mode to a high power mode. The photosensor can be disposed in the packaging unit and not be exposed to light with the packaging unit unopened. With the packaging unit opened, the photosensor is exposed to light. The photosensor's exposure to light can trigger the packaging unit's power source to begin providing power to the packaging unit's communications interface.

In some embodiments, a packaging unit can be configured to move from a no power mode to a power on mode. In the no power mode, a communications interface of the packaging unit is not powered. In the power on mode, the communications interface is powered. The packaging unit is configured to be in the no power mode with the packaging unit in an unopened, closed state and to be in the power on mode with the packaging unit in an open state. The packaging unit is thus configured to move automatically from the no power mode to the power on mode in response to the packaging unit being opened, e.g., moving from the closed state to the open state. The packaging unit includes a power source configured to facilitate movement of the packaging unit from the no power mode to the power on mode. The power source is light sensitive. With the packaging unit in the closed state, the power source is dormant and not powered. The packaging unit being opened is configured to activate the power source by exposing the power source to light. The packaging unit is thus made of a material configured to prevent light passage therethrough to the power source inside of the packaging unit. The packaging unit is thus passive and unpowered until the packaging unit is opened. By not including an active power source such as a battery, the packaging unit may be disposed of in a safer and/or more environmentally friendly way than a packaging unit that includes an active power source.

In an exemplary embodiment, the packaging unit configured to move from the no power mode to the power on mode includes a degradable element configured to degrade in response to exposure to an environmental condition such as humidity, temperature, oxygen, or irradiation. In the power on mode, the communications interface is configured to communicate data indicative of a state of the degradable element to a surgical hub or other computer system, as discussed herein. The state of the degradable element corresponds to the degradable element's exposure to the environmental condition, thereby providing the surgical hub or other computer system exposure condition information that can be used as discussed herein.

Figure 55:
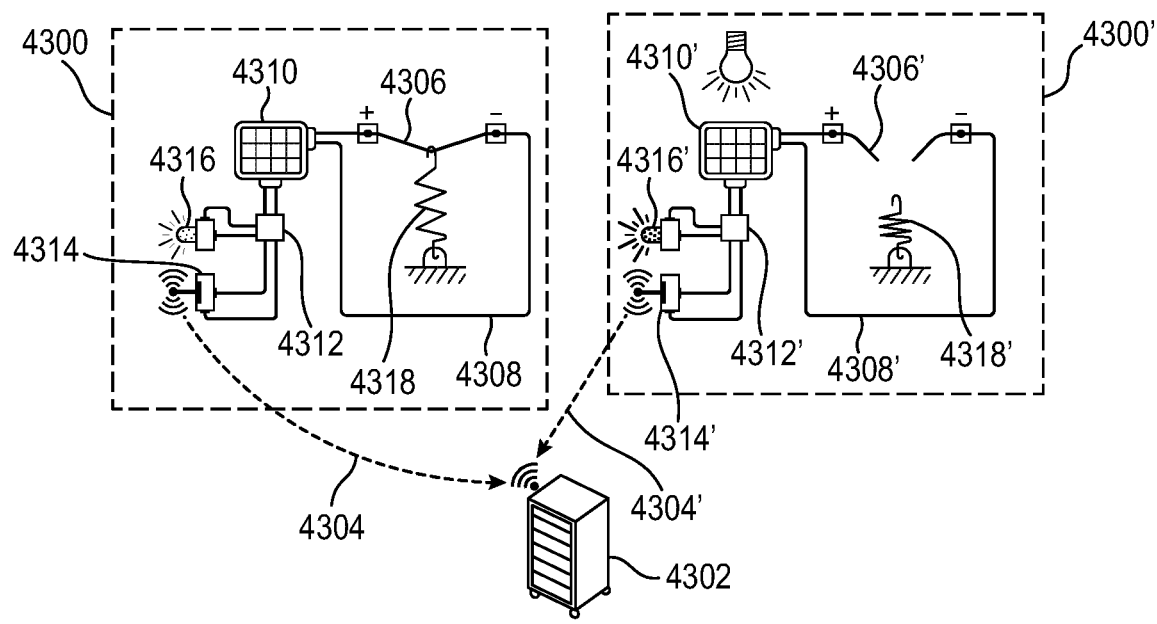
FIG. 55 is a schematic view of another embodiment of a communication network including another embodiment of a packaging unit and another embodiment of a surgical hub.

FIG. 55 illustrates an embodiment of a packaging unit 4300, 4300' configured to move from a no power mode to a power on mode. The no power mode is the initial, default mode. The packaging unit 4300, 4300' is shown communicating 4304, 4304' wirelessly with a surgical hub 4302 in this illustrated embodiment, but as discussed herein can communicate with another external device.

The packaging unit 4300, 4300' includes a degradable element 4306, 4306' configured to degrade in response to exposure to an environmental condition such as humidity (including moisture or water level), temperature, oxygen, or irradiation. The degradable element 4306 is thus generally configured as a sensor configured to monitor an exposure condition. The degradable element 4306 is intact in the no power mode. In other words, an initial state of the degradable element 4306 is non-degraded with the packaging unit 4300 in a closed state. A circuit 4308 that includes the degradable element 4306 is thus closed in the no power mode.

In the power on mode, the degradable element is either intact (non-degraded) or degraded. The packaging unit shown to the left of FIG. 55 as packaging unit 4300 illustrates the packaging unit in the power on mode with the degradable element 4306 intact. The circuit 4308 is thus closed in the power on mode with the degradable element 4306 not being degraded. The packaging unit shown to the right of FIG. 55 as packaging unit 4300', with use of hash marks for the elements corresponding to those same elements of the other illustrated packaging unit 4300, illustrates the packaging unit in the power on mode with the degradable element 4306' degraded. The circuit 4308' is thus open in the power on mode with the degradable element 4306' being degraded.

With the packaging unit 4300 in the no power mode, if the degradable element 4306 has been exposed to the environmental condition for a sufficient amount of time, e.g., because packaging unit 4300 has been in a high temperature environment long enough to degrade the degradable element 4306, because packaging unit 4300 has been in a high humidity environment long enough to degrade the degradable element 4306, because packaging unit 4300 has been in a high radiation environment long enough to degrade the degradable element 4306, because packaging unit 4300 has been exposed to oxygen long enough to degrade the degradable element 4306, etc., then the degradable element moves from being intact (degradable element 4306) to being degraded (degradable element 4306'), thereby moving the circuit from being closed (circuit 4308) to being open (circuit 4308').

The degradable element 4306, 4306' is made from an environmentally sensitive material. In an exemplary embodiment, the degradable element 4306, 4306' is conductive. The degradable element 4306, 4306' being conductive allows for the circuit 4308 to be closed with the degradable 4306 intact. The degradable element 4306, 4306' can be infused with or made from an absorbable polymer and doped conductive particles that are configured to degrade in the presence of the environmental condition it is set to monitor. When energized, the conductivity of the degradable element 4306, 4306' is directly proportionate to the exposure the packaging unit 4300, 4300' has experienced. The degradable element 4306, 4306' can be infused with or made from a polymer that break down as fast or faster than the adjunct being monitored, e.g., than the adjunct packaged by the packaging unit 4300, 4300'. In an exemplary embodiment, as shown in FIG. 55, the degradable element 4306, 4306' includes a filament (either a single filament or a plurality of filaments) that forms a portion of the circuit 4308, 4308'.

The degradable element 4306, 4306' can be selected based on the adjunct and/or the medicant(s) packaged by the packaging unit 4300, 4300' so that the degradable element's susceptibility to one or more environmental conditions corresponds to or is more sensitive than the adjunct's and/or the medicant(s)' susceptibility to the one or more environmental conditions. The degradable element's susceptibility corresponding to the adjunct's and/or the medicant(s)' susceptibility allows the degradable element's degradation to correspond to effectiveness of the adjunct and/or the medicant(s). In this way, the degradable element degrading so as to no longer be intact can indicate that the adjunct and/or the medicant(s) should not be used. The degradable element's susceptibility being more sensitive than the adjunct's and/or the medicant(s)' susceptibility allows the degradable element's degradation to occur faster than a reduction in effectiveness of the adjunct and/or the medicant(s). The degradable element's degradation can thus lead the reduction in the effectiveness, which may help ensure that non-use of an ineffective adjunct and/or medicant(s).

The packaging unit 4300, 4300' also includes light sensitive element 4310, 4310' in the circuit 4308, 4308'. The light sensitive element 4310, 4310' is in series with the degradable element 4306, 4306'. With the packaging unit 4300, 4300' in the power on mode (with the degradable element 4306, 4306' degraded or non-degraded), the light sensitive element 4310, 4310' is configured to provide power to a controller 4312, 4312' of the packaging unit 4300, 4300', to a communications interface 4314, 4314' of the packaging unit 4300, 4300', and to a light 4316, 4316' of the packaging unit 4300. The light sensitive element 4310, 4310' thus serves as a power source. In the no power mode, the light sensitive element 4310 does not provide power to any of the controller 4312, the communications interface 4314, and the light 4316.

The light sensitive element 4310, 4310' is configured to begin providing power to the controller 4312, 4312', the communications interface 4314, 4314', and the light 4316, 4316' in response to being exposed to light. Thus, the opening of the packaging unit 4300, 4300', e.g., moving from the closed state to the open state, is configured to activate the light sensitive element 4310, 4310' by allowing the light sensitive element 4310, 4310' to become exposed to light, either artificial light, sunlight, or both artificial light and sunlight, in a room in which the packaging unit is opened. In an exemplary embodiment, the light sensitive element 4310, 4310' includes a solar cell (either a single solar cell or a plurality of solar cells).

The communications interface 4314, 4314' includes a wireless transmitter in this illustrated embodiment and is configured to communicate wirelessly with the surgical hub 4302 with the communications interface 4314' being powered by the light sensitive element 4314'. Data communicated to the surgical hub 4302 using the communications interface 4314' regards a state of the degradable element 4306'. With the degradable element 4306' being conductive, a conductivity of the degradable element 4306' is proportional to an amount of degradation of the degradable element 4306', e.g., a resistance of the conductive degradable element 4306' changing based on its amount of degradation. The data communicated by the communications interface 4314' can thus include an amount of degradation of the degradable element 4306'. The communications interface 4314 cannot wirelessly communicate with the surgical hub 4302 (or with anything else) with the packaging unit 4300 in the no power mode. The controller 4312, 4312' is configured to control the communications interface 4314, 4314' based on the sensed condition of the circuit 4308, 4308'. With the circuit 4308 being closed, the controller 4312 is configured to cause the communications interface 4314 to communicate to the surgical hub 4302 that the packaging unit 4300, and thus its packaged components, meets quality standards, e.g., because the packaging unit 4300 has not experienced an adverse environmental condition indicative of ineffective adjunct and/or ineffective medicant. With the circuit 4308' being open, the controller 4312' is configured to cause the communications interface 4314' to communicate to the surgical hub 4302 that the packaging unit 4300', and thus its packaged components, does not meet quality standards, e.g., because the packaging unit 4300' has experienced an adverse environmental condition indicative of ineffective adjunct and/or ineffective medicant. Such an unmet quality standards communication can cause the surgical hub 4302 to provide a warning, as discussed herein.

The light 4316, 4316' includes a single LED in this illustrated embodiment but can include another type of light and/or a plurality of lights. In the no power mode, the light 4316 is off (not illuminated). In the power on mode, the light 4316, 4316' is on (illuminated). The light 4316, 4316' being on thus provides a visual indication that the packaging unit 4300, 4300' is open and is in the power on mode. A color of the light's illumination in the power on mode depends on whether or not the degradable element is degraded (degradable element 4306') or intact (degradable element 4306). In this illustrated embodiment, the light 4316 is illuminated in green with the degradable element 4306 intact, and the light 4316' is illuminated in red with the degradable element 4306' degraded, but other colors can be used. In other embodiments, instead of being different colors, the light 4316' can be continuously illuminated when the degradable element is degraded (degradable element 4306'), and the light 4316 can be blinking when the degradable element is not degraded (degradable element 4306). Alternatively, the light 4316' can be blinking when the degradable element is degraded (degradable element 4306'), and the light 4316 can be continuously illuminated when the degradable element is not degraded (degradable element 4306).

The controller 4312, 4312' is configured to sense whether the circuit is closed (circuit 4308, degradable element 4306 not degraded) or open (circuit 4308', degradable element 4306' degraded). The controller 4312, 4312' is configured to control the light 4316, 4316' based on the sensed condition of the circuit 4308, 4308'. For example, as shown in this illustrated embodiment, the controller 4312, 4312' causes the light 4316 to illuminate in green with the circuit 4308 being closed and causes the light 4316' to illuminate in red with the circuit 4308' being open.

As in this illustrated embodiment, the packaging unit 4300, 4300' can include a force element 4318, 4318', e.g., a coil spring, an elastic filament, or other force element, configured to provide a force to the degradable element 4306 with the packaging unit 4300 in the no power mode. The force element 4318, 4318' is configured to facilitate breakage of the intact degradable element 4306 that has been weakened by exposure to the environmental condition. The force element can thus help ensure that the circuit 4308' is open with the degradable element 4306' degraded. The force element 4318, 4318' is not conductive, such as by being formed of a non-conductive material and/or having an insulative coating, so as to not form a part of the circuit 4308, 4308'.

Figure 56:
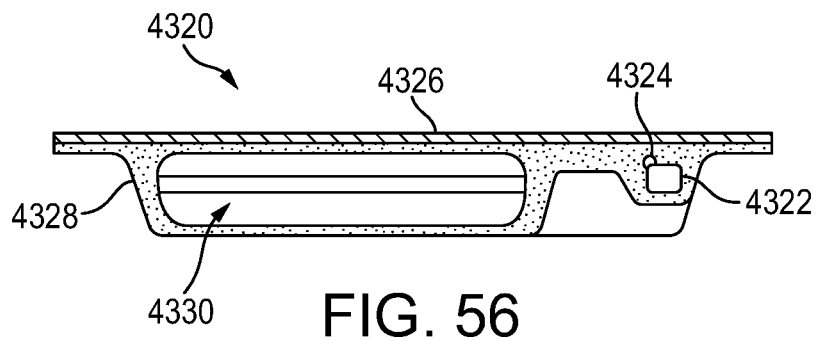
FIG. 56 is a longitudinal cross-sectional view of another embodiment of a packaging unit with a cover of the packaging unit closed.
Figure 57:
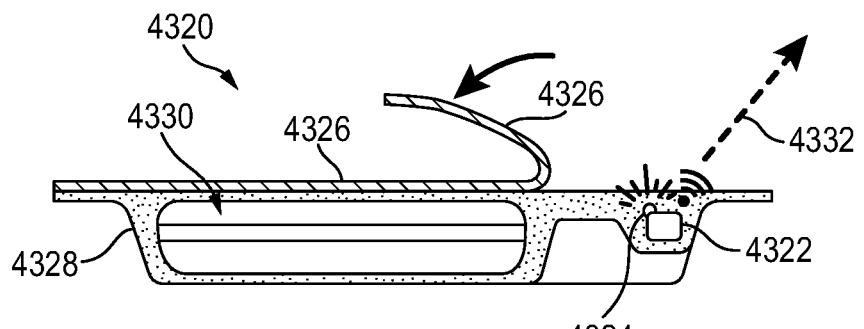
FIG. 57 is a longitudinal cross-sectional view of the packaging unit of FIG. 56 with the cover of the packaging unit open.

FIG. 56 and FIG. 57 illustrate another embodiment of a packaging unit 4320 configured to move from a no power mode to a power on mode. The packaging unit 4320 is generally configured and used similar to the packaging unit 4300, 4300' of FIG. 55 discussed above, e.g., includes a degradable element (obscured in FIG. 56 and FIG. 57), a circuit (obscured in FIG. 56 and FIG. 57), a light sensitive element 4322, a controller (obscured in FIG. 56 and FIG. 57), a communications interface 4322, a light 4324, and a force element (obscured in FIG. 56 and FIG. 57). As shown in FIG. 56 and FIG. 57, the light sensitive element and the communications interface are integrated together in this illustrated embodiment. The light sensitive element 4322 in this illustrated embodiment includes a solar cell (either a single solar cell or a plurality of solar cells). The communications interface 4322 in this illustrated embodiment includes a wireless transmitter.

The packaging unit 4320 in this illustrated embodiment includes a foil pouch having a cover 4326. The cover 4326 is configured to be manually removed (fully or partially) from a housing 4328 of the packaging unit 4320 that houses packaged elements in a cavity 4330 thereof. The packaged elements are not shown in FIG. 56 and FIG. 57 but can include elements as discussed herein, e.g., an adjunct releasably retaining medicant(s) therein, a plurality of adjuncts each releasably retaining a medicant therein, a staple cartridge having an adjunct releasably attached thereto with the adjunct releasably retaining medicant(s) therein, a plurality of staple cartridges each having an adjunct releasably attached thereto with the adjunct releasably retaining medicant(s) therein, etc. As discussed herein, the packaging unit 4320 can be packaged in a bulk packaging unit and removed therefrom for use.

As shown in FIG. 56 and FIG. 57, the light sensitive element 4322, the communications interface 4322, and the light 4324 can be embedded in the housing 4328. The obscured degradable element, circuit, controller, and force element are similarly embedded in the housing 4328. Embedding these elements in the housing 4328 may help protect the elements from being damaged during the packaging unit's progression through the supply chain.

FIG. 56 illustrates the packaging unit 4320 in the no power mode. The cover 4326 is thus closed, such that the light sensitive element 4322 is not exposed to light. The light 4324 is off. The degradable element is subject to environmental conditions in the no power mode and is thus able to degrade if warranted.

FIG. 57 illustrates the packaging unit 4320 in the power on mode. The cover 4326 is thus open, such that the light sensitive element 4322 is exposed to light. The light 4324 is on. A color (and/or a blinking/continuous illumination state) of the illuminated light 4324 depends on whether or not the degradable element is degraded or intact, as discussed above. Now receiving power from the light sensitive element 4322 with the packaging unit 4320 in the power on mode, the communications interface 4322 is shown transmitting 4332 data regarding a state of the degradable element to a surgical hub or other computer system as discussed above.

In some embodiments, instead of a packaging unit that is configured to move from a no power mode to a power on mode including a light sensitive element configured to provide power to elements of the packaging unit, the packaging unit can include a magnetic-field powered element such as an RFID tag or other passively magnetically powered element. The magnetic-field powered element is configured to only be powered when in the presence of a magnetic field. Thus, when exposed to a magnetic field, such as that provided by an RFID reader or other device, the magnetic-field powered element can allow a communications interface of the packaging unit to communicate data as discussed above.

Post-Implantation Adjunct Monitoring

As discussed above, an adjunct can be absorbable. The adjunct can thus be configured to degrade in a patient's body. The adjunct's absorbable configuration can be exploited to help monitor the patient's healing. Monitoring the adjunct's breakdown (generally referred to herein as the adjunct "degrading") in the patient's body after the adjunct has been implanted can serve as a means to monitor the patient's healing. The adjunct's degradation generally corresponds to the patient's healing since tissue heals over time and since any medicants releasably retained by the adjunct are releasable over time after the adjunct has been implanted in the patient's body. Monitoring the adjunct's degradation may therefore allow for assessment of the patient's healing.

The adjunct's monitoring can occur non-invasively from outside the patient's body. The patient therefore does not need any surgical intervention to assess the adjunct's absorption state and the patient's healing after the adjunct has been implanted.

An implanted adjunct's degradation can be monitored in a variety of ways. For example, the monitoring can include imaging the adjunct for visualization of radio-opaque markers releasable from the adjunct in the body of the patient. For another example, the monitoring can include tracking a waste byproduct of the adjunct that is releasable from the implanted adjunct into the body of the patient. For yet another example, the monitoring can include monitoring waste of the patient. For still another example, in embodiments in which the adjunct is delivered using a surgical stapler, the monitoring can include tracking a trackable element delivered to the patient from a surgical stapler that stapled the adjunct in the patient. Each of these examples is discussed further below.

Information gathered regarding the implanted adjunct's degradation can be communicated to a surgical hub or other computer system, such as via a communications interface of a device that gathers images, trackable material data, etc. as discussed further below. The surgical hub or other computer system can be configured to provide a notification of the adjunct's monitoring to the patient's surgeon or other medical care professional(s), similar to that discussed above regarding providing a notification of compatibility, to facilitate the patient's treatment.

In some embodiments, monitoring an implanted adjunct's breakdown in a patient's body can include imaging the adjunct for visualization of radio-opaque markers releasable from the adjunct in the body of the patient. In such embodiments, the radio-opaque markers are retained by the adjunct when the adjunct is implanted, similar to that discussed herein regarding the adjunct releasably retaining a medicant when the adjunct is implanted. As the adjunct breaks down and is bioabsorbed, the radio-opaque markers will be moved from their original implanted location where the adjunct was stapled or otherwise attached to the patient. The adjunct's degradation, and thus patient healing, can thereby be monitored.

The patient can be imaged at a plurality of different times, e.g., a plurality of different days sequential with one another and/or separated by one or more days, for visualization of the radio-opaque markers. The adjunct's degradation can thus be monitored over time, with each subsequent imaging providing an updated indication of the patient's healing. Comparing each of the images can thus provide an indication of the radio-opaque markers' movement in the patient's body over time and, thus, the adjunct's degradation and the patient's healing over time.

In embodiments in which an adjunct is compressible, such as by being a tissue thickness compensator, a comparison of images taken over time can show if the adjunct is breaking down such that the radio-opaque markers are moving closer together as the adjunct degrades or are moving apart from one another as the adjunct holding them constrained degrades and the radio-opaque markers are free to migrate.

The radio-opaque markers can be formed from any of a variety of biocompatible radio-opaque materials and can be releasably retained by the adjunct in a variety of ways. For example, in embodiments in which the adjunct is formed from a foam, the radio-opaque markers can be embedded throughout the foam such that, as the foam degrades, the radio-opaque markers are released. Any medicants releasably retained by the foam adjunct are similarly releasable, as discussed herein. For another example, in embodiments in which the adjunct is formed from a fibrous structure, the radio-opaque markers can be trapped between fibers forming the fibrous structure such that, as the fibrous structure degrades, the radio-opaque markers are released. Any medicants releasably retained by the fibrous structure adjunct are similarly releasable, as discussed herein.

In an exemplary embodiment, the radio-opaque markers are independent elements from the adjunct and the medicant(s) retained by the adjunct, as well as from device(s) that facilitate the delivery of the adjunct and medicant(s) to tissue, such as a surgical stapler that applies the staples and the adjunct. Existing adjuncts and existing medicants thus do not need to be modified, nor do future adjuncts or medicants need to be particularly designed, in order to be used with radio-opaque markers as discussed herein.

Figure 58:
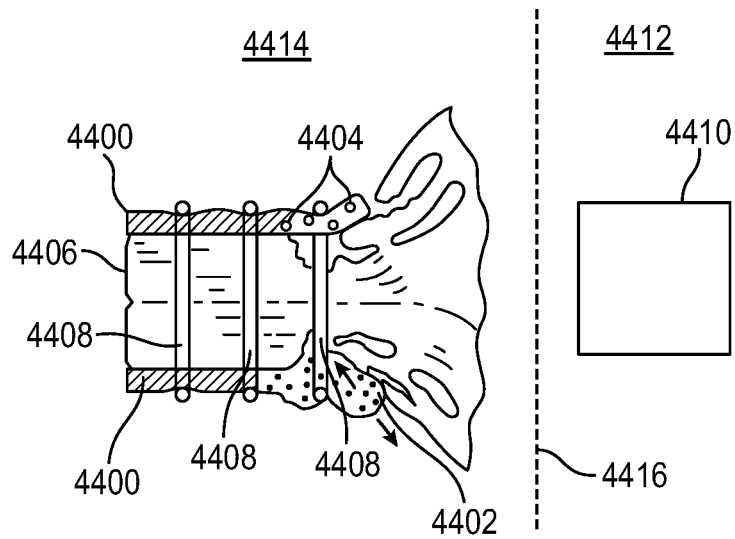
FIG. 58 is a perspective view of an imaging system located outside of a body of a patient and another embodiment of an adjunct stapled inside the patient.

FIG. 58 illustrates an embodiment of an adjunct 4400 releasably retaining a medicant 4402 and a plurality of radio-opaque markers 4404. The adjunct 4400 is retaining a single medicant 4402 but as discussed herein can retain a plurality of medicants. In this illustrated embodiment, the adjunct 4400 is configured to change conformation.

FIG. 58 shows the adjunct 4400 implanted at an edge of a tissue 4406 of a patient by deployment of staples 4408 deployed into the tissue 4406. With the adjunct 4400 implanted in the patient, the patient can be imaged using an imaging system 4410, such as a fluoroscopy system, an x-ray system, or other system, that is configured to provide an image allowing visualization of the radio-opaque markers 4404. The imaging system 4410 is located outside 4412 the patient's body, and the adjunct 4400, the medicant 4402, and the radio-opaque markers 4404 are located inside 4414 the patient's body. The imaging system 4410 is thus configured to image the patient from outside 4410 the patient's body. An external surface of the patient is schematically represented by a dotted line 4416. Each image taken using the imaging system 4410 can be taken at a location of known adjunct 4400 implantation, which in this illustrated embodiment is at the edge of the tissue 4406, or a plurality of images at two or more different locations can be taken using the imaging system 4410. One or more of the two or more locations can include the location of known adjunct 4400 implantation. Taking at least one image at the location of known adjunct 4400 implantation may allow for the monitoring of healing of the tissue 4406 at the location of known adjunct 4400 implantation. Taking at least one image that does not include the location of known adjunct 4400 implantation may allow for the monitoring of healing away from the location of known adjunct 4400 implantation, either at the tissue 4406 or other location. Healing away from the location of known adjunct 4400 implantation can be caused by the medicant 4402 moving within the patient's body. Taking at least one image that does not include the location of known adjunct 4400 implantation may allow for monitoring of how the degrading adjunct 4400 and/or the released medicant 4402 moves in the patient's body, which may help facilitate post-operative analysis useful for the patient and/or future patients who receive a similar adjunct and/or similar medicant.

Figure 59:
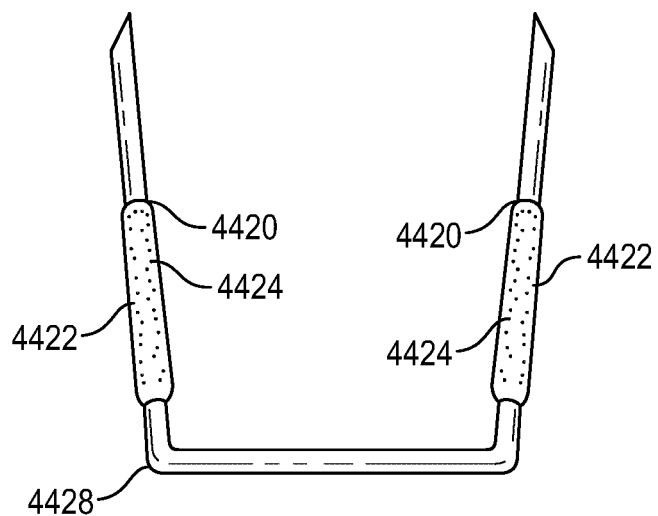
FIG. 59 is a perspective view of one exemplary embodiment of a staple having an adjunct disposed thereon.
Figure 60:
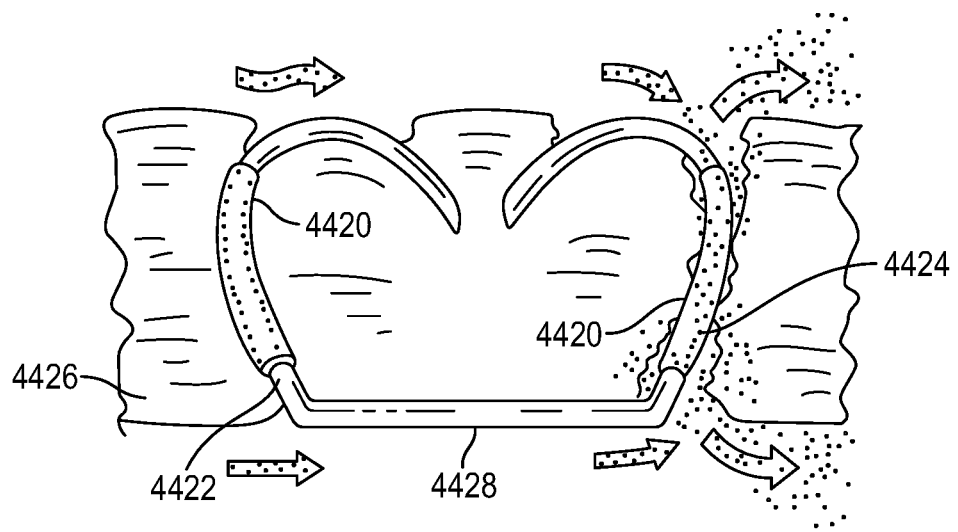
FIG. 60 is a partial cross-sectional side view of the staple of FIG. 59 applied to tissue.

FIG. 59 and FIG. 60 illustrate another embodiment of an adjunct 4420 releasably retaining a medicant 4422 and releasably retaining a plurality of radio-opaque markers 4424. FIG. 59 illustrates the adjunct 4420 before implantation, and FIG. 60 illustrates the adjunct 4420 implanted in a body of a patient with the adjunct 4420 stapled to tissue 4426 of the patient. In this illustrated embodiment, a surgical staple 4428 includes the adjunct 4420 disposed over each leg of the staple 4428 configured to be used in delivering the adjunct 4420 to the tissue 4426. The adjunct 4420 is thus a two-part adjunct in this illustrated embodiment with each part of the adjunct 4420 releasably retaining the medicant 4422 and the radio-opaque markers 4424. In other embodiments, one part of the adjunct 4420 can releasably retain the medicant 442, and the other part of the adjunct 4420 can releasably retain the radio-opaque markers 4424. In some embodiments, only one staple leg can have an adjunct thereon, or one or both staple legs can have more than one adjunct thereon.

Figure 61:
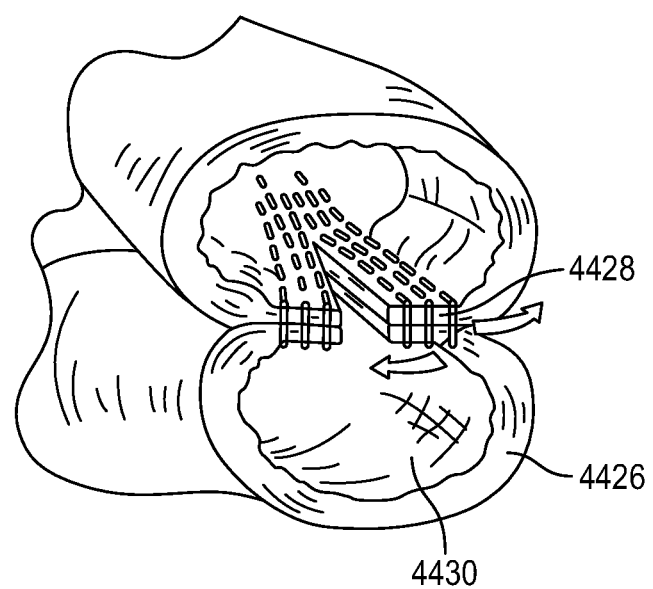
FIG. 61 is a perspective, zoomed-out view of the tissue of FIG. 60 having the staple and a plurality of additional staples applied thereto.

The medicant 4422 and the radio-opaque markers 4424 are configured to be released from the adjunct 4420 when the staple 4428 is deformed upon deployment of the staple 4428 into the tissue 4426 of a patient, e.g., a bowel, a lung, etc., as shown in FIG. 60. Some of the medicant 4422 and/or some the radio-opaque markers 4424 can remain in the adjunct 4420 upon stapling and be released from the adjunct 4420 as the adjunct 4420 degrades. FIG. 61 shows the staple 4428 and a plurality of additional similar staples each also having an adjunct disposed thereon similar to the disposal of the adjunct 4420 on the staple 4428. FIG. 61 illustrates a side-to-side anastomosis, but the staple 4428 can be used in other surgical procedures. The medicant 4222 and/or the radio-opaque markers 4424 can be released from the adjunct 4420 into a passageway 4430 extending through the tissue 4426. Imaging the passageway at the location of the adjunct's implantation at the tissue 4426 and/or away from the location of the adjunct's implantation at the tissue 4426 may thus allow for visualization of the radio-opaque markers 4424.

In some embodiments, monitoring an implanted adjunct's breakdown in a patient's body can include tracking a waste byproduct of the adjunct that is releasable from the implanted adjunct into the body of the patient. In such embodiments, the adjunct includes the waste byproduct releasable from the implanted adjunct into the body of the patient. Similar to that discussed above regarding radio-opaque markers releasable from an adjunct, as the adjunct releasably retaining the waste byproduct breaks down and is bioabsorbed, the waste byproduct will be moved from their original implanted location where the adjunct was stapled or otherwise attached to the patient. The adjunct's degradation, and thus patient healing, can thereby be monitored.

The waste byproduct can be formed from any of a variety of biocompatible materials. For example, the adjunct can be formed from an absorbable material and a non-absorbable material. The non-absorbable material, such as a non-absorbable polymer, can define the waste byproduct. As the absorbable material of the adjunct breaks down in a patient's body, the waste byproduct will be released from the adjunct to allow for monitoring of the waste byproduct. The adjunct can be formed from the absorbable material and the non-absorbable material in a variety of ways, such as by the adjunct formed from a fibrous structure that includes a plurality of absorbable fibers and a plurality of non-absorbable fibers, the adjunct formed from at least one absorbable film attached to at least one non-absorbable film, or other adjunct configuration. For another example, the waste byproduct can include a ferrous material configured to be detected by a metal detector. The adjunct can include the ferrous material similar to that discussed above regarding an adjunct including radio-opaque markers. For another example, the waste byproduct can include a radioactive material configured to be detected by a radiation detector. The adjunct can include the radioactive material similar to that discussed above regarding an adjunct including radio-opaque markers. The radioactive material is slightly radioactive so as to be a safe level. For yet another example, the waste byproduct can include a physiologic bi-product. For still another example, the waste byproduct can include a metabolism marker or degradation decomposition product. As mentioned above, an adjunct can be formed from an absorbable polymer. Absorbable polymers tend to break down into sub components, including a component that is metabolized by the body and another component that is not metabolized by the body and is released from the body as waste. The component that is not metabolized can be the waste byproduct. As one example, with PLGA, metabolized product can include a material that acts as a sugar and waste byproduct including lactic acid and glycolic acid excreted by the kidneys. As another example, with PLA, metabolized product can include a material that acts as a sugar and waste byproduct including lactic acid excreted by the kidneys.

The waste byproduct can be monitored locally using a monitoring device. The monitoring device can be configured to monitor a concentration and a location of the waste product in a patient's body. The monitoring device is located outside of the patient's body similar to that discussed above regarding the imaging system 4410 of FIG. 58 that is configured to monitor a material released from an implanted adjunct. In an exemplary embodiment, the monitoring device is a wearable monitor, which may allow a patient to be easily and non-invasively monitored.

In some embodiments, the waste byproduct can include a ferrous material, and the monitoring device can include a metal detector configured to monitor a concentration and a location of the ferrous material in a patient's body. At time zero when the adjunct releasably retaining the ferrous material is implanted in the patient's body, the concentration of the ferrous material would be known. The monitoring device can then track any changes to this concentration or dispersion of the ferrous material away from the site of implantation.

In some embodiments, the waste byproduct can include a radioactive material, and the monitoring device can include a radiation detector configured to monitor a concentration and a location of the radioactive material in a patient's body. At time zero when the adjunct releasably retaining the radioactive material is implanted in the patient's body, the concentration of the radioactive material would be known. The monitoring device can then track any changes to this concentration or dispersion of the radioactive material away from the site of implantation.

In some embodiments, monitoring an implanted adjunct's breakdown in a patient's body can include monitoring waste of the patient. An adjunct can be implanted at a variety of locations in a patient, such as at a lung, a gastrointestinal tract, or a liver. In situations where the adjunct is implanted at a gastrointestinal tract, such as at a colon, the adjunct's location can be exploited to facilitate monitoring of the adjunct's degradation in the patient's body. In such situations, the adjunct's waste byproduct can be released into a passageway of the gastrointestinal tract similar to that discussed above regarding release of the radio-opaque markers 4424 of FIG. 61 being released from the adjunct 4420 into the passageway 4430.

Monitoring the waste of the patient can include tracking a waste byproduct of the adjunct that is releasable from the implanted adjunct into the body of the patient and released with the waste. In such embodiments, the waste byproduct can be monitored systemically after the waste byproduct has exited the patient as waste. The waste byproduct can thus be monitored from outside of the patient's body. The waste byproduct that is monitored after its release from a patient's body can include a metabolism marker or degradation decomposition product.

A toilet can include a smart computer system monitor, similar to a urinal puck, that is configured to track the metabolism marker or degradation decomposition product. The smart monitor can be configured to provide a notification of the adjunct's monitoring to the patient's surgeon or other medical care professional(s), or the smart monitor can be configured to communicate data gathered thereby to a surgical hub or other computer system configured to provide such a notification.

In addition to or in alternative to using a smart monitor, a patient's feces can be collected for detection of the waste byproduct in the feces. The waste byproduct can be detected in the feces in any of a variety of ways, such as by the waste byproduct including a dye that, if present in the waste, will be visually observable. For another example, the waste byproduct can include a reactive chemical that, if present in the waste, will react with a reactor, such as litmus paper or an activator chemical, applied to the feces. Thus, pH can be used to detect the waste byproduct. Bacterial load or other mineral reactors could also be used.

In some embodiments, monitoring an implanted adjunct's breakdown in a patient's body can include tracking a trackable element delivered to the patient from a surgical stapler that stapled the adjunct in the patient. In situations where an adjunct is implanted at a gastrointestinal tract, such as at a colon, the adjunct's location can be exploited to facilitate monitoring of the adjunct's degradation in the patient's body. In such situations, the trackable element can be released into a passageway of the gastrointestinal tract similar to that discussed above regarding release of the radio-opaque markers 4424 of FIG. 61 being released from the adjunct 4420 into the passageway 4430. The trackable element can be configured to interact with a microbiome of the gastrointestinal tract, such as at a colon. A tracked magnitude of the release of the tracking element can be used as a means to analyze a balance of the intestinal micro biome and/or the healing response over time. Parameters within the colon that can be used as an interactive measure linked to the microbiome balance or healing include pH, $O_2$, and $CO_2$. $CO_2$ concentrations cause a shift in pH in organic structures. Additional testing may be done if increased pH is detected in order to determine the source of the pH change, which could lead to a $O_2/CO_2$ balance measure. Different bacteria use $O_2$ and $CO_2$ differently and some excrete them. The balance measure can indicate the bacterial load of the gut and therefore shed light on the balance of good bacteria to bad bacteria in the microbiome.

In an exemplary embodiment, the trackable element is delivered to the patient separately from the adjunct. Each of the trackable element and the adjunct can be delivered to the patient using a same device, e.g., a surgical stapler as discussed herein, but can each be delivered separately from the device. Adjuncts thus need not be modified in order to be used with a trackable element.

Implantable Adjuncts Having Adjustable Degradation Profile

As discussed above, embodiments of adjuncts can be employed for a variety of functions, such as reinforcement of tissue at a treatment site, minimizing tissue movement in and around staple puncture sites, tissue thickness compensation, and the like. This functionality relies upon one or more mechanical properties of the adjunct, such as strength (e.g., compressive strength, tensile strength), elastic modulus/stiffness, etc., remaining at or above a predetermined level after implantation in order to ensure that the functionality of the adjunct is achieved. However, after implantation, the adjunct can absorb bodily fluids (e.g., water and/or water-containing fluids). The bodily fluids can chemically react with the adjunct material (e.g., via hydrolysis) and cause the adjunct material to degrade over time, resulting in a change in the mechanical properties of the adjunct.

For a given adjunct, the change in mechanical properties as a function of time can be characterized in the form of a degradation profile. However, it can be appreciated that a surgeon may desire to adjust the degradation profile of the adjunct based on considerations such as the implantation location, type of surgery, etc. Accordingly, as discussed in detail below, embodiments of the disclosure provide compressible adjuncts having adjustable degradation profiles.

In one embodiment, a compressible adjunct kit can be provided for use with a staple cartridge and the kit can include a biocompatible adjunct material and a pretreatment fluid. The adjunct material is configured to be releasably retained on a staple cartridge body or anvil and is configured to be delivered to tissue by deployment of staples in the cartridge body. The adjunct material can be in the form of a porous polymer body. Prior to implantation, the pretreatment fluid can be applied to the adjunct material to change the adjunct material from a stock or untreated state that is configured to exhibit a first degradation profile when delivered to tissue, to a treated state that is configured to exhibit a second degradation profile when delivered to tissue. The first and second degradation profiles can differ from one another.

Figure 62:
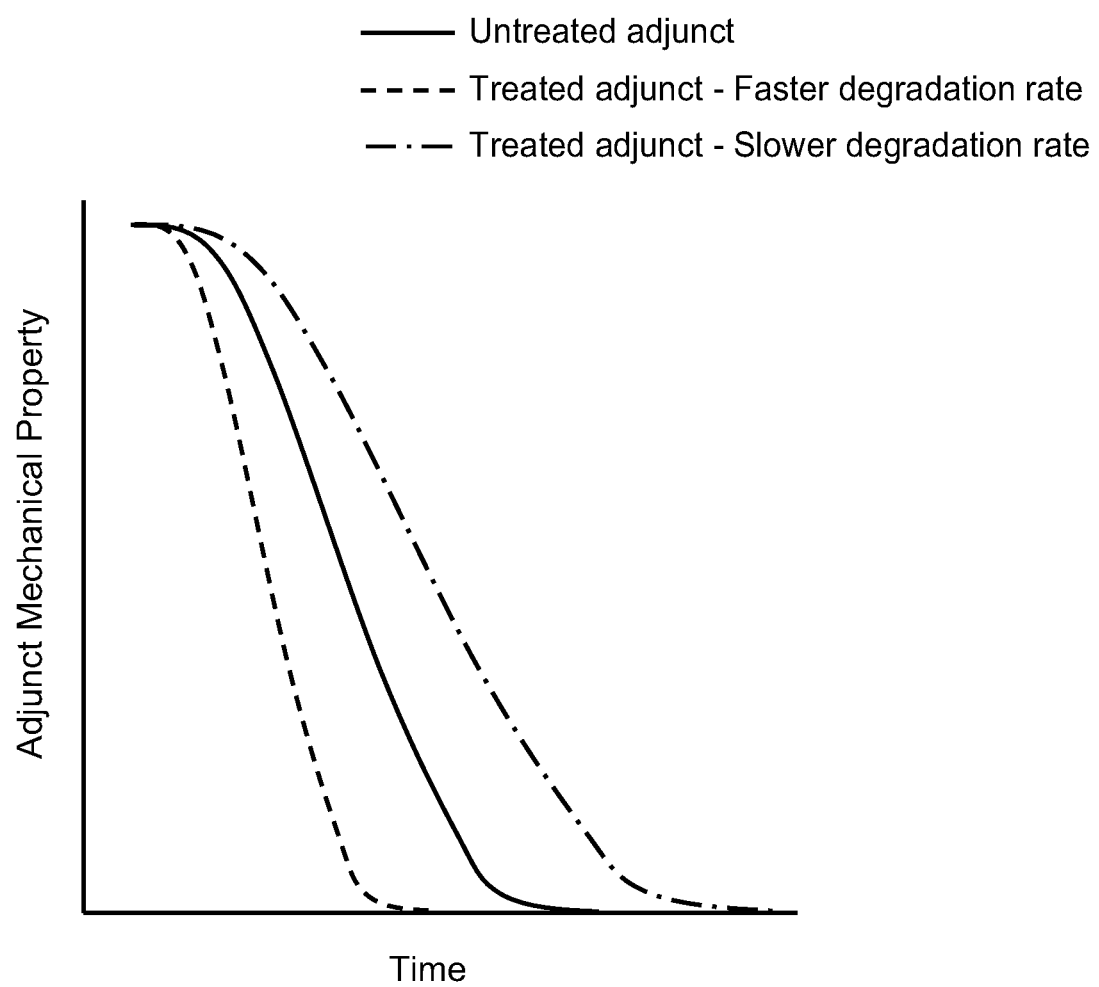
FIG. 62 is a plot illustrating exemplary degradation profiles for adjunct materials in an untreated state and a treated state after application of a pretreatment fluid.

FIG. 62 is a plot illustrating several exemplary degradation profiles, one for an untreated adjunct and two for treated adjuncts. The degradation profiles are in the form of curves representing the value of a given adjunct mechanical property as a function of time. As shown, a degradation rate of a treated adjunct, represented by the slope of the degradation profile, can be greater than or less than a degradation rate of the untreated adjunct. Embodiments of the kit can include at least one pretreatment fluid configured to increase or decrease the degradation rate. In certain embodiments, the kit can include a plurality of pretreatment fluids configured to increase or decrease the degradation rate to a predetermined degradation rate, thus allowing a user to select a pretreatment fluid configured to produce a desired degradation rate.

As discussed in greater detail below, the pretreatment fluid can employ a variety of mechanisms to increase or decrease the degradation rate of the adjunct material when delivered to tissue. In one aspect, the pretreatment fluid can increase or decrease the rate of chemical reaction between bodily fluids containing water (e.g., hydrolysis) and the treated adjunct material, as compared to the untreated adjunct. In another aspect, the pretreatment fluid can be configured to promote or inhibit absorption of bodily fluids by the adjunct material to increase or decrease, respectively, a surface area of the adjunct material that contacts, and can therefore chemically react with, the bodily fluids. By increasing or decreasing the surface area of the treated adjunct material in contact with the bodily fluids, as compared to the untreated adjunct, the degradation rate of the treated adjunct material can be increased or decreased, relative to the untreated adjunct.

In additional embodiments, compressive force can be applied to the adjunct material, prior to attachment to the staple cartridge or anvil, to alter the connectivity between pores of the adjunct material, and therefore the relative ease of fluid flow into the interior of the adjunct material. As discussed above the pores of the adjunct material can be classified as either open or closed. Open pores can allow flow of fluid therethrough while closed pores cannot. In one embodiment, compressive force applied to the adjunct material can form channels (e.g., cracks) between adjacent pores, converting closed pores to open pores. Opening the porosity in this manner can promote fluid flow through the adjunct material, increasing the surface area of the adjunct material that is available to contact bodily fluids and, therefore, increasing the degradation rate of the adjunct material. In other embodiments, compressive force applied to the adjunct material can close channels between adjacent pores, converting open pores to closed pores. Closing the porosity in this manner can inhibit fluid flow through the adjunct material, decreasing the surface area of the adjunct material that is available to contact bodily fluids and, therefore, decreasing the degradation rate of the adjunct material.

The pretreatment fluid can be applied to the adjunct material in a variety of ways. In one aspect, the adjunct material can be immersed in a vessel containing the pretreatment fluid. In another aspect, the pretreatment fluid can be applied to the adjunct material using a delivery device (e.g., a pipette, eyedropper, etc.) In certain embodiments, the pretreatment fluid is applied to the adjunct when the adjunct is separated from the staple cartridge. In other embodiments, the pretreatment fluid is applied to the adjunct when the adjunct is retained on the staple cartridge or anvil.

Certain embodiments of the pretreatment fluid can be configured to increase the degradation rate of the treated adjunct as compared to the untreated adjunct using a variety of mechanisms. In one aspect, the pretreatment fluid is configured to change (e.g., raise) the pH of any water-containing tissue or water-containing fluids adjacent to the adjunct material once implanted. As an example, the pretreatment fluid can mix with water contained in fluids contacting the adjunct material and/or water-containing fluids adjacent to the adjunct. By raising the pH at the location of the adjunct, the rate of hydrolysis of the adjunct material can be increased, thereby increasing the degradation rate of the treated adjunct. Examples of pretreatment fluids effective to increase the pH include, but are not limited to, fluids including one or more salts, bicarbonates, or other buffered aspects. In an embodiment, the pretreatment fluid is a solution of sodium chloride and water (e.g., saline solution).

In another aspect, the pretreatment fluid is configured to make the adjunct material more hydrophilic. As an example, the pretreatment fluid can form a coating or film on at least a portion of the surfaces of the adjunct material (e.g., exterior surfaces, interior surfaces of pores, etc.) In general, when water contacts the surface of a material that is hydrophilic, the water tends to spread out or "wet" the surface. As the degree of hydrophilicity of a surface increases, the area of contact between a given volume of water and the surface increases. Therefore, increasing the hydrophilicity of the adjunct can increase the degradation rate of the adjunct material due to increasing the area of contact between the adjunct material and water and/or water-containing bodily fluids. Examples of pretreatment fluids effective to increase the hydrophilicity of the adjunct material include, but are not limited to, wetting agents or surfactants such as loosely cross-linked polymers.

In further embodiments, cross-linking can be employed to increase the hydrophilicity of the adjunct material, alone or in combination with a pretreatment fluid. For example, the adjunct material can be physically cross-linked (e.g., irradiated by ultraviolet (UV) and gamma radiation and dehydrothermal treatment) or chemically cross-linked (e.g., use of chemical cross-linker(s), such as genipin and glutaraldehyde). In certain embodiments, the pretreatment fluid can include one or more chemical cross-linkers. Non-limiting examples of the chemical cross-linkers include bi-/multi-functional molecules, which bridge free carboxylic acid groups, amino groups, and hydroxyl groups between adjacent polymer molecules (e.g., glutaraldehyde, polyepoxides, and isocyanates), chromium sulphate, aldehydes, and isocyanates.

In alternative embodiments, the pretreatment fluid can be configured to decrease the degradation rate of the adjunct material as compared to the untreated adjunct using a variety of mechanisms. In one aspect, the pretreatment fluid can configured to make the adjunct material more hydrophobic. As an example, the pretreatment fluid can form a coating or film on at least a portion of the surfaces of the adjunct material (e.g., exterior surfaces, interior surfaces of pores, etc.) In general, when water contacts the surface of a material that is hydrophobic, the water tends to form beads, rather than spreading out or "wetting" the surface. As the degree of hydrophobicity of a surface increases, the area of contact between a given volume of water and the surface increases. Therefore, increasing the hydrophobicity of the adjunct can decrease the degradation rate of the adjunct material due to decreasing the area of contact between the adjunct material and water and/or water-containing bodily fluids. Examples of such pretreatment fluids include, but are not limited to, silicones and other materials suitable for increasing the hydrophobicity of surfaces of the adjunct material.

In another aspect, the pretreatment fluid can be configured to form a coating that is deposited on at least a portion of the surfaces of the adjunct (e.g., exterior surfaces, interior surfaces of pores, etc.) in the treated state. The coating forms a barrier that inhibits contact between the adjunct material and water and/or water-containing bodily fluids. That is, the water or water-containing fluids are required to penetrate the coating (e.g., via diffusion) before reacting with and degrading the adjunct material. As penetration of the coating is not instantaneous and requires some time to accomplish, the presence of the coating delays the onset of hydrolysis and increases the time to achieve a given amount of degradation, thereby decreasing the degradation rate. Examples of such pretreatment fluids can include, but are not limited to, oils (e.g., mineral oils, food grade oils), greases, biocompatible lubricants, and perfluoropolyether (PFPE)).

In a further aspect, the pretreatment fluid is configured to form a sealant that seals at least a portion of the pores of the porous polymer body, inhibiting ingress of water or water-containing bodily fluids within the bulk of the adjunct material. As an example, the sealant formed by the pretreatment fluid can be positioned on the surface and/or the interior of the adjunct material so as to partially and/or completely obstruct respective flow passageways leading from the surface of adjunct material to pores within the bulk of the adjunct material. Therefore, the sealant can decrease the degradation rate of the adjunct material due to decreasing the area of contact between the adjunct material and water and/or water-containing bodily fluids. Examples of such pretreatment fluids can include, but are not limited to, oils (e.g., mineral oils, food grade oils), greases, biocompatible lubricants, and other highly viscous materials capable of blocking fluid flow into pores of the adjunct material, and perfluoropolyether (PFPE)).

In another aspect, the pretreatment fluid is configured to react with the adjunct material (e.g., via a substitution reaction) to change a terminal functional group of at least a portion of a polymer chains forming the porous polymer body in the treated state as compared to the untreated state. The difference in terminal functional groups inhibits contact between the polymer adjunct material and water or water-containing bodily fluids. Therefore, the terminal functional group can decrease the degradation rate of the adjunct material due to decreasing the area of contact between the adjunct material and water and/or water-containing bodily fluids. Examples of such pretreatment fluids can include, but are not limited to, saline and acids (e.g., carbonic acid).

As an additional example, the pretreatment fluid can configured to terminate at least a portion of a plurality of polymer chains of the porous polymer body. As a result, an average length of the plurality of polymer chains of the polymer body in the treated state is less than an average length of the plurality of polymer chains of the polymer body in the untreated state. The decrease in average chain length decreases the area of contact between the polymer adjunct material and water, thereby decreasing the rate of degradation of the adjunct material.

As indicated above, the adjunct can be used with a staple cartridge or anvil for treating tissue. Prior to implantation, the adjunct material can be treated with the pretreatment fluid, either prior to or after attachment to a staple cartridge, e.g., such as staple cartridge 102 shown in FIG. 6 or anvil (e.g., upper jaw surface 34) shown in FIG. 2. As a result, the pretreatment fluid can be present on at least the surface of the adjunct material. In certain embodiments, the pretreatment fluid can also flow from the surface of the adjunct material to the interior or bulk of the adjunct material via open pores. Once properly treated, and with the treated adjunct material releasably retained on the anvil or staple cartridge and the cartridge disposed within a jaw of a surgical staple, such as stapler 10 or FIG. 1, the device can be manipulated to engage tissue between the jaws 32, 34 and to actuate the device thereby firing staples through the adjunct material and the tissue to secure the adjunct material to the tissue, as shown for example in FIG. 7.

Once implanted, the pretreated adjunct material can interact with water adjacent to the adjunct material. Such water can be in the form of water alone or a mixture with other bodily fluids. Additionally, the water can be located at the surface of the adjunct material and within at least a portion of the interior of the adjunct material (e.g., via flow through fluid passageways such as open pores in fluid communication with the surface of the adjunct material).

The configuration of the pretreatment fluid dictates whether the pretreatment fluid increases or decreases the degradation rate of the adjunct material. Embodiments of the pretreatment material that are configured to increase the degradation rate of the adjunct material can do so by increasing the rate of chemical reaction (e.g., hydrolysis) between the adjunct material and the water or by increasing the area of contact between the water and the adjunct material. In one example, the pretreatment fluid can mix with water that contacts surfaces of the adjunct (e.g., exterior surfaces or interior surfaces of pores). The mixture of pretreatment fluid and water can possess a higher pH than the water alone and accelerate the rate of hydrolysis reactions with the adjunct material. In another example, the pretreatment fluid can form a coating or film on the surfaces of the adjunct material (e.g., exterior surfaces or interior surfaces of pores) that increases the hydrophilicity of these surfaces. The increased hydrophilicity causes water contacting these surfaces to spread out and wet the surfaces, increasing the surface area of contact between the adjunct material and the water, thereby increasing the degradation rate of the adjunct material.

Embodiments of the pretreatment material that are configured to increase the degradation rate of the adjunct material can do so by decreasing the area of contact between the water and the adjunct material, via physical or chemical mechanisms. Pretreatment fluids that physically decrease the area of contact can include coatings or sealants. Coatings of the pretreatment fluid can be formed by flow of the pretreatment fluid onto surfaces of the adjunct material (e.g., exterior surfaces or interior surfaces of pores). Once present on the surfaces of the adjunct material, the coatings can form a physical barrier to interaction between the water and the adjunct material. The pretreatment fluid can form sealants by flowing to and residing between adjacent surfaces of the adjunct material that function as fluid passageways between the exterior surface of the adjunct material and the interior of the adjunct material. Once present in the flow passageways, the sealants can block flow of water therethrough, isolating interior regions of the adjunct material from interaction with water. Alternatively, the pretreatment fluid can react with the polymer chains forming the adjunct material to sever these polymer chains, physically reducing the length of the polymer chains and, therefore, reducing the area of the adjunct material that can contact the water. Pretreatment fluids that chemically decrease the area of contact can include hydrophobic agents and substitution agents. Hydrophobic agents can form a coating or film on the surfaces of the adjunct material (e.g., exterior surfaces or interior surfaces of pores) that increases the hydrophobicity of these surfaces. The increased hydrophobicity causes water contacting these surfaces to ball up, rather than spreading out to wet the surfaces. Substitution agents can chemically react with the polymer chains forming the adjunct material, changing the terminal group of the polymer chains to a functional group that inhibits interaction of water therewith.

Implantable Adjuncts Having Compressive Properties that Degrade Based Upon Healing Progression When implanting an adjunct adjacent to the cut tissue, one function of the adjunct can be application of pressure to the tissue (e.g., a cut line) when stapled thereto to facilitate the healing process (e.g., hemostasis). As healing progresses, it can be further desirable to reduce the pressure (compressive pressure) applied to the tissue in order to facilitate formation of blood vessels (vascularization). Existing adjuncts can be configured to degrade as a function of time, and therefore decrease the pressure applied to tissue, by degradation due to chemical reaction with water (hydrolysis). However, such degradation and reduction in pressure is not directly correlated to tissue healing. Thus, the level of pressure maintained by existing degradable adjuncts at a given time can be inappropriate for the degree of healing progression at that time and, actually inhibit, rather than facilitate the healing process.

Accordingly, in further embodiments, implantable adjuncts are provided that can be configured to exhibit a decrease in stiffness after implantation. The decrease in stiffness can result from degradation of the adjunct material due to chemical reaction with physiologic elements released during the healing process. When stapled to the tissue, the decrease in stiffness further results in a decrease in pressure applied by the adjunct to the tissue. In this manner, the applied pressure is correlated to the advancement of healing progression of the tissue, rather than merely time exposed to water.

In one embodiment, a biocompatible adjunct material is configured to be releasably retained on a staple cartridge and is configured to be delivered to tissue by deployment of staples in the staple cartridge. The adjunct material can be in the form of a porous polymer body exhibiting a first compressive stiffness that is approximately constant during a first time period from contact with the tissue. The porous polymer body can further exhibit a second compressive stiffness following the first time period that is less than the first compressive property. The second compressive property can decrease with time due to interaction (e.g., chemical reaction) with at least one physiological element released from the tissue during healing progression of the tissue. In other words, as the healing process progresses, physiological elements released from the tissue during different stages of the healing process can interact with the adjunct thereby causing the compressive properties of the adjunct to change. As discussed in greater detail below, examples of interaction of the porous polymer body with the at least one physiological element can include oxidation, enzyme-catalyzed hydrolysis, and change of pH adjacent to the adjunct.

The first time period represents a time duration prior to substantive reaction of the porous polymer body with the at least one physiological element. That is, a time duration over which any change in the first compressive stiffness is negligible (e.g., less than about 5%, less that about 4%, less than about 3%, less than about 2%, less than about 1%, etc.) In contrast, the second time period can represent a time duration during which reaction of the porous polymer body with the at least one physiological element occurs.

In one embodiment, the interaction of the porous polymer body with the at least one physiological element results in enzymatic degradation due to progression of the healing response and the body's introduction of the at least one physiological element into the healing site as the wound is remodeled.

As indicated above, in one embodiment, the interaction between the porous polymer body and the at least one physiological element is an oxidation reaction, where the at least one physiological element is an oxygen containing enzyme. In general, wound healing can be divided into four phases, hemostasis, inflammation, proliferation, and remodeling, and nearly every phase in the wound healing process can require oxygen, as outlined below.

Healing tissue requires energy, which is generated from oxidative metabolism of glucose. In aerobic metabolism of glucose, cells use oxygen to generate adenosine triphosphate (ATP), which fuels a majority of cellular processes during wound healing. Thus, healing tissue has increased oxygen demand. Increased oxygen consumption in turn causes hypoxia and activates the initial steps of the healing process by boosting activity of reactive oxygen species.

During the inflammatory phase of healing progression, the area of inflammation is a site for significant production of reactive oxygen species. In one aspect, this production is due to the occurrence of phagocytosis, the ingestion of cells or other materials by phagocytes as a defense against infection and invasion by foreign substances. The presence of reactive oxygen species further stimulate other functions necessary for wound repair, such as recruitment and activation of inflammatory cells such a leukocytes (white blood cells) at the wound site and the activation of fibroblasts. Examples of leukocytes include neutrophils, basophils, eosinophils, lymphocytes, monocytes, and macrophages. These inflammatory cells are also able to produce the at least one physiological element in the form of highly reactive oxygen species. Examples of classes of highly reactive oxygen species can include at least one of oxygen containing enzymes, free radicals, superoxides, and peroxides. Specific examples of the reactive oxygen species can include at least one of $O^{2-}$, $H_2O_2$, NO, and HOCl. At this time, a set of growth factors can be released that stimulate and attract the components of wound healing, such as wound leukocytes and fibroblasts. Hydrogen peroxide ($H_2O_2$) can be a mediator of these interactions. As wound healing progresses, cell proliferation and migration occur due to redox signaling of the reactive oxygen species. The last step or phase of wound healing is remodeling. During remodeling, the wound gains tensile strength, and the collagen fibers contract so the wound shrinks. The most prominent mediators of collagen processes are compounds released by macrophages, keratinocytes, endothelial cells, and fibroblasts/fibrocytes, all of which are dependent on oxygen.

In further embodiments, reactive oxygen species can be directed to a wound healing site from other regions in the body. In general, cells typically consume oxygen during their function. For the body to keep them alive it typically provides the oxygen via biologic processes like hemoglobin transport. As the body sees more cells in a region, angiogenesis grows blood pathways to the site to supply nutrients and oxygen to the site to sustain the cellular populations.

From the forgoing, it can be appreciated that the healing process results in the production and/or attraction of reactive oxygen species to the site of wound healing. These reactive oxygen species can participate in oxidation reactions with the polymer adjunct material to cause polymer chain scission and contribute to degradation of the adjunct. In particular, $O^{2-}$ can accelerate the degradation of polymers such as aliphatic polyesters by cleavage of ester bonds via nucleophilic attack. The oxygen-induced degradation chemically breaks down the polymer adjunct material, causing it to weaken and become less stiff, thus changing the applied pressure (e.g., compressive force) applied to the tissue. Because the concentration of reactive oxygen species available to react with the polymer adjunct material is a function of the healing process, the degree of oxygen-induced degradation of the polymer adjunct material, and therefore the pressure applied to the tissue by the adjunct, is also a function of the healing process.

In further embodiments, enzyme-catalyzed hydrolysis can contribute to degradation of the polymer body and attendant reduction in stiffness of the adjunct material. As an example, the adsorption and rate of hydrolysis reaction can be affected by (i) the physiochemical properties of the polymer body (e.g., molecular weight, chemical composition, crystallinity, surface area, etc.), (ii) the characteristics of a specific enzyme (e.g., activity, stability, local concentration, amino acid composition, and three-dimensional conformation), and (iii) medium conditions such as pH and temperature. The presence of stabilizers, activators, and/or inhibitory products in the local environment adjacent to the adjunct (e.g., resulting from degradation of the adjunct material or leaching out of processing additives) can also affect enzyme-catalyzed reactions by influencing enzyme adsorption and activity. Examples of such enzymes can include, but are not limited to, hydrolyzes such as proteases, esterases, glycosidases, phosphatases, and other suitable hydrolytic enzymes.

In additional embodiments, chemical modification of the polymer body (e.g., cross-linking, removal or introduction of chemical groups into the polymer chain) can affect the enzymatic degradation rate. Notably, depending on the degree of chemical modification, it can compromise the ability of the enzyme to recognize the modified polymer body. As an example, lysozyme, the enzyme responsible for degradation of peptidoglycan and chitin materials, exhibits low activity towards chitosans with high degrees of deacetylation or cross-linked chitosan. Examples of such enzymes can include, but are not limited to, lysozyme.

In other embodiments, degradation can be linked to other physiologic chemical changes in situ. For example, pH is one of the most impacted changes within the local chemical environment due to healing progression of infection development. The pH value adjacent to a wound directly and indirectly influences at least a portion of, and up to all of, the biochemical reactions taking place in the process of wound healing. As an example, the surface pH of a wound plays an important role in wound healing, as it helps control infection and increase anti-microbial activity, oxygen release, angiogenesis, protease activity, and biological toxicity. Accordingly, pH value can affect regular cellular events in wound healing.

Additionally, wounds with a high alkaline pH have a lower healing rate in both acute and chronic wounds as compared to wounds with a pH closer to neutral. That is, wound healing progression decreases when pH is elevated to alkaline levels. The environment of acute, as well as chronic wounds, progresses from an alkaline state to a neutral state, and then to an acidic state, when healing begins.

Accordingly, embodiments of the adjunct can be configured to adopt the second stiffness in response to a decrease in pH in the local environment adjacent to the polymer body resulting from the presence of the at least one physiological element. As discussed above, the pH of water or water-containing biological material participating in hydrolysis reactions can influence the rate of hydrolysis. Specifically, the rate of hydrolysis can decrease with decreasing pH. As the pH in the local environment of a wound decreases with healing progression, it can be expected that the reduction in pH will also be experienced by water and water-containing fluids participating in hydrolysis reaction with the adjunct material. Therefore, the rate of hydrolysis of the adjunct material, and relative contribution of hydrolysis to degradation of the adjunct material can decrease over time as compared to the relative contribution of oxidation to degradation of the adjunct material. However, it can be appreciated that the overall rate of degradation of the adjunct material resulting from combination of oxidation and hydrolysis processes can exceed the rate of degradation due to oxidation alone.

As indicated above, the adjunct can be used with a staple cartridge or anvil of the surgical stapler 10 for treating tissue e.g., such as staple cartridge 102 shown in FIG. 6 or anvil (e.g., upper jaw surface 34) shown in FIG. 2. During implantation, the adjunct material can be delivered to tissue by deployment of staples in the staple cartridge body, securing the adjunct material to the tissue and causing the adjunct material to apply pressure (e.g., compressive pressure) to a wound (e.g., a cut line).

In use, the healing process occurs within the tissue coupled to the adjunct material. The healing process begins with hemostasis, where flow of blood from the wound is stopped. In general, it is beneficial for the adjunct to apply a relatively high pressure (compressive pressure) to the wound to facilitate hemostasis. As discussed above, the adjunct can be compressed (e.g., by upper and lower jaws 22, 34 when delivered to the tissue by deployment of staples and can expand when released. Accordingly, the adjunct material can be configured to exhibit a first stiffness in compression such that, when the adjunct is deployed, a compressive pressure exerted by the adjunct when expanded against the tissue is sufficiently high to assist hemostasis of the tissue.

The adjunct can be further configured to maintain the first stiffness at an approximately constant level during a first time period from contact with the tissue. That is, the adjunct material can experience little to no degradation due to reaction (e.g., oxidation, enzyme-catalyzed hydrolysis, etc.) with bodily fluids such as water or water-containing fluids during the first time period. By maintaining the first stiffness at an approximately constant level during the first time period, the compressive pressure applied by the adjunct material to the tissue is also maintained at an approximately constant level.

The adjunct material can be configured to maintain the first stiffness over the first time period in a variety of ways. As discussed above, in one aspect, the adjunct material can be treated, as discussed above, with a pretreatment fluid to reduce the rate of degradation of the adjunct material. In another aspect, the adjunct material can be mechanically compressed to close at least a portion of the porosity of the adjunct material to inhibit flow of bodily fluids. It can be appreciated that one or more other mechanisms for reducing the rate of degradation of the adjunct material can be employed, alone or in any combination with those discussed above, can be employed without limit.

As healing progression continues into the inflammation, proliferation, and remodeling stages, it can be desirable to reduce the compressive pressure applied by the adjunct material to the tissue to facilitate formation of blood vessels. Accordingly, the adjunct material can be configured to exhibit a second stiffness, less than the first stiffness, during a second time period following the first time period.

As an example, during the second time period, these later healing stages can occur and the tissue can release the at least one physiological element to facilitate healing. For example, the at least one physiological element can include a reactive oxygen species. While the reactive oxygen species is produced to provide energy for the healing process, it can also interact with the adjunct material to cause degradation. Examples of such interactions can include oxidation via reaction with the reactive oxygen species, hydrolysis that is catalyzed by an enzyme (e.g., oxygen-containing enzyme), and change of pH resulting from the presence of the at least one physiological element in the fluid environment local to the adjunct material. Oxidation can contribute to degradation of the adjunct material by polymer chain scission, while enzyme-catalyzed hydrolysis can contribute to degradation by chemical breakdown of the polymer adjunct material. pH can contribute to degradation by influencing the rate of degradation, where the increased rate of degradation can be greatest when the pH is relatively high (e.g., alkaline relatively early within the healing process). A least oxidation can be a function of the healing process, as it depends upon the concentration of reactive oxygen species e produced during healing. As a result, degradation of the adjunct material can be a function of the healing progression, which results in the adjunct material exhibiting a second stiffness that is less than the first stiffness, that decreases with advancement of the healing process. Beneficially, as noted above, the reduction in stiffness of the adjunct material from the first stiffness to the second stiffness can promote vascularization.

Tissue Thickness Compensating Adjunct Having Regions of Differential Expansion

As discussed above, in certain embodiments, adjuncts can be configured to compensate for variations in tissue thickness when stapled to tissue, exhibiting an uncompressed (un-deformed), or pre-deployed, height, and being configured to deform to one of a plurality of compressed (deformed), or deployed, heights. It can be appreciated that leakage of bodily fluids (e.g., blood, air, gastrointestinal fluids, etc.) can occur when staples penetrate the adjunct and tissue. Notably, penetration of the adjunct the staples can form holes in the adjunct that are larger than the diameter of the staple legs. Furthermore, when tissue is cut, prior to onset of hemostasis, blood can flow along a cut line. Accordingly, it can be desirable to employ the adjunct material to seal staple puncture holes and/or apply pressure to the staple line to facilitate hemostasis.

In further embodiments discussed in detail below, tissue thickness compensating adjuncts are provided that are formed from a material that swells when exposed to moisture and that have a structure that varies in thickness and/or pressure as a function of position within the adjunct. As an example, predefined portions of the adjunct are configured to permit or restrain expansion of the adjunct, thus altering the sealing pressure applied to the tissue at those predefined portions of the adjunct. In one aspect, portions of the adjunct adjacent to respective incipient staple lines, where staple legs are intended to penetrate the adjunct material, can be configured expand when exposed to moisture as compared to portions of the adjunct distanced from the incipient staple lines. This expansion of the adjunct can urge the adjunct material in contact with the staple legs and sealing the staple holes. In another aspect, portions of the adjunct adjacent to an incipient cut line, where a knife is expected to pass and cut the tissue and adjunct, can be configured to expand when exposed to moisture, as compared to portions of the adjunct distanced from the incipient cut line. This expansion of the adjunct can allow the adjunct to apply a compressive pressure to the cut line and/or regions of the tissue adjacent to the cut line to promote hemostasis.

Figure 63:
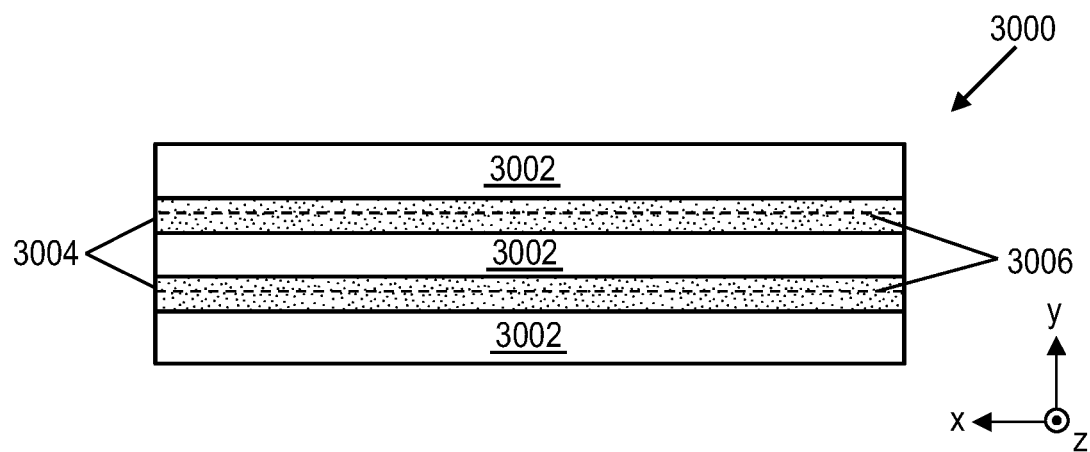
FIG. 63 is a schematic diagram illustrating a top view of an upper tissue contacting surface of one exemplary embodiment of a tissue thickness compensating adjunct in an un-deformed or pre-deployed state configured for sealing staples along a staple line.

FIG. 63 is a schematic diagram illustrating a top view (e.g., an x-y plane) of an upper tissue contacting surface of one exemplary embodiment of a tissue thickness compensating adjunct 3000 in the un-deformed or pre-deployed state. The adjunct 3000 includes at one or more first portions 3002 and one or more second portions 3004. While the adjunct 3000 is configured to be releasably retained on a staple cartridge or anvil of a stapling assembly, the adjunct 3000 is shown in isolation for clarity.

The first portions 3002 of the adjunct 3000 can be formed from a first material that is configured to exhibit a first expansion behavior in response to receipt of a unit volume of fluid. The second portion 3004 of the adjunct 3000 can be configured to exhibit a second expansion behavior, different from the first expansion behavior, in response to receipt of the unit volume of fluid. The expansion behavior can include, but is not limited to, expansion volume and expansion rate. In certain embodiments the volume of expansion and/or rate of expansion given by the second expansion behavior of the second material is greater than a corresponding volume of expansion and/or rate of expansion given by the first expansion behavior of the first material.

The first portions 3002 can be formed from a biocompatible porous polymer material, as discussed above. In contrast, the second portions 3004 can be formed from a swellable material that is different from the biocompatible porous polymer material of the first portions 3002. Examples of swellable materials can include, but are not limited to, hydrogels, a low molecular weight polymers (e.g., polymers having an average molecular weight sufficient to be cleared from the patient's body, such as less than about 30,000 kDa), polymers having a relatively low degree of cross-linking.

It can be appreciated that alternative embodiments of the adjunct can be configured to change the relative expansion characteristics (e.g., volume of expansion, rate of expansion, etc.) of the first and second portions from those discussed above. For example, the volume of expansion and/or rate of expansion of the first portions of the adjunct can be greater than that of the second portions in response to receipt of approximately the same volume of moisture. Furthermore, while not shown, additional embodiments of the adjunct can include greater than two regions, each configured to swell by different respective amount in response to receipt of approximately the same volume of moisture.

As noted above, a common problem encountered when employing surgical staples with adjuncts is seepage of one or more fluids (e.g., water, blood, air, gastrointestinal fluids, etc.) through the openings formed by the staples, even after the staple is fully formed. Accordingly, in further embodiments of the adjunct 3000, the relative placement of the first and second portions 3002, 3004 can be configured to apply pressure to staples along staple lines to seal holes formed within the adjunct by staples. As shown in the top view of FIG. 63, incipient staple lines 3006 extend along the length of the adjunct 3000 (e.g., in the longitudinal or x-direction). The second portions 3004 are approximately aligned with (e.g., approximately parallel to) the incipient staple lines 3006 and have a width greater than the incipient staple lines 3006. Under circumstances where multiple incipient staple lines 3006 are present, they can be separated from one another in a width direction (e.g., the y-direction) by the first portions 3002 and extend in a longitudinal direction of the adjunct (e.g., the x-direction), aligned with respective staple lines 3006.

Figure 64:
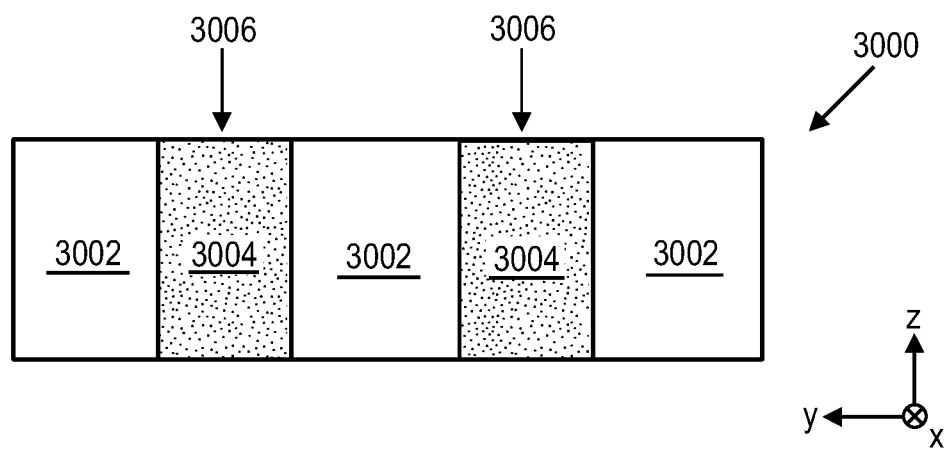
FIG. 64 is a schematic diagram illustrating an end-on view of the tissue thickness compensating adjunct of FIG. 63 in the un-deformed or un-deployed state.

FIG. 64 is an end-on view (e.g., a y-z plane) of the adjunct 3000 of FIG. 63. As shown, the second portions 3004 can extend through an entirety of the thickness (e.g., z-direction) of the adjunct 3000.

Figure 65:
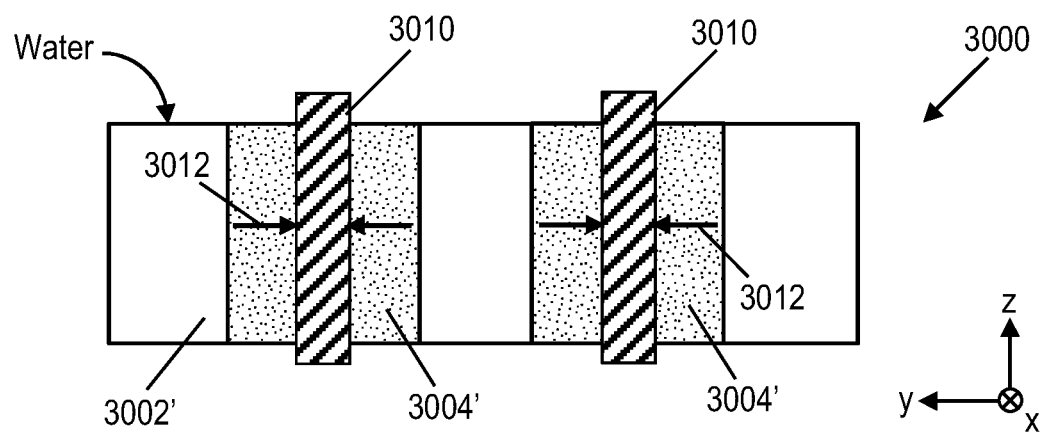
FIG. 65 is a schematic diagram illustrating an end-on view of the tissue thickness compensating adjunct of FIG. 63 in a deformed or deployed state where expanded portions of the adjunct exert a sealing pressure against staples extending therethrough.

Prior to deployment, and receipt of water or other physiological fluids, the adjunct 3000 has a first shape. Once implanted, and upon receipt of water or other fluids, the second portions 3004 expand to form corresponding expanded second portions 3004" and adopt a second shape, different from the first shape, as shown in FIG. 65. As a result, the of expansion, the second portions 3004 exert a compressive force or pressure (arrows 3012) on the staples 3010 thereby partially or substantially completely sealing the holes formed through the adjunct 3000 by passage of the staples 3010 therethrough. The expansion behavior of respective expanded second portions 3004' can be the same or different as a function of position along the staple line 3006 (e.g., along the x-direction).

Figure 66:
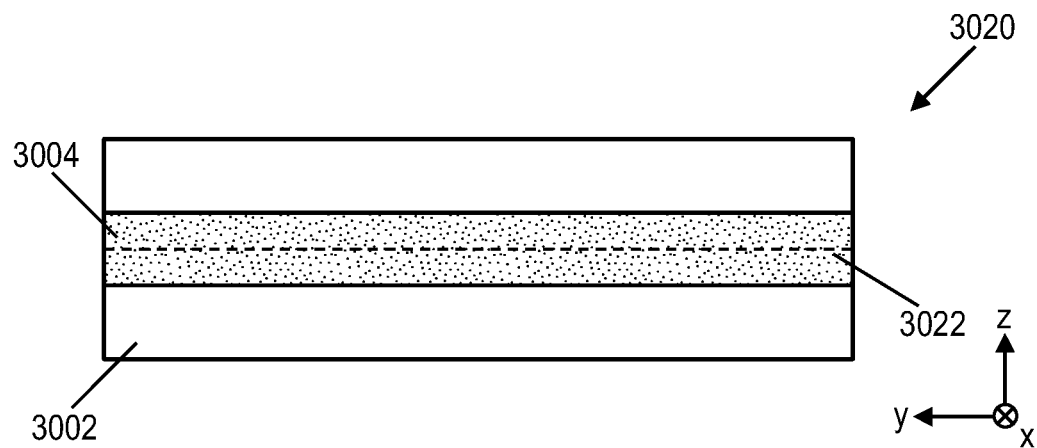
FIG. 66 is a schematic diagram illustrating a top view of an upper tissue contacting surface of another exemplary embodiment of an adjunct configured to apply pressure along a tissue cut line.
Figure 67:
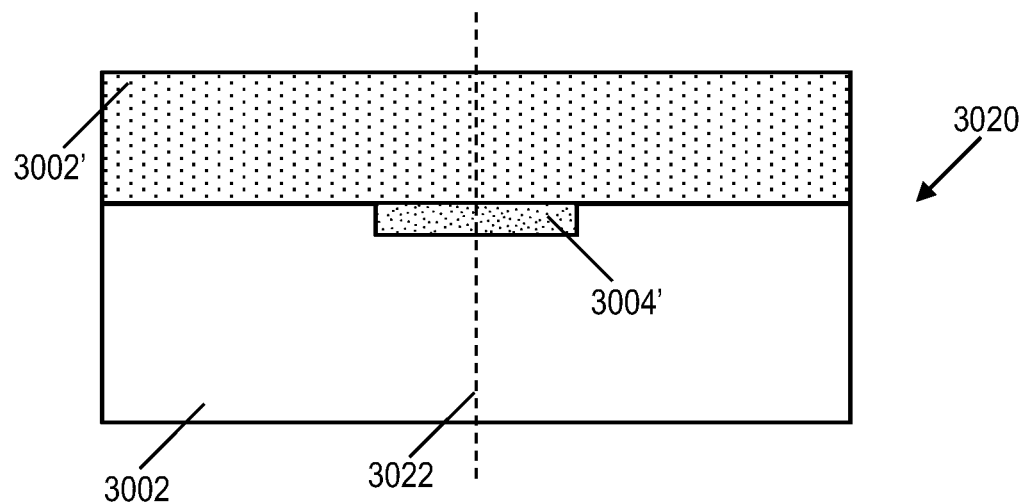
FIG. 67 is a schematic diagram illustrating an end-on view of the tissue thickness compensating adjunct of FIG. 66 in the un-deformed or un-deployed state.
Figure 68:
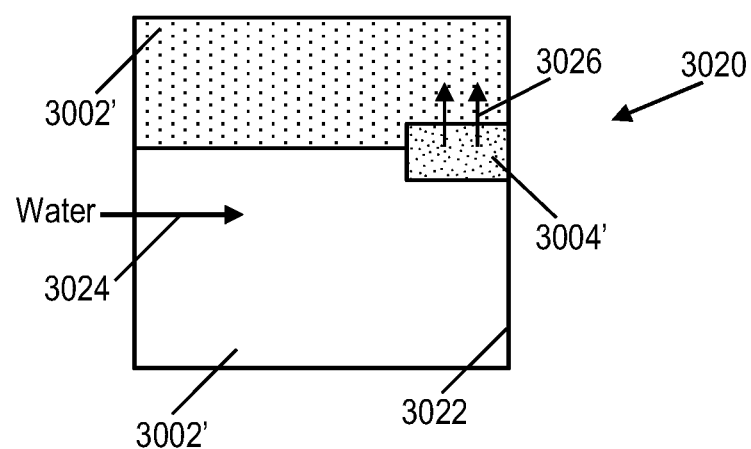
FIG. 68 is a schematic diagram illustrating an end-on view of the tissue thickness compensating adjunct of FIG. 67 in the deformed or deployed state.

In another embodiment, the relative placement of the first and second portions 3002 and 3004 can be configured such that expansion of at least one of the first and second portions 3002, 3004 exerts pressure along and/or adjacent to a tissue cut line that is sufficient to provide hemostasis. FIG. 66 is a schematic diagram illustrating a top view of an upper tissue contacting surface another exemplary embodiment of a tissue thickness compensating adjunct 3020 in the un-deformed or pre-deployed state. FIG. 67 is an end-on view of the adjunct 3020 of FIG. 66. FIG. 68 is an end-on view of the adjunct 3020 in the deformed or deployed state. While the adjunct 3000 is configured to be releasably retained on a staple cartridge or anvil of a stapling assembly, the adjunct 3020 is shown in isolation for clarity.

As shown in FIG. 66 and FIG. 67, similar to the adjunct 3000, the adjunct 3020 includes first and second portions 3002, 3004. However, in contrast to the adjunct 3000, the second portion(s) 3004 overlie at least the first portion(s) 3002 on and/or adjacent to an incipient tissue cut line 3022. In other embodiments, the second portion(s) can overlie substantially the entire first portion(s). The adjunct 3020 can be positioned on the staple cartridge of a stapling assembly, with the first portion(s) 3022 spaced a distance from an expected path of a knife 36, as shown in FIG. 3 that defines the incipient tissue cut line 3022 and the second portion(s) 3004 positioned on or adjacent to the knife path/incipient tissue cut line 3022. So configured, receipt of water or other fluids by the adjunct 3020 (arrow 3024) results in expansion of the second portion(s) 3004 relative to the first portion(s) 3002 to form expanded second portion(s) 3004', as shown in FIG. 68. The expanded second portion(s) 3004' exert pressure (arrows 3026) along the cut line 3022 to promote hemostasis. The expansion behavior of respective expanded second portions 3004' can be the same or different as a function of position along the knife path/incipient tissue cut line 3022.

In further embodiments of the adjuncts 3000, 3020, the second portions 3004 can be formed from a porous, solid material and housed in a compressed state within a fluid soluble capsule. The capsule can be configured to degrade relatively quickly in response to contact with water and/or other physiological fluids after a predetermined time period (e.g., on the order of seconds to minutes) for release of the second portions therefrom. Beneficially, such encapsulation provides for time-release control of pressure applied by the adjuncts 3000, 3020 to tissue.

In other embodiments, tissue thickness compensating adjuncts can be configured to degrade over time, providing a short-term mechanism for compression of tissue. As discussed in greater detail below, such adjuncts can be combined with other mechanisms that provide comparatively longer-term compression (e.g., staples). Together, these short- and long-term compression mechanisms can promote tissue healing.

In general, the mechanical properties of bioabsorbable adjunct materials change (e.g., reduce) over time as the degree of degradation of the adjunct increases. In one embodiment, the adjunct 3020 can be configured to degrade at a rate that maintains sufficient compression (e.g., by the expanded second portions 3004') to allow the body to coagulate/clot bleeding within the region of the cut line 3022. Compressive pressure provided by staples can be provided to further reinforce the cut line for a longer time duration and lower magnitude, as compared to that provided by the adjunct. Beneficially, the relative high compressive pressure provided in the short-term by the adjunct 3020 facilitates clotting while the relatively lower compressive pressure provided in the long-term by the staples provides reinforcement without restricting flow of blood to the cut line 3022.

Figure 69:
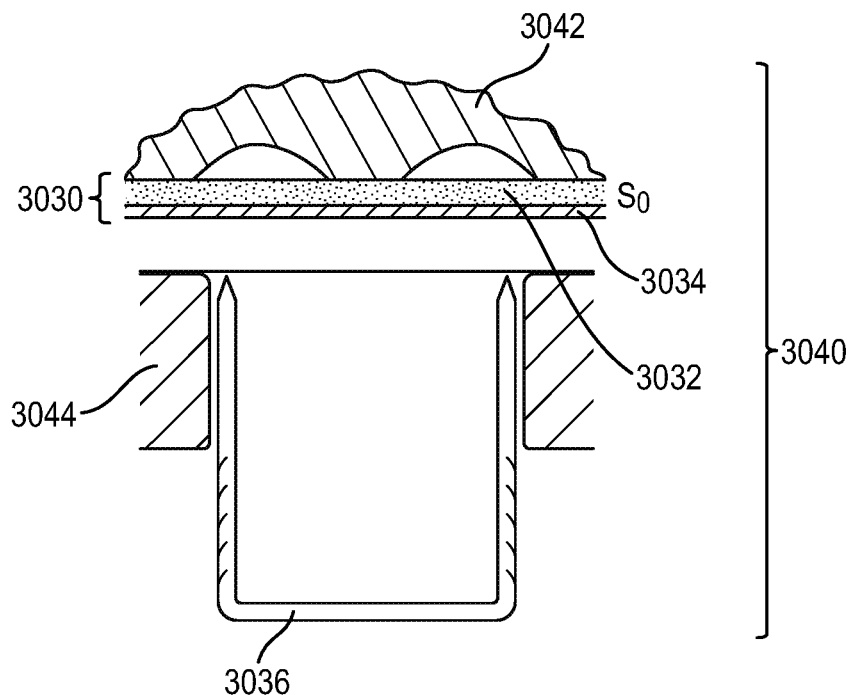
FIG. 69 is a schematic diagram illustrating a side cross-sectional view of a stapling assembly in a pre-firing configuration including an anvil and staple cartridge with another embodiment of a tissue compensating adjunct mounted on an anvil, the adjunct being configured to work in combination with staples fired from the staple cartridge to inhibit retraction of the adjunct from contact with the tissue after staple firing.

In another embodiment, a tissue thickness compensating adjunct 3030 is provided and is configured to work in combination with staples 3036 to inhibit retraction of the adjunct 3030 from contact with the tissue 3038 after expansion. FIG. 69 is a schematic diagram illustrating a side cross-sectional view of a stapling assembly 3040 in a pre-firing configuration that includes a first jaw having an anvil 3042 (shown in part) opposite a staple cartridge 3044 housing a plurality of staples (only one staple 3036 is shown). The adjunct 3020 is positioned on the anvil 3042 and includes one or more first portions 3032 underlying one or more second portions 3034. The first portion 3032 contacts the anvil 3042 and the second portion 3034 is spaced apart from the anvil 3042 and faces tissue. The adjunct 3030 has a total initial thickness $s_o$ in this pre-firing configuration. As shown, the first and second portions 3032, 3034 are generally planar. However, other non-planar configurations can be employed without limit. Additionally, while the embodiment of FIG. 69 illustrates the adjunct positioned on the anvil, in alternative embodiments, the adjunct can be positioned on the staple cartridge.

Figure 70:
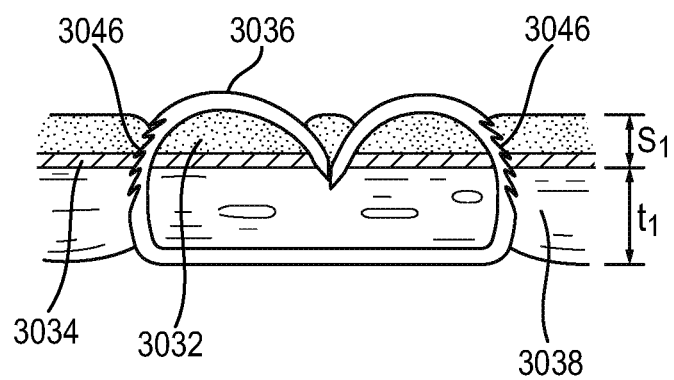
FIG. 70 is a schematic diagram illustrating the stapling assembly and adjunct of FIG. 69 immediately after firing of a staple from the staple cartridge, through the adjunct and tissue, and release of the adjunct and tissue from the stapling assembly.

In operation, as shown in FIG. 70, the tissue 3038 is clamped between the anvil 3042 and the staple cartridge 3044 and one or more staples 3036 are fired from the staple cartridge, through the adjunct 330, and into the tissue 3038 to thereby staple the adjunct 3030 to the tissue 3038. As further illustrated in FIG. 71, the adjunct 3030 and tissue 3038 are subsequently released from the stapling assembly 3040 after staple firing. The total thickness of the adjunct 3030 after release from the stapling assembly 3040 increases from the initial thickness $s_o$ to an implanted thickness $s_1$ due to removal of the clamping force applied by the stapling assembly 3040. The tissue 3038 has a thickness $t_1$.

After being stapled to the tissue 3038, the adjunct receives a unit volume of fluid (e.g., water and/or other physiological fluids). At least one of the first and second portions 3032, 3034 is formed from a polymer configured to expand in response to receipt of the water and/or other physiological fluids. In certain embodiments, the first portions 3032 can be formed from a moisture absorbing, swellable polymer. The second portions 3034 can be formed from a semi-porous film. The first portions 3032 are configured to expand according to a first expansion behavior in response to receipt of a unit volume of fluid. The second portions 3034 can be configured to expand according to a second expansion behavior, different from the first expansion behavior, in response to receipt of the unit volume of fluid. The second portions 3034 can further overlie the first portions 3032 and can be mechanically coupled thereto (e.g., by a biocompatible adhesive or other fixation mechanism). As the second portions 3034 are semi-porous, a portion of the water and/or other physiological fluids received by the second portions 3034 and not absorbed can flow through the second portions 3034 (e.g., via open porosity) for receipt by the first portions 3032.

Figure 71:
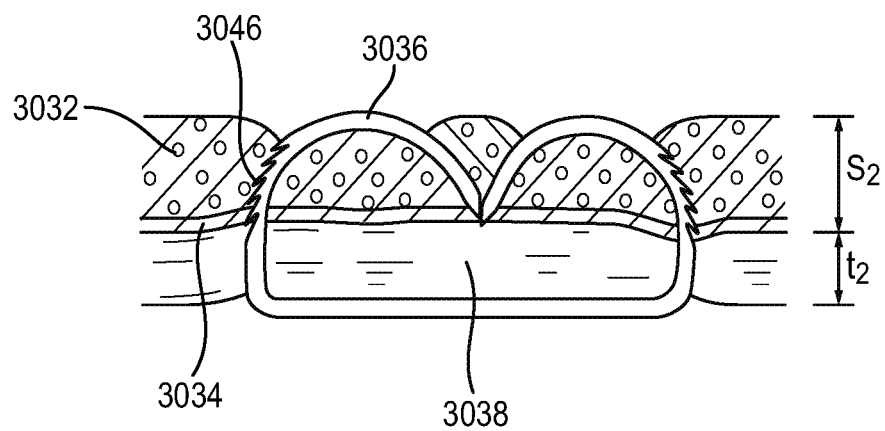
FIG. 71 is a schematic diagram illustrating the stapling assembly and adjunct of FIG. 70 after absorption of water and/or other physiological fluids from the body.

Expansion of the first portions 3032 applies a first pressure (e.g., compressive pressure) to the tissue 3038, and expansion of the second portions, 3034 results in application of second pressure to the tissue 3038. As a result of expansion of the adjunct 3030 and application of pressure by the adjunct 3030 to the tissue 3038, the thickness of the adjunct increases to a third thickness $s_2$ and the thickness $t_2$ of the tissue 3038 decreases, as shown in FIG. 71. In alternative embodiments, the second portion(s) do not substantially expand when receiving water and/or other physiological fluids, or expand to a degree that is significantly less than that of the first portions(s).

In other embodiments, the staples 3036 can include one or more features 3046 configured to permit expansion of the adjunct 3030 in a first direction (e.g., a direction towards the tissue 3038) and to inhibit retraction of the adjunct 3030 in a second direction, opposite the first direction (e.g., a direction away from the tissue 3038). As shown in FIG. 70 and FIG. 71, the one or more features 3046 can include a plurality of barbs extending along one or more of the legs of the staples 3036. The plurality of barbs are positioned such that, after firing into the adjunct, the barbs extend toward the base of the staple, opposite the direction of insertion of the staple into tissue 3038. As the adjunct 3030 expands (e.g., via expansion of the first and/or second portions 3032, 3034), the plurality of barbs engage at least the second portions 3034. As the second portions 3034 are mechanically coupled to the first portions 3032, engagement of the barbs with the second portions 3034 provides a ratcheting-like effect that inhibits retraction of the adjunct 3030 away from the tissue 3038 after expansion of the adjunct 3030.

Embodiments of any portion of any of the adjuncts 3000, 3020, 3030 can be configured to exhibit a change of color in response to expansion. As an example, the portion(s) of the adjuncts 3000, 3020, 3030 exhibiting a color change can include a color transition dye. Examples of the color transition dye can include a hydrochromic ink that is configured to change color in response to at least one fluid, such as water and lipids. In further embodiments, expandable portions of the adjuncts 3030, 3020, 3030 formed from water or lipid sensitive polymers can be in a thin and dry state when un-deployed and expand to a taller state when deployed and hydrated.

The ability of selected portions of the adjuncts 3000, 3020, 3030 to exhibit color change when expanding can allow for rapid, visual identification of expansion behavior. This can be beneficial for confirming that the selected portions of the adjuncts 3000, 3020, 3030 have in fact expanded and therefore, functionality enabled by expansion, such as staple sealing or application of pressure to the cut line is accomplished, without requiring time consuming measurements.

It can be appreciated that such visual identification of the expansion of portions of the adjuncts 3000, 3020, 3030 can be employed for sealing staple It can be appreciated that, because the mass of the portion(s) of the adjuncts 3000, 3020, 3020 exhibiting a color change is constant, the increase in volume resulting from expansion decreases the density of these portions.

Composite Adjuncts that Degrade Through Multiple Different Mechanisms

As discussed above, it can be desirable to employ adjuncts that exhibit compressive properties that degrade as a function of the healing process in order to correlate the amount of compression applied to tissue with that most suitable to facilitate tissue healing. In one aspect, degradation can be correlated to the healing process by use of adjunct materials that degrade in response to reaction with at least one physiological element that is released from tissue during the healing process. In one example, physiological elements including a reactive oxygen species can facilitate degradation by participation in oxidation reactions with the adjunct material. In another example, enzymes released during healing process can catalyze hydrolysis reactions, increasing the rate of degradation of the adjunct material by hydrolysis. This concept can be further employed in the context of composite adjuncts formed from two or more polymers, each of which degrades by a different mechanisms. In this manner, the rate of degradation and attendant change in mechanical properties of the adjunct can be controlled via two mechanisms, rather than a single mechanism, providing greater functionality.

Figure 72:
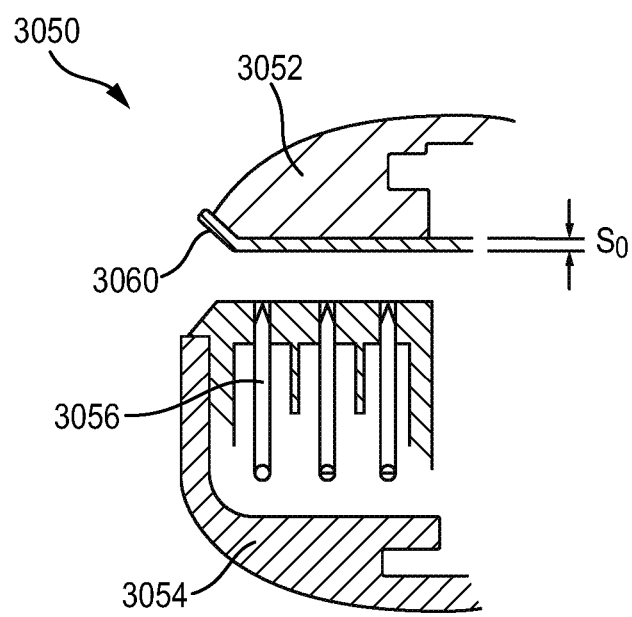
FIG. 72 is a schematic diagram illustrating a side cross-sectional view of a stapling assembly in a pre-firing configuration including an exemplary embodiment of a composite adjunct including first and second polymers.

FIG. 72 is a schematic diagram illustrating a side cross-sectional view of a stapling assembly 3050 in a pre-firing configuration that includes a first jaw having an anvil 3052 opposite a staple cartridge 3054 housing a plurality of staples 3056. As shown, an exemplary embodiment of a composite adjunct 3060 is releasably retained on the anvil 3052 and has a thickness S. In alternative embodiments (not shown), the composite adjunct 3060 can be releasably retained on either or both of staple cartridge or anvil for delivery to tissue by deployment of staples in the staple cartridge.

Figure 73:
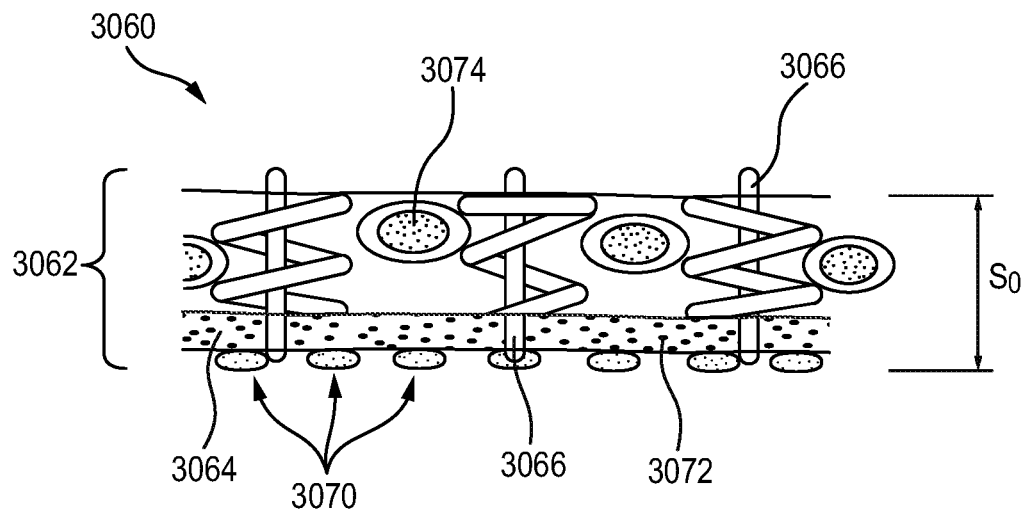
FIG. 73 is a schematic diagram illustrating a side cross-sectional view of the composite adjunct of FIG. 72.

The composite adjunct 3060 is illustrated in greater detail in FIG. 73. The composite adjunct 3060 is formed as a porous polymer body 3062 that includes a first polymer 3064 and a second polymer 3066. The first polymer 3064 overlies the second polymer 3066 and the second polymer 3066 is compressed beneath the first polymer 3064. While first and second polymers 3064, 3066 are shown, the adjunct can include any number of polymers. In certain embodiments, the first polymer 3064 retains at least one first drug 3070 therein. In certain embodiments, the at least one first drug 3070 is a hemostat. In further embodiments, the second polymer 3066 retains at least one second drug 3074 therein configured to encourage tissue remodeling. The compression response of the first and second polymers 3064, 3066 and corresponding amount of first and second drugs 3070, 3074 released are illustrated in FIG. 78B and FIG. 78C, respectively, discussed in greater detail below. Healing mechanisms occurring as a function of time are further illustrated in FIG. 78A.

The first polymer 3064 can be configured to degrade according to a first degradation profile as a function of at least one of hydrolysis in response to interaction with water 3072 and heating to a physiological temperature. The first polymer 3064 can further be configured to expand in response to absorption of water 3072 and/or other physiological fluids. Example of the first polymer 3064 include at least one of moisture absorbing powders and moisture absorbing foams.

The second polymer 3066 can be configured to degrade according to a second degradation profile as a function of at least one of oxidation, enzyme-catalyzed hydrolysis, and change of pH resulting from interaction with at least one physiological element 3076 released from the tissue during healing progression of the tissue (FIG. 77), as discussed in greater detail below. The second polymer 3066 is further configured to expand in response to degradation of the first polymer 3064.

Figure 75:
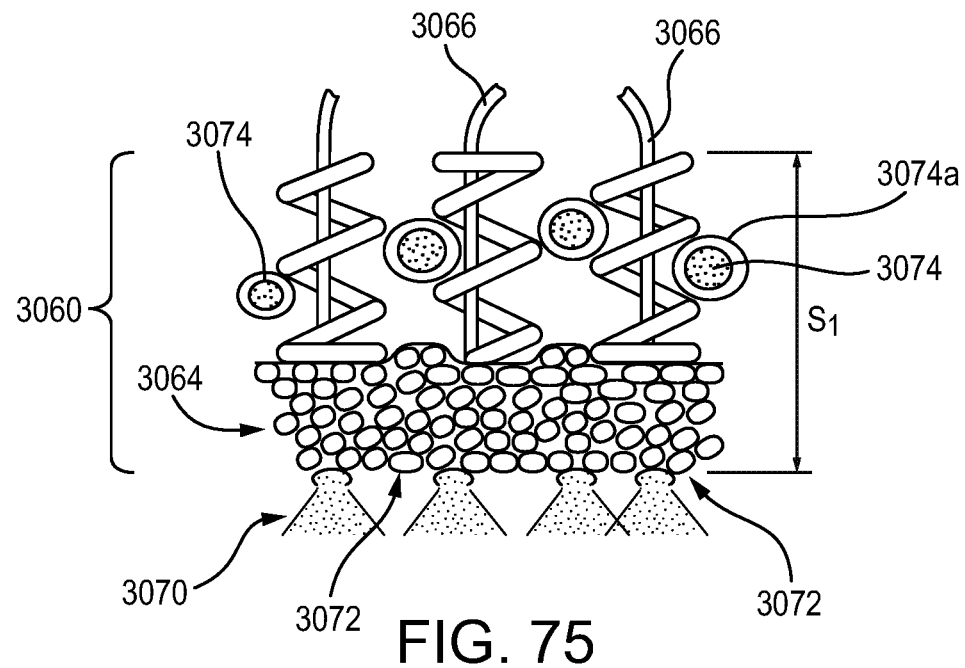
FIG. 75 is a schematic diagram illustrating a magnified side cross-sectional view of the composite adjunct of FIG. 74.

As shown in FIG. 73 and FIG. 75, the first polymer 3064 overlies the second polymer 3064, and therefore mechanically constrains the second polymer 3064. As a result, during the first time window A, the compressive pressure applied by the second polymer 3064 to the tissue 3068 (FIG. 78B) is relatively low and increases relatively slowly as compared to the first polymer 3064. The relatively slow rate of increase of the compressive pressure can be attributed to modest degradation of the first polymer 3064 and attendant relaxation of the constraint of the second polymer 3064.

Examples of the second polymer 3066 include porous structures. Examples of the at least one physiological element can include, but are not limited to, reactive oxygen species. The reactive oxygen species can include at least one of an oxygen containing enzyme, a free radical, a superoxide, and a peroxide.

In certain embodiments, the second polymer 3064 retains the second drug 3074 therein. Examples of the at least one second drug 3074 can include, but are not limited to, drugs configured to promote tissue remodeling. As shown in FIG. 78C, prior to firing (condition time window A, none of the at least one second drug 3074 is released.

In certain embodiments, the at least one second drug 3074 can be configured for at least one of bolus release or gradual release. In one example, as shown in FIG. 21, the second drug 3074 can be encapsulated by a material 3074a that that is configured for gradual release of the second drug 3074 (e.g., a material that degrades relatively slowly in response to interaction with water 3072 and/or other physiological fluids). In another example, graduated release can be provided by one or more relatively large reservoirs formed within the second polymer configured to provide a release of a relatively small volume of the second drug therefrom during a relatively short time period during degradation of the second polymer. As an example, a fluid limiting device, such as a valve, can be employed in combination with a relatively large reservoir for graduated release. In other embodiments, graduated release can be provided by a plurality of relatively smaller volume reservoirs that are configured to independently release relatively small volumes of the second drug over time via degradation of the second polymer (e.g., release of the second drug into respective fluid passageways that are not in fluid communication with one another).

In further embodiments, bolus release of the second drug can be provided by one or more relatively large reservoirs formed within the second polymer that are configured to provide a release of a relatively large volume of the second drug upon during degradation of the second polymer. In alternative embodiments, bolus containment can be provided by a plurality of smaller reservoirs that are configured to concurrently combine respective volumes of the second drug released therefrom during a relatively short time period during degradation of the second polymer (e.g., release of the second drug into one or more common fluid passageways).

Figure 74:
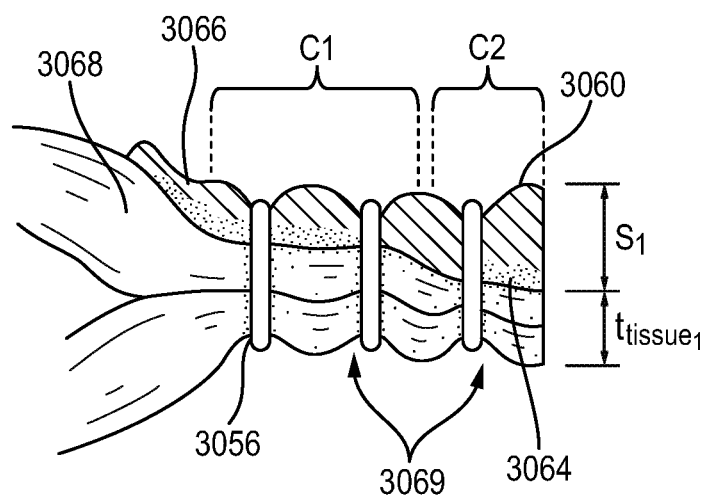
FIG. 74 is a schematic diagram illustrating a side cross-sectional view of the composite adjunct of FIG. 73 coupled to tissue by staples immediately after firing of the stapling assembly.

FIG. 74 is a schematic diagram illustrating the adjunct 3060 immediately after firing the staples 3056 through the adjunct 3060 and tissue 3068 (time window B, FIG. 78A). FIG. 21 is a schematic diagram illustrating the adjunct 3060 in greater detail. As shown, the first polymer 3064 expands in response to interaction with water 3072. As a result of this expansion, the first polymer 3064 exerts a first compressive pressure 3080 on the tissue 3068.

The first degradation profile of the first polymer 3064 during the time window B (FIG. 78A) is a function of interaction (e.g., chemical reaction) with water 3072 (hydrolysis). This configuration can be beneficial for hemostasis, as it results in a first degradation profile that exhibits a relatively rapid rate of decrease of the first compressive pressure 3080 from a peak value. Accordingly, in certain embodiments, a degradation rate of the first polymer 3064 according to the first degradation profile is greater than a degradation rate of the second polymer 3066 according to the second degradation profile.

Concurrently, a release rate 3086 of the first drug 3070 also exhibits a relatively rapid decrease, falling from a maximum value with degradation of the first polymer 3064. That is to say, the at least one first drug 3070 is configured for relatively rapid release. As discussed above, the at least one first drug 3070 can be a hemostat. Accordingly, rapid release of the at least one first drug 3070 can further promote rapid hemostasis.

With compression of the second polymer 3066 beneath the first polymer 3064, the first polymer 3064 can constrain expansion of the second polymer 3066. This is reflected in FIG. 78B as a relatively slow rate of increase of the second compressive pressure 3082. However, the ability of the first polymer 3064 to constrain the second polymer 3066 diminishes with continued degradation of the first polymer 3064, and the rate of increase of the second compressive stress 2412 on the tissue 3068 rises as time progresses within the second time window B. As a result, the thickness of the adjunct 3060 can increase from an initial thickness $S_o$ to a first thickness $S_1$. The tissue thickness has an initial thickness $t_{tissue1}$. The combination of the first and second compressive pressure 3080, 3082 further promotes hemostasis, providing a region 3069 of restricted blood flow for clotting.

In certain embodiments, at least one of the first polymer and the second polymer can include a hydrogel that is configured to expand by a larger amount than the surrounding polymer material. In this way, the resulting composite adjunct can exhibit varying amounts of expansion. In this manner, different levels of compression can be applied by the adjunct to different regions of the tissue (e.g., cut line, staple line, etc.) As shown in FIG. 20, the composite adjunct 3060 applies two different levels of compression C1 and C2 at different regions. For example, the compression C2 can be greater than the compression C1 and positioned proximate to a cut line to thereby increase local pressure to seal the region until healing.

As healing progresses during the second time window B (e.g., the inflammation phase and release of neutrophils), the concentration of the at least one physiological element 3076 received at the composite adjunct 3060 increases. As an example, neutrophils can be released, along with corresponding ones of the at least one physiological element 3076. Concurrently, degradation of the first polymer 3064 progresses with time, reducing the ability of the first polymer 3064 to inhibit interaction of the second polymer 3066 with the at least one physiological element 3076. Thus, the rate of degradation of the second polymer 3066 increases, reflected as an increase in release rate 2086 of the at least one second drug 3074 from the second polymer 3066 as time progresses within the second time window B.

Figure 76:
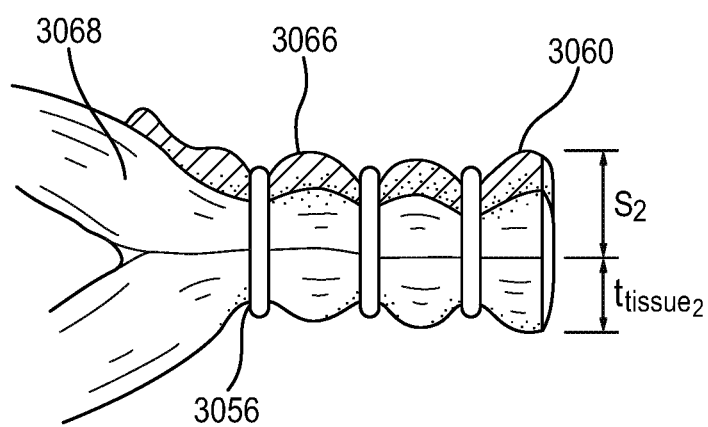
FIG. 76 is a schematic diagram illustrating a side cross-sectional view of the composite adjunct of FIG. 73 coupled to tissue by staples at a predetermined time duration after firing of the stapling assembly.

FIG. 76 is a schematic diagram illustrating the adjunct 3060 at a predetermined time after firing the staples 3056 through the adjunct 3060 and tissue 3068 (time window C, FIG. 78C). FIG. 77 is a schematic diagram illustrating the adjunct 3060 in greater detail. As shown, degradation of the first polymer 3064 is substantially complete, by the relatively low magnitude of the first compressive pressure 3080, and relatively low release rate 3084 of the at least one first drug 3070. That is, substantially all of the at least one first drug 3070 has been released. Furthermore, due to the reduction in the first compressive pressures 3080, the thickness of the adjunct 3060 decreases from the first thickness $S_1$ to a second thickness $S_2$ and the thickness of the tissue 3068 increases from an initial tissue thickness $t_{tissue1}$ to a second tissue thickness $t_{tissue2}$. Beneficially, the combination of first and second compressive pressures 3080, 3082 applied to the tissue 3068 are at a level sufficient to allow vascularization.

Concurrently, healing continues to progress from the inflammation to the proliferation and maturation stages, resulting in release of macrophages, fibroblasts, and lymphocytes, as illustrated in FIG. 78A and corresponding ones of the at least one physiological element 3076. With the high degree of degradation of the first polymer 3064 during time window C, the ability of the at least one first polymer 3064 to inhibit interaction of the second polymer 3066 with the at least one physiological element 3076 is significantly reduced. Thus, the at least one physiological element 3076 can freely flow into the pores of the second polymer 3066. This increases the degradation rate of the second polymer 3066, decreasing the second compressive pressure 3082.

The release rate 3086 of the at least one second drug increases to a peak with increasing degradation of the second polymer 3066, then decreases from the peak. The relatively slow release of the at least one second drug 3074 can encourage tissue remodeling. Examples of drugs configured to encourage tissue remodeling can include drugs that are configured to treat pain or inflammation. Further examples of such drugs can include, but are not limited to, MMP inhibitors. Examples of MMP inhibitors can be found in U.S. Pat. Nos. 10,939,911 and 10,569,071 and U.S. Patent Publication Nos. 2018/0353659, 2018/0353175, and 2018/0353174, each of which is incorporated by reference in their entirety.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for treating tissue, comprising:
   securing, by one or more staples, a biocompatible porous polymer adjunct material to tissue, the adjunct material receiving at least one physiological element released from the tissue during healing progression of the tissue, and the adjunct material exhibiting a first stiffness in compression that is approximately constant during a first time period from contact with the tissue and exhibiting a second stiffness in compression during a second time period following the first time period, the second stiffness being less than the first stiffness and decreasing with time as a function of at least one of oxidation, enzyme-catalyzed hydrolysis, and change of pH resulting from interaction with the at least one physiological element.

2. The method of claim 1, wherein the adjunct material adopts the second stiffness in response to oxidation of the adjunct due to reaction with the at least one physiological element comprising a reactive oxygen species.

3. The method of claim 2, wherein the reactive oxygen species is at least one of an oxygen containing enzyme, a free radical, a superoxide, or a peroxide.

4. The method of claim 2, wherein the reactive oxygen species is at least one of $O^{2-}$, $H_2O_2$, NO, and HOCl.

5. The method of claim 1, wherein the adjunct material oxidizes in response to reaction with the at least one physiological element comprising a reactive oxygen species released by at least one of a mature blood cell, a fybrocyte, and an inflammatory cell.

6. The method of claim 3, wherein the inflammatory cell is at least one of a leukocyte and a macrophage.

7. The method of claim 1, wherein the adjunct material adopts the second stiffness in response to hydrolysis catalyzed by an enzyme.

8. The method of claim 7, wherein the enzyme comprises a lysozyme.

9. The method of claim 1, wherein the adjunct adopts the second stiffness in response to a decrease in pH resulting from the presence of the at least one physiological element.

10. A surgical method, comprising:
   clamping tissue and a biocompatible porous polymer adjunct between opposed first and second jaws;
   firing a plurality of staples from one of the first and second jaws, through the adjunct, and into the tissue to thereby staple the adjunct to the tissue;
   wherein the adjunct, after being stapled to the tissue, receives a unit volume of fluid that causes at least one first portion of the adjunct to expand according to a first expansion behavior to thereby apply a first pressure to the tissue, and that causes at least one second portion of the adjunct to expand according to a second expansion behavior that is different from the first expansion behavior to thereby apply a second pressure to the tissue that is different than the first pressure.

11. The method of claim 10, wherein one of the first and second jaws includes a staple cartridge having a knife slot, and where the at least one first portion of the adjunct is positioned adjacent to the knife slot, and the at least one second portion of the adjunct is spaced apart from the knife slot.

12. The method of claim 10, wherein the one or more second portions of the adjunct comprise a swellable material, different from the adjunct material, positioned at the one or more second portions.

13. The method of claim 12, wherein the swellable material comprises a hydrogel.

14. The method of claim 12, wherein the swellable material comprises a porous, solid material and wherein the swellable material is housed in a compressed state within a fluid-soluble capsule.

15. The method of claim 14, wherein the capsule releases the swellable material after a predetermined time period from contact with the fluid.

16. The method of claim 10, wherein the amount of expansion of the adjunct is sufficient to provide hemostasis when the tissue is cut.

17. The method of claim 10, wherein the amount of expansion of the adjunct is sufficient to seals holes created by staples when ejected therethrough.

18. The method of claim 17, wherein at least one staple of the plurality of staples comprises at least one leg including a plurality of barbs, and wherein, when the plurality of staples are ejected into the adjunct and tissue, the barbs permit expansion of adjunct in a first direction towards the tissue and inhibit retraction of the adjunct in a second direction, opposite the first direction.

19. The method of claim 10, wherein the at least one second portion of the adjunct comprises a film overlying a surface of the adjunct.

20. The method of claim 10, wherein the adjunct further comprises a color transition dye and the method further comprises changing, by the dye, the color of the adjunct during expansion.

* * * * *